United States Patent
Cheruvallath et al.

(10) Patent No.: US 8,163,779 B2
(45) Date of Patent: Apr. 24, 2012

(54) GLUCOKINASE ACTIVATORS

(75) Inventors: Zacharia Cheruvallath, San Diego, CA (US); Jun Feng, Carlsbad, CA (US); Prasuna Guntupalli, San Diego, CA (US); Stephen L. Gwaltney, Escondido, CA (US); Joanne Miura, San Diego, CA (US); Mark Sabat, San Diego, CA (US); Mingnam Tang, San Diego, CA (US); Haxia Wang, San Diego, CA (US)

(73) Assignee: Takeda San Diego, Inc., San Diego, CA (US)

( * ) Notice: Subject to any disclaimer, the term of this patent is extended or adjusted under 35 U.S.C. 154(b) by 1126 days.

(21) Appl. No.: 11/958,271

(22) Filed: Dec. 17, 2007

(65) Prior Publication Data
US 2009/0105255 A1    Apr. 23, 2009

Related U.S. Application Data

(60) Provisional application No. 60/870,929, filed on Dec. 20, 2006.

(51) Int. Cl.
*A61K 31/4439* (2006.01)
*C07D 417/14* (2006.01)
*C07D 417/12* (2006.01)

(52) U.S. Cl. .................... 514/342; 546/270.7
(58) Field of Classification Search ............ 546/270.7; 514/342
See application file for complete search history.

(56) References Cited

U.S. PATENT DOCUMENTS

| | | |
|---|---|---|
| 3,956,287 A | 5/1976 | Bambury et al. |
| 4,900,423 A | 2/1990 | Iida et al. |
| 4,959,212 A | 9/1990 | Stancesco et al. |
| 5,239,080 A | 8/1993 | Sohda et al. |
| 5,424,204 A | 6/1995 | Aoyama et al. |
| 5,501,965 A | 3/1996 | Iwata et al. |
| 5,541,060 A | 7/1996 | Bell et al. |
| 5,854,067 A | 12/1998 | Newgard et al. |
| 6,252,082 B1 | 6/2001 | Lassalle et al. |
| 6,320,050 B1 | 11/2001 | Bizzarro et al. |
| 6,353,111 B1 | 3/2002 | Corbett et al. |
| 6,369,232 B1 | 4/2002 | Sidduri |
| 6,384,220 B2 | 5/2002 | Corbett et al. |
| 6,388,071 B2 | 5/2002 | Mahaney |
| 6,388,088 B1 | 5/2002 | Sidduri |
| 6,433,188 B1 | 8/2002 | Corbett et al. |
| 6,441,180 B1 | 8/2002 | Sidduri |
| 6,441,184 B1 | 8/2002 | Corbett et al. |
| 6,448,399 B1 | 9/2002 | Corbett et al. |
| 6,482,951 B2 | 11/2002 | Guertin |
| 6,486,184 B2 | 11/2002 | Kester et al. |
| 6,486,380 B1 | 11/2002 | Epstein |
| 6,489,485 B2 | 12/2002 | Bizzarro et al. |
| 6,503,887 B1 | 1/2003 | During |
| 6,528,543 B1 | 3/2003 | Bizzarro et al. |
| 6,545,155 B2 | 4/2003 | Corbett et al. |
| 6,566,109 B2 | 5/2003 | Kawase et al. |
| 6,583,288 B2 | 6/2003 | Goodnow, Jr. et al. |
| 6,608,218 B2 | 8/2003 | Kester et al. |
| 6,610,846 B1 | 8/2003 | Bizzarro et al. |
| 6,784,298 B2 | 8/2004 | Goodnow, Jr. et al. |
| 6,881,844 B2 | 4/2005 | Corbett et al. |
| 2001/0039344 A1 | 11/2001 | Bizzarro et al. |
| 2001/0051731 A1 | 12/2001 | Bizzarro et al. |
| 2001/0053851 A1 | 12/2001 | Mahaney |
| 2001/0056191 A1 | 12/2001 | Goodnow, Jr. et al. |
| 2002/0002190 A1 | 1/2002 | Corbett et al. |
| 2002/0032330 A1 | 3/2002 | Nomura et al. |
| 2002/0035266 A1 | 3/2002 | Sidduri |
| 2002/0035267 A1 | 3/2002 | Sidduri |
| 2002/0042512 A1 | 4/2002 | Kester et al. |
| 2002/0065239 A1 | 5/2002 | Caplan et al. |
| 2002/0065275 A1 | 5/2002 | Sidduri |
| 2002/0082260 A1 | 6/2002 | Guertin |
| 2002/0103199 A1 | 8/2002 | Corbett et al. |
| 2002/0103241 A1 | 8/2002 | Corbett et al. |
| 2002/0107396 A1 | 8/2002 | Corbett et al. |
| 2002/0110863 A1 | 8/2002 | Kawase et al. |
| 2002/0111372 A1 | 8/2002 | Corbett et al. |

(Continued)

FOREIGN PATENT DOCUMENTS

DE    4341665 A1    6/1995

(Continued)

OTHER PUBLICATIONS

Goda, F. E. et al. "Synthesis and Biological Evaluation of Novel n-nitro-5-substituted Aminoquinolines as Local Anesthetic and Anti-Arrhythmic Agents: Molecular Modeling Study" Bioorganic & Medicinal Chem. vol. 13, 2005, pp. 3175-3183, XP002498208.

Kojima et al. "Synthesis of Novel Structurally Constrained (S)-Histidyl (S)-Histidine Derivatives and Their Cooper (II) Complexes" Chem. Ltrs. vol. 1995, pp. 797-798, XP009106427.

Mohamed et al. Efficient Synthesis of Substituted Oxopiperazines From Amino Acids Tetrahedron Ltrs, vol. 39, 1998, pp. 87213-8216, XP002498215.

Piercey, et al. "Analgesic Activities of Spinal Cord Substance P Antagonists Implicate Substance P as a Neurotransmitter of Pain Sensation" Brain Research, vol. 385, 1986, pp. 74-85, XP002498209.

(Continued)

*Primary Examiner* — Patricia Morris
(74) *Attorney, Agent, or Firm* — Matthew J. Russo; Mitchell R. Brustein

(57) ABSTRACT

Compounds of the following formula are provided for use with glucokinase:

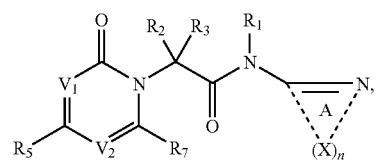

wherein the variables are as defined herein. Also provided are pharmaceutical compositions, kits and articles of manufacture comprising such compounds; methods and intermediates useful for making the compounds; and methods of using said compounds.

18 Claims, 1 Drawing Sheet

U.S. PATENT DOCUMENTS

| | | |
|---|---|---|
| 2002/0198200 A1 | 12/2002 | Kester et al. |
| 2003/0060625 A1 | 3/2003 | Bizzarro et al. |
| 2003/0082700 A1 | 5/2003 | Baker et al. |
| 2003/0082706 A1 | 5/2003 | Baker et al. |
| 2003/0082728 A1 | 5/2003 | Baker et al. |
| 2003/0092106 A1 | 5/2003 | Baker et al. |
| 2003/0096964 A1 | 5/2003 | Baker et al. |
| 2003/0096967 A1 | 5/2003 | Baker et al. |
| 2003/0100725 A1 | 5/2003 | Baker et al. |
| 2003/0100730 A1 | 5/2003 | Baker et al. |
| 2003/0129691 A1 | 7/2003 | Baker et al. |
| 2003/0129694 A1 | 7/2003 | Baker et al. |
| 2003/0138416 A1 | 7/2003 | Lau |
| 2003/0171411 A1 | 9/2003 | Kodra et al. |
| 2003/0181653 A1 | 9/2003 | Eaton et al. |
| 2003/0181657 A1 | 9/2003 | Eaton et al. |
| 2003/0181684 A1 | 9/2003 | Eaton et al. |
| 2003/0181686 A1 | 9/2003 | Eaton et al. |
| 2003/0181707 A1 | 9/2003 | Eaton et al. |
| 2003/0190716 A1 | 10/2003 | Eaton et al. |
| 2003/0194779 A1 | 10/2003 | Baker et al. |
| 2003/0194793 A1 | 10/2003 | Baker et al. |
| 2003/0199025 A1 | 10/2003 | Baker et al. |
| 2003/0199027 A1 | 10/2003 | Baker et al. |
| 2003/0207385 A1 | 11/2003 | Baker et al. |
| 2003/0219887 A1 | 11/2003 | Corbett et al. |
| 2003/0225283 A1 | 12/2003 | Corbett et al. |
| 2003/0225286 A1 | 12/2003 | Goodnow, Jr. et al. |
| 2003/0232370 A1 | 12/2003 | Trifiro |
| 2003/0232846 A1 | 12/2003 | Golec et al. |
| 2004/0009492 A1 | 1/2004 | Kim et al. |
| 2004/0014968 A1 | 1/2004 | Bizzarro et al. |
| 2004/0039164 A1 | 2/2004 | Baker et al. |
| 2004/0043457 A1 | 3/2004 | Schumacher et al. |
| 2004/0044179 A1 | 3/2004 | Baker et al. |
| 2004/0044180 A1 | 3/2004 | Baker et al. |
| 2004/0048332 A1 | 3/2004 | Baker et al. |
| 2004/0048333 A1 | 3/2004 | Baker et al. |
| 2004/0048334 A1 | 3/2004 | Baker et al. |
| 2004/0048335 A1 | 3/2004 | Baker et al. |
| 2004/0053245 A1 | 3/2004 | Tang et al. |
| 2004/0053397 A1 | 3/2004 | Iwamoto et al. |
| 2004/0058398 A1 | 3/2004 | Sarvetnick et al. |
| 2004/0063156 A1 | 4/2004 | Rademacher et al. |
| 2004/0067222 A1 | 4/2004 | Walker et al. |
| 2004/0067939 A1 | 4/2004 | Corbett et al. |
| 2004/0081981 A1 | 4/2004 | Egashira et al. |
| 2004/0086875 A1 | 5/2004 | Agee et al. |
| 2004/0086954 A1 | 5/2004 | Goueli et al. |
| 2004/0091959 A1 | 5/2004 | Baker et al. |
| 2004/0091972 A1 | 5/2004 | Baker et al. |
| 2004/0106555 A1 | 6/2004 | German |
| 2004/0108226 A1 | 6/2004 | Polychronakos et al. |
| 2004/0110246 A1 | 6/2004 | Ebinuma et al. |
| 2004/0116423 A1 | 6/2004 | Nivorozhkin et al. |
| 2004/0122235 A1 | 6/2004 | Polisetti et al. |
| 2004/0126839 A1 | 7/2004 | Baker et al. |
| 2004/0127400 A1 | 7/2004 | Smith et al. |
| 2004/0128707 A1 | 7/2004 | Ishino et al. |
| 2004/0132679 A1 | 7/2004 | Chan et al. |
| 2004/0137517 A1 | 7/2004 | Andrews et al. |
| 2004/0142373 A1 | 7/2004 | Gonye et al. |
| 2004/0142901 A1 | 7/2004 | German |
| 2004/0143110 A1 | 7/2004 | Krolewski et al. |
| 2004/0143854 A1 | 7/2004 | Klebl et al. |
| 2004/0146922 A1 | 7/2004 | Gonye et al. |
| 2004/0147017 A1 | 7/2004 | Ashkenazi et al. |
| 2004/0147725 A1 | 7/2004 | Chuntharapai et al. |
| 2004/0147748 A1 | 7/2004 | Chen et al. |
| 2004/0175740 A1 | 9/2004 | Brennan et al. |
| 2004/0180808 A1 | 9/2004 | Nye et al. |
| 2004/0180845 A1 | 9/2004 | Newgard et al. |
| 2004/0181067 A1 | 9/2004 | Fyfe et al. |
| 2004/0185531 A1 | 9/2004 | Ashkenazi et al. |
| 2004/0185548 A1 | 9/2004 | Ji |
| 2004/0186290 A1 | 9/2004 | Fyfe et al. |
| 2004/0191901 A1 | 9/2004 | Assady et al. |
| 2004/0197792 A1 | 10/2004 | Whyte et al. |
| 2004/0198969 A1 | 10/2004 | Baldwin et al. |
| 2004/0209797 A1 | 10/2004 | Karas |
| 2004/0213769 A1 | 10/2004 | Ferber |
| 2004/0214187 A1 | 10/2004 | Van Der Vuurst De Vries et al. |
| 2004/0214265 A1 | 10/2004 | Baker et al. |
| 2004/0214266 A1 | 10/2004 | Baker et al. |
| 2004/0214267 A1 | 10/2004 | Baker et al. |
| 2004/0214268 A1 | 10/2004 | Hayter et al. |
| 2004/0214269 A1 | 10/2004 | Baker et al. |
| 2004/0223964 A1 | 11/2004 | Ashkenazi et al. |
| 2005/0009129 A1 | 1/2005 | Rizzo et al. |
| 2005/0031605 A1 | 2/2005 | Bunn et al. |
| 2005/0032711 A1 | 2/2005 | Patel et al. |
| 2005/0032712 A1 | 2/2005 | Urbanski |
| 2005/0043391 A1 | 2/2005 | Fong et al. |
| 2005/0049310 A1 | 3/2005 | Mjalli et al. |
| 2005/0054715 A1 | 3/2005 | Hayter et al. |

FOREIGN PATENT DOCUMENTS

| | | |
|---|---|---|
| GB | 921315 | 3/1963 |
| WO | WO 99/14203 | 3/1999 |
| WO | WO 00/53756 A2 | 9/2000 |
| WO | WO 00/53756 A3 | 9/2000 |
| WO | WO 00/58293 A2 | 10/2000 |
| WO | WO 00/58293 A3 | 10/2000 |
| WO | WO 01/04103 | 1/2001 |
| WO | WO 01/44216 A1 | 6/2001 |
| WO | WO 01/83465 A2 | 11/2001 |
| WO | WO 01/83465 A3 | 11/2001 |
| WO | WO 01/83478 A2 | 11/2001 |
| WO | WO 01/83478 A3 | 11/2001 |
| WO | WO 01/85706 A1 | 11/2001 |
| WO | WO 01/85707 A1 | 11/2001 |
| WO | WO 01/88088 A2 | 11/2001 |
| WO | WO 01/88088 A3 | 11/2001 |
| WO | WO 01/90325 A2 | 11/2001 |
| WO | WO 01/90325 A3 | 11/2001 |
| WO | WO 01/92523 A2 | 12/2001 |
| WO | WO 01/92523 A3 | 12/2001 |
| WO | WO 01/98454 A2 | 12/2001 |
| WO | WO 02/00691 A2 | 1/2002 |
| WO | WO 02/00691 A3 | 1/2002 |
| WO | WO 02/06339 A2 | 1/2002 |
| WO | WO 02/06339 A3 | 1/2002 |
| WO | WO 02/08209 A1 | 1/2002 |
| WO | WO 02/08277 A2 | 1/2002 |
| WO | WO 02/08277 A3 | 1/2002 |
| WO | WO 02/08288 A2 | 1/2002 |
| WO | WO 02/08288 A3 | 1/2002 |
| WO | WO 02/08289 A2 | 1/2002 |
| WO | WO 02/08289 A3 | 1/2002 |
| WO | WO 02/14312 A1 | 2/2002 |
| WO | WO 02/14358 A2 | 2/2002 |
| WO | WO 02/14358 A3 | 2/2002 |
| WO | WO 02/14500 A2 | 2/2002 |
| WO | WO 02/14500 A3 | 2/2002 |
| WO | WO 02/16578 A2 | 2/2002 |
| WO | WO 02/16578 A3 | 2/2002 |
| WO | WO 02/16599 A2 | 2/2002 |
| WO | WO 02/16599 A3 | 2/2002 |
| WO | WO 02/18409 A1 | 3/2002 |
| WO | WO 02/18621 A2 | 3/2002 |
| WO | WO 02/26801 A2 | 4/2002 |
| WO | WO 02/26801 A3 | 4/2002 |
| WO | WO 02/32939 A2 | 4/2002 |
| WO | WO 02/32939 A3 | 4/2002 |
| WO | WO 02/46173 A1 | 6/2002 |
| WO | WO 02/46409 A2 | 6/2002 |
| WO | WO 02/46409 A3 | 6/2002 |
| WO | WO 02/48106 A2 | 6/2002 |
| WO | WO 02/48106 A3 | 6/2002 |
| WO | WO 02/48361 A2 | 6/2002 |
| WO | WO 02/48361 A3 | 6/2002 |
| WO | WO 02/49423 A1 | 6/2002 |
| WO | WO 02/50277 A2 | 6/2002 |
| WO | WO 02/50277 A3 | 6/2002 |
| WO | WO 02/055704 A2 | 7/2002 |
| WO | WO 02/055704 A3 | 7/2002 |
| WO | WO 02/055705 A2 | 7/2002 |

| | | |
|---|---|---|
| WO | WO 02/055705 A3 | 7/2002 |
| WO | WO 02/057450 A2 | 7/2002 |
| WO | WO 02/057450 A3 | 7/2002 |
| WO | WO 02/057453 A2 | 7/2002 |
| WO | WO 02/057453 A3 | 7/2002 |
| WO | WO 02/059315 A2 | 8/2002 |
| WO | WO 02/059315 A3 | 8/2002 |
| WO | WO 02/064791 A2 | 8/2002 |
| WO | WO 02/064791 A3 | 8/2002 |
| WO | WO 02/065985 A2 | 8/2002 |
| WO | WO 02/065985 A3 | 8/2002 |
| WO | WO 02/068649 A3 | 9/2002 |
| WO | WO 02/068680 A2 | 9/2002 |
| WO | WO 02/068680 A3 | 9/2002 |
| WO | WO 02/070539 A2 | 9/2002 |
| WO | WO 02/070539 A3 | 9/2002 |
| WO | WO 02/072757 A2 | 9/2002 |
| WO | WO 02/072757 A3 | 9/2002 |
| WO | WO 02/072875 A1 | 9/2002 |
| WO | WO 02/081498 A2 | 10/2002 |
| WO | WO 02/081498 A3 | 10/2002 |
| WO | WO 02/081517 A2 | 10/2002 |
| WO | WO 02/081517 A3 | 10/2002 |
| WO | WO 02/093127 A2 | 11/2002 |
| WO | WO 02/093127 A3 | 11/2002 |
| WO | WO 02/097434 A1 | 12/2002 |
| WO | WO 02/098355 A2 | 12/2002 |
| WO | WO 02/098355 A3 | 12/2002 |
| WO | WO 02/101074 A2 | 12/2002 |
| WO | WO 02/101074 A3 | 12/2002 |
| WO | WO 03/000262 A1 | 1/2003 |
| WO | WO 03/000267 A1 | 1/2003 |
| WO | WO 03/015774 A1 | 2/2003 |
| WO | WO 03/047626 A1 | 6/2003 |
| WO | WO 03/054198 A1 | 7/2003 |
| WO | WO 03/055482 A1 | 7/2003 |
| WO | WO 03/080585 A1 | 10/2003 |
| WO | WO 03/095438 A1 | 11/2003 |
| WO | WO 03/097824 A1 | 11/2003 |
| WO | WO 03/101284 A2 | 12/2003 |
| WO | WO 03/101284 A3 | 12/2003 |
| WO | WO 03/102161 A2 | 12/2003 |
| WO | WO 03/102161 A3 | 12/2003 |
| WO | WO 03/102163 A2 | 12/2003 |
| WO | WO 03/103597 A2 | 12/2003 |
| WO | WO 03/103597 A3 | 12/2003 |
| WO | WO 03/103601 A2 | 12/2003 |
| WO | WO 03/103601 A3 | 12/2003 |
| WO | WO 03/105879 A1 | 12/2003 |
| WO | WO 2004/002481 A1 | 1/2004 |
| WO | WO 2004/026226 | 4/2004 |
| WO | WO 2004/031179 A1 | 4/2004 |
| WO | WO 2004/037797 | 5/2004 |
| WO | WO 2004/039954 A2 | 5/2004 |
| WO | WO 2004/039954 A3 | 5/2004 |
| WO | WO 2004/045614 A1 | 6/2004 |
| WO | WO 2004/046139 A1 | 6/2004 |
| WO | WO 2004/050645 A1 | 6/2004 |
| WO | WO 2004/052869 A1 | 6/2004 |
| WO | WO 2004/063179 A1 | 7/2004 |
| WO | WO 2004/063194 A1 | 7/2004 |
| WO | WO 2004/072031 A2 | 8/2004 |
| WO | WO 2004/072031 A3 | 8/2004 |
| WO | WO 2004/072066 | 8/2004 |
| WO | WO 2004/072066 A1 | 8/2004 |
| WO | WO 2004/076420 A1 | 9/2004 |
| WO | WO 2004/081001 A1 | 9/2004 |
| WO | WO 2004/099246 A2 | 11/2004 |
| WO | WO 2004/100944 A1 | 11/2004 |
| WO | WO 2004/101505 A1 | 11/2004 |
| WO | WO 2005/030032 A2 | 4/2005 |
| WO | WO 2005/030032 A3 | 4/2005 |
| WO | WO 2005/054200 A1 | 6/2005 |
| WO | WO 2005/054233 A1 | 6/2005 |
| WO | WO 2005/095360 | 10/2005 |
| WO | WO 2006/016194 | 2/2006 |
| WO | WO 2007/104034 | 9/2007 |
| WO | WO 2007/147217 | 12/2007 |

OTHER PUBLICATIONS

Sugihara et al. "Novel Non-Peptide Fibrinogen Receptor Antagonists. 1 Synthesis and Glycoprotein IIb-IIIa Antagonistic Activities of 1,2,4-trisubstitued 2-Oxopiperazine Derivatives Incorporating Side Chain Functions of RGDF Peptide" Journal of Med. Chem. vol. 41, 1998, pp. 589-502, XP002498214.

Takenaka et al. "Synthesis of Met-and Leu-Enkephal in Analogues Containing Chiral N,N'-Ethylene-bridged Phenylalanyl-Methionine and -Leucine" Journal of Chem. Soc., Perkin, Transaction I, vol. 1993, pp. 933-937, XP008062468.

Yamashita et al. "Synthesis and Opiate Activity of Pseudo-Tetrapeptides Containing Chiral Piperazin-2-one and Piperazine Derivatives" Chem. and Pharma. Bulletin, vol. 45, No. 12, 1997, pp. 1940-1944, XP002498212.

Yamashita et al.: Structure-Activity Relationshps of Dermorphin analogues Containing Chiral Piperazine-2-one and Piperazine derivative Chem. and Pharma. Bulletin, vol. 44, No. 4, 1996, pp. 856-859, XP002498213.

Benhida et al. "A mild and effective iodination method using iodine in the presence of Bis-(trifluoroacetoxy) iodobenzene" Tetrahedron ltrs., vol. 39, No. 38 (Sep. 17, 1998) pp. 6849-6852 XP004132621.

Database C.A. Demirayak, Seref et al. "Some 6-Substituted3-Aryl-7-oxothiazolo[4,5-d]pyrimidin-2(3H)-thione Derivatives and Their Antimicrobial Activities" XP002503463 DB accession No. 2007:660570.

Database C.A. Nakahira, Hiroyuki et al. "Preparation of fused imidazole derivatives as DPP-IV inhibitirs" XP002503464 DB accession No. 2004:965251.

M.L. Edwards and Co. "Beta-latam antiboiotics derived from nitrogen heterocyclic acetic acids" J. of Med Chem. vol. 20, 204, 1977, pp. 560-563. XP002503461.

Houria-Nacera Kherf and Co "Reactivie des esters de la . . . " J. of Heterocyclic Chem. vol. 27, 1990, pp. 1401-1406. XP002503462.

Malamas M. S. et al.: "Quinazolineacetic Acids and Related Analogues as Aldose Reductase Inhibitors" Journal of Medicinal Chemistry, American Chemical Society. Washington, US, vol. 34, 1991, pp. 1492-1503, XP002928778 ISSN: 0022-2623 table 1.

Billon F. et al.: "Aldose Reductase Inhibition by 2,4-OXO and Thioxo Derivatives of 1,2,3,4-Tetrahydroquinazoline" European Journal of Medicinal Chemistry, Editions Scientifique Elsevier, Paris, FR, vol. 25, No. 2, 1990, pp. 121-126, XP000654239 ISSN: 0223-5234 table 1.

Yamashita J. et al.: "Studies on Antitumor Agents. V" Chemical and Pharmaceutical Bulletin, Pharmaceutical Society of Japan, Tokyo, JP, vol. 12, No. 30, 1982, pp. 4258-4267, XP002077368 ISSN: 0009-2363 Example 25.

Evans, J. Johnson, T.B.: "Researches on Pyrimidines. CXIX. Determination of the Constitution of Alkylation Products of Phenyluracil and Phenylhydrouracil" Journal of the American Chemical Society, Dec. 1930, pp. 4993-5005, XP002449771 Example VI.

[SEQ. I.D. No. 1]

MKLMALTLVEQILAEFQLQEEDLKKVMRRMQKEMDRGLRLETHEEASVKMLPTYVRSTPE
GSEVGDFLSLDLGGTNFRVMLVKVGEGEEGQWSVKTKHQMYSIPEDAMTGTAEMLFDYIS
ECISDFLDKHQMKHKKLPLGFTPSFPVRHEDIDKGILLNWTKGFKASGAEGNNVVGLLRD
AIKRRGDFEMDVVAMVNDTVATMISCYYEDHQCEVGMIVGTGCNACYMEDMQNVELVEGD
EGRMCVNTEWGAFGDSGELDEFLLEYDRLVDESSANPGQQLYEKLIGGKYMGELVRLVLL
RLVDENLLFHGEASEQLRTPGAFETRFVSQVESDTGDRKQIYNILSTLGLRPSTTDCDIV
RRACESVSTRAAHMCSAGLAGVINRMRESRSEDVMRITVGVDGSVYKLHPSFKERFHASV
RRLTPSCEITFIESEEGSGRGAALVSAVACKKACMLGQ

GLUCOKINASE ACTIVATORS

RELATED APPLICATION

This application claims the benefit of U.S. Provisional Application No. 60/870,929, filed Dec. 20, 2006, which is incorporated herein by reference.

FIELD OF THE INVENTION

The present invention relates to compounds that may be used to activate hexokinases, as well as compositions of matter, kits and articles of manufacture comprising these compounds. The invention also relates to methods for activating hexokinases and treatment methods using compounds according to the present invention. In addition, the invention relates to methods of making the compounds of the present invention, as well as intermediates useful in such methods. In particular, the present invention relates to glucokinase activators; compositions of matter, kits and articles of manufacture comprising these compounds; methods for activating glucokinase; and methods and intermediates useful for making the glucokinase activators.

BACKGROUND OF THE INVENTION

Glucokinase (GK, Hexokinase IV) is one of four hexokinases that are found in mammals (Colowick, S. P., in The Enzymes, Vol. 9 (P. Boyer, ed.) Academic Press, New York, N.Y., pages 1-48, 1973). The hexokinases catalyze the first step in the metabolism of glucose, i.e., the conversion of glucose to glucose-6-phosphate. Glucokinase is found principally in pancreatic β-cells and liver parenchymal cells, two cell types that are known to play critical roles in whole-body glucose homeostasis. Specifically, GK is a rate-controlling enzyme for glucose metabolism in these two cell types (Chipkin, S. R., Kelly, K. L., and Ruderman, N. B. in Joslin's Diabetes (C. R. Khan and G. C. Wier, eds.), Lea and Febiger, Philadelphia, Pa., pages 97-115, 1994).

The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting levels (5 mM) to postprandial levels following a carbohydrate-containing meal (about 10-15 mM) (Printz, R. G., Magnuson, M. A., and Granner, D. K. in Ann. Rev. Nutrition Vol. 13 (R. E. Olson, D. M. Bier, and D. B. McCormick, eds.), Annual Review, Inc., Palo Alto, Calif., pages 463-496, 1993). These findings suggest that GK functions as a glucose sensor in β-cells and hepatocytes (Meglasson, M. D. and Matschinsky, F. M. Amer. J. Physiol. 246, E1-E13, 1984).

More recently, studies in transgenic animals confirmed that GK does indeed play a critical role in whole-body glucose homeostasis. Animals that do not express GK die within days of birth with severe diabetes, while animals overexpressing GK have improved glucose tolerance (Grupe, A., Hultgren, B., Ryan, A. et al., Cell 83, 69-78, 1995; Ferrie, T., Riu, E., Bosch, F. et al., FASEB J., 10, 1213-1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., Biochem. J. 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., New England J. Med. 338, 226-230, 1998). Accordingly, compounds that activate GK and, thereby, increase the sensitivity of the GK sensor system are expected to be useful in the treatment of the hyperglycemia characteristic of all type II diabetes. Glucokinase activators should increase the flux of glucose metabolism in β-cells and hepatocytes, which will be coupled to increased insulin secretion.

There is a continued need to find new therapeutic agents to treat human diseases. The hexokinases, specifically but not limited to glucokinase, are especially attractive targets for the discovery of new therapeutics due to their important role in diabetes, hyperglycemia and other diseases.

SUMMARY OF THE INVENTION

The present invention relates to compounds that activate glucokinase. The present invention also provides compositions, articles of manufacture and kits comprising these compounds. In addition, the invention relates to methods of making the compounds of the present invention, as well as intermediates useful in such methods.

In one embodiment, a pharmaceutical composition is provided that comprises a glucokinase activator according to the present invention as an active ingredient. Pharmaceutical compositions according to the invention may optionally comprise 0.001%-100% of one or more activators of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

The invention is also directed to kits and other articles of manufacture for treating disease states associated with glucokinase.

In one embodiment, a kit is provided that comprises a composition comprising at least one glucokinase activator of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one glucokinase activator of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to modulate glucokinase. In particular, the compounds, compositions, kits and articles of manufacture can be used to activate glucokinase.

In another embodiment, the compounds, compositions, kits and articles of manufacture are used to treat a disease state for which increasing glucokinase activity ameliorates the pathology and/or symptomology of the disease state.

In another embodiment, a compound is administered to a subject wherein glucokinase activity within the subject is altered and, in one embodiment, increased.

In another embodiment, a prodrug of a compound is administered to a subject that is converted to the compound in vivo where it activates glucokinase.

In another embodiment, a method of activating glucokinase is provided that comprises contacting glucokinase with a compound according to the present invention.

In another embodiment, a method of activating glucokinase is provided that comprises causing a compound according to the present invention to be present in a subject in order to activate glucokinase in vivo.

In another embodiment, a method of activating glucokinase is provided that comprises administering a first compound to a subject that is converted in vivo to a second compound wherein the second compound activates glucokinase in vivo. It is noted that the compounds of the present invention may be the first or second compounds.

In another embodiment, a therapeutic method is provided that comprises administering a compound according to the present invention.

In another embodiment, a method of treating a condition in a patient that is known to be mediated by glucokinase, or which is known to be treated by glucokinase activators, is provided comprising administering to the patient a therapeutically effective amount of a compound according to the present invention.

In another embodiment, a method is provided for treating a disease state for which increasing glucokinase activity ameliorates the pathology and/or symptomology of the disease state, the method comprising: causing a compound according to the present invention to be present in a subject in a therapeutically effective amount for the disease state.

In another embodiment, a method is provided for treating a disease state for which increasing glucokinase activity ameliorates the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which increasing glucokinase activity ameliorates the pathology and/or symptomology of the disease state, the method comprising: administering a compound according to the present invention to a subject such that the compound is present in the subject in a therapeutically effective amount for the disease state.

In another embodiment, a method is provided for using a compound according to the present invention in order to manufacture a medicament for use in the treatment of a disease state that is known to be mediated by glucokinase, or that is known to be treated by glucokinase activators.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well known in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula," "compound having the formula" and "compound of the formula" is intended to encompass the compound and all pharmaceutically acceptable ionized forms and solvates, all possible stereoisomers, and all possible resonance forms and tautomers unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to activating glucokinase and thus may themselves be prodrugs for another compound. Such prodrugs of another compound may or may not themselves independently have glucokinase activity.

BRIEF DESCRIPTION OF THE FIGURES

FIG. 1 illustrates SEQ. ID No. 1 referred to in this application.

DEFINITIONS

Unless otherwise stated, the following terms used in the specification and claims shall have the following meanings for the purposes of this application.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with ($C_{3-8}$) rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkenyl" means a straight or branched, carbon chain that contains at least one carbon-carbon double bond (—CR=CR'— or —CR=CR'R", wherein R, R' and R" are each independently hydrogen or further substituents). Examples of alkenyl include vinyl, allyl, isopropenyl, pentenyl, hexenyl, heptenyl, 1-propenyl, 2-butenyl, 2-methyl-2-butenyl, and the like. In particular embodiments, "alkenyl," either alone or represented along with another radical, can be a ($C_{2-20}$)alkenyl, a ($C_{2-15}$)alkenyl, a ($C_{2-10}$)alkenyl, a ($C_{2-5}$) alkenyl or a ($C_{2-3}$)alkenyl. Alternatively, "alkenyl," either alone or represented along with another radical, can be a ($C_2$)alkenyl, a ($C_3$)alkenyl or a ($C_4$)alkenyl.

"Alkenylene" means a straight or branched, divalent carbon chain having one or more carbon-carbon double bonds (—CR=CR'—, wherein R and R' are each independently hydrogen or further substituents). Examples of alkenylene include ethene-1,2-diyl, propene-1,3-diyl, methylene-1,1-diyl, and the like. In particular embodiments, "alkenylene," either alone or represented along with another radical, can be a ($C_{2-20}$) alkenylene, a ($C_{2-15}$) alkenylene, a ($C_{2-10}$) alkenylene, a ($C_{2-5}$) alkenylene or a ($C_{2-3}$) alkenylene. Alternatively, "alkenylene," either alone or represented along with another radical, can be a ($C_2$) alkenylene, a ($C_3$) alkenylene or a ($C_4$) alkenylene.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with one or more of the carbon atoms being replaced with oxygen (See "oxaalkyl"), a carbonyl group (See "oxoalkyl"), sulfur (See "thioalkyl"), and/or nitrogen (See "azaalkyl"). ($C_X$)alkyl and ($C_{X-Y}$)alkyl are typically used where X and Y indicate the number of carbon atoms in the chain. For example, ($C_{1-6}$)alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl and the like) means a straight or branched, saturated or unsaturated aliphatic divalent radical having the number of atoms indicated or when no atoms are indicated means a bond (e.g., ($C_{6-10}$)aryl($C_{1-3}$) alkyl includes, benzyl, phenethyl, 1-phenylethyl, 3-phenylpropyl, 2-thienylmethyl, 2-pyridinylmethyl and the like). In particular embodiments, "alkyl," either alone or represented along with another radical, can be a ($C_{1-20}$)alkyl, a ($C_{1-15}$) alkyl, a ($C_{1-10}$)alkyl, a ($C_{1-5}$)alkyl or a ($C_{1-3}$)alkyl. Alternatively, "alkyl," either alone or represented along with another radical, can be a ($C_1$)alkyl, a ($C_2$)alkyl or a ($C_3$)alkyl.

"Alkylene", unless indicated otherwise, means a straight or branched, saturated or unsaturated, aliphatic, divalent radical. ($C_X$)alkylene and ($C_{X-Y}$)alkylene are typically used where X and Y indicate the number of carbon atoms in the chain. For example, ($C_{1-6}$)alkylene includes methylene (—$CH_2$—), ethylene (—$CH_2CH_2$—), trimethylene (—$CH_2CH_2CH_2$—), tetramethylene (—$CH_2CH_2CH_2CH_2$—) 2-butenylene (—$CH_2CH=CHCH_2$—), 2-methyltetramethylene (—$CH_2CH(CH_3)CH_2CH_2$—), pentamethylene (—$CH_2CH_2CH_2CH_2CH_2$—) and the like. In particular embodiments, "alkylene," either alone or represented along with another radical, can be a ($C_{1-20}$)alkylene, a ($C_{1-15}$)alkylene, a ($C_{1-10}$)alkylene, a ($C_{1-5}$)alkylene or a ($C_{1-3}$)alkylene. Alternatively, "alkylene," either alone or represented along with another radical, can be a ($C_1$)alkylene, a ($C_2$)alkylene or a ($C_3$)alkylene.

"Alkylidene" means a straight or branched, saturated or unsaturated, aliphatic radical connected to the parent molecule by a double bond. ($C_X$)alkylidene and ($C_{X-Y}$)alkylidene are typically used where X and Y indicate the number of carbon atoms in the chain. For example, ($C_{1-6}$)alkylidene includes methylene (=$CH_2$), ethylidene (=$CHCH_3$), isopropylidene (=$C(CH_3)_2$), propylidene (=$CHCH_2CH_3$), allylidene (=CH—CH=$CH_2$), and the like. In particular embodiments, "alkylidene," either alone or represented along with another radical, can be a ($C_{1-20}$)alkylidene, a ($C_{1-15}$) alkylidene, a ($C_{1-10}$)alkylidene, a ($C_{1-5}$)alkylidene or a ($C_{1-3}$)alkylidene. Alternatively, "alkylidene," either alone or represented along with another radical, can be a ($C_1$)alkylidene, a ($C_2$)alkylidene or a ($C_3$)alkylidene.

"Alkynyl" means a straight or branched, carbon chain that contains at least one carbon-carbon triple bond (—C≡C— or —C≡CR, wherein R is hydrogen or a further substituent). Examples of alkynyl include ethynyl, propargyl, 3-methyl-1-pentynyl, 2-heptynyl and the like. In particular embodiments, "alkynyl," either alone or represented along with another radical, can be a ($C_{2-20}$)alkynyl, a ($C_{2-15}$)alkynyl, a ($C_{2-10}$) alkynyl, a ($C_{2-5}$)alkynyl or a ($C_{2-3}$)alkynyl. Alternatively, "alkynyl," either alone or represented along with another radical, can be a ($C_2$)alkynyl, a ($C_3$)alkynyl or a ($C_4$)alkynyl.

"Alkynylene" means a straight or branched, divalent carbon chain having one or more carbon-carbon triple bonds (—CR≡CR'—, wherein R and R' are each independently hydrogen or further substituents). Examples of alkynylene include ethyne-1,2-diyl, propyne-1,3-diyl, and the like. In particular embodiments, "alkynylene," either alone or represented along with another radical, can be a ($C_{2-20}$) alkynylene, a ($C_{2-15}$) alkynylene, a ($C_{2-10}$) alkynylene, a ($C_{2-5}$) alkynylene or a ($C_{2-3}$) alkynylene. Alternatively, "alkynylene," either alone or represented along with another radical, can be a ($C_2$) alkynylene, a ($C_3$) alkynylene or a ($C_4$) alkynylene.

"Amido" means the radical —C(=O)—NR—, —C(=O)—NRR', —NR—C(=O)— and/or —NR—C (=O)R', wherein each R and R' are independently hydrogen or a further substituent.

"Amino" means a nitrogen moiety having two further substituents where, for example, a hydrogen or carbon atom is attached to the nitrogen. For example, representative amino groups include —$NH_2$, —$NHCH_3$, —$N(CH_3)_2$, —NH (($C_{1-10}$)alkyl), —N(($C_{1-10}$)alkyl)$_2$, —NH(aryl), —NH(heteroaryl), —N(aryl)$_2$, —N(heteroaryl)$_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are $sp^2$ hybridized and the total number of pi electrons is equal to 4n+2. An aromatic ring may be such that the ring atoms are only carbon atoms or may include carbon and non-carbon atoms (See "heteroaryl").

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. ($C_X$)aryl and ($C_{X-Y}$)aryl are typically used where X and Y indicate the number of carbon atoms in the ring. In particular embodiments, "aryl," either alone or represented along with another radical, can be a $(C_{3-14})$aryl, a $(C_{3-10})$aryl, a $(C_{3-7})$aryl, a $(C_{8-10})$aryl or a $(C_{5-7})$aryl. Alternatively, "aryl," either alone or represented along with another radical, can be a $(C_5)$aryl, a $(C_6)$aryl, a $(C_7)$aryl, a $(C_8)$aryl, a $(C_9)$aryl or a $(C_{10})$aryl.

"Azaalkyl" and "aminoalkyl" mean an alkyl, as defined above, except where one or more of the carbon atoms forming the alkyl chain are replaced with substituted or unsubstituted nitrogen atoms (—NR— or —NRR', wherein R and R' are each independently hydrogen or further substituents). For example, a $(C_{1-10})$azaalkyl refers to a chain comprising between 1 and 10 carbons and one or more nitrogen atoms.

"Bicycloalkyl" means a saturated or partially unsaturated fused, spiro or bridged bicyclic ring assembly. In particular embodiments, "bicycloalkyl," either alone or represented along with another radical, can be a $(C_{4-15})$bicycloalkyl, a $(C_{4-10})$bicycloalkyl, a $(C_{6-10})$bicycloalkyl or a $(C_{8-10})$bicycloalkyl. Alternatively, "bicycloalkyl," either alone or represented along with another radical, can be a $(C_8)$bicycloalkyl, a $(C_9)$bicycloalkyl or a $(C_{10})$bicycloalkyl.

"Bicycloaryl" means a fused, spiro or bridged bicyclic ring assembly wherein at least one of the rings comprising the assembly is aromatic. $(C_X)$bicycloaryl and $(C_{X-Y})$bicycloaryl are typically used where X and Y indicate the number of carbon atoms in the bicyclic ring assembly and directly attached to the ring. In particular embodiments, "bicycloaryl," either alone or represented along with another radical, can be a (a $(C_{4-15})$bicycloaryl, a $(C_{4-10})$bicycloaryl, a $(C_{6-10})$bicycloaryl or a $(C_{8-10})$bicycloaryl. Alternatively, "bicycloalkyl," either alone or represented along with another radical, can be a $(C_8)$bicycloaryl, a $(C_9)$bicycloaryl or a $(C_{10})$bicycloaryl.

"Bridging ring" and "bridged ring" as used herein refer to a ring that is bonded to another ring to form a compound having a bicyclic or polycyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NRR', wherein R and R' are each independently hydrogen or further substituents.

"Carbocycle" means a ring consisting of carbon atoms.

"Carbonyl" means the radical —C(=O)— and/or —C(=O)R, wherein R is hydrogen or a further substituent. It is noted that the carbonyl radical may be further substituted with a variety of substituents to form different carbonyl groups including acids, acid halides, aldehydes, amides, esters, and ketones.

"Carboxy" means the radical —C(=O)—O— and/or —C(=O)—OR, wherein R is hydrogen or a further substituent. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, bicyclic or polycyclic ring assembly. $(C_X)$cycloalkyl and $(C_{X-Y})$cycloalkyl are typically used where X and Y indicate the number of carbon atoms in the ring assembly. For example, $(C_{3-10})$cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like. In particular embodiments, "cycloalkyl," either alone or represented along with another radical, can be a $(C_{3-14})$cycloalkyl, a $(C_{3-10})$cycloalkyl, a $(C_{3-7})$cycloalkyl, a $(C_{8-10})$cycloalkyl or a $(C_{5-7})$cycloalkyl. Alternatively, "cycloalkyl," either alone or represented along with another radical, can be a $(C_5)$cycloalkyl, a $(C_6)$cycloalkyl, a $(C_7)$cycloalkyl, a $(C_8)$cycloalkyl, a $(C_9)$cycloalkyl or a $(C_{10})$cycloalkyl.

"Cycloalkylene" means a divalent, saturated or partially unsaturated, monocyclic, bicyclic or polycyclic ring assembly. $(C_X)$cycloalkylene and $(C_{X-Y})$cycloalkylene are typically used where X and Y indicate the number of carbon atoms in the ring assembly. In particular embodiments, "cycloalkylene," either alone or represented along with another radical, can be a $(C_{3-14})$cycloalkylene, a $(C_{3-10})$cycloalkylene, a $(C_{3-7})$cycloalkylene, a $(C_{8-10})$cycloalkylene or a $(C_{5-7})$cycloalkylene. Alternatively, "cycloalkylene," either alone or represented along with another radical, can be a $(C_5)$cycloalkylene, a $(C_6)$cycloalkylene, a $(C_7)$cycloalkylene, a $(C_8)$cycloalkylene, a $(C_9)$cycloalkylene or a $(C_{10})$cycloalkylene.

"Disease" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a ring that is bonded to another ring to form a compound having a bicyclic structure where the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Heteroalkyl" means alkyl, as defined in this application, provided that one or more of the atoms within the alkyl chain is a heteroatom. In particular embodiments, "heteroalkyl," either alone or represented along with another radical, can be a hetero$(C_{1-20})$alkyl, a hetero$(C_{1-5})$alkyl, a hetero$(C_{1-10})$alkyl, a hetero$(C_{1-5})$alkyl, a hetero$(C_{1-3})$alkyl or a hetero$(C_{1-2})$alkyl. Alternatively, "heteroalkyl," either alone or represented along with another radical, can be a hetero$(C_1)$alkyl, a hetero$(C_2)$alkyl or a hetero$(C_3)$alkyl.

"Heteroaryl" means a monocyclic, bicyclic or polycyclic aromatic group wherein at least one ring atom is a heteroatom and the remaining ring atoms are carbon. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted. In particular embodiments, "heteroaryl," either alone or represented along with another radical, can be a hetero($C_{1-13}$)aryl, a hetero($C_{2-13}$)aryl, a hetero($C_{2-6}$)aryl, a hetero($C_{3-9}$)aryl or a hetero($C_{5-9}$)aryl. Alternatively, "heteroaryl," either alone or represented along with another radical, can be a hetero($C_3$)aryl, a hetero($C_4$)aryl, a hetero($C_5$)aryl, a hetero($C_6$)aryl., a hetero($C_7$)aryl, a hetero($C_8$)aryl or a hetero($C_9$)aryl.

"Heteroatom" refers to an atom that is not a carbon atom. Particular examples of heteroatoms include, but are not limited to, nitrogen, oxygen, and sulfur.

"Heteroatom moiety" includes a moiety where the atom by which the moiety is attached is not a carbon. Examples of heteroatom moieties include —NR—, —N$^+$(O$^-$)=, —O—, —S— or —S(O)$_2$—, wherein R is hydrogen or a further substituent.

"Heterobicycloalkyl" means bicycloalkyl, as defined in this application, provided that one or more of the atoms within the ring is a heteroatom. For example hetero($C_{9-12}$) bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like. In particular embodiments, "heterobicycloalkyl," either alone or represented along with another radical, can be a hetero($C_{1-14}$)bicycloalkyl, a hetero($C_{4-14}$)bicycloalkyl, a hetero($C_{4-9}$)bicycloalkyl or a hetero($C_{5-9}$)bicycloalkyl. Alternatively, "heterobicycloalkyl," either alone or represented along with another radical, can be a hetero($C_5$)bicycloalkyl, hetero($C_6$)bicycloalkyl, hetero($C_7$)bicycloalkyl, hetero($C_8$)bicycloalkyl or a hetero($C_9$)bicycloalkyl.

"Heterobicycloaryl" means bicycloaryl, as defined in this application, provided that one or more of the atoms within the ring is a heteroatom. For example, hetero($C_{4-12}$)bicycloaryl as used in this application includes, but is not limited to, 2-amino-4-oxo-3,4-dihydropteridin-6-yl, tetrahydroisoquinolinyl, and the like. In particular embodiments, "heterobicycloaryl," either alone or represented along with another radical, can be a hetero($C_{1-14}$)bicycloaryl, a hetero($C_{4-14}$) bicycloaryl, a hetero($C_{4-9}$)bicycloaryl or a hetero($C_{5-9}$)bicycloaryl. Alternatively, "heterobicycloaryl," either alone or represented along with another radical, can be a hetero($C_5$) bicycloaryl, hetero($C_6$)bicycloaryl, hetero($C_7$)bicycloaryl, hetero($C_8$)bicycloaryl or a hetero($C_9$)bicycloaryl.

"Heterocycloalkyl" means cycloalkyl, as defined in this application, provided that one or more of the atoms forming the ring is a heteroatom selected, independently from N, O, or S, Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like. In particular embodiments, "heterocycloalkyl," either alone or represented along with another radical, can be a hetero($C_{1-13}$)cycloalkyl, a hetero ($C_{1-9}$)cycloalkyl, a hetero($C_{1-6}$)cycloalkyl, a hetero($C_{5-9}$)cycloalkyl or a hetero($C_{2-6}$)cycloalkyl. Alternatively, "heterocycloalkyl," either alone or represented along with another radical, can be a hetero($C_2$)cycloalkyl, a hetero($C_3$)cycloalkyl, a hetero($C_4$)cycloalkyl, a hetero($C_5$)cycloalkyl, a hetero($C_6$)cycloalkyl, hetero($C_7$)cycloalkyl, hetero($C_8$)cycloalkyl or a hetero($C_9$)cycloalkyl.

"Heterocycloalkylene" means cycloalkylene, as defined in this application, provided that one or more of the ring member carbon atoms is replaced by a heteroatom. In particular embodiments, "heterocycloalkylene," either alone or represented along with another radical, can be a hetero($C_{1-13}$) cycloalkylene, a hetero($C_{1-9}$)cycloalkylene, a hetero($C_{1-6}$) cycloalkylene, a hetero($C_{5-9}$)cycloalkylene or a hetero($C_{2-6}$) cycloalkylene. Alternatively, "heterocycloalkylene," either alone or represented along with another radical, can be a hetero($C_2$)cycloalkylene, a hetero($C_3$)cycloalkylene, a hetero ($C_4$)cycloalkylene, a hetero($C_5$)cycloalkylene, a hetero($C_6$) cycloalkylene, hetero($C_7$)cycloalkylene, hetero($C_8$)cycloalkylene or a hetero($C_9$)cycloalkylene.

"Hydroxy" means the radical —OH.

"IC$_{50}$" means the molar concentration of an inhibitor that produces 50% inhibition of the target enzyme.

"Imino" means the radical —CR(=NR') and/or —C(=NR')—, wherein R and R' are each independently hydrogen or a further substituent.

"Isomers" means compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Leaving group" means the group with the meaning conventionally associated with it in synthetic organic chemistry, i.e., an atom or group displaceable under reaction (e.g., alkylating) conditions. Examples of leaving groups include, but are not limited to, halo (e.g., F, Cl, Br and I), alkyl (e.g., methyl and ethyl) and sulfonyloxy (e.g., mesyloxy, ethanesulfonyloxy, benzenesulfonyloxy and tosyloxy), thiomethyl, thienyloxy, dihalophosphinoyloxy, tetrahalophosphoxy, benzyloxy, isopropyloxy, acyloxy, and the like.

"Moiety providing X atom separation" and "linker providing X atom separation" between two other moieties mean that the chain of atoms directly linking the two other moieties is X atoms in length. When X is given as a range (e.g., $X_1$-$X_2$), then the chain of atoms is at least $X_1$ and not more than $X_2$ atoms in length. It is understood that the chain of atoms can be formed from a combination of atoms including, for example, carbon, nitrogen, sulfur and oxygen atoms. Further, each atom can optionally be bound to one or more substituents, as valencies allow. In addition, the chain of atoms can form part of a ring. Accordingly, in one embodiment, a moiety providing X atom separation between two other moieties (R and R') can be represented by R-(L)$_X$-R' where each L is independently selected from the group consisting of CR"R''', NR"", O, S, CO, CS, C=NR''''', SO, SO$_2$, and the like, where any two or more of R", R''', R"" and R''''' can be taken together to form a substituted or unsubstituted ring.

"Nitro" means the radical —NO$_2$.

"Oxaalkyl" means an alkyl, as defined above, except where one or more of the carbon atoms forming the alkyl chain are replaced with oxygen atoms (—O— or —OR, wherein R is hydrogen or a further substituent). For example, an oxa($C_{1-10}$)alkyl refers to a chain comprising between 1 and 10 carbons and one or more oxygen atoms.

"Oxoalkyl" means an alkyl, as defined above, except where one or more of the carbon atoms forming the alkyl chain are replaced with carbonyl groups (—C(=O)— or —C(=O)—R, wherein R is hydrogen or a further substituent). The carbonyl group may be an aldehyde, ketone, ester, amide, acid or acid halide. For example, an oxo($C_{1-10}$)alkyl refers to a chain comprising between 1 and 10 carbon atoms and one or more carbonyl groups.

"Oxy" means the radical —O— or —OR, wherein R is hydrogen or a further substituent. Accordingly, it is noted that the oxy radical may be further substituted with a variety of substituents to form different oxy groups including hydroxy, alkoxy, aryloxy, heteroaryloxy or carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Polycyclic ring" includes bicyclic and multi-cyclic rings. The individual rings comprising the polycyclic ring can be fused, spiro or bridging rings.

"Prodrug" means a compound that is convertible in vivo metabolically into an active species according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-b-hydroxynaphthoates, gentisates, isethionates, di-p-toluoyl-tartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

"Protected derivatives" means derivatives of compounds in which a reactive site or sites are blocked with protecting groups. Protected derivatives are useful in the preparation of pharmaceutical agents or in themselves may be active as pharmaceutical agents. A comprehensive list of suitable protecting groups can be found in T. W. Greene, *Protecting Groups in Organic Synthesis*, 3rd edition, John Wiley & Sons, Inc. 1999.

"Ring" and "ring assembly" means a carbocyclic or a heterocyclic system and includes aromatic and non-aromatic systems. The system can be monocyclic, bicyclic or polycyclic. In addition, for bicyclic and polycyclic systems, the individual rings comprising the polycyclic ring can be fused, spiro or bridging rings.

"Subject" and "patient" includes humans, non-human mammals (e.g., dogs, cats, rabbits, cattle, horses, sheep, goats, swine, deer, and the like) and non-mammals (e.g., birds, and the like).

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, t-butoxycarbonyl [(CH$_3$)$_3$C—OCO—], benzyloxycarbonyl, p-methoxybenzyloxycarbonyl, vinyloxycarbonyl, β-(p-toluenesulfonyl)ethoxycarbonyl, and the like. Examples of suitable amino acid residues include amino acid residues per se and amino acid residues that are protected with a protecting group. Suitable amino acid residues include, but are not limited to, residues of Gly (glycine), Ala (alanine; CH$_3$CH(NH$_2$)CO—), Arg (arginine), Asn (asparagine), Asp (aspartic acid), Cys (cysteine), Glu (glutamic acid), His (histidine), Ile (isoleucine), Leu (leucine; (CH$_3$)$_2$CHCH$_2$CH(NH$_2$)CO—), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [(CH$_3$)$_3$C—OCO-], and the like. Suitable peptide residues include peptide residues comprising two to five, and optionally two to three, of the aforesaid amino acid residues. Examples of such peptide residues include, but are not limited to, residues of such peptides as Ala-Ala [CH$_3$CH(NH$_2$)CO—NHCH(CH$_3$)CO-], Gly-Phe, Nva-Nva, Ala-Phe, Gly-Gly, Gly-Gly-Gly, Ala-Met, Met-Met, Leu-Met and Ala-Leu. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [(CH$_3$)$_3$C—OCO—], and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxybenzyloxycarbonyl); and halogenoethoxycarbonyl groups (such as β,β,β-trichloroethoxycarbonyl and β-iodoethoxycarbonyl).

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —CH$_3$. In general, a non-hydrogen substituent may be any substituent that may be bound to an atom of the given moiety that is specified to be substituted. Examples of substituents include, but are not limited to, aldehyde, alicyclic, aliphatic, (C$_{1-10}$)alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted. In one particular embodiment, examples of substituents include, but are not limited to, hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl (C$_{1-10}$)alkyl, sulfinyl(C$_{1-10}$)alkyl, (C$_{1-10}$)azaalkyl, imino (C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl (C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero (C$_{4-12}$)bicycloaryl. In addition, the substituent is itself optionally substituted by a further substituent. In one particular embodiment, examples of the further substituent include, but are not limited to, hydrogen, halo, nitro, cyano, thio, oxy, hydroxy, carbonyloxy, (C$_{1-10}$)alkoxy, (C$_{4-12}$)aryloxy, hetero (C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl (C$_{1-10}$)alkyl, sulfinyl(C$_{1-10}$)alkyl, (C$_{1-10}$)azaalkyl, imino (C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl (C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero (C$_{4-12}$)bicycloaryl.

"Sulfinyl" means the radical —SO— and/or —SO—R, wherein R is hydrogen or a further substituent. It is noted that the sulfinyl radical may be further substituted with a variety of substituents to form different sulfinyl groups including sulfinic acids, sulfinamides, sulfinyl esters, and sulfoxides.

"Sulfonyl" means the radical —SO$_2$— and/or —SO$_2$—R, wherein R is hydrogen or a further substituent. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thio" denotes replacement of an oxygen by a sulfur and includes, but is not limited to, —SR, —S— and =S containing groups.

"Thioalkyl" means an alkyl, as defined above, except where one or more of the carbon atoms forming the alkyl chain are replaced with sulfur atoms (—S— or —S—R, wherein R is hydrogen or a further substituent). For example, a thio(C$_{1-10}$)alkyl refers to a chain comprising between 1 and 10 carbons and one or more sulfur atoms.

"Thiocarbonyl" means the radical —C(=S)— and/or —C(=S)—R, wherein R is hydrogen or a further substituent. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a (C$_1$)alkyl comprises methyl (i.e., —CH$_3$) as well as —CRR'R" where R, R', and R" may each independently be hydrogen or a further substituent where the atom attached to the carbon is a heteroatom or cyano. Hence, $CF_3$, $CH_2OH$ and $CH_2CN$, for example, are all ($C_1$)alkyls. Similarly, terms such as alkylamino and the like comprise dialkylamino and the like.

A compound having a formula that is represented with a dashed bond is intended to include the formulae optionally having zero, one or more double bonds, as exemplified and shown below:

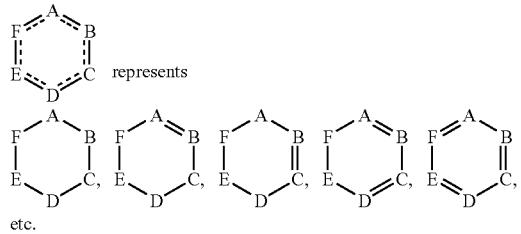

etc.

DETAILED DESCRIPTION OF THE INVENTION

The present invention relates to compounds that may be used to activate hexokinases and, in particular glucokinase (referred to herein as GK). The present invention also relates to pharmaceutical compositions, kits and articles of manufacture comprising such compounds. In addition, the present invention relates to methods and intermediates useful for making the compounds. Further, the present invention relates to methods of using said compounds. It is noted that the compounds of the present invention may also possess activity for other hexokinase family members and thus may be used to address disease states associated with these other family members.

Glucokinase Activators

In one of its aspects, the present invention relates to compounds that are useful as glucokinase activators. In one embodiment, glucokinase activators of the present invention have the formula:

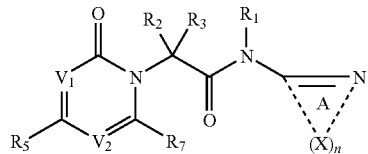

or a polymorph, solvate, ester, tautomer, enantiomer, pharmaceutically acceptable salt or prodrug thereof, wherein n is selected from the group consisting of 3, 4 and 5;

$V_1$ is selected from the group consisting of $CR_4$ and N;

$V_2$ is selected from the group consisting of $CR_6$ and N;

each X is independently selected from the group consisting of $CR_8R_9$, CO, CS, $NR_{10}$, O, S, SO and $SO_2$;

$R_1$ is selected from the group consisting of hydrogen and a substituent convertible to hydrogen in vivo;

$R_2$ and $R_3$ are each independently selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_2$ and $R_3$ are taken together to form a substituted or unsubstituted ring;

$R_4$, $R_5$, $R_6$ and $R_7$ are each independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or any two of $R_4$, $R_5$, $R_6$ and $R_7$ are taken together to form a substituted or unsubstituted ring;

$R_8$ and $R_9$ are each independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that $R_9$ is absent when the atom to which it is bound forms part of a double bond; and $R_{10}$ is selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, with the proviso that $R_{10}$ is absent when the atom to which it is bound forms part of a double bond, or any two $R_8$, $R_9$ and $R_{10}$ are taken together to form a substituted or unsubstituted ring.

In another embodiment, glucokinase activators of the present invention have the formula:

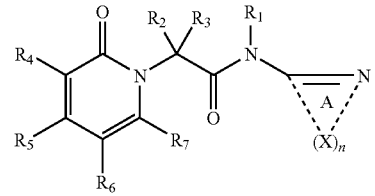

or a polymorph, solvate, ester, tautomer, enantiomer, pharmaceutically acceptable salt or prodrug thereof.

In still another embodiment, glucokinase activators of the present invention have the formula:

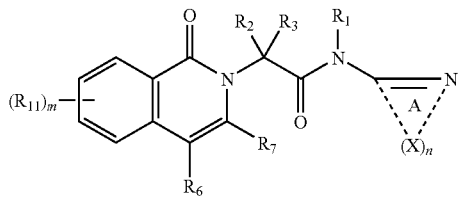

or a polymorph, solvate, ester, tautomer, enantiomer, pharmaceutically acceptable salt or prodrug thereof, wherein
m is selected from the group consisting of 0, 1, 2, 3 and 4; and
each $R_{11}$ is independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{11}$ and $R_6$ or two $R_{11}$ are taken together to form a substituted or unsubstituted ring.

In yet another embodiment, glucokinase activators of the present invention have the formula:

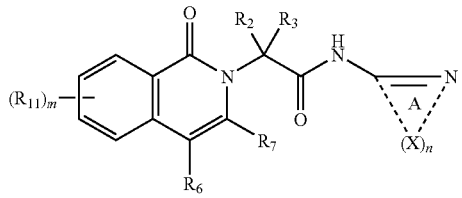

or a polymorph, solvate, ester, tautomer, enantiomer, pharmaceutically acceptable salt or prodrug thereof, wherein
m is selected from the group consisting of 0, 1, 2, 3 and 4; and
each $R_{11}$ is independently selected from the group consisting of hydrogen, halo, nitro, cyano, thio, hydroxy, alkoxy, aryloxy, heteroaryloxy, carbonyl, amino, $(C_{1-10})$ alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_{11}$ and $R_6$ or two $R_{11}$ are taken together to form a substituted or unsubstituted ring.

In a further embodiment, glucokinase activators of the present invention have the formula:

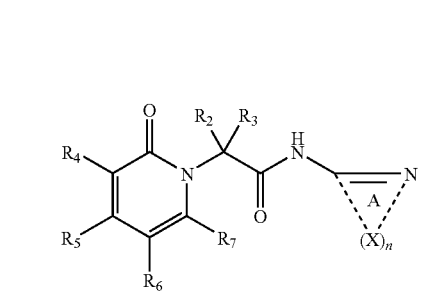

or a polymorph, solvate, ester, tautomer, enantiomer, pharmaceutically acceptable salt or prodrug thereof.

In still a further embodiment, glucokinase activators of the present invention have the formula:

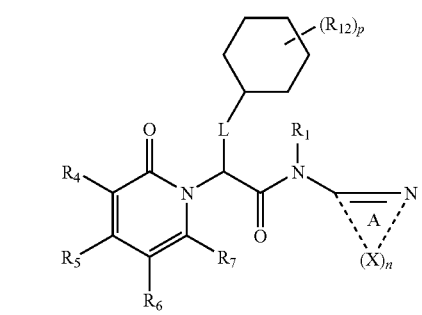

or a polymorph, solvate, ester, tautomer, enantiomer, pharmaceutically acceptable salt or prodrug thereof, wherein
p is selected from the group consisting of 0, 1, 2, 3, 4, 5, 6, 7, 8, 9, 10 and 11;
L is a linker providing 0, 1, 2, 3, 4, 5 or 6 atom separation between the C and the ring to which L is attached, wherein the atoms of the linker providing the separation are selected from the group consisting of carbon, oxygen, nitrogen, and sulfur; and
each $R_{12}$ is independently selected from the group consisting of hydrogen, halo, nitro, cyano, thio, hydroxy, alkoxy, aryloxy, heteroaryloxy, carbonyl, amino, $(C_{1-10})$ alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or two $R_{12}$ are taken together to form a substituted or unsubstituted ring.

In yet a further embodiment, glucokinase activators of the present invention have the formula:

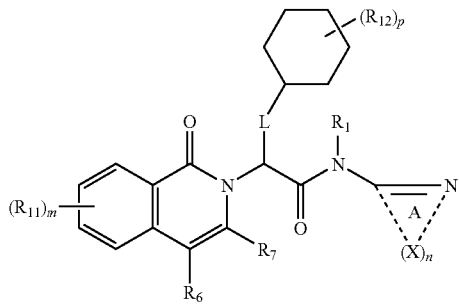

or a polymorph, solvate, ester, tautomer, enantiomer, pharmaceutically acceptable salt or prodrug thereof, wherein
p is selected from the group consisting of 0, 1, 2, 3, 4, 5, 6, 7, 8, 9, 10 and 11;
m is selected from the group consisting of 0, 1, 2, 3 and 4;
each $R_{11}$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or two $R_{11}$ are taken together to form a substituted or unsubstituted ring; and
each $R_{12}$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or two $R_{12}$ are taken together to form a substituted or unsubstituted ring.

In another embodiment, glucokinase activators of the present invention have the formula:

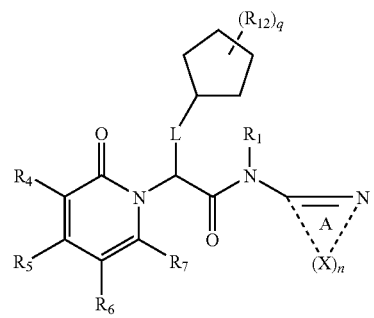

or a polymorph, solvate, ester, tautomer, enantiomer, pharmaceutically acceptable salt or prodrug thereof, wherein
q is selected from the group consisting of 0, 1, 2, 3, 4, 5, 6, 7, 8 and 9;
L is a linker providing 0, 1, 2, 3, 4, 5 or 6 atom separation between the C and the ring to which L is attached, wherein the atoms of the linker providing the separation are selected from the group consisting of carbon, oxygen, nitrogen, and sulfur; and
each $R_{12}$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or two $R_{12}$ are taken together to form a substituted or unsubstituted ring.

In still another embodiment, glucokinase activators of the present invention have the formula:

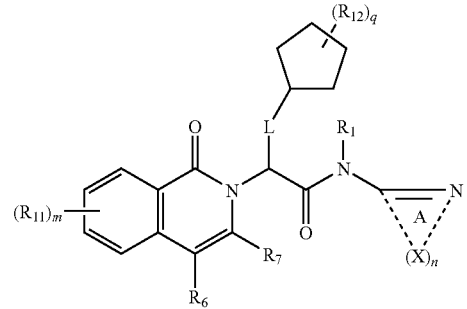

or a polymorph, solvate, ester, tautomer, enantiomer, pharmaceutically acceptable salt or prodrug thereof, wherein
q is selected from the group consisting of 0, 1, 2, 3, 4, 5, 6, 7, 8 and 9;
m is selected from the group consisting of 0, 1, 2, 3 and 4;
each $R_{11}$ is independently selected from the group consisting of hydrogen, halo, nitro, cyano, thio, hydroxy, alkoxy, aryloxy, heteroaryloxy, carbonyl, amino, ($C_{1-10}$)

alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{11}$ are taken together to form a substituted or unsubstituted ring; and each $R_{12}$ is independently selected from the group consisting of hydrogen, halo, nitro, cyano, thio, hydroxy, alkoxy, aryloxy, heteroaryloxy, carbonyl, amino, $(C_{1-10})$ alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{12}$ are taken together to form a substituted or unsubstituted ring.

In yet another embodiment, glucokinase activators of the present invention have the formula:

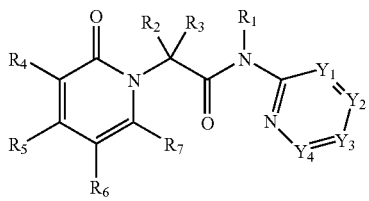

or a polymorph, solvate, ester, tautomer, enantiomer, pharmaceutically acceptable salt or prodrug thereof, wherein
$Y_1, Y_2, Y_3$ and $Y_4$ are each independently selected from the group consisting of $CR_{13}$ and N; and
each $R_{13}$ is independently selected from the group consisting of hydrogen, halo, nitro, cyano, thio, hydroxy, alkoxy, aryloxy, heteroaryloxy, carbonyl, amino, $(C_{1-10})$ alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or two $R_{13}$ are taken together to form a substituted or unsubstituted ring.

In a further embodiment, glucokinase activators of the present invention have the formula:

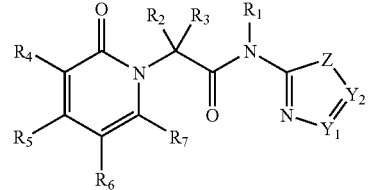

or a polymorph, solvate, ester, tautomer, enantiomer, pharmaceutically acceptable salt or prodrug thereof, wherein
$Y_1$ and $Y_2$ are each independently selected from the group consisting of $CR_{13}$ and N;
Z is selected from the group consisting of $CR_{13}R_{14}$, $NR_{15}$, O and S;
each $R_{13}$ and $R_{14}$ is independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two of $R_{13}$ and $R_{14}$ are taken together to form a substituted or unsubstituted ring, or $R_{13}$ and $R_{14}$ are taken together to form C=O, C=S or C=$NR_{15}$; and
$R_{15}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two $R_{13}$, $R_{14}$ and $R_{15}$ are taken together to form a substituted or unsubstituted ring.

In still a further embodiment, glucokinase activators of the present invention have the formula:

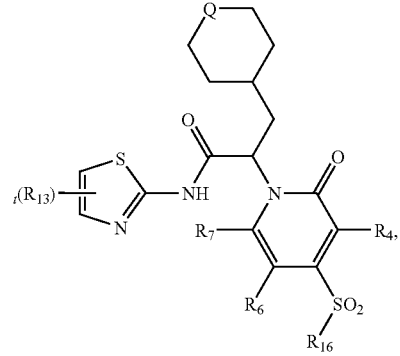

or a polymorph, solvate, ester, tautomer, enantiomer, pharmaceutically acceptable salt or prodrug thereof, wherein t is selected from the group consisting of 0, 1 and 2;

Q is selected from the group consisting of O, S, CS, CO, SO, $SO_2$, $CR_{17}R_{18}$ and $NR_{19}$;

$R_4$, $R_6$ and $R_7$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two of $R_4$, $R_6$ and $R_7$ are taken together to form a substituted or unsubstituted ring;

each $R_{13}$ is independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;

$R_{16}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{17}$ and $R_{18}$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and $R_{19}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In yet a further embodiment, glucokinase activators of the present invention have the formula:

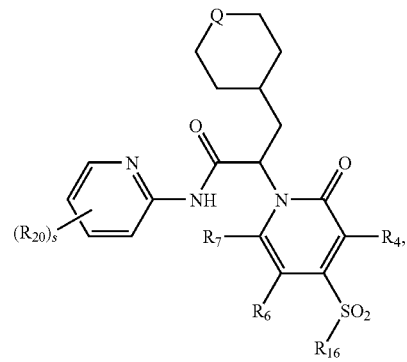

or a polymorph, solvate, ester, tautomer, enantiomer, pharmaceutically acceptable salt or prodrug thereof, wherein s is selected from the group consisting of 0, 1, 2, 3 and 4;

Q is selected from the group consisting of O, S, CS, CO, SO, $SO_2$, $CR_{17}R_{18}$ and $NR_{19}$;

$R_4$, $R_6$ and $R_7$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two of $R_4$, $R_6$ and $R_7$ are taken together to form a substituted or unsubstituted ring;

$R_{16}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$ bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted;

$R_{17}$ and $R_{18}$ are each independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted;

$R_{19}$ is selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted; and $R_{20}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted.

In another embodiment, glucokinase activators of the present invention have the formula:

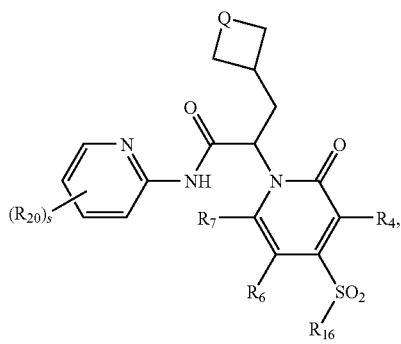

or a polymorph, solvate, ester, tautomer, enantiomer, pharmaceutically acceptable salt or prodrug thereof, wherein s is selected from the group consisting of 0, 1, 2, 3 and 4;

Q is selected from the group consisting of O, S, CS, CO, SO, $SO_2$, $CR_{17}R_{18}$ and $NR_{19}$;

$R_4$, $R_6$ and $R_7$ are each independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or any two of $R_4$, $R_6$ and $R_7$ are taken together to form a substituted or unsubstituted ring;

$R_{16}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$) alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl ($C_{1-10}$)alkyl, aryl($C_{1-10}$)alkyl, hetero($C_{1-10}$)aryl($C_{1-5}$) alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted;

$R_{17}$ and $R_{18}$ are each independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted;

$R_{19}$ is selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted; and $R_{20}$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$) alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted.

In a further embodiment, glucokinase activators of the present invention have the formula:

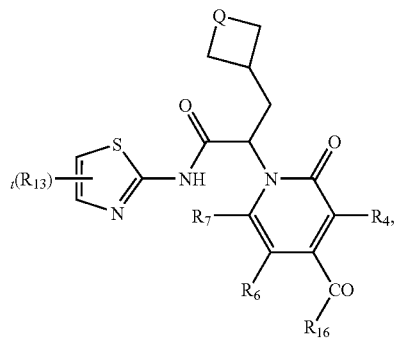

or a polymorph, solvate, ester, tautomer, enantiomer, pharmaceutically acceptable salt or prodrug thereof, wherein t is selected from the group consisting of 0, 1 and 2;

Q is selected from the group consisting of O, S, CS, CO, SO, $SO_2$, $CR_{17}R_{18}$ and $NR_{19}$;

$R_4$, $R_6$ and $R_7$ are each independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or any two of $R_4$, $R_6$ and $R_7$ are taken together to form a substituted or unsubstituted ring;

each $R_{13}$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted;

$R_{16}$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$) alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl ($C_{1-10}$)alkyl, aryl($C_{1-10}$)alkyl, hetero($C_{1-10}$)aryl($C_{1-5}$) alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$) bicycloaryl, each substituted or unsubstituted;

$R_{17}$ and $R_{18}$ are each independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$) cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero ($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted; and $R_{19}$ is selected from the group consisting of hydrogen, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl ($C_{1-5}$)alkyl, hetero($C_{3-12}$)cycloalkyl($C_{1-5}$)alkyl, aryl($C_{1-10}$) alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero ($C_{4-12}$)bicycloaryl, each substituted or unsubstituted.

In still another embodiment, glucokinase activators of the present invention have the formula:

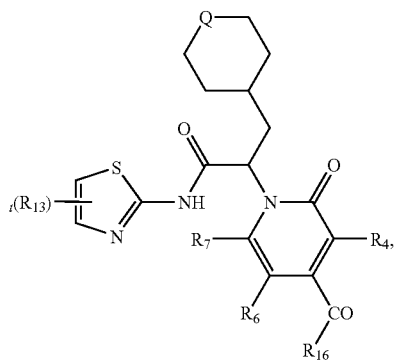

or a polymorph, solvate, ester, tautomer, enantiomer, pharmaceutically acceptable salt or prodrug thereof, wherein t is selected from the group consisting of 0, 1 and 2;

Q is selected from the group consisting of O, S, CS, CO, SO, SO₂, CR₁₇R₁₈ and NR₁₉;

R₄, R₆ and R₇ are each independently selected from the group consisting of hydrogen, halo, nitro, cyano, thio, hydroxy, alkoxy, aryloxy, heteroaryloxy, carbonyl, amino, (C₁₋₁₀)alkylamino, sulfonamido, imino, sulfonyl, sulfinyl, (C₁₋₁₀)alkyl, halo(C₁₋₁₀)alkyl, carbonyl(C₁₋₃)alkyl, thiocarbonyl(C₁₋₃)alkyl, sulfonyl(C₁₋₃)alkyl, sulfinyl(C₁₋₃)alkyl, amino (C₁₋₁₀)alkyl, imino(C₁₋₃)alkyl, (C₃₋₁₂)cycloalkyl(C₁₋₅)alkyl, hetero(C₃₋₁₂)cycloalkyl(C₁₋₅)alkyl, aryl(C₁₋₁₀)alkyl, heteroaryl(C₁₋₅)alkyl, (C₉₋₁₂)bicycloaryl(C₁₋₅)alkyl, hetero(C₈₋₁₂)bicycloaryl(C₁₋₅)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, aryl, heteroaryl, (C₉₋₁₂)bicycloaryl and hetero(C₄₋₁₂)bicycloaryl, each substituted or unsubstituted, or any two of R₄, R₆ and R₇ are taken together to form a substituted or unsubstituted ring;

each R₁₃ is independently selected from the group consisting of hydrogen, halo, nitro, cyano, thio, hydroxy, alkoxy, aryloxy, heteroaryloxy, carbonyl, amino, (C₁₋₁₀)alkylamino, sulfonamido, imino, sulfonyl, sulfinyl, (C₁₋₁₀)alkyl, halo(C₁₋₁₀)alkyl, carbonyl(C₁₋₃)alkyl, thiocarbonyl(C₁₋₃)alkyl, sulfonyl(C₁₋₃)alkyl, sulfinyl(C₁₋₃)alkyl, amino (C₁₋₁₀)alkyl, imino(C₁₋₃)alkyl, (C₃₋₁₂)cycloalkyl(C₁₋₅)alkyl, hetero(C₃₋₁₂)cycloalkyl(C₁₋₅)alkyl, aryl(C₁₋₁₀)alkyl, heteroaryl(C₁₋₅)alkyl, (C₉₋₁₂)bicycloaryl(C₁₋₅)alkyl, hetero(C₈₋₁₂)bicycloaryl(C₁₋₅)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, aryl, heteroaryl, (C₉₋₁₂)bicycloaryl and hetero(C₄₋₁₂)bicycloaryl, each substituted or unsubstituted;

R₁₆ is selected from the group consisting of hydrogen, halo, nitro, cyano, thio, oxy, hydroxy, carbonyloxy, (C₁₋₁₀)alkoxy, (C₄₋₁₂)aryloxy, hetero(C₁₋₁₀)aryloxy, carbonyl, oxycarbonyl, aminocarbonyl, amino, (C₁₋₁₀)alkylamino, sulfonamido, imino, sulfonyl, sulfinyl, (C₁₋₁₀)alkyl, halo(C₁₋₁₀)alkyl, hydroxy(C₁₋₁₀)alkyl, carbonyl(C₁₋₁₀)alkyl, thiocarbonyl(C₁₋₁₀)alkyl, sulfonyl(C₁₋₁₀)alkyl, sulfinyl(C₁₋₁₀)alkyl, aza(C₁₋₁₀)alkyl, (C₁₋₁₀)Oxaalkyl, (C₁₋₁₀)Oxoalkyl, imino(C₁₋₁₀)alkyl, (C₃₋₁₂)cycloalkyl(C₁₋₅)alkyl, hetero(C₃₋₁₂)cycloalkyl(C₁₋₁₀)alkyl, aryl(C₁₋₁₀)alkyl, hetero(C₁₋₁₀)aryl(C₁₋₅)alkyl, (C₉₋₁₂)bicycloaryl(C₁₋₅)alkyl, hetero(C₈₋₁₂)bicycloaryl(C₁₋₅)alkyl, hetero(C₁₋₁₀)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, (C₄₋₁₂)aryl, hetero(C₁₋₁₀)aryl, (C₉₋₁₂)bicycloaryl and hetero(C₄₋₁₂)bicycloaryl, each substituted or unsubstituted;

R₁₇ and R₁₈ are each independently selected from the group consisting of hydrogen, halo, nitro, cyano, thio, hydroxy, alkoxy, aryloxy, heteroaryloxy, carbonyl, amino, (C₁₋₁₀)alkylamino, sulfonamido, imino, sulfonyl, sulfinyl, (C₁₋₁₀)alkyl, halo(C₁₋₁₀)alkyl, carbonyl(C₁₋₃)alkyl, thiocarbonyl(C₁₋₃)alkyl, sulfonyl(C₁₋₃)alkyl, sulfinyl(C₁₋₃)alkyl, amino (C₁₋₁₀)alkyl, imino(C₁₋₃)alkyl, (C₃₋₁₂)cycloalkyl(C₁₋₅)alkyl, hetero(C₃₋₁₂)cycloalkyl(C₁₋₅)alkyl, aryl(C₁₋₁₀)alkyl, heteroaryl(C₁₋₅)alkyl, (C₉₋₁₂)bicycloaryl(C₁₋₅)alkyl, hetero(C₈₋₁₂)bicycloaryl(C₁₋₅)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, aryl, heteroaryl, (C₉₋₁₂)bicycloaryl and hetero(C₄₋₁₂)bicycloaryl, each substituted or unsubstituted; and R₁₉ is selected from the group consisting of hydrogen, hydroxy, alkoxy, aryloxy, heteroaryloxy, carbonyl, amino, (C₁₋₁₀)alkylamino, sulfonamido, imino, sulfonyl, sulfinyl, (C₁₋₁₀)alkyl, halo(C₁₋₁₀)alkyl, carbonyl(C₁₋₃)alkyl, thiocarbonyl(C₁₋₃)alkyl, sulfonyl(C₁₋₃)alkyl, sulfinyl(C₁₋₃)alkyl, amino (C₁₋₁₀)alkyl, imino(C₁₋₃)alkyl, (C₃₋₁₂)cycloalkyl(C₁₋₅)alkyl, hetero(C₃₋₁₂)cycloalkyl(C₁₋₅)alkyl, aryl(C₁₋₁₀)alkyl, heteroaryl(C₁₋₅)alkyl, (C₉₋₁₂)bicycloaryl(C₁₋₅)alkyl, hetero(C₈₋₁₂)bicycloaryl(C₁₋₅)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, aryl, heteroaryl, (C₉₋₁₂)bicycloaryl and hetero(C₄₋₁₂)bicycloaryl, each substituted or unsubstituted.

In yet another embodiment, glucokinase activators of the present invention have the formula:

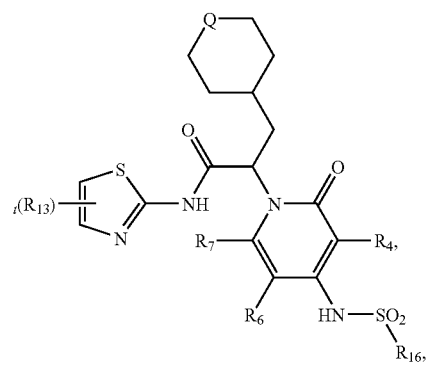

or a polymorph, solvate, ester, tautomer, enantiomer, pharmaceutically acceptable salt or prodrug thereof, wherein t is selected from the group consisting of 0, 1 and 2;

Q is selected from the group consisting of O, S, CS, CO, SO, SO₂, CR₁₇R₁₈ and NR₁₉;

R₄, R₆ and R₇ are each independently selected from the group consisting of hydrogen, halo, nitro, cyano, thio, hydroxy, alkoxy, aryloxy, heteroaryloxy, carbonyl, amino, (C₁₋₁₀)alkylamino, sulfonamido, imino, sulfonyl, sulfinyl, (C₁₋₁₀)alkyl, halo(C₁₋₁₀)alkyl, carbonyl(C₁₋₃)alkyl, thiocarbonyl(C₁₋₃)alkyl, sulfonyl(C₁₋₃)alkyl, sulfinyl(C₁₋₃)alkyl, amino (C₁₋₁₀)alkyl, imino(C₁₋₃)alkyl, (C₃₋₁₂)cycloalkyl(C₁₋₅)alkyl, hetero(C₃₋₁₂)cycloalkyl(C₁₋₅)alkyl, aryl(C₁₋₁₀)alkyl, heteroaryl(C₁₋₅)alkyl, (C₉₋₁₂)bicycloaryl(C₁₋₅)alkyl, hetero(C₈₋₁₂)bicycloaryl(C₁₋₅)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, aryl, heteroaryl, (C₉₋₁₂)bicycloaryl and hetero(C₄₋₁₂)bicycloaryl, each substituted or unsubstituted, or any two of R₄, R₆ and R₇ are taken together to form a substituted or unsubstituted ring;

each R₁₃ is independently selected from the group consisting of hydrogen, halo, nitro, cyano, thio, hydroxy, alkoxy, aryloxy, heteroaryloxy, carbonyl, amino, (C₁₋₁₀)alkylamino, sulfonamido, imino, sulfonyl, sulfinyl, (C₁₋₁₀)alkyl, halo(C₁₋₁₀)alkyl, carbonyl(C₁₋₃)alkyl, thiocarbonyl(C₁₋₃)alkyl, sulfonyl(C₁₋₃)alkyl, sulfinyl(C₁₋₃)alkyl, amino (C₁₋₁₀)alkyl, imino(C₁₋₃)alkyl, (C₃₋₁₂)cycloalkyl(C₁₋₅)alkyl, hetero(C₃₋₁₂)cycloalkyl(C₁₋₅)alkyl, aryl(C₁₋₁₀)alkyl, heteroaryl(C₁₋₅)alkyl, (C₉₋₁₂)bicycloaryl(C₁₋₅)alkyl, hetero(C₈₋₁₂)bicycloaryl(C₁₋₅)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, aryl, heteroaryl, (C₉₋₁₂)bicycloaryl and hetero(C₄₋₁₂)bicycloaryl, each substituted or unsubstituted;

R₁₆ is selected from the group consisting of hydrogen, halo, nitro, cyano, thio, oxy, hydroxy, carbonyloxy, alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl $(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{17}$ and $R_{18}$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and $R_{19}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In a further embodiment, glucokinase activators of the present invention have the formula:

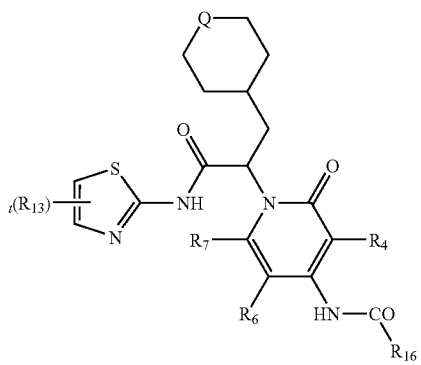

or a polymorph, solvate, ester, tautomer, enantiomer, pharmaceutically acceptable salt or prodrug thereof, wherein t is selected from the group consisting of 0, 1 and 2;

Q is selected from the group consisting of O, S, CS, CO, SO, $SO_2$, $CR_{17}R_{18}$ and $NR_{19}$;

$R_4$, $R_6$ and $R_7$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two of $R_4$, $R_6$ and $R_7$ are taken together to form a substituted or unsubstituted ring;

each $R_{13}$ is independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted;

$R_{16}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{17}$ and $R_{18}$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted; and $R_{19}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In another of its aspects, the present invention relates to methods of making compounds that are useful as glucokinase activators. In one embodiment, the methods comprise the steps of:

reacting a compound having the formula

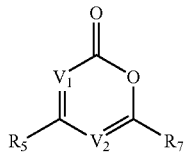

with a compound having the formula

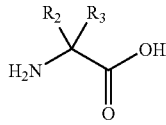

under conditions that form a first reaction product having the formula

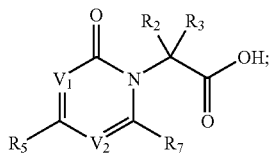

and reacting the first reaction product with a compound having the formula

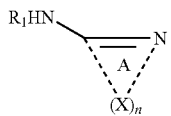

under conditions that form a product having the formula

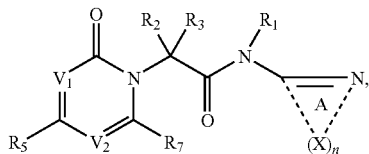

wherein n is selected from the group consisting of 3, 4 and 5;

$V_1$ is selected from the group consisting of $CR_4$ and N;

$V_2$ is selected from the group consisting of $CR_6$ and N;

each X is independently selected from the group consisting of $CR_8R_9$, CO, CS, $NR_{10}$, O, S, SO and $SO_2$;

$R_1$ is selected from the group consisting of hydrogen and a substituent convertible to hydrogen in vivo;

$R_2$ and $R_3$ are each independently selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_2$ and $R_3$ are taken together to form a substituted or unsubstituted ring;

$R_4$, $R_5$, $R_6$ and $R_7$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two of $R_4$, $R_5$, $R_6$ and $R_7$ are taken together to form a substituted or unsubstituted ring;

$R_8$ and $R_9$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_9$ is absent when the atom to which it is bound forms part of a double bond; and $R_{10}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{10}$ is absent when the atom to which it is bound forms part of a double bond.

In another embodiment, the methods comprise the steps of: treating a compound having the formula

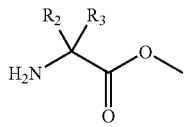

under conditions that form a first reaction product having the formula

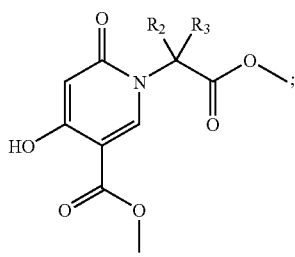

treating the first reaction product under conditions that form a second reaction product having the formula

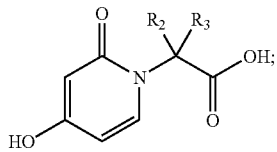

treating the second reaction product under conditions that form a third reaction product having the formula

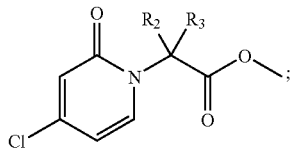

reacting the third reaction product with a compound having the formula

$R_5$—$R_a$ under conditions that form a fourth reaction product having the formula

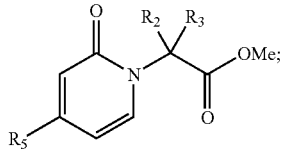

treating the fourth reaction product under conditions that form a fifth reaction product having the formula

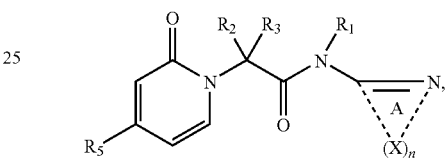

and reacting the fifth reaction product with a compound having the formula $$R_1HN\underset{(X)_n}{\overset{A}{\diagdown}}N \qquad D$$

under conditions that form a product having the formula wherein n is selected from the group consisting of 3, 4 and 5;

each X is independently selected from the group consisting of $CR_8R_9$, CO, CS, $NR_{10}$, O, S, SO and $SO_2$;

$R_a$ is a metal;

$R_1$ is selected from the group consisting of hydrogen and a substituent convertible to hydrogen in vivo;

$R_2$ and $R_3$ are each independently selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_2$ and $R_3$ are taken together to form a substituted or unsubstituted ring;

$R_5$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero $(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero $(C_{3-12})$bicycloalkyl, aryl, heteroaryl, $(C_{9-12})$bicycloaryl and hetero$(C_{4-12})$bicycloaryl, each substituted or unsubstituted;

$R_8$ and $R_9$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_9$ is absent when the atom to which it is bound forms part of a double bond; and $R_{10}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{10}$ is absent when the atom to which it is bound forms part of a double bond.

In still another embodiment, the methods comprise the steps of:

treating a compound having the formula

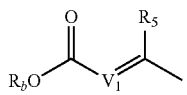

under conditions that form a first reaction product having the formula

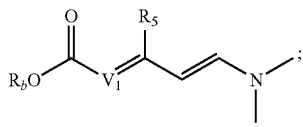

treating the first reaction product under conditions that form a second reaction product having the formula

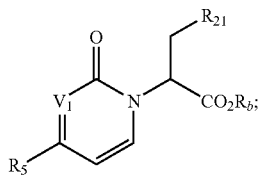

treating the second reaction product under conditions that form a third reaction product having the formula

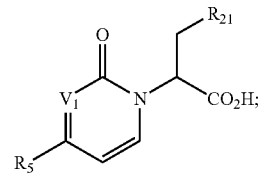

and reacting the third reaction product with a compound having the formula

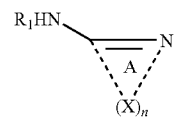

under conditions that form a product having the formula

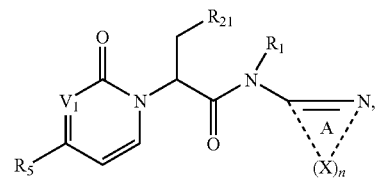

wherein n is selected from the group consisting of 3, 4 and 5;

$V_1$ is selected from the group consisting of $CR_4$ and N;

each X is independently selected from the group consisting of $CR_8R_9$, CO, CS, $NR_{10}$, O, S, SO and $SO_2$;

$R_b$ is a $(C_{1-3})$alkyl;

$R_1$ is selected from the group consisting of hydrogen and a substituent convertible to hydrogen in vivo;

$R_4$ and $R_5$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_4$ and $R_5$ are taken together to form a substituted or unsubstituted ring;

$R_8$ and $R_9$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$ bicycloalkyl, aryl, heteroaryl, $(C_{9-12})$bicycloaryl and hetero$(C_{4-12})$bicycloaryl, each substituted or unsubstituted, with the proviso that $R_9$ is absent when the atom to which it is bound forms part of a double bond;

$R_{10}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{10}$ is absent when the atom to which it is bound forms part of a double bond; and $R_{21}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In yet another embodiment, the methods comprise the steps of:

reacting a compound having the formula

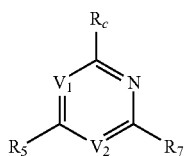

with a compound having the formula

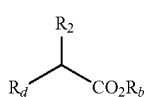

under conditions that form a first reaction product having the formula

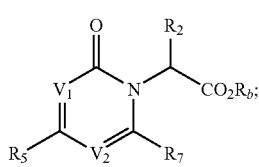

treating the first reaction product under conditions that form a second reactin product having the formula

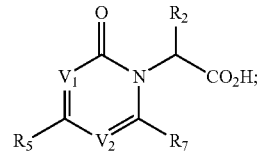

and reacting the second reaction product with a compound having the formula

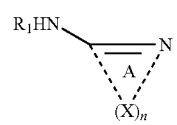

under conditions that form a product having the formula

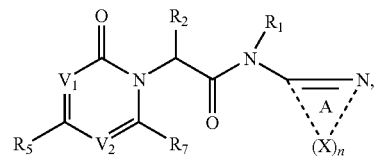

wherein n is selected from the group consisting of 3, 4 and 5;

$V_1$ is selected from the group consisting of $CR_4$ and N;

$V_2$ is selected from the group consisting of $CR_6$ and N;

each X is independently selected from the group consisting of $CR_8R_9$, CO, CS, $NR_{10}$, O, S, SO and $SO_2$;

$R_b$ is a $(C_{1-3})$alkyl;

$R_c$ and $R_d$ are each independently a leaving group;

$R_1$ is selected from the group consisting of hydrogen and a substituent convertible to hydrogen in vivo;

$R_2$ is selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero $(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero $(C_{3-12})$bicycloalkyl, aryl, heteroaryl, $(C_{9-12})$bicycloaryl and hetero$(C_{4-12})$bicycloaryl, each substituted or unsubstituted;

$R_4, R_5, R_6$ and $R_7$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two of $R_4$, $R_5$, $R_6$ and $R_7$ are taken together to form a substituted or unsubstituted ring;

$R_8$ and $R_9$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_9$ is absent when the atom to which it is bound forms part of a double bond; and $R_{10}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{10}$ is absent when the atom to which it is bound forms part of a double bond.

In a further embodiment, the methods comprise the steps of:

reacting a compound having the formula

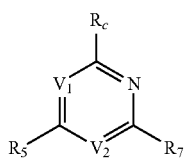

with a compound having the formula

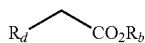

under conditions that form a first reaction product having the formula

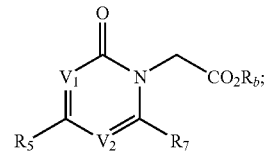

reacting the first reaction product with a compound having the formula

$R_{21}CHO$ under conditions that form a second reaction product having the formula

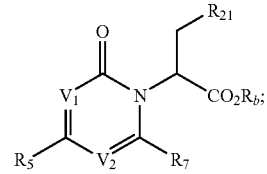

treating the second reaction product under conditions that form a third reaction product having the formula

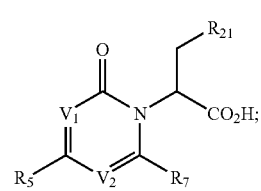

and reacting the third reaction product with a compound having the formula

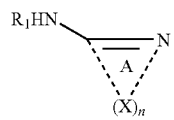

under conditions that form a product having the formula

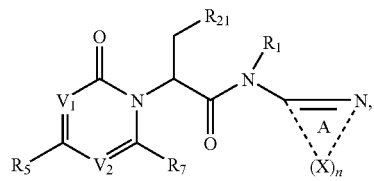

wherein n is selected from the group consisting of 3, 4 and 5;

$V_1$ is selected from the group consisting of $CR_4$ and N;

$V_2$ is selected from the group consisting of $CR_6$ and N;

each X is independently selected from the group consisting of $CR_8R_9$, CO, CS, $NR_{10}$, O, S, SO and $SO_2$;

$R_b$ is a $(C_{1-3})$alkyl;

$R_c$ and $R_d$ are each independently a leaving group;

$R_1$ is selected from the group consisting of hydrogen and a substituent convertible to hydrogen in vivo;

$R_4$, $R_5$, $R_6$ and $R_7$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two of $R_4$, $R_5$, $R_6$ and $R_7$ are taken together to form a substituted or unsubstituted ring;

$R_8$ and $R_9$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_9$ is absent when the atom to which it is bound forms part of a double bond;

$R_{10}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{10}$ is absent when the atom to which it is bound forms part of a double bond; and $R_{21}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In still a further embodiment, the methods comprise the steps of:

reacting a compound having the formula

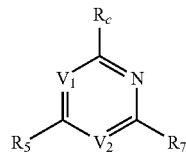

with a compound having the formula

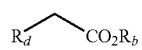

under conditions that form a first reaction product having the formula

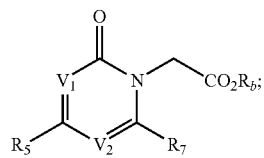

reacting the first reaction product with a compound having the formula

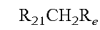

under conditions that form a second reaction product having the formula

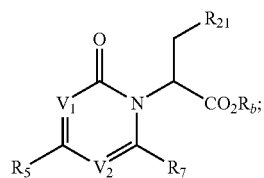

treating the second reaction under conditions that form a third reaction product having the formula

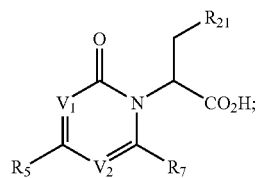

and reacting the third reaction product with a compound having the formula

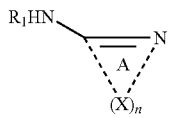

under conditions that form a product having the formula

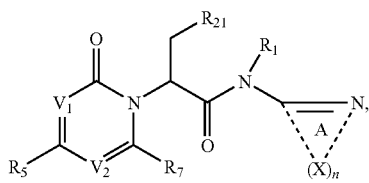

wherein n is selected from the group consisting of 3, 4 and 5;
$V_1$ is selected from the group consisting of $CR_4$ and N;
$V_2$ is selected from the group consisting of $CR_6$ and N;
each X is independently selected from the group consisting of $CR_8R_9$, CO, CS, $NR_{10}$, O, S, SO and $SO_2$;
$R_b$ is a $(C_{1-3})$alkyl;
$R_c$, $R_d$ and $R_e$ are each independently a leaving group;
$R_1$ is selected from the group consisting of hydrogen and a substituent convertible to hydrogen in vivo;
$R_4$, $R_5$, $R_6$ and $R_7$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or any two of $R_4$, $R_5$, $R_6$ and $R_7$ are taken together to form a substituted or unsubstituted ring;
$R_8$ and $R_9$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_9$ is absent when the atom to which it is bound forms part of a double bond;
$R_{10}$ is selected from the group consisting of hydrogen, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, with the proviso that $R_{10}$ is absent when the atom to which it is bound forms part of a double bond; and
$R_{21}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In still another of its aspects, the present invention relates to intermediates that are useful in making glucokinase activators. In one embodiment, the intermediates have the formula

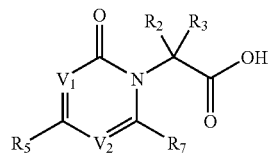

wherein $V_1$ is selected from the group consisting of $CR_4$ and N;
$V_2$ is selected from the group consisting of $CR_6$ and N;
$R_2$ and $R_3$ are each independently selected from the group consisting of hydrogen, carbonyl, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted, or $R_2$ and $R_3$ are taken together to form a substituted or unsubstituted ring; and
$R_4$, $R_5$, $R_6$ and $R_7$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$ cycloalkyl($C_{1-5}$)alkyl, aryl($C_{1-10}$)alkyl, heteroaryl ($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or any two of $R_4$, $R_5$, $R_6$ and $R_7$ are taken together to form a substituted or unsubstituted ring.

In another embodiment, the intermediates have the formula

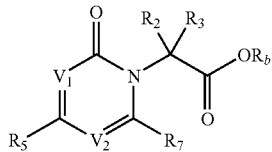

wherein $V_1$ is selected from the group consisting of $CR_4$ and N;

$V_2$ is selected from the group consisting of $CR_6$ and N;

$R_b$ is a ($C_{1-3}$)alkyl;

$R_2$ and $R_3$ are each independently selected from the group consisting of hydrogen, carbonyl, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or $R_2$ and $R_3$ are taken together to form a substituted or unsubstituted ring; and $R_4$, $R_5$, $R_6$ and $R_7$ are each independently selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or any two of $R_4$, $R_5$, $R_6$ and $R_7$ are taken together to form a substituted or unsubstituted ring.

In one variation of each of the above embodiments, ring A is a substituted or unsubstituted heteroaryl. In another variation of each of the above embodiments, ring A is selected from the group consisting of thiazolyl and pyridyl; each substituted or unsubstituted. In still another variation of each of the above embodiments, ring A is selected from the group consisting of thiazol-2-yl; 2-pyridyl; 5-methyl-thiazol-2-yl; 6-methyl-pyrid-2-yl; 4-methyl-pyrid-2-yl; 5-bromo-6-methyl-pyrid-2-yl; 5-phenyl-pyrid-2-yl; benzothiazol-2-yl; a nicotinic acid methyl ester; and 5-bromo-pyrid-2-yl.

In yet another variation of each of the above embodiments, ring A comprises:

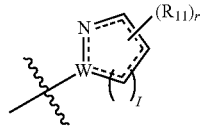

wherein l is selected from the group consisting of 1 and 2;

r is selected from the group consisting of 0, 1, 2, 3, 4, 5, 6, 7 and 8;

W is selected from the group consisting of $CR_{12}$ or N;

each $R_{11}$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or any two $R_{11}$ are taken together to form a ring; and $R_{12}$ is selected from the group consisting of hydrogen, ($C_{1-3}$)alkyl, aryl and heteroaryl, each substituted or unsubstituted, or $R_{11}$ and $R_{12}$ are taken together to form a ring.

In a further variation of each of the above embodiments, ring A comprises:

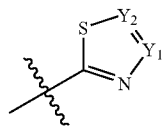

wherein $Y_1$ and $Y_2$ are each independently selected from the group consisting of $CR_{13}$ and N; and each $R_{13}$ is independently selected from the group consisting of hydrogen, halo, nitro, cyano, thio, hydroxy, alkoxy, aryloxy, heteroaryloxy, carbonyl, amino, ($C_{1-10}$) alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl and hetero($C_{4-12}$)bicycloaryl, each substituted or unsubstituted, or two $R_{13}$ are taken together to form a substituted or unsubstituted ring.

In still a further variation of each of the above embodiments, ring A comprises:

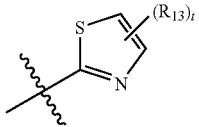

wherein t is selected from the group consisting of 0, 1 and 2; and each $R_{13}$ is independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In yet a further variation of each of the above embodiments, ring A comprises:

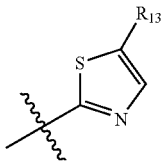

wherein $R_{13}$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl, heteroaryl, $(C_{9-12})$bicycloaryl and hetero$(C_{4-12})$bicycloaryl, each substituted or unsubstituted.

In another variation of each of the above embodiments, ring A comprises:

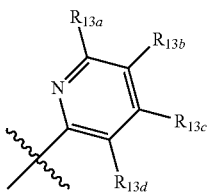

wherein $R_{13a}$, $R_{13b}$, $R_{13c}$ and $R_{13d}$ are each independently selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl $(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero $(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero $(C_{3-12})$bicycloalkyl, aryl, heteroaryl, $(C_{9-12})$bicycloaryl and hetero$(C_{4-12})$bicycloaryl, each substituted or unsubstituted, or two of $R_{13a}$, $R_{13b}$, $R_{13c}$ and $R_{13d}$ are taken together to form a substituted or unsubstituted ring.

In another variation of each of the above embodiments and variations, $Y_1$ is $CR_{13}$. In still another variation of each of the above embodiments and variations, $Y_2$ is $CR_{13}$. In yet another variation of each of the above embodiments and variations, $Y_3$ is $CR_{13}$. In a further variation of each of the above embodiments and variations, $Y_4$ is $CR_{13}$.

In still a further variation of each of the above embodiments and variations, Z is S.

In yet a further variation of each of the above embodiments and variations, n is 3 or 4.

In another variation of each of the above embodiments and variations, $R_1$ is hydrogen.

In still another variation of each of the above embodiments and variations, W is $CR_{12}$.

In yet another variation of each of the above embodiments and variations, l is 1.

In a further variation of each of the above embodiments and variations, r is 1.

In still a further variation of each of the above embodiments and variations, $R_2$ is hydrogen. In yet a further variation of each of the above embodiments and variations, $R_2$ comprises —$CH_2R_{21}$ and $R_{21}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo $(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$ oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted.

In another variation of each of the above embodiments and variations, $R_2$ comprises

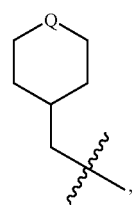

wherein
Q is selected from the group consisting of O, S, CS, CO, SO, SO$_2$, CR$_{17}$R$_{18}$ and NR$_{19}$;

R$_{17}$ and R$_{18}$ are each independently selected from the group consisting of hydrogen, halo, nitro, cyano, thio, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$) alkyl, sulfinyl(C$_{1-3}$)alkyl, amino (C$_{1-10}$)alkyl, imino (C$_{1-3}$)alkyl, (C$_{3-12}$)cycloalkyl(C$_{1-5}$)alkyl, hetero(C$_{3-12}$) cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{8-12}$)bicycloaryl(C$_{1-5}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted; and R$_{19}$ is selected from the group consisting of hydrogen, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$) alkyl, sulfinyl(C$_{1-3}$)alkyl, amino (C$_{1-10}$)alkyl, imino (C$_{1-3}$)alkyl, (C$_{3-12}$)cycloalkyl(C$_{1-5}$)alkyl, hetero(C$_{3-12}$) cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{8-12}$)bicycloaryl(C$_{1-5}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted.

In still another variation of each of the above embodiments and variations, R$_2$ comprises

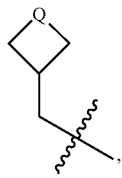,

Q is selected from the group consisting of O, S, CS, CO, SO, SO$_2$, CR$_{17}$R$_{18}$ and NR$_{19}$;

R$_{17}$ and R$_{18}$ are each independently selected from the group consisting of hydrogen, halo, nitro, cyano, thio, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$) alkyl, sulfinyl(C$_{1-3}$)alkyl, amino (C$_{1-10}$)alkyl, imino (C$_{1-3}$)alkyl, (C$_{3-12}$)cycloalkyl(C$_{1-5}$)alkyl, hetero(C$_{3-12}$) cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{8-12}$)bicycloaryl(C$_{1-5}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted; and R$_{19}$ is selected from the group consisting of hydrogen, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$) alkyl, sulfinyl(C$_{1-3}$)alkyl, amino (C$_{1-10}$)alkyl, imino (C$_{1-3}$)alkyl, (C$_{3-12}$)cycloalkyl(C$_{1-5}$)alkyl, hetero(C$_{3-12}$) cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{8-12}$)bicycloaryl(C$_{1-5}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted.

In yet another variation of each of the above embodiments and variations, R$_3$ is selected from the group consisting of carbonyl, (C$_{1-10}$)alkyl, halo(C$_{1-10}$)alkyl, carbonyl(C$_{1-10}$) alkyl, thiocarbonyl(C$_{1-3}$)alkyl, sulfonyl(C$_{1-3}$)alkyl, sulfinyl (C$_{1-3}$)alkyl, amino (C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl (C$_{1-10}$)alkyl, heteroaryl(C$_{1-5}$)alkyl, (C$_{9-12}$)bicycloaryl(C$_{1-5}$) alkyl, hetero(C$_{8-12}$)bicycloaryl(C$_{1-5}$)alkyl, (C$_{3-12}$) cycloalkyl, hetero(C$_{3-12}$)cycloalkyl, (C$_{9-12}$)bicycloalkyl, hetero(C$_{3-12}$)bicycloalkyl, aryl, heteroaryl, (C$_{9-12}$)bicycloaryl and hetero(C$_{4-12}$)bicycloaryl, each substituted or unsubstituted.

In a further variation of each of the above embodiments and variations, R$_3$ is selected from the group consisting of hydrogen, (C$_{1-10}$)alkyl, (C$_{3-12}$)cycloalkyl(C$_{1-5}$)alkyl, hetero(C$_{3-12}$) cycloalkyl(C$_{1-5}$)alkyl, aryl(C$_{1-10}$)alkyl, and heteroaryl(C$_{1-5}$) alkyl, each substituted or unsubstituted. In still a further variation of each of the above embodiments and variations, R$_3$ is selected from the group consisting of (C$_{1-10}$)alkyl, (C$_{3-12}$)cycloalkyl(C$_{1-5}$)alkyl, hetero(C$_{3-12}$)cycloalkyl(C$_{1-5}$) alkyl, aryl(C$_{1-10}$)alkyl, and heteroaryl(C$_{1-5}$)alkyl, each substituted or unsubstituted. In yet a further variation of each of the above embodiments and variations, R$_3$ is selected from the group consisting of hydrogen; butyl; cyclohexylmethyl; benzyl; imidazol-4-ylmethyl and phenyl. In another variation of each of the above embodiments and variations, R$_3$ is selected from the group consisting of butyl; cyclohexylmethyl; benzyl; imidazol-4-ylmethyl and phenyl.

In still another variation of each of the above embodiments and variations, R$_4$ is selected from the group consisting of halo, (C$_{1-10}$)alkyl, (C$_{1-10}$)alkoxy, —CO—NH—R$_{16}$, —NH—CO—R$_{16}$, —SO$_2$—R$_{16}$, —NH—SO$_2$—R$_{16}$ and —SO$_2$—NH—R$_{16}$; and R$_{16}$ is selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$) aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$)alkyl, sulfinyl(C$_{1-10}$)alkyl, aza(C$_{1-10}$)alkyl, (C$_{1-10}$)oxaalkyl, (C$_{1-10}$) oxoalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero (C$_{1-10}$)aryl(C$_{1-5}$)alkyl, (C$_{9-12}$)bicycloaryl(C$_{1-5}$)alkyl, hetero (C$_{8-12}$)bicycloaryl(C$_{1-5}$)alkyl, hetero(C$_{1-10}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, (C$_{4-12}$)aryl, hetero(C$_{1-10}$)aryl, (C$_{9-12}$) bicycloaryl and hetero(C$_{4-12}$)bicycloaryl, each substituted or unsubstituted.

In yet another variation of each of the above embodiments and variations, R$_4$ is a substituted or unsubstituted (C$_{1-5}$) alkyl. In a further variation of each of the above embodiments and variations, R$_4$ is methyl. In still a further variation of each of the above embodiments and variations, R$_4$ is halo and, in particular, chloro.

In still a further variation of each of the above embodiments and variations, R$_4$ and R$_7$ are taken together to form a ring.

In yet a further variation of each of the above embodiments and variations, R$_5$ is selected from the group consisting of halo, $(C_{1-10})$alkyl, $(C_{1-10})$alkoxy, —CO—$R_{16}$, —CO—NH—$R_{16}$, —NH—CO—$R_{16}$, —SO$_2$—$R_{16}$, —NH—SO$_2$—$R_{16}$ and —SO$_2$—NH—$R_{16}$; and $R_{16}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In another variation of each of the above embodiments and variations, $R_5$ is a substituted or unsubstituted $(C_{1-5})$alkyl. In still another variation of each of the above embodiments and variations, $R_5$ is —SO$_2$—$R_{16}$; and $R_{16}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In yet another variation of each of the above embodiments and variations, $R_5$ is —CO—$R_{16}$; and $R_{16}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In a further variation of each of the above embodiments and variations, $R_5$ is —NH—SO$_2$—$R_{16}$; and $R_{16}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$Oxaalkyl, $(C_{1-10})$Oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In still a further variation of each of the above embodiments and variations, $R_5$ is —NH—CO—$R_{16}$; and $R_{16}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In still a further variation of each of the above embodiments and variations, $R_5$ is halo and, in particular, chloro. In yet a further variation of each of the above embodiments and variations, $R_5$ is $(C_{1-3})$alkyl and, in particular, methyl.

In yet a further variation of each of the above embodiments and variations, $R_6$ is selected from the group consisting of hydrogen, halo, $(C_{1-10})$alkyl, $(C_{1-10})$alkoxy, —CO—NH—$R_{16}$, —NH—CO—$R_{16}$, —SO$_2$—$R_{16}$, —NH—SO$_2$—$R_{16}$ and —SO$_2$—NH—$R_{16}$; and $R_{16}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In another variation of each of the above embodiments and variations, $R_6$ is hydrogen. In still another variation of each of the above embodiments and variations, $R_6$ is a substituted or unsubstituted $(C_{1-5})$alkyl. In yet another variation of each of the above embodiments and variations, $R_6$ is methyl.

In a further variation of each of the above embodiments and variations, $R_7$ is selected from the group consisting of hydrogen, halo, $(C_{1-10})$alkyl, $(C_{1-10})$alkoxy, —CO—NH—$R_{16}$, —NH—CO—$R_{16}$, —SO$_2$—$R_{16}$, —NH—SO$_2$—$R_{16}$ and —SO$_2$—NH—$R_{16}$; and $R_{16}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted. In still a further variation of each of the above embodiments and variations, $R_7$ is methyl. In another variation of each of the above embodiments and variations, $R_7$ is selected from the group consisting of hydrogen and a substituted or unsubstituted $(C_{1-10})$alkyl.

In still a further variation of each of the above embodiments and variations, $R_7$ is halo and, in particular, chloro. In yet a further variation of each of the above embodiments and variations, $R_7$ is $(C_{1-3})$alkyl and, in particular, methyl.

In yet a further variation of each of the above embodiments and variations, $R_8$ is selected from the group consisting of hydrogen, halo, $(C_{1-5})$alkyl and carboxamido, each substituted or unsubstituted.

In another variation of each of the above embodiments and variations, $R_9$ is selected from the group consisting of hydrogen, halo and a substituted or unsubstituted $(C_{1-5})$alkyl.

In still another variation of each of the above embodiments and variations, $R_{10}$ is $(C_{1-5})$alkyl.

In yet another variation of each of the above embodiments and variations, $R_{11}$ is selected from the group consisting of hydrogen, halo, cyano, —$OR_{16}$, —$SO_2$—$R_{16}$, —NH—$SO_2$—$R_{16}$ and —$SO_2$—NH—$R_{16}$; and $R_{16}$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl $(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In a further variation of each of the above embodiments and variations, m is 1 or 2.

In still a further variation of each of the above embodiments and variations, $R_{12}$ is selected from the group consisting of halo, $(C_{1-5})$alkyl, oxa$(C_{1-5})$alkyl and oxo$(C_{1-5})$alkyl, each substituted or unsubstituted.

In yet a further variation of each of the above embodiments and variations, p is 1 or 2.

In another variation of each of the above embodiments and variations, q is 1 or 2.

In still another variation of each of the above embodiments and variations, each $R_{13}$ is independently selected from the group consisting of halo, $(C_{1-5})$alkyl and carboxamido, each substituted or unsubstituted. In yet another variation of each of the above embodiments and variations, each $R_{13}$ is independently selected from the group consisting of halo, $(C_{1-5})$alkyl and carboxamido, each substituted or unsubstituted. In a further variation of each of the above embodiments and variations, $R_{13}$ is hydrogen.

In still a further variation of each of the above embodiments and variations, $R_{13a}$ is selected from the group consisting of halo, $(C_{1-5})$alkyl and carboxamido, each substituted or unsubstituted. In yet a further variation of each of the above embodiments and variations, $R_{13a}$ is hydrogen.

In still a further variation of each of the above embodiments and variations, $R_{13b}$ is selected from the group consisting of halo, $(C_{1-5})$alkyl and carboxamido, each substituted or unsubstituted. In yet a further variation of each of the above embodiments and variations, $R_{13b}$ is hydrogen.

In still a further variation of each of the above embodiments and variations, $R_{13c}$ is selected from the group consisting of halo, $(C_{1-5})$alkyl and carboxamido, each substituted or unsubstituted. In yet a further variation of each of the above embodiments and variations, $R_{13c}$ is hydrogen.

In still a further variation of each of the above embodiments and variations, $R_{13d}$ is selected from the group consisting of halo, $(C_{1-5})$alkyl and carboxamido, each substituted or unsubstituted. In yet a further variation of each of the above embodiments and variations, $R_{13d}$ is hydrogen.

In another variation of each of the above embodiments and variations, $R_{14}$ is selected from the group consisting of halo and a substituted or unsubstituted $(C_{1-5})$alkyl.

In still another variation of each of the above embodiments and variations, $R_{15}$ is a substituted or unsubstituted $(C_{1-5})$alkyl.

In yet another variation of each of the above embodiments and variations, L is selected from the group consisting of —$CH_2$—, —$CH_2CH_2$—, —$CH_2CH_2CH_2$—, —$C(O)$—, —$CH_2C(O)$—, —$C(O)CH_2$—, —$CH_2$—$C(O)CH_2$—, —$C(O)CH_2CH_2$—, —$CH_2CH_2C(O)$—, —O—, —$OCH_2$—, —$CH_2O$—, —$CH_2OCH_2$—, —$OCH_2CH_2$—, —$CH_2CH_2O$—, —$N(CH_3)$—, —$NHCH_2$—, —$CH_2NH$—, —$CH_2NHCH_2$—, —$NHCH_2CH_2$—, —$CH_2CH_2NH$—, —NH—$C(O)$—, —$NCH_3$—$C(O)$—, —$C(O)NH$—, —$C(O)NCH_3$—, —$NHC(O)CH_2$—, —$C(O)NHCH_2$—, —$C(O)CH_2NH$—, —$CH_2NHC(O)$—, —$CH_2C(O)NH$—, —$NHCH_2C(O)$—, —S—, —$SCH_2$—, —$CH_2S$—, —$SCH_2CH_2$—, —$CH_2SCH_2$—, —$CH_2CH_2S$—, —$C(O)S$—, —$C(O)SCH_2$—, —$CH_2C(O)S$—, —$C(O)CH_2S$—, and —$CH_2SC(O)$—, each substituted or unsubstituted.

In a further variation of each of the above embodiments and variations, Q is —$CR_{17}R_{18}$—. In still a further variation of each of the above embodiments and variations, Q is —$CH_2$—. In yet a further variation of each of the above embodiments and variations, Q is —$NR_{19}$—. In another variation of each of the above embodiments and variations, Q is —NH—.

Particular examples of compounds according to the present invention include, but are not limited to:

3-cyclohexyl-2-(4-hydroxy-6-methyl-2-oxopyridin-1 (2H)-yl)-N-(thiazol-2-yl)propanamide;
3-cyclohexyl-2-(4-methoxy-6-methyl-2-oxopyridin-1 (2H)-yl)-N-(thiazol-2-yl)propanamide;
3-cyclohexyl-2-(6-methyl-4-(methylsulfonyl)-2-oxopyridin-1(2H)-yl)-N-(thiazol-2-yl)propanamide;
3-cyclohexyl-2-(4-(ethylsulfonyl)-6-methyl-2-oxopyridin-1(2H)-yl)-N-(thiazol-2-yl)propanamide;
3-cyclohexyl-2-(4-(cyclopentylsulfonyl)-6-methyl-2-oxopyridin-1(2H)-yl)-N-(thiazol-2-yl)propanamide;
6-(3-cyclohexyl-2-(4-(cyclopentylsulfonyl)-6-methyl-2-oxopyridin-1(2H)-yl)propanamido)nicotinamide;
2-(6-methyl-4-(methylsulfonyl)-2-oxopyridin-1(2H)-yl)-3-(tetrahydro-2H-pyran-4-yl)-N-(thiazol-2-yl)propanamide;
3-cyclohexyl-2-(4-(cyclopentylsulfonyl)-2-oxopyridin-1 (2H)-yl)-N-(thiazol-2-yl)propanamide;
3-(2-chloro-5-fluorophenyl)-N-(5-chlorothiazol-2-yl)-2-(4-(methylsulfonyl)-2-oxopyridin-1(2H)-yl)propanamide;
2-(4-(cyclopentylsulfonyl)-6-methyl-2-oxopyridin-1 (2H)-yl)-N-(thiazol-2-yl)-3-p-tolylpropanamide;
2-(4-(cyclopentylsulfonyl)-6-methyl-2-oxopyridin-1 (2H)-yl)-4-methyl-N-(thiazol-2-yl)pentanamide;

2-(4-(cyclopentylsulfonyl)-6-methyl-2-oxopyridin-1(2H)-yl)-3-cyclopropyl-N-(thiazol-2-yl)propanamide;

(S)-3-cyclohexyl-2-(4-(cyclopentylsulfonyl)-2-oxopyridin-1(2H)-yl)-N-(thiazol-2-yl)propanamide;

3-cyclopentyl-2-(4-(cyclopentylsulfonyl)-6-methyl-2-oxopyridin-1(2H)-yl)-N-(thiazol-2-yl)propanamide;

N-(5-chlorothiazol-2-yl)-2-(4-(methylsulfonyl)-2-oxopyridin-1(2H)-yl)-3-(thiophen-3-yl)propanamide;

2-(4-(cyclopentylsulfonyl)-6-methyl-2-oxopyridin-1(2H)-yl)-3-(tetrahydro-2H-pyran-4-yl)-N-(thiazol-2-yl)propanamide;

N-(5-chlorothiazol-2-yl)-3-(2,6-dichlorophenyl)-2-(4-(methylsulfonyl)-2-oxopyridin-1(2H)-yl)propanamide;

2-(4-(cyclopentylsulfonyl)-6-methyl-2-oxopyridin-1(2H)-yl)-N-(thiazol-2-yl)hexanamide;

2-(4-(cyclopentylsulfonyl)-6-methyl-2-oxopyridin-1(2H)-yl)-5-methyl-N-(thiazol-2-yl)hexanamide;

2-(4-(cyclopentylsulfonyl)-6-methyl-2-oxopyridin-1(2H)-yl)-3-(3-methoxyphenyl)-N-(thiazol-2-yl)propanamide;

2-(4-(cyclopentylsulfonyl)-6-methyl-2-oxopyridin-1(2H)-yl)-3-(furan-2-yl)-N-(thiazol-2-yl)propanamide;

(R)-N-(5-chlorothiazol-2-yl)-2-(4-(methylsulfonyl)-2-oxopyridin-1(2H)-yl)-3-(tetrahydro-2H-pyran-4-yl)propanamide;

(S)-N-(5-chlorothiazol-2-yl)-2-(4-(methylsulfonyl)-2-oxopyridin-1(2H)-yl)-3-(tetrahydro-2H-pyran-4-yl)propanamide;

N-(5-chlorothiazol-2-yl)-3-(3,5-dimethylphenyl)-2-(4-(methylsulfonyl)-2-oxopyridin-1(2H)-yl)propanamide;

N-(5-chlorothiazol-2-yl)-2-(4-(cyclopropylsulfonyl)-6-methyl-2-oxopyridin-1(2H)-yl)-4,4-dimethylpentanamide;

N-(5-chlorothiazol-2-yl)-2-(4-(methylsulfonyl)-2-oxopyridin-1(2H)-yl)hex-4-ynamide;

2-(4-(cyclopentylsulfonyl)-6-methyl-2-oxopyridin-1(2H)-yl)-3-(4-methoxyphenyl)-N-(thiazol-2-yl)propanamide;

2-(4-(cyclopentylsulfonyl)-6-methyl-2-oxopyridin-1(2H)-yl)-3-(4-hydroxyphenyl)-N-(thiazol-2-yl)propanamide;

(R)-N-(5-chlorothiazol-2-yl)-2-(4-(cyclopropylsulfonyl)-2-oxopyridin-1(2H)-yl)-3-(tetrahydro-2H-pyran-4-yl)propanamide;

(S)-N-(5-chlorothiazol-2-yl)-2-(4-(cyclopropylsulfonyl)-2-oxopyridin-1(2H)-yl)-3-(tetrahydro-2H-pyran-4-yl)propanamide;

(R)-N-(5-chlorothiazol-2-yl)-2-(4-(cyclopentylsulfonyl)-2-oxopyridin-1(2H)-yl)-3-(tetrahydro-2H-pyran-4-yl)propanamide;

(S)-N-(5-chlorothiazol-2-yl)-2-(4-(cyclopentylsulfonyl)-2-oxopyridin-1(2H)-yl)-3-(tetrahydro-2H-pyran-4-yl)propanamide;

(R)-2-(4-(cyclopentylsulfonyl)-2-oxopyridin-1(2H)-yl)-N-(5-fluorothiazol-2-yl)-3-(tetrahydro-2H-pyran-4-yl)propanamide;

(S)-2-(4-(cyclopentylsulfonyl)-2-oxopyridin-1(2H)-yl)-N-(5-fluorothiazol-2-yl)-3-(tetrahydro-2H-pyran-4-yl)propanamide;

(S)-2-(4-(cyclopropylsulfonyl)-2-oxopyridin-1(2H)-yl)-N-(5-fluorothiazol-2-yl)-3-(tetrahydro-2H-pyran-4-yl)propanamide;

(R)-2-(4-(cyclopropylsulfonyl)-2-oxopyridin-1(2H)-yl)-N-(5-fluorothiazol-2-yl)-3-(tetrahydro-2H-pyran-4-yl)propanamide;

(R)-N-(5-chlorothiazol-2-yl)-2-(4-(cyclopentylsulfonyl)-6-methyl-2-oxopyridin-1(2H)-yl)-3-(tetrahydro-2H-pyran-4-yl)propanamide;

(S)-N-(5-chlorothiazol-2-yl)-2-(4-(cyclopentylsulfonyl)-6-methyl-2-oxopyridin-1(2H)-yl)-3-(tetrahydro-2H-pyran-4-yl)propanamide;

(R)-2-(4-(cyclopentylsulfonyl)-6-methyl-2-oxopyridin-1(2H)-yl)-N-(5-fluorothiazol-2-yl)-3-(tetrahydro-2H-pyran-4-yl)propanamide;

(S)-2-(4-(cyclopentylsulfonyl)-6-methyl-2-oxopyridin-1(2H)-yl)-N-(5-fluorothiazol-2-yl)-3-(tetrahydro-2H-pyran-4-yl)propanamide;

(R)-N-(5-chloropyridin-2-yl)-2-(4-(cyclopentylsulfonyl)-2-oxopyridin-1(2H)-yl)-3-(tetrahydro-2H-pyran-4-yl)propanamide;

(S)-N-(5-chloropyridin-2-yl)-2-(4-(cyclopentylsulfonyl)-2-oxopyridin-1(2H)-yl)-3-(tetrahydro-2H-pyran-4-yl)propanamide;

N-(5-fluorothiazol-2-yl)-4,4-dimethyl-2-(6-methyl-2-oxo-4-tosylpyridin-1(2H)-yl)pentanamide;

(R)-methyl 2-(2-(4-(cyclopentylsulfonyl)-2-oxopyridin-1(2H)-yl)-3-(tetrahydro-2H-pyran-4-yl)propanamido)thiazole-5-carboxylate;

(S)-methyl 2-(2-(4-(cyclopentylsulfonyl)-2-oxopyridin-1(2H)-yl)-3-(tetrahydro-2H-pyran-4-yl)propanamido)thiazole-5-carboxylate;

(S)-6-(2-(4-(cyclopentylsulfonyl)-2-oxopyridin-1(2H)-yl)-3-(tetrahydro-2H-pyran-4-yl)propanamido)nicotinamide;

(R)-6-(2-(4-(cyclopentylsulfonyl)-2-oxopyridin-1(2H)-yl)-3-(tetrahydro-2H-pyran-4-yl)propanamido)nicotinamide;

(R)-2-(4-(cyclopropylsulfonyl)-2-oxopyridin-1(2H)-yl)-N-(5-methoxythiazolo[5,4-b]pyridin-2-yl)-3-(tetrahydro-2H-pyran-4-yl)propanamide;

(S)-2-(4-(cyclopropylsulfonyl)-2-oxopyridin-1(2H)-yl)-N-(5-methoxythiazolo[5,4-b]pyridin-2-yl)-3-(tetrahydro-2H-pyran-4-yl)propanamide;

N-(5-fluorothiazol-2-yl)-2-(2-oxo-4-(pyridin-2-ylsulfonyl)pyridin-1(2H)-yl)-3-(tetrahydro-2H-pyran-4-yl)propanamide;

(R)-2-(4-(cyclopropylsulfonyl)-2-oxopyridin-1(2H)-yl)-3-(tetrahydro-2H-pyran-4-yl)-N-(thiazolo[5,4-b]pyridin-2-yl)propanamide;

(S)-2-(4-(cyclopropylsulfonyl)-2-oxopyridin-1(2H)-yl)-3-(tetrahydro-2H-pyran-4-yl)-N-(thiazolo[5,4-b]pyridin-2-yl)propanamide;

3-(2-(2-(4-(methylsulfonyl)-2-oxopyridin-1(2H)-yl)-3-(tetrahydro-2H-pyran-4-yl)propanamido)thiazol-5-yl)propanoic acid;

N-(5-chlorothiazol-2-yl)-3-cyclohexyl-2-(6-methyl-4-(2-methylfuran-3-ylsulfonyl)-2-oxopyridin-1(2H)-yl)propanamide;

2-(4-(benzyloxy)-2-oxopyridin-1(2H)-yl)-N-(5-methylthiazol-2-yl)-3-(tetrahydro-2H-pyran-4-yl)propanamide;

(R)-N-(5-cyanothiazol-2-yl)-2-(4-(cyclopentylsulfonyl)-2-oxopyridin-1(2H)-yl)-3-(tetrahydro-2H-pyran-4-yl)propanamide;

(S)-N-(5-cyanothiazol-2-yl)-2-(4-(cyclopentylsulfonyl)-2-oxopyridin-1(2H)-yl)-3-(tetrahydro-2H-pyran-4-yl)propanamide;

(R)-2-(4-(cyclopentylsulfonyl)-2-oxopyridin-1(2H)-yl)-N-(5-methoxythiazolo[5,4-b]pyridin-2-yl)-3-(tetrahydro-2H-pyran-4-yl)propanamide;

(S)-2-(4-(cyclopentylsulfonyl)-2-oxopyridin-1(2H)-yl)-N-(5-methoxythiazolo[5,4-b]pyridin-2-yl)-3-(tetrahydro-2H-pyran-4-yl)propanamide;

N-(5-chlorothiazol-2-yl)-3-cyclohexyl-2-(6-methyl-2-oxo-4-(thiophen-2-ylsulfonyl)pyridin-1(2H)-yl)propanamide;

(S)-2-(4-bromo-6-methyl-2-oxopyridin-1(2H)-yl)-3-cyclohexyl-N-(thiazol-2-yl)propanamide;

(S)-N-(5-methoxythiazolo[5,4-b]pyridin-2-yl)-2-(6-methyl-4-(2-methylfuran-3-ylsulfonyl)-2-oxopyridin-1(2H)-yl)-3-(tetrahydro-2H-pyran-4-yl)propanamide;

(R)-N-(5-methoxythiazolo[5,4-b]pyridin-2-yl)-2-(6-methyl-4-(2-methylfuran-3-ylsulfonyl)-2-oxopyridin-1(2H)-yl)-3-(tetrahydro-2H-pyran-4-yl)propanamide;

(S)-N-(5-chlorothiazol-2-yl)-2-(6-methyl-4-(2-methylfuran-3-ylsulfonyl)-2-oxopyridin-1(2H)-yl)-3-(tetrahydro-2H-pyran-4-yl)propanamide;

(R)-N-(5-chlorothiazol-2-yl)-2-(6-methyl-4-(2-methylfuran-3-ylsulfonyl)-2-oxopyridin-1(2H)-yl)-3-(tetrahydro-2H-pyran-4-yl)propanamide;

2-(4-(cyclopropylsulfonyl)-2-oxopyridin-1(2H)-yl)-N-(1-methyl-1H-pyrazol-3-yl)-3-(tetrahydro-2H-pyran-4-yl)propanamide;

2-(4-(3-hydroxypropylsulfonyl)-2-oxopyridin-1(2H)-yl)-N-(5-methoxythiazolo[5,4-b]pyridin-2-yl)-3-(tetrahydro-2H-pyran-4-yl)propanamide;

3-cyclohexyl-2-(4-(cyclopropylsulfonyl)-2-oxopyridin-1(2H)-yl)-N-(5-methoxythiazolo[5,4-b]pyridin-2-yl)propanamide;

(R)-2-(4-(cyclopropylsulfonyl)-2-oxopyridin-1(2H)-yl)-N-(pyrazin-2-yl)-3-(tetrahydro-2H-pyran-4-yl)propanamide;

(S)-2-(4-(cyclopropylsulfonyl)-2-oxopyridin-1(2H)-yl)-N-(pyrazin-2-yl)-3-(tetrahydro-2H-pyran-4-yl)propanamide;

(R)-2-(4-(3-hydroxypropylsulfonyl)-2-oxopyridin-1(2H)-yl)-N-(5-methoxythiazolo[5,4-b]pyridin-2-yl)-3-(tetrahydro-2H-pyran-4-yl)propanamide;

(S)-2-(4-(3-hydroxypropylsulfonyl)-2-oxopyridin-1(2H)-yl)-N-(5-methoxythiazolo[5,4-b]pyridin-2-yl)-3-(tetrahydro-2H-pyran-4-yl)propanamide;

(R)-2-(4-(cyclopropylsulfonyl)-2-oxopyridin-1(2H)-yl)-N-(1-methyl-1H-pyrazol-3-yl)-3-(tetrahydro-2H-pyran-4-yl)propanamide;

(S)-2-(4-(cyclopropylsulfonyl)-2-oxopyridin-1(2H)-yl)-N-(1-methyl-1H-pyrazol-3-yl)-3-(tetrahydro-2H-pyran-4-yl)propanamide;

(R)-3-cyclohexyl-2-(4-(cyclopropylsulfonyl)-2-oxopyridin-1(2H)-yl)-N-(5-methoxythiazolo[5,4-b]pyridin-2-yl)propanamide;

(S)-3-cyclohexyl-2-(4-(cyclopropylsulfonyl)-2-oxopyridin-1(2H)-yl)-N-(5-methoxythiazolo[5,4-b]pyridin-2-yl)propanamide;

(S)-2-(3-chloro-4-(cyclopropylsulfonyl)-6-methyl-2-oxopyridin-1(2H)-yl)-N-(5-chlorothiazol-2-yl)-3-cyclohexylpropanamide;

(R)-2-(3-chloro-4-(cyclopropylsulfonyl)-6-methyl-2-oxopyridin-1(2H)-yl)-N-(5-chlorothiazol-2-yl)-3-cyclohexylpropanamide;

3-cyclohexyl-2-(6-methyl-4-morpholino-2-oxopyridin-1(2H)-yl)-N-(thiazol-2-yl)propanamide;

N-(5-chlorothiazol-2-yl)-3-cyclohexyl-2-(6-methyl-2-oxo-4-(thiophen-2-ylmethylsulfonyl)pyridin-1(2H)-yl)propanamide;

3-cyclohexyl-2-(4-(furan-2-ylmethylsulfonyl)-6-methyl-2-oxopyridin-1(2H)-yl)-N-(thiazol-2-yl)propanamide;

3-cyclohexyl-2-(4-(cyclopentylsulfonyl)-6-methyl-2-oxopyridin-1(2H)-yl)-N-(5-(4-fluorobenzyl)thiazol-2-yl)propanamide;

N-(5-chlorothiazol-2-yl)-3-cyclohexyl-2-(4-(2,5-dimethylfuran-3-ylsulfonyl)-6-methyl-2-oxopyridin-1(2H)-yl)propanamide;

2-(4-(cyclopropylsulfonyl)-2-oxopyridin-1(2H)-yl)-N-(6-hydroxybenzo[d]thiazol-2-yl)-3-(tetrahydro-2H-pyran-4-yl)propanamide;

(S)-N-(5-chlorothiazol-2-yl)-3-cyclohexyl-2-(6-methyl-2-oxo-4-(thiophen-2-ylmethylsulfonyl)pyridin-1(2H)-yl)propanamide;

(R)-N-(5-chlorothiazol-2-yl)-3-cyclohexyl-2-(6-methyl-2-oxo-4-(thiophen-2-ylmethylsulfonyl)pyridin-1(2H)-yl)propanamide;

3-cyclohexyl-2-(6-methyl-2-oxo-4-(pyrrolidin-1-yl)pyridin-1(2H)-yl)-N-(thiazol-2-yl)propanamide;

2-(4-(4-methoxy-2-methylbutan-2-ylsulfonyl)-2-oxopyridin-1(2H)-yl)-N-(5-methoxythiazolo[5,4-b]pyridin-2-yl)-3-(tetrahydro-2H-pyran-4-yl)propanamide;

3-cyclohexyl-2-(4-(cyclopentylsulfonyl)-6-methyl-2-oxopyridin-1(2H)-yl)-N-(5-(morpholinomethyl)thiazol-2-yl)propanamide;

(S)-3-cyclohexyl-2-(6-methyl-2-oxo-4-phenylpyridin-1(2H)-yl)-N-(thiazol-2-yl)propanamide;

(S)-2-(4-(2-chlorophenyl)-6-methyl-2-oxopyridin-1(2H)-yl)-3-cyclohexyl-N-(thiazol-2-yl)propanamide;

(S)-2-(4-(3-chlorophenyl)-6-methyl-2-oxopyridin-1(2H)-yl)-3-cyclohexyl-N-(thiazol-2-yl)propanamide;

(S)-2-(4-(4-chlorophenyl)-6-methyl-2-oxopyridin-1(2H)-yl)-3-cyclohexyl-N-(thiazol-2-yl)propanamide;

(S)-3-cyclohexyl-2-(4-(2-methoxyphenyl)-6-methyl-2-oxopyridin-1(2H)-yl)-N-(thiazol-2-yl)propanamide;

(S)-3-cyclohexyl-2-(4-(3-methoxyphenyl)-6-methyl-2-oxopyridin-1(2H)-yl)-N-(thiazol-2-yl)propanamide;

(S)-3-cyclohexyl-2-(4-(4-methoxyphenyl)-6-methyl-2-oxopyridin-1(2H)-yl)-N-(thiazol-2-yl)propanamide;

(S)-2-(4-(3-cyanophenyl)-6-methyl-2-oxopyridin-1(2H)-yl)-3-cyclohexyl-N-(thiazol-2-yl)propanamide;

(S)-2-(4-(4-cyanophenyl)-6-methyl-2-oxopyridin-1(2H)-yl)-3-cyclohexyl-N-(thiazol-2-yl)propanamide;

(S)-3-cyclohexyl-2-(4-(furan-3-yl)-6-methyl-2-oxopyridin-1(2H)-yl)-N-(thiazol-2-yl)propanamide;

(S)-3-cyclohexyl-2-(6-methyl-2-oxo-4-(pyridin-3-yl)pyridin-1(2H)-yl)-N-(thiazol-2-yl)propanamide;

(S)-3-cyclohexyl-2-(6-methyl-4-(4-(methylsulfonyl)phenyl)-2-oxopyridin-1(2H)-yl)-N-(thiazol-2-yl)propanamide;

(S)-3-cyclohexyl-2-(4-(4-(ethylsulfonyl)phenyl)-6-methyl-2-oxopyridin-1(2H)-yl)-N-(thiazol-2-yl)propanamide;

(S)-2-(4-(5-chloro-2-methoxyphenyl)-6-methyl-2-oxopyridin-1(2H)-yl)-3-cyclohexyl-N-(thiazol-2-yl)propanamide;

(S)-2-(4-(benzofuran-2-yl)-6-methyl-2-oxopyridin-1(2H)-yl)-3-cyclohexyl-N-(thiazol-2-yl)propanamide;

(S)-3-cyclohexyl-2-(4-(4-fluorophenyl)-6-methyl-2-oxopyridin-1(2H)-yl)-N-(thiazol-2-yl)propanamide;

(S)-2-(4-(3-chloro-4-fluorophenyl)-6-methyl-2-oxopyridin-1(2H)-yl)-3-cyclohexyl-N-(thiazol-2-yl)propanamide;

(S)-2-(4-(benzo[b]thiophen-3-yl)-6-methyl-2-oxopyridin-1(2H)-yl)-3-cyclohexyl-N-(thiazol-2-yl)propanamide;

(S)-2-(4-(benzo[b]thiophen-2-yl)-6-methyl-2-oxopyridin-1(2H)-yl)-3-cyclohexyl-N-(thiazol-2-yl)propanamide;

(S)-3-cyclohexyl-2-(4-(3-fluorophenyl)-6-methyl-2-oxopyridin-1(2H)-yl)-N-(thiazol-2-yl)propanamide;

(S)-3-cyclohexyl-2-(4-(2-fluorophenyl)-6-methyl-2-oxopyridin-1(2H)-yl)-N-(thiazol-2-yl)propanamide;

(S)-3-cyclohexyl-2-(6-methyl-4-(4-methylthiophen-2-yl)-2-oxopyridin-1(2H)-yl)-N-(thiazol-2-yl)propanamide;

(S)-3-cyclohexyl-2-(6-methyl-4-(3-(methylsulfonamido)phenyl)-2-oxopyridin-1(2H)-yl)-N-(thiazol-2-yl)propanamide;

(S)-3-cyclohexyl-2-(6-methyl-2-oxo-4-(1H-pyrazol-4-yl)pyridin-1(2H)-yl)-N-(thiazol-2-yl)propanamide;

(S)-3-cyclohexyl-2-(6-methyl-4-(3-(N-methylsulfamoyl)phenyl)-2-oxopyridin-1(2H)-yl)-N-(thiazol-2-yl)propanamide;

(S)-3-cyclohexyl-2-(6-methyl-4-(4-(N-methylsulfamoyl)phenyl)-2-oxopyridin-1(2H)-yl)-N-(thiazol-2-yl)propanamide;

ethyl 2-(2-(4-(cyclopropylsulfonyl)-2-oxopyridin-1(2H)-yl)-3-(tetrahydro-2H-pyran-4-yl)propanamido)thiazole-5-carboxylate;

2-(4-(cyclopropylsulfonyl)-2-oxopyridin-1(2H)-yl)-N-(5-(2-hydroxypropan-2-yl)thiazol-2-yl)-3-(tetrahydro-2H-pyran-4-yl)propanamide;

N-(5-chlorothiazol-2-yl)-2-(4-(cyclopentylsulfonyl)-3,5,6-trimethyl-2-oxopyridin-1(2H)-yl)-3-(tetrahydro-2H-pyran-4-yl)propanamide;

N-(5-chlorothiazol-2-yl)-2-(4-(2,5-dichlorothiophen-3-ylsulfonyl)-6-methyl-2-oxopyridin-1(2H)-yl)-3-(tetrahydro-2H-pyran-4-yl)propanamide;

(R)-2-(4-(4-methoxy-2-methylbutan-2-ylsulfonyl)-2-oxopyridin-1(2H)-yl)-N-(5-methoxythiazolo[5,4-b]pyridin-2-yl)-3-(tetrahydro-2H-pyran-4-yl)propanamide;

(S)-2-(4-(4-methoxy-2-methylbutan-2-ylsulfonyl)-2-oxopyridin-1(2H)-yl)-N-(5-methoxythiazolo[5,4-b]pyridin-2-yl)-3-(tetrahydro-2H-pyran-4-yl)propanamide;

(R)-3-cyclohexyl-2-(4-(cyclopropylsulfonyl)-6-methyl-2-oxopyridin-1(2H)-yl)-N-(5-methoxythiazolo[5,4-b]pyridin-2-yl)propanamide;

(S)-3-cyclohexyl-2-(4-(cyclopropylsulfonyl)-6-methyl-2-oxopyridin-1(2H)-yl)-N-(5-methoxythiazolo[5,4-b]pyridin-2-yl)propanamide;

2-(7-chloro-4-oxothieno[3,2-c]pyridin-5(4H)-yl)-N-(5-chlorothiazol-2-yl)-3-cyclohexylpropanamide;

2-(4-((S)-3-hydroxypyrrolidin-1-yl)-2-oxopyridin-1(2H)-yl)-N-(5-methoxythiazolo[5,4-b]pyridin-2-yl)-3-(tetrahydro-2H-pyran-4-yl)propanamide;

(S)-3-cyclohexyl-2-(6-methyl-4-(3-(methylsulfonyl)phenyl)-2-oxopyridin-1(2H)-yl)-N-(thiazol-2-yl)propanamide;

2-(4-(cyclopropylsulfonyl)-2-oxopyridin-1(2H)-yl)-N-(6-methoxybenzo[d]thiazol-2-yl)-3-(tetrahydro-2H-pyran-4-yl)propanamide;

2-(4-(cyclopropylsulfonyl)-2-oxopyridin-1(2H)-yl)-N-(5-(dimethylamino)thiazolo[5,4-b]pyridin-2-yl)-3-(tetrahydro-2H-pyran-4-yl)propanamide;

N-(5-chlorothiazol-2-yl)-3-cyclohexyl-2-(2-oxo-4-(pyrrolidine-1-carbonyl)pyridin-1(2H)-yl)propanamide;

N-(6-chlorobenzo[d]thiazol-2-yl)-2-(4-(cyclopropylsulfonyl)-2-oxopyridin-1(2H)-yl)-3-(tetrahydro-2H-pyran-4-yl)propanamide;

2-(4-(cyclopropylsulfonyl)-2-oxopyridin-1(2H)-yl)-N-(6-fluorobenzo[d]thiazol-2-yl)-3-(tetrahydro-2H-pyran-4-yl)propanamide;

(R)-2-(4-(cyclopropylsulfonyl)-2-oxopyridin-1(2H)-yl)-N-(5-(2-methoxypropan-2-yl)thiazol-2-yl)-3-(tetrahydro-2H-pyran-4-yl)propanamide;

(S)-2-(4-(cyclopropylsulfonyl)-2-oxopyridin-1(2H)-yl)-N-(5-(2-methoxypropan-2-yl)thiazol-2-yl)-3-(tetrahydro-2H-pyran-4-yl)propanamide;

N-(5-chlorothiazol-2-yl)-2-(6-methyl-2-oxo-4-(thiophen-2-ylmethylsulfonyl)pyridin-1(2H)-yl)-3-(tetrahydro-2H-pyran-4-yl)propanamide;

(S)-N-(5-chlorothiazol-2-yl)-2-(4-(cyclopentylsulfonyl)-3,5,6-trimethyl-2-oxopyridin-1(2H)-yl)-3-(tetrahydro-2H-pyran-4-yl)propanamide;

(R)-N-(5-chlorothiazol-2-yl)-2-(4-(cyclopentylsulfonyl)-3,5,6-trimethyl-2-oxopyridin-1(2H)-yl)-3-(tetrahydro-2H-pyran-4-yl)propanamide;

N-(5-chlorothiazol-2-yl)-2-(4-(3-hydroxyprop-1-ynyl)-6-methyl-2-oxopyridin-1(2H)-yl)-3-(tetrahydro-2H-pyran-4-yl)propanamide;

2-(4-(cyclopropylsulfonyl)-2-oxopyridin-1(2H)-yl)-N-(5-(4-fluorobenzyl)thiazol-2-yl)-3-(tetrahydro-2H-pyran-4-yl)propanamide;

2-(2-oxo-5-(pyrrolidin-1-ylsulfonyl)pyridin-1(2H)-yl)-3-(tetrahydro-2H-pyran-4-yl)-N-(thiazol-2-yl)propanamide;

N-(5-chlorothiazol-2-yl)-2-(2-oxo-5-(pyrrolidin-1-ylsulfonyl)pyridin-1(2H)-yl)-3-(tetrahydro-2H-pyran-4-yl)propanamide;

(S)-N-(5-chlorothiazol-2-yl)-2-(4-(furan-2-ylmethylsulfonyl)-6-methyl-2-oxopyridin-1(2H)-yl)-3-(tetrahydro-2H-pyran-4-yl)propanamide;

(R)-N-(5-chlorothiazol-2-yl)-2-(4-(furan-2-ylmethylsulfonyl)-6-methyl-2-oxopyridin-1(2H)-yl)-3-(tetrahydro-2H-pyran-4-yl)propanamide;

N-(5-chlorothiazol-2-yl)-3-cyclohexyl-2-(6-methyl-4-(oxazol-2-yl)-2-oxopyridin-1(2H)-yl)propanamide;

N-(5-(4-fluorobenzyl)thiazol-2-yl)-2-(4-(furan-2-ylmethylsulfonyl)-6-methyl-2-oxopyridin-1(2H)-yl)-3-(tetrahydro-2H-pyran-4-yl)propanamide;

2-(4-(cyclopropylsulfonyl)-2-oxopyridin-1(2H)-yl)-N-(5-(morpholinomethyl)thiazol-2-yl)-3-(tetrahydro-2H-pyran-4-yl)propanamide;

N-(5-chlorothiazol-2-yl)-2-(2-oxo-4-(2,2,2-trifluoroethylsulfonyl)pyridin-1(2H)-yl)-3-(tetrahydro-2H-pyran-4-yl)propanamide;

2-(4-(cyclopropylsulfonyl)-2-oxopyridin-1(2H)-yl)-N-(5-((4-methylpiperazin-1-yl)methyl)thiazol-2-yl)-3-(tetrahydro-2H-pyran-4-yl)propanamide;

(R)-N-(5-chlorothiazol-2-yl)-2-(2-oxo-4-(2,2,2-trifluoroethylsulfonyl)pyridin-1(2H)-yl)-3-(tetrahydro-2H-pyran-4-yl)propanamide;

(S)-N-(5-chlorothiazol-2-yl)-2-(2-oxo-4-(2,2,2-trifluoroethylsulfonyl)pyridin-1(2H)-yl)-3-(tetrahydro-2H-pyran-4-yl)propanamide;

2-(4-(cyclopropylsulfonyl)-2-oxopyridin-1(2H)-yl)-N-(5-((4-(2-(dimethylamino)-2-oxoethyl)piperazin-1-yl)methyl)thiazol-2-yl)-3-(tetrahydro-2H-pyran-4-yl)propanamide;

(S)-2-(4-(cyclopentylsulfonyl)-5,6-dimethyl-2-oxopyridin-1(2H)-yl)-N-(5-fluorothiazol-2-yl)-3-(tetrahydro-2H-pyran-4-yl)propanamide;

2-(4-(cyclopropylsulfonyl)-6-methyl-2-oxopyridin-1(2H)-yl)-N-(5-fluorothiazol-2-yl)-3-(tetrahydro-2H-pyran-4-yl)propanamide;

(R)-2-(4-(cyclopentylsulfonyl)-5,6-dimethyl-2-oxopyridin-1(2H)-yl)-N-(5-fluorothiazol-2-yl)-3-(tetrahydro-2H-pyran-4-yl)propanamide;

(R)-2-(3-amino-4-(cyclopropylsulfonyl)-6-methyl-2-oxopyridin-1(2H)-yl)-3-cyclopentyl-N-(5-fluorothiazol-2-yl)propanamide;

(S)-2-(3-amino-4-(cyclopropylsulfonyl)-6-methyl-2-oxopyridin-1(2H)-yl)-3-cyclopentyl-N-(5-fluorothiazol-2-yl)propanamide;
2-(5-acetamido-2-oxopyridin-1(2H)-yl)-N-(5-chlorothiazol-2-yl)-3-(tetrahydro-2H-pyran-4-yl)propanamide;
N-(5-chlorothiazol-2-yl)-2-(4-(cyclopropylsulfonyl)-6-methyl-2-oxopyridin-1(2H)-yl)-3-(tetrahydro-2H-pyran-4-yl)propanamide;
N-(5-chlorothiazol-2-yl)-2-(4-(3-fluorophenylsulfonyl)-6-methyl-2-oxopyridin-1(2H)-yl)-3-(tetrahydro-2H-pyran-4-yl)propanamide;
2-(4-(3-fluorophenylsulfonyl)-6-methyl-2-oxopyridin-1(2H)-yl)-N-(5-fluorothiazol-2-yl)-3-(tetrahydro-2H-pyran-4-yl)propanamide;
N-(5-chlorothiazol-2-yl)-2-(4-(1,1-dioxotetrahydrothiopyran-4-ylsulfonyl)-6-methyl-2-oxopyridin-1(2H)-yl)-3-cyclohexylpropanamide;
N-(5-fluorothiazol-2-yl)-2-(4-(1,1-dioxotetrahydrothiopyran-4-ylsulfonyl)-6-methyl-2-oxopyridin-1(2H)-yl)-3-cyclohexylpropanamide;
(S)-3-cyclopentyl-2-(4-(cyclopropylsulfonyl)-6-methyl-2-oxopyridin-1(2H)-yl)-N-(5-fluorothiazol-2-yl)propanamide;
(R)-3-cyclopentyl-2-(4-(cyclopropylsulfonyl)-6-methyl-2-oxopyridin-1(2H)-yl)-N-(5-fluorothiazol-2-yl)propanamide;
(R)-2-(4-(cyclopentylsulfonyl)-6-methyl-2-oxopyridin-1(2H)-yl)-N-(5-fluoropyridin-2-yl)-3-(tetrahydro-2H-pyran-4-yl)propanamide;
(S)-2-(4-(cyclopentylsulfonyl)-6-methyl-2-oxopyridin-1(2H)-yl)-N-(5-fluoropyridin-2-yl)-3-(tetrahydro-2H-pyran-4-yl)propanamide;
(S)-N-(5-chloropyridin-2-yl)-2-(4-(cyclopentylsulfonyl)-6-methyl-2-oxopyridin-1(2H)-yl)-3-(tetrahydro-2H-pyran-4-yl)propanamide;
(R)-N-(5-chloropyridin-2-yl)-2-(4-(cyclopentylsulfonyl)-6-methyl-2-oxopyridin-1(2H)-yl)-3-(tetrahydro-2H-pyran-4-yl)propanamide;
(S)-2-(4-(3-chlorophenylsulfonyl)-6-methyl-2-oxopyridin-1(2H)-yl)-N-(5-fluorothiazol-2-yl)-3-(tetrahydro-2H-pyran-4-yl)propanamide;
(R)-2-(4-(3-chlorophenylsulfonyl)-6-methyl-2-oxopyridin-1(2H)-yl)-N-(5-fluorothiazol-2-yl)-3-(tetrahydro-2H-pyran-4-yl)propanamide;
(R)-3-cyclopentyl-2-(4-(cyclopropylsulfonyl)-6-methyl-2-oxopyridin-1(2H)-yl)-N-(pyrazin-2-yl)propanamide;
(S)-3-cyclopentyl-2-(4-(cyclopropylsulfonyl)-6-methyl-2-oxopyridin-1(2H)-yl)-N-(pyrazin-2-yl)propanamide;
(S)-N-(5-chlorothiazol-2-yl)-2-(4-(cyclopropylsulfonyl)-6-methyl-2-oxopyridin-1(2H)-yl)-3-(tetrahydro-2H-pyran-4-yl)propanamide;
(R)-N-(5-chlorothiazol-2-yl)-2-(4-(cyclopropylsulfonyl)-6-methyl-2-oxopyridin-1(2H)-yl)-3-(tetrahydro-2H-pyran-4-yl)propanamide;
N-(5-chlorothiazol-2-yl)-3-cyclopentyl-2-(6-methyl-2-oxo-4-(tetrahydro-2H-pyran-4-ylsulfonyl)pyridin-1(2H)-yl)propanamide;
3-cyclopentyl-N-(5-fluorothiazol-2-yl)-2-(6-methyl-2-oxo-4-(tetrahydro-2H-pyran-4-ylsulfonyl)pyridin-1(2H)-yl)propanamide;
2-(4-(cyclopentylsulfonyl)-6-methyl-2-oxopyridin-1(2H)-yl)-N-(1-methyl-1H-pyrazol-3-yl)-3-(tetrahydro-2H-pyran-4-yl)propanamide;
2-(4-(cyclopentylsulfonyl)-6-methyl-2-oxopyridin-1(2H)-yl)-N-(pyrazin-2-yl)-3-(tetrahydro-2H-pyran-4-yl)propanamide;
N-(5-chlorothiazol-2-yl)-3-cyclopentyl-2-(4-(cyclopropylsulfonyl)-6-methyl-2-oxopyridin-1(2H)-yl)propanamide;
2-(5-chloro-4-(cyclopropylsulfonyl)-2-oxopyridin-1(2H)-yl)-N-(5-chlorothiazol-2-yl)-3-(tetrahydro-2H-pyran-4-yl)propanamide;
(S)-6-(3-cyclopentyl-2-(4-(cyclopropylsulfonyl)-6-methyl-2-oxopyridin-1(2H)-yl)propanamido)nicotinamide;
(R)-6-(2-(4-(cyclopentylsulfonyl)-6-methyl-2-oxopyridin-1(2H)-yl)-3-(tetrahydro-2H-pyran-4-yl)propanamido)nicotinamide;
(S)-6-(2-(4-(cyclopentylsulfonyl)-6-methyl-2-oxopyridin-1(2H)-yl)-3-(tetrahydro-2H-pyran-4-yl)propanamido)nicotinamide;
(S)-N-(5-chlorothiazol-2-yl)-3-cyclopentyl-2-(4-(cyclopropylsulfonyl)-6-methyl-2-oxopyridin-1(2H)-yl)propanamide;
(R)-N-(5-chlorothiazol-2-yl)-3-cyclopentyl-2-(4-(cyclopropylsulfonyl)-6-methyl-2-oxopyridin-1(2H)-yl)propanamide;
2-(5-chloro-4-(cyclopentylsulfonyl)-2-oxopyridin-1(2H)-yl)-N-(5-chlorothiazol-2-yl)-3-(tetrahydro-2H-pyran-4-yl)propanamide;
2-(5-chloro-4-(cyclopentylsulfonyl)-2-oxopyridin-1(2H)-yl)-N-(5-fluorothiazol-2-yl)-3-(tetrahydro-2H-pyran-4-yl)propanamide;
(S)-N-(5-chlorothiazol-2-yl)-2-(4-(1,1-dioxotetrahydrothiopyran-4-ylsulfonyl)-6-methyl-2-oxopyridin-1(2H)-yl)-3-cyclohexylpropanamide;
(R)-N-(5-chlorothiazol-2-yl)-2-(4-(1,1-dioxotetrahydrothiopyran-4-ylsulfonyl)-6-methyl-2-oxopyridin-1(2H)-yl)-3-cyclohexylpropanamide;
(S)-2-(4-(3-fluorophenylsulfonyl)-6-methyl-2-oxopyridin-1(2H)-yl)-N-(5-fluorothiazol-2-yl)-3-(tetrahydro-2H-pyran-4-yl)propanamide;
(R)-2-(4-(3-fluorophenylsulfonyl)-6-methyl-2-oxopyridin-1(2H)-yl)-N-(5-fluorothiazol-2-yl)-3-(tetrahydro-2H-pyran-4-yl)propanamide;
(S)-N-(5-chlorothiazol-2-yl)-3-cyclopentyl-2-(6-methyl-2-oxo-4-(tetrahydro-2H-pyran-4-ylsulfonyl)pyridin-1(2H)-yl)propanamide;
(R)-N-(5-chlorothiazol-2-yl)-3-cyclopentyl-2-(6-methyl-2-oxo-4-(tetrahydro-2H-pyran-4-ylsulfonyl)pyridin-1(2H)-yl)propanamide;
(S)-3-cyclopentyl-N-(5-fluorothiazol-2-yl)-2-(6-methyl-2-oxo-4-(tetrahydro-2H-pyran-4-ylsulfonyl)pyridin-1(2H)-yl)propanamide;
(R)-3-cyclopentyl-N-(5-fluorothiazol-2-yl)-2-(6-methyl-2-oxo-4-(tetrahydro-2H-pyran-4-ylsulfonyl)pyridin-1(2H)-yl)propanamide;
(R)-2-(5-chloro-4-(cyclopropylsulfonyl)-2-oxopyridin-1(2H)-yl)-N-(5-chlorothiazol-2-yl)-3-(tetrahydro-2H-pyran-4-yl)propanamide;
(S)-2-(5-chloro-4-(cyclopropylsulfonyl)-2-oxopyridin-1(2H)-yl)-N-(5-chlorothiazol-2-yl)-3-(tetrahydro-2H-pyran-4-yl)propanamide;
(R)-2-(5-chloro-4-(cyclopropylsulfonyl)-2-oxopyridin-1(2H)-yl)-N-(5-fluorothiazol-2-yl)-3-(tetrahydro-2H-pyran-4-yl)propanamide;
(S)-2-(5-chloro-4-(cyclopropylsulfonyl)-2-oxopyridin-1(2H)-yl)-N-(5-fluorothiazol-2-yl)-3-(tetrahydro-2H-pyran-4-yl)propanamide;
3-cyclohexyl-2-(1-oxoisoquinolin-2(1H)-yl)-N-(thiazol-2-yl)propanamide; and
2-(2-oxo-1,6-naphthyridin-1(2H)-yl)-3-(tetrahydro-2H-pyran-4-yl)-N-(thiazol-2-yl)propanamide.

In addition, particular examples of compounds according to the present invention include, but are not limited to:

- 3-cyclohexyl-2-(4-(cyclopentylsulfonyl)-6-methyl-2-oxopyridin-1(2H)-yl)-N-(thiazol-2-yl)propanamide;
- 6-(3-cyclohexyl-2-(4-(cyclopentylsulfonyl)-6-methyl-2-oxopyridin-1(2H)-yl)propanamido)nicotinamide;
- 3-cyclohexyl-2-(4-(cyclopentylsulfonyl)-2-oxopyridin-1(2H)-yl)-N-(thiazol-2-yl)propanamide;
- 2-(4-(cyclopentylsulfonyl)-6-methyl-2-oxopyridin-1(2H)-yl)-4-methyl-N-(thiazol-2-yl)pentanamide;
- (S)-3-cyclohexyl-2-(4-(cyclopentylsulfonyl)-2-oxopyridin-1(2H)-yl)-N-(thiazol-2-yl)propanamide;
- 3-cyclopentyl-2-(4-(cyclopentylsulfonyl)-6-methyl-2-oxopyridin-1(2H)-yl)-N-(thiazol-2-yl)propanamide;
- N-(5-chlorothiazol-2-yl)-2-(4-(cyclopropylsulfonyl)-6-methyl-2-oxopyridin-1(2H)-yl)-4,4-dimethylpentanamide;
- (S)-N-(5-chlorothiazol-2-yl)-2-(4-(cyclopropylsulfonyl)-2-oxopyridin-1(2H)-yl)-3-(tetrahydro-2H-pyran-4-yl)propanamide;
- (S)-N-(5-chlorothiazol-2-yl)-2-(4-(cyclopentylsulfonyl)-2-oxopyridin-1(2H)-yl)-3-(tetrahydro-2H-pyran-4-yl)propanamide;
- (S)-2-(4-(cyclopentylsulfonyl)-2-oxopyridin-1(2H)-yl)-N-(5-fluorothiazol-2-yl)-3-(tetrahydro-2H-pyran-4-yl)propanamide;
- (S)-2-(4-(cyclopropylsulfonyl)-2-oxopyridin-1(2H)-yl)-N-(5-fluorothiazol-2-yl)-3-(tetrahydro-2H-pyran-4-yl)propanamide;
- (S)-N-(5-chlorothiazol-2-yl)-2-(4-(cyclopentylsulfonyl)-6-methyl-2-oxopyridin-1(2H)-yl)-3-(tetrahydro-2H-pyran-4-yl)propanamide;
- (S)-2-(4-(cyclopentylsulfonyl)-6-methyl-2-oxopyridin-1(2H)-yl)-N-(5-fluorothiazol-2-yl)-3-(tetrahydro-2H-pyran-4-yl)propanamide;
- (S)-N-(5-chloropyridin-2-yl)-2-(4-(cyclopentylsulfonyl)-2-oxopyridin-1(2H)-yl)-3-(tetrahydro-2H-pyran-4-yl)propanamide;
- (S)-methyl 2-(2-(4-(cyclopentylsulfonyl)-2-oxopyridin-1(2H)-yl)-3-(tetrahydro-2H-pyran-4-yl)propanamido)thiazole-5-carboxylate;
- (S)-6-(2-(4-(cyclopentylsulfonyl)-2-oxopyridin-1(2H)-yl)-3-(tetrahydro-2H-pyran-4-yl)propanamido)nicotinamide;
- (S)-2-(4-(cyclopropylsulfonyl)-2-oxopyridin-1(2H)-yl)-N-(5-methoxythiazolo[5,4-b]pyridin-2-yl)-3-(tetrahydro-2H-pyran-4-yl)propanamide;
- N-(5-fluorothiazol-2-yl)-2-(2-oxo-4-(pyridin-2-ylsulfonyl)pyridin-1(2H)-yl)-3-(tetrahydro-2H-pyran-4-yl)propanamide;
- N-(5-chlorothiazol-2-yl)-3-cyclohexyl-2-(6-methyl-4-(2-methylfuran-3-ylsulfonyl)-2-oxopyridin-1(2H)-yl)propanamide;
- (S)-2-(4-(cyclopentylsulfonyl)-2-oxopyridin-1(2H)-yl)-N-(5-methoxythiazolo[5,4-b]pyridin-2-yl)-3-(tetrahydro-2H-pyran-4-yl)propanamide;
- N-(5-chlorothiazol-2-yl)-3-cyclohexyl-2-(6-methyl-2-oxo-4-(thiophen-2-ylsulfonyl)pyridin-1(2H)-yl)propanamide;
- 3-cyclohexyl-2-(4-(cyclopropylsulfonyl)-2-oxopyridin-1(2H)-yl)-N-(5-methoxythiazolo[5,4-b]pyridin-2-yl)propanamide;
- (S)-3-cyclohexyl-2-(4-(cyclopropylsulfonyl)-2-oxopyridin-1(2H)-yl)-N-(5-methoxythiazolo[5,4-b]pyridin-2-yl)propanamide;
- (S)-2-(3-chloro-4-(cyclopropylsulfonyl)-6-methyl-2-oxopyridin-1(2H)-yl)-N-(5-chlorothiazol-2-yl)-3-cyclohexylpropanamide;
- 3-cyclohexyl-2-(4-(furan-2-ylmethylsulfonyl)-6-methyl-2-oxopyridin-1(2H)-yl)-N-(thiazol-2-yl)propanamide;
- 3-cyclohexyl-2-(4-(cyclopentylsulfonyl)-6-methyl-2-oxopyridin-1(2H)-yl)-N-(5-(4-fluorobenzyl)thiazol-2-yl)propanamide;
- N-(5-chlorothiazol-2-yl)-3-cyclohexyl-2-(4-(2,5-dimethylfuran-3-ylsulfonyl)-6-methyl-2-oxopyridin-1(2H)-yl)propanamide;
- (S)-N-(5-chlorothiazol-2-yl)-3-cyclohexyl-2-(6-methyl-2-oxo-4-(thiophen-2-ylmethylsulfonyl)pyridin-1(2H)-yl)propanamide;
- 3-cyclohexyl-2-(4-(cyclopentylsulfonyl)-6-methyl-2-oxopyridin-1(2H)-yl)-N-(5-(morpholinomethyl)thiazol-2-yl)propanamide;
- N-(5-chlorothiazol-2-yl)-2-(4-(cyclopentylsulfonyl)-3,5,6-trimethyl-2-oxopyridin-1(2H)-yl)-3-(tetrahydro-2H-pyran-4-yl)propanamide;
- (S)-3-cyclohexyl-2-(4-(cyclopropylsulfonyl)-6-methyl-2-oxopyridin-1(2H)-yl)-N-(5-methoxythiazolo[5,4-b]pyridin-2-yl)propanamide;
- 2-(4-(cyclopropylsulfonyl)-2-oxopyridin-1(2H)-yl)-N-(5-(dimethylamino)thiazolo[5,4-b]pyridin-2-yl)-3-(tetrahydro-2H-pyran-4-yl)propanamide;
- N-(5-chlorothiazol-2-yl)-2-(6-methyl-2-oxo-4-(thiophen-2-ylmethylsulfonyl)pyridin-1(2H)-yl)-3-(tetrahydro-2H-pyran-4-yl)propanamide;
- (S)-N-(5-chlorothiazol-2-yl)-2-(4-(cyclopentylsulfonyl)-3,5,6-trimethyl-2-oxopyridin-1(2H)-yl)-3-(tetrahydro-2H-pyran-4-yl)propanamide;
- (S)-N-(5-chlorothiazol-2-yl)-2-(4-(furan-2-ylmethylsulfonyl)-6-methyl-2-oxopyridin-1(2H)-yl)-3-(tetrahydro-2H-pyran-4-yl)propanamide;
- (S)-2-(4-(cyclopentylsulfonyl)-5,6-dimethyl-2-oxopyridin-1(2H)-yl)-N-(5-fluorothiazol-2-yl)-3-(tetrahydro-2H-pyran-4-yl)propanamide;
- (R)-2-(4-(cyclopentylsulfonyl)-5,6-dimethyl-2-oxopyridin-1(2H)-yl)-N-(5-fluorothiazol-2-yl)-3-(tetrahydro-2H-pyran-4-yl)propanamide;
- N-(5-chlorothiazol-2-yl)-2-(4-(3-fluorophenylsulfonyl)-6-methyl-2-oxopyridin-1(2H)-yl)-3-(tetrahydro-2H-pyran-4-yl)propanamide;
- (S)-3-cyclopentyl-2-(4-(cyclopropylsulfonyl)-6-methyl-2-oxopyridin-1(2H)-yl)-N-(5-fluorothiazol-2-yl)propanamide;
- (S)-N-(5-chloropyridin-2-yl)-2-(4-(cyclopentylsulfonyl)-6-methyl-2-oxopyridin-1(2H)-yl)-3-(tetrahydro-2H-pyran-4-yl)propanamide;
- (S)-2-(4-(3-chlorophenylsulfonyl)-6-methyl-2-oxopyridin-1(2H)-yl)-N-(5-fluorothiazol-2-yl)-3-(tetrahydro-2H-pyran-4-yl)propanamide;
- (S)-N-(5-chlorothiazol-2-yl)-2-(4-(cyclopropylsulfonyl)-6-methyl-2-oxopyridin-1(2H)-yl)-3-(tetrahydro-2H-pyran-4-yl)propanamide;
- N-(5-chlorothiazol-2-yl)-3-cyclopentyl-2-(4-(cyclopropylsulfonyl)-6-methyl-2-oxopyridin-1(2H)-yl)propanamide; and
- (S)-N-(5-chlorothiazol-2-yl)-3-cyclopentyl-2-(4-(cyclopropylsulfonyl)-6-methyl-2-oxopyridin-1(2H)-yl)propanamide.

It is noted that the compounds of the present invention may be in the form of a pharmaceutically acceptable salt, biohydrolyzable ester, biohydrolyzable amide, biohydrolyzable carbamate, solvate, hydrate or prodrug thereof. For example, the compound optionally comprises a substituent that is convertible in vivo to a different substituent, such as hydrogen.

It is further noted that the compound may be present as a mixture of stereoisomers, or the compound may be present as a single stereoisomer.

In another of its aspects, there is provided a pharmaceutical composition comprising as an active ingredient a compound according to any one of the above embodiments and variations. In one particular variation, the composition is a solid formulation adapted for oral administration. In another particular variation, the composition is a liquid formulation adapted for oral administration. In yet another particular variation, the composition is a tablet. In still another particular variation, the composition is a liquid formulation adapted for parenteral administration.

In another of its aspects, there is provided a pharmaceutical composition comprising a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In yet another of its aspects, there is provided a kit comprising a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound of any one of the above embodiments and variations; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound of any one of the above embodiments and variations to a subject.

In another of its aspects, there is provided a method of activating glucokinase comprising contacting glucokinase with a compound of any one of the above embodiments and variations.

In yet another of its aspects, there is provided a method of activating glucokinase comprising causing a compound of any one of the above embodiments and variations to be present in a subject in order to activate glucokinase in vivo.

In a further of its aspects, there is provided a method of activating glucokinase comprising administering a first compound to a subject that is converted in vivo to a second compound wherein the second compound activates glucokinase in vivo, the second compound being a compound according to any one of the above embodiments and variations.

In another of its aspects, there is provided a method of treating a disease state for which increasing glucokinase activity ameliorates the pathology and/or symptomology of the disease state, the method comprising causing a compound of any one of the above embodiments and variations to be present in a subject in a therapeutically effective amount for the disease state.

In yet another of its aspects, there is provided a method of treating a disease state for which increasing glucokinase activity ameliorates the pathology and/or symptomology of the disease state, the method comprising administering a compound of any one of the above embodiments and variations to a subject, wherein the compound is present in the subject in a therapeutically effective amount for the disease state.

In a further of its aspects, there is provided a method of treating a disease state for which increasing glucokinase activity ameliorates the pathology and/or symptomology of the disease state, the method comprising administering a first compound to a subject that is converted in vivo to a second compound wherein the second compound activates glucokinase in vivo, the second compound being a compound according to any one of the above embodiments and variations.

In one variation of each of the above methods the disease state is selected from the group consisting of hyperglycemia, diabetes, dyslipidaemia, obesity, insulin resistance, metabolic syndrome X, impaired glucose tolerance, polycystic ovary syndrome, and cardiovascular disease.

Salts, Hydrates, and Prodrugs of Glucokinase Activators

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptonate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen-containing groups may be quaternized with such agents as ($C_{1-4}$) alkyl halides, e.g., methyl, ethyl, iso-propyl and tert-butyl chlorides, bromides and iodides; di ($C_{1-4}$) alkyl sulfates, e.g., dimethyl, diethyl and diamyl sulfates; ($C_{10-18}$) alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water-soluble and oil-soluble compounds of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), *Bioorganic and Medicinal Chemistry Letters*, Vol. 4, p. 1985.

Protected derivatives of compounds of the present invention can also be made. Examples of techniques applicable to the creation of protecting groups and their removal can be found in T. W. Greene, Protecting *Groups in Organic Synthesis*, 3$^{rd}$ edition, John Wiley & Sons, Inc. 1999.

Compounds of the present invention may also be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Compositions Comprising Glucokinase Activators

A wide variety of compositions and administration methods may be used in conjunction with the compounds of the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The glucokinase activators and compositions comprising them may be administered or coadministered in any conventional dosage form. Co-administration in the context of this invention is intended to mean the administration of more than one therapeutic agent, one of which includes a glucokinase activator, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When compounds according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding compounds according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more compounds according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of an activator of the present invention to increase glucokinase activity in vivo, thereby treating the disease state of the subject.

Dosage forms or compositions may optionally comprise one or more compounds according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more glucokinase activators, optionally 0.1-95%, and optionally 1-95%.

Salts, preferably sodium salts, of the activators may be prepared with carriers that protect the compound against rapid elimination from the body, such as time release formulations or coatings. The formulations may further include other active compounds to obtain desired combinations of properties.

Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, compounds according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose, and starch paste.

Examples of lubricants that may be used include, but are not limited to, talc, starch, magnesium or calcium stearate, *lycopodium* and stearic acid.

Examples of diluents that may be used include, but are not limited to, lactose, sucrose, starch, kaolin, salt, mannitol, and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof, and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate, and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The compounds of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate, and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

Injectables, Solutions, and Emulsions

The present invention is also directed to compositions designed to administer the compounds of the present invention by parenteral administration, generally characterized by subcutaneous, intramuscular or intravenous injection. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions includes EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of an activator in the parenteral formulation may be adjusted so that an injection administers a pharmaceutically effective amount sufficient to produce the desired pharmacological effect. The exact concentration of an activator and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is known and practiced in the art.

Injectables may be designed for local and systemic administration. Typically a therapeutically effective dosage is formulated to contain a concentration of at least about 0.1% w/w up to about 90% w/w or more, preferably more than 1% w/w of the glucokinase activator to the treated tissue(s). The activator may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The glucokinase activator may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

Lyophilized Powders

The compounds of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a glucokinase activator is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the activator.

Topical Administration

The compounds of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The glucokinase activators may be formulated as aerosols for topical application, such as by inhalation (see, U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The activators may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the glucokinase activator alone or in combination with other pharmaceutically acceptable excipients can also be administered.

Formulations for Other Routes of Administration

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
|---|---:|
| Compound of the Present Invention | 10-100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
|---|---:|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
|---|---|
| Compound of the Present Invention | 1% |
| Microcrystalline Cellulose | 73% |
| Stearic Acid | 25% |
| Colloidal Silica | 1%. |

Kits Comprising Glucokinase Activators

The invention is also directed to kits and other articles of manufacture for treating diseases associated with glucokinase. It is noted that diseases are intended to cover all conditions for which increasing glucokinase activity (e.g., upregulation of glucokinase) ameliorates the pathology and/or symptomology of the condition.

In one embodiment, a kit is provided that comprises a composition comprising at least one activator of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one activator of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Dosage, Host and Safety

The compounds of the present invention are stable and can be used safely. In particular, the compounds of the present invention are useful as GK activators for a variety of subjects (e.g., humans, non-human mammals and non-mammals). The optimal dose may vary depending upon such conditions as, for example, the type of subject, the body weight of the subject, the route of administration, and specific properties of the particular compound being used. In general, the daily dose for oral administration to an adult (body weight of about 60 kg) is about 1 to 1000 mg, about 3 to 300 mg, or about 10 to 200 mg. It will be appreciated that the daily dose can be given in a single administration or in multiple (e.g., 2 or 3) portions a day.

Combination Therapies

A wide variety of therapeutic agents may have a therapeutic additive or synergistic effect with GK activators according to the present invention. In particular, the present invention also relates to the use of the GK activators of the present invention in combination with one or more other antidiabetic compounds. Examples of such other antidiabetic compounds include, but are not limited to S9 proteases, like dipeptidyl peptidase IV (DPP-IV) inhibitors; insulin signaling pathway modulators, like protein tyrosine phosphatase (PTPase) inhibitors, and glutamine-fructose-6-phosphate amidotransferase (GFAT) inhibitors; compounds influencing a dysregulated hepatic glucose production, like glucose-6-phosphatase (G6Pase) inhibitors, fructose-1,6-bisphosphatase (F-1,6-BPase) inhibitors, glycogen phosphorylase (GP) inhibitors, glucagon receptor antagonists and phosphoenolpyruvate carboxykinase (PEPCK) inhibitors; pyruvate dehydrogenase kinase (PDHK) inhibitors; insulin sensitivity enhancers (insulin sensitizers); insulin secretion enhancers (insulin secretagogues); alpha-glucosidase inhibitors; inhibitors of gastric emptying; other glucokinase (GK) activators; GLP-1 receptor agonists; UCP modulators; RXR modulators; GSK-3 inhibitors; PPAR modulators; metformin; insulin; and $\alpha_2$-adrenergic antagonists. The compound of the present invention may be administered with such at least one other antidiabetic compound either simultaneously as a single dose, at the same time as separate doses, or sequentially (i.e., where one is administered before or after the other is administered).

In the case of combination therapy with compounds of the present invention, the other antidiabetic compound may be administered (e.g., route and dosage form) in a manner known per se for such compound. Compounds of the present invention and the other antidiabetic compound may be administered sequentially (i.e., at separate times) or at the same time, either one after the other separately in two separate dose forms or in one combined, single dose form. In one particular embodiment, the other antidiabetic compound is administered with compounds of the present invention as a single, combined dosage form. The dose of the antidiabetic compound may be selected from the range known to be clinically employed for such compound. Any of the therapeutic compounds of diabetic complications, antihyperlipemic compounds or antiobestic compounds can be used in combination with compounds of the present invention in the same manner as the above antidiabetic compounds.

EXAMPLES

Preparation of Glucokinase Activators

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (i.e., enantiomers and diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) and can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in T. W. Greene, *Protecting Groups in Organic Synthesis,* 3d edition, John Wiley & Sons, Inc. 1999.

Compounds according to the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/ resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

ing detector (ELSD). Thin-layer chromatography was performed on 0.25 mm E. Merck silica gel plates (60F-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

| | |
|---|---|
| μL (microliters) | Ac (acetyl) |
| atm (atmosphere) | ATP (Adenosine Triphophatase) |
| BOC (tert-butyloxycarbonyl) | BOP (bis(2-oxo-3-oxazolidinyl)phosphinic chloride) |
| BSA (Bovine Serum Albumin) | CBZ (benzyloxycarbonyl) |
| CDI (1,1-carbonyldiimidazole) | DCC (dicyclohexylcarbodiimide) |
| DCE (dichloroethane) | DCM (dichloromethane) |
| DMAP (4-dimethylaminopyridine) | DME (1,2-dimethoxyethane) |
| DMF (N,N-dimethylformamide) | DMPU (N,N'-dimethylpropyleneurea) |
| DMSO (dimethylsulfoxide) | EDCI (ethylcarbodiimide hydrochloride) |
| EDTA (Ethylenediaminetetraacetic acid) | Et (ethyl) |
| Et$_2$O (diethyl ether) | EtOAc (ethyl acetate) |
| FMOC (9-fluorenylmethoxycarbonyl) | g (grams) |
| h (hours) | HOAc or AcOH (acetic acid) |
| HOBT (1-hydroxybenzotriazole) | HOSu (N-hydroxysuccinimide) |
| HPLC (high pressure liquid chromatography) | Hz (Hertz) |
| i.v. (intravenous) | IBCF (isobutyl chloroformate) |
| i-PrOH (isopropanol) | L (liters) |
| M (molar) | mCPBA (meta-chloroperbenzoic acid) |
| Me (methyl) | MeOH (methanol) |
| mg (milligrams) | MHz (megahertz) |
| min (minutes) | mL (milliliters) |
| mM (millimolar) | mmol (millimoles) |
| mol (moles) | MOPS (Morpholinepropanesulfonic acid) |
| mp (melting point) | NaOAc (sodium acetate) |
| OMe (methoxy) | psi (pounds per square inch) |
| RP (reverse phase) | RT (ambient temperature) |
| SPA (Scintillation Proximity Assay) | TBAF (tetra-n-butylammonium fluoride) |
| TBS (t-butyldimethylsilyl) | tBu (tert-butyl) |
| TEA (triethylamine) | TFA (trifluoroacetic acid) |
| TFAA (trifluoroacetic anhydride) | THF (tetrahydrofuran) |
| TIPS (triisopropylsilyl) | TLC (thin layer chromatography) |
| TMS (trimethylsilyl) | TMSE (2-(trimethylsilyl)ethyl) |
| Tr (retention time) | |

All references to ether or Et$_2$O are to diethyl ether; and brine refers to a saturated aqueous solution of NaCl. Unless otherwise indicated, all temperatures are expressed in ° C. (degrees Centigrade). All reactions are conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scatter- The entire disclosures of all documents cited throughout this application are incorporated herein by reference.

Synthetic Schemes for Compounds of the Present Invention

Compounds according to the present invention may be synthesized according to the reaction schemes shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W.

Greene and P. G. M. Wuts in "Protective Groups in Organic Chemistry" John Wiley and Sons, 1991.

Scheme 1:

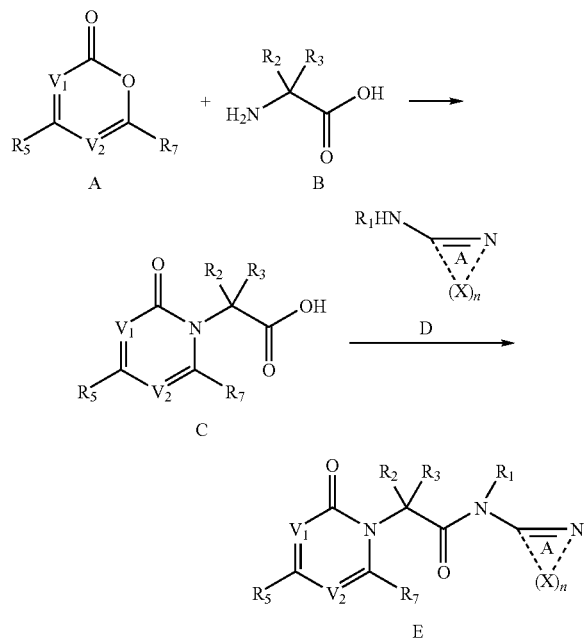

Referring to Scheme 1, compound A is condensed with amino acid B to give compound C. Compound C is coupled with amino heterocycle D to give compound E.

Scheme 2:

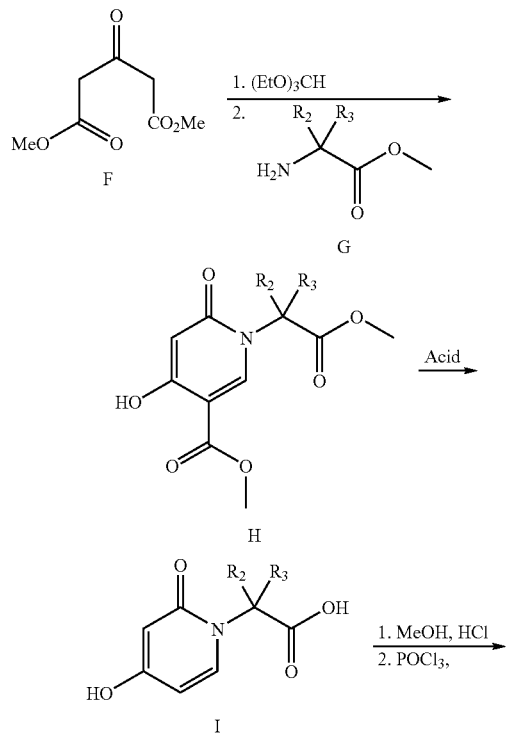

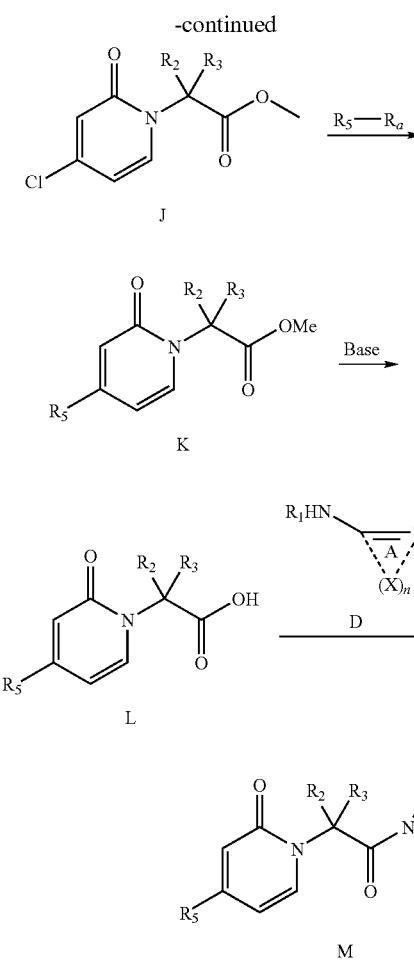

Referring to Scheme 2, dimethyl 1,3-acetonedicarboxylate F is condensed with triethyl orthoformate, and then cyclized with amino ester G to give compound H. Decarboxylation in conc. HBr provides compound I, which is then esterified and chlorinated to obtain compound J. Displacement of the chloride with nucleophile $R_5$-$R_a$ (where $R_a$ is a metal (e.g., Na or Li)) gives compound K. Compound K is treated with base (e.g., LiOH) to form acid L. Acid L is coupled with amino heterocycle D to obtain compound M.

Scheme 3:

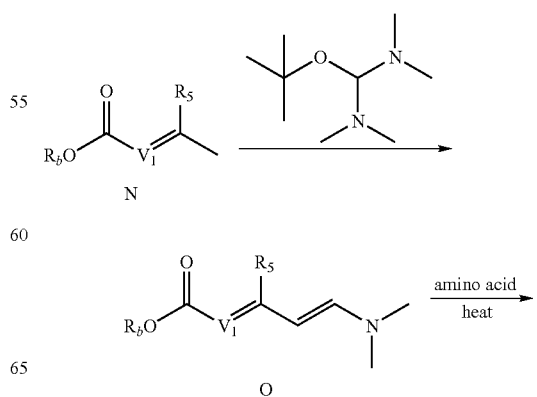

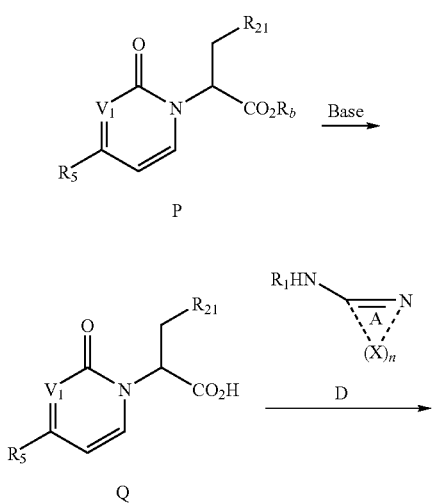

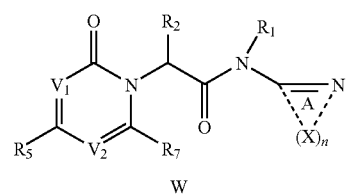

Referring to Scheme 4, 2-hydroxy-, 2-alkoxy- or 2-halo-pyridine derivative S is alkylated with ester T, where $R_b$ is a $(C_{1-3})$alkyl and $R_d$ is a leaving group (e.g., halo), to obtain compound U. Compound U is treated with base (e.g., LiOH) to form acid V. Acid V is coupled with amino heterocycle D to obtain compound W.

Scheme 5:

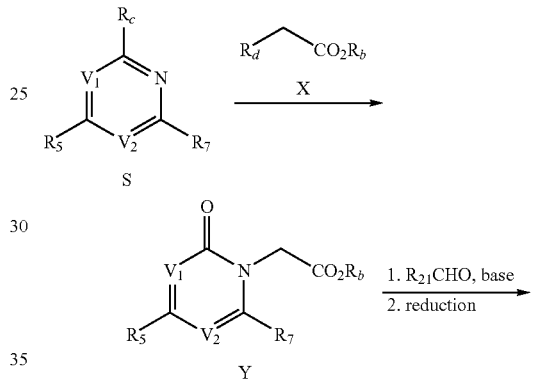

Referring to Scheme 3, butenoate ester N, where $R_b$ is a $(C_{1-3})$alkyl, is converted to aminopentadienoate O, which is then cyclized with an amino ester to obtain compound P. Compound P is treated with base (e.g., LiOH) to form acid Q. Acid Q is coupled with amino heterocycle D to obtain compound R.

Scheme 4:

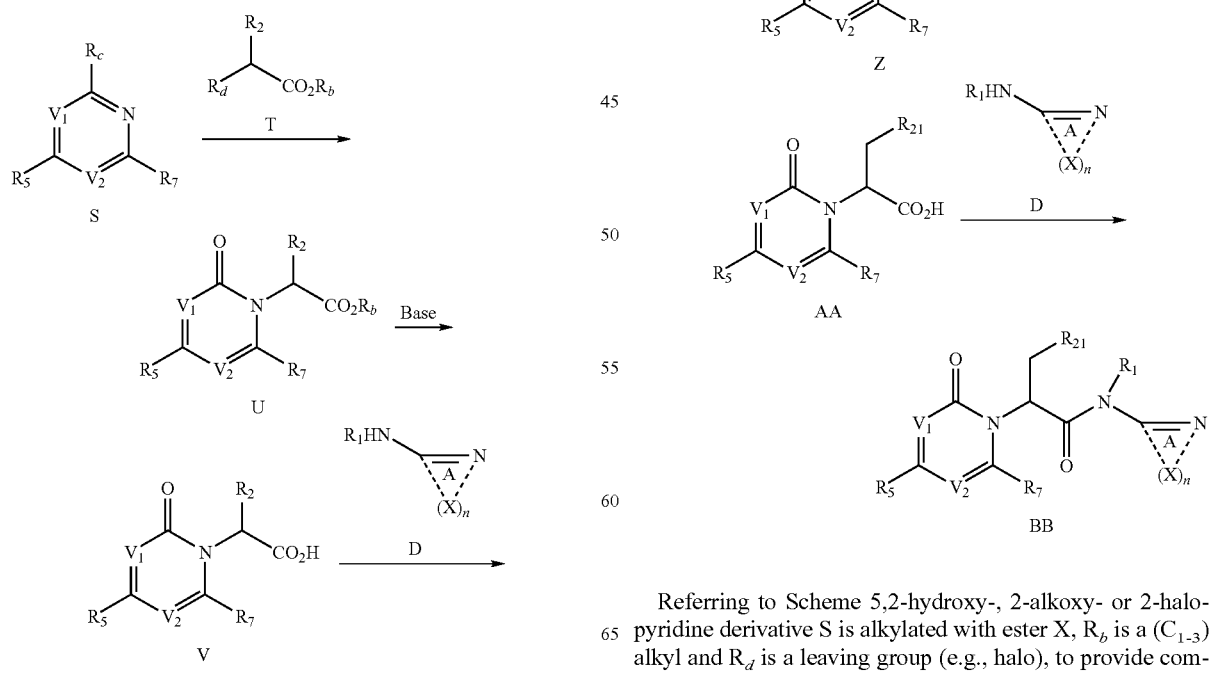

Referring to Scheme 5, 2-hydroxy-, 2-alkoxy- or 2-halo-pyridine derivative S is alkylated with ester X, $R_b$ is a $(C_{1-3})$ alkyl and $R_d$ is a leaving group (e.g., halo), to provide compound Y. An aldol condensation followed by reduction yields compound Z. Compound Z is treated with base (e.g., LiOH) to form acid AA. Acid AA is coupled with amino heterocycle D to obtain compound BB.

Scheme 6:

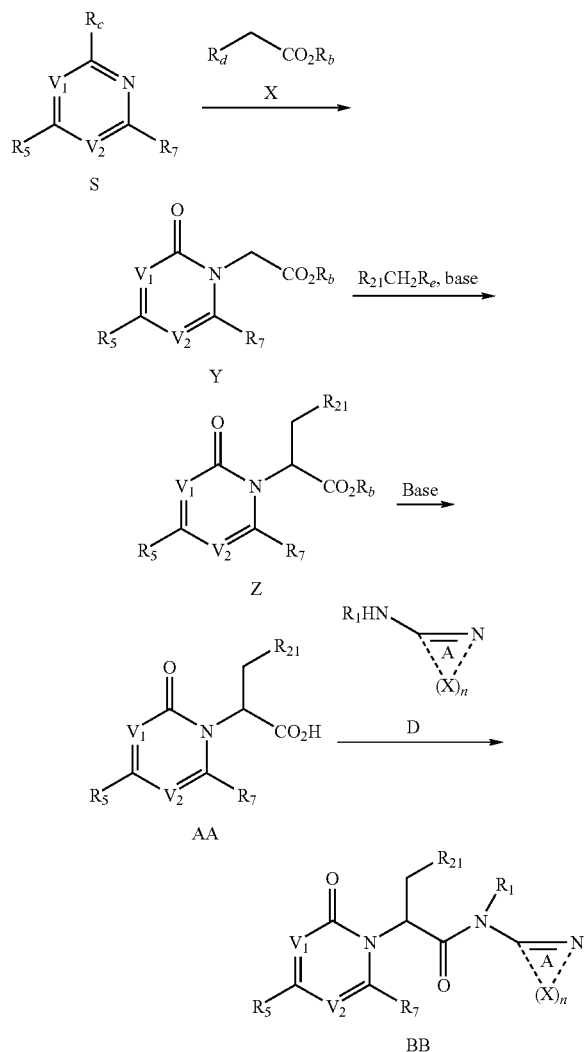

Referring to Scheme 6, 2-hydroxy-, 2-alkoxy- or 2-halopyridine derivative S is alkylated with ester X, $R_b$ is a ($C_{1-3}$) alkyl and $R_d$ is a leaving group (e.g., halo), to provide compound Y. Alkylation of the unsubstituted alpha carbon of compound Y by $R_{21}CH_2R_e$, where $R_e$ is a leaving group (e.g., halo, ($C_{1-3}$)alkyl), provides compound Z. Compound Z is treated with base (e.g., LiOH) to form acid AA. Acid AA is coupled with amino heterocycle D to obtain compound BB.

Chiral components can be separated and purified using any of a variety of techniques known to those skilled in the art. For example, chiral components can be purified using supercritical fluid chromatography (SFC). In one particular variation, chiral analytical SFC/MS analyses are conducted using a Berger analytical SFC system (AutoChem, Newark, Del.) which consists of a Berger SFC dual pump fluid control module with a Berger FCM 1100/1200 supercritical fluid pump and FCM 1200 modifier fluid pump, a Berger TCM 2000 oven, and an Alcott 718 autosampler. The integrated system can be controlled by BI-SFC Chemstation software version 3.4. Detection can be accomplished with a Watrers ZQ 2000 detector operated in positive mode with an ESI interface and a scan range from 200-800 Da with 0.5 second per scan. Chromatographic separations can be performed on a ChiralPak AD-H, ChiralPak AS-H, ChiralCel OD-H, or ChiralCel OJ-H column (5µ, 4.6×250 mm; Chiral Technologies, Inc. West Chester, Pa.) with 10 to 40% methanol as the modifier and with or without ammonium acetate (10 mM). Any of a variety of flow rates can be utilized including, for example, 1.5 or 3.5 mL/min with an inlet pressure set at 100 bar. Additionally, a variety of sample injection conditions can be used including, for example, sample injections of either 5 or 10 µL in methanol at 0.1 mg/mL in concentration.

In another variation, preparative chiral separations are performed using a Berger MultiGram II SFC purification system. For example, samples can be loaded onto a ChiralPak AD column (21×250 mm, 10µ). In particular variations, the flow rate for separation can be 70 mL/min, the injection volume up to 2 mL, and the inlet pressure set at 130 bar. Stacked injections can be applied to increase the efficiency.

In each of the above reaction procedures or schemes, the various substituents may be selected from among the various substituents otherwise taught herein.

Descriptions of the syntheses of particular compounds according to the present invention based on the above reaction scheme are set forth herein.

Examples of Glucokinase Activators

The present invention is further exemplified, but not limited by, the following examples that describe the synthesis of particular compounds according to the invention.

Method A

Compounds designated in Table 1 below as being prepared using Method A were prepared using a procedure analogous to that described in connection with Example 1.

Example 1

3-cyclohexyl-2-(4-hydroxy-6-methyl-2-oxopyridin-1 (2H)-yl)-N-(thiazol-2-yl)propanamide trifluoroacetic acid salt

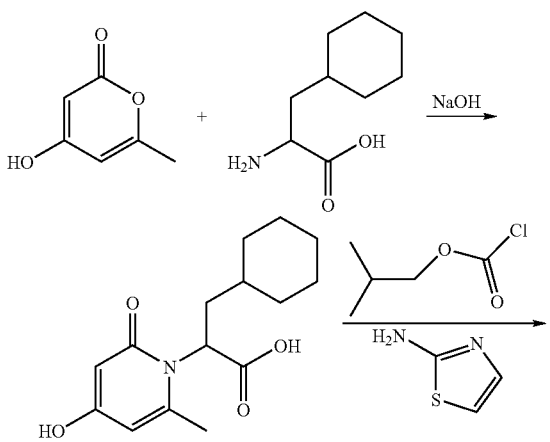

91

-continued

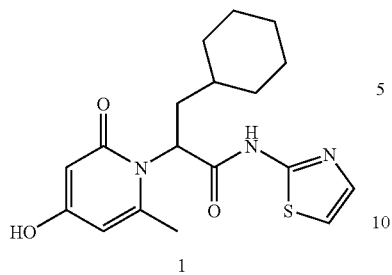

1

4-Hydroxy-6-methyl-2-pyrone (1.10 g) was added in portions at room temperature to a solution of 2-amino-3-cyclohexylpropanoic acid (1.5 g) in 9 ml of 1N aqueous NaOH. The mixture was heated under reflux overnight, cooled and acidified with 9 ml of 1N hydrochloric acid. The reaction mixture was then concentrated to half its volume and the precipitate was filtered, washed with cold water and dried to give compound 1A. $^1$H NMR (400 MHz, MeOD) δ 0.8-1.93 (m, 13H), 2.30 (m, 1H), 2.36 (s, 3H), 5.67 (s, 1 H), 5.93 (d, J=4Hz, 1 H). [M+H] calc'd for $C_{15}H_{21}NO_4$, 280.33; found, 280.3.

To compound 1A (0.16 mg) in 3 ml of THF was added N-methylmorpholine (NMM, 0.09 ml) and the flask cooled to 0° C. To this reaction mixture was added isobutylchloroformate (0.081 ml) dropwise. After 20 min, 2-aminothiazole (0.057 mg) was added and the reaction was allowed to warm to room temperature and stirred overnight. The reaction mixture was diluted with ethyl acetate, and washed with water and brine, dried over $Na_2SO_4$, and concentrated in vacuo. Purification by HPLC afforded the title compound as a colorless solid (36 mg). $^1$H NMR (400 MHz, MeOD) δ 0.9-1.93 (m, 13 H), 2.40 (m, 1 H), 2.44 (s, 3H), 5.67 (d, J=4Hz, 1 H), 6.02 (s, 1 H), 7.11 (s, 1 H), 7.40 (s, 1 H). [M+H] calc'd for $C_{18}H_{23}N_3O_3S$, 362.4; found, 362.5.

Method B

Compounds designated in Table 1 below as being prepared using Method B were prepared using a procedure analogous to that described in connection with Example 2.

Example 2

3-cyclohexyl-2-(4-methoxy-6-methyl-2-oxopyridin-1(2H)-yl)-N-(thiazol-2-yl)propanamide trifluoroacetic acid salt

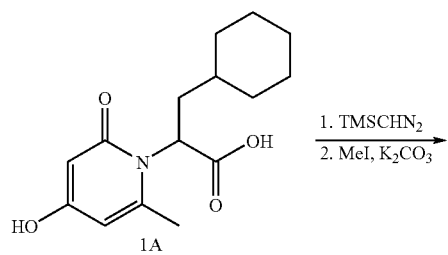

92

-continued

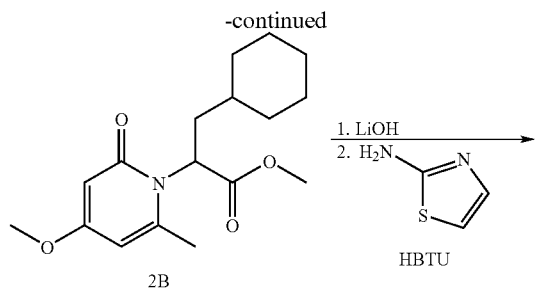

Compound 1A (0.36 g) in 13 ml of acetonitrile at 0° C. was treated with trimethylsilyldiazomethane (1.93 ml of a 2M solution) and the reaction was allowed to warm to room temperature and stirred overnight. The reaction mixture was concentrated on a rotary evaporator and redissolved in DMF (5 ml). To this solution was added $K_2CO_3$ and methyl iodide (3 equiv each) and the reaction was stirred overnight at room temperature. The product was extracted into ethyl acetate, and washed with water and brine, dried over $Na_2SO_4$, and concentrated in vacuo to yield compound 2B. [M+H] calc'd for $C_{17}H_{25}NO_4$, 308.38 found, 308.4.

To a solution of compound 2B (0.131 g) in dioxane (4 ml) was added 1.27 ml of a 1N LiOH solution and the reaction mixture stirred overnight at room temperature. The reaction mixture was diluted with ethyl acetate and the separated aqueous layer was acidified with 1N hydrochloric acid to pH 2. The aqueous layer was extracted with ethyl acetate (2×), and washed with water and brine, dried over $Na_2SO_4$, and concentrated in vacuo to obtain the intermediate acid. [M+H] calc'd for $C_{16}H_{23}NO_4$, 294.36 found, 294.4.

To the intermediate acid in DMF (3 ml) was added HBTU (0.33 g) and $Et_3N$ (0.15 ml). After 20 min., 2-aminothiazole (0.065 g) was added and the reaction mixture stirred overnight at room temperature. The reaction mixture was diluted with ethyl acetate, and the mixture was washed with water and brine, dried over $Na_2SO_4$, and concentrated in vacuo to yield compound 2. $^1$H NMR (400 MHz, $CDCl_3$) δ 0.9-1.38 (m, 7 H), 1.58-1.82 (m, 5 H), 2.39 (s, 3 H), 2.46 (m, 1 H), 3.76 (s, 3 H), 5.81 (s, 1 H), 5.84 (s, 1 H), 6.97 (d, J=4 Hz, 1 H), 7.42 (d, J=4 Hz, 1 H). [M+H] calc'd for $C_{18}H_{23}N_3O_3S$, 376.49; found, 376.4.

Method C

Compounds designated in Table 1 below as being prepared using Method C were prepared using a procedure analogous to that described in connection with Example 3.

Example 3

3-cyclohexyl-2-(6-methyl-4-(methylsulfonyl)-2-oxopyridin-1(2H)-yl)-N-(thiazol-2-yl)propanamide trifluoroacetic acid salt

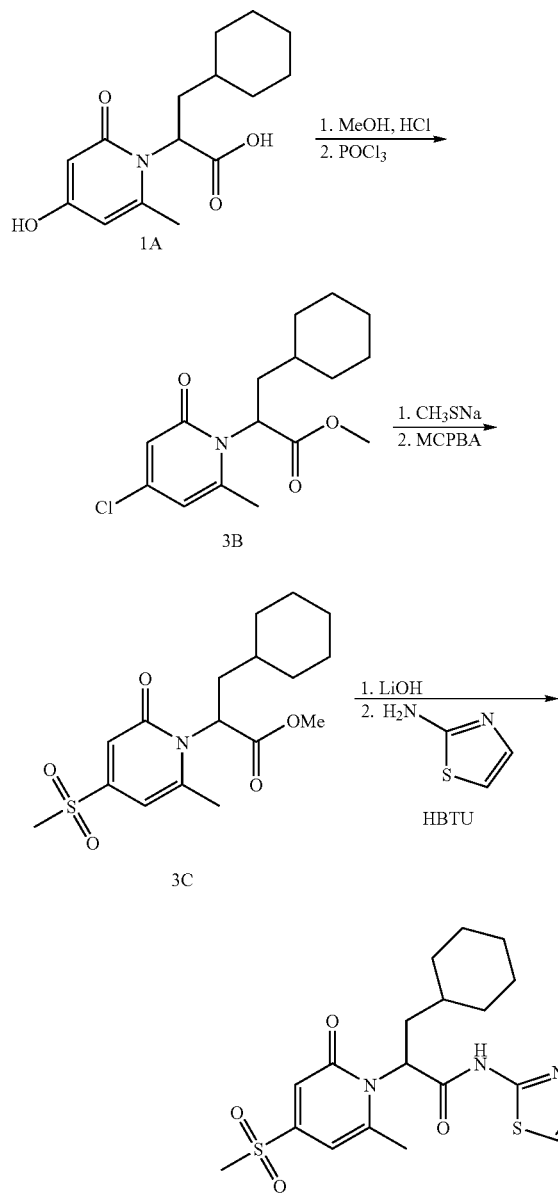

To a solution of compound 1A (2 g) in 30 ml of methanol was added concentrated HCl (2 ml) in one portion. The solution was refluxed for 3 h, cooled to room temperature, concentrated, and poured on crushed ice. The solid obtained was filtered, washed with cold water and dried to yield the corresponding ester in quantitative yield.

To a rapidly stirring solution of the intermediate ester of compound 1A (0.53 g), Et$_4$NCl (1.19 g) and dry N,N-dimethylaniline (0.22 ml) in anhydrous acetonitrile (5 ml) was added POCl$_3$ (0.41 ml) at ambient temperature under nitrogen. The reaction was placed in a preheated oil bath and refluxed at 100° C. for 15 min. The reaction mixture was then evaporated on a rotary evaporator and the resulting oil was dissolved in dichloromethane and poured onto crushed ice. The layers were separated, and the organic phase was washed with water, 5% NaHCO$_3$ and brine, dried over Na$_2$SO$_4$, and concentrated in vacuo to yield compound 3B. $^1$H NMR (400 MHz, CDCl$_3$) δ 0.8-1.7 (m, 13 H), 2.27 (s, 3H), 2.35 (m, 1H), 3.64 (s, 3 H), 6.03 (d, J=4 Hz, 1 H), 6.40 (d, J=4 Hz, 1 H). [M+H] calc'd for C$_{16}$H$_{22}$ClNO$_3$, 312.80 found, 312.8.

To compound 3B (0.29 g) in 5 ml of DMSO was added sodium methylthiolate (0.066 g) and the solution was heated at 80° C. overnight. The reaction mixture was allowed to cool to room temperature, extracted into ethyl acetate, washed with water and brine, dried over Na$_2$SO$_4$, and concentrated in vacuo to obtain an oil. To the oil in 6 ml of dichloromethane was added MCPBA (0.318 g) and the reaction stirred at room temperature for 3 h. The excess MCPBA was quenched with aqueous sodium sulfite, and the organic layer was washed with water, 5% NaHCO$_3$ and brine, dried over Na$_2$SO$_4$, and concentrated in vacuo to yield compound 3C. [M+H] calc'd for C$_{17}$H$_{25}$NO$_5$S, 356.50 found, 356.5

To a solution of compound 3C (0.131 g) in dioxane (4 ml) was added 1.27 ml of a 1N LiOH solution and the reaction mixture stirred overnight at room temperature. The reaction mixture was diluted with ethyl acetate, and the separated aqueous layer was acidified with 1N hydrochloric acid to pH 2. The aqueous layer was extracted with ethyl acetate (2×), and washed with water and brine, dried over Na$_2$SO$_4$, and concentrated in vacuo to obtain the intermediate acid. [M+H] calc'd for C$_{16}$H$_{23}$NO$_5$S, 342.42 found, 342.5

To the intermediate acid in DMF (3 ml) was added HBTU (0.33 g) and Et$_3$N (0.15 ml). After 20 min., 2-aminothiazole (0.065 g) was added and the reaction mixture stirred overnight at room temperature. The reaction mixture was extracted into ethyl acetate, and the organic layer was washed with water and brine, dried over Na$_2$SO$_4$, and concentrated in vacuo. Purification by HPLC afforded the title compound (3) as a colorless solid. $^1$H NMR (400 MHz, CDCl$_3$) δ 0.9-1.35 (m, 7 H), 1.60-1.82 (m, 5 H), 2.47 (m, 1 H), 2.52 (s, 3 H), 3.08 (s, 3 H), 5.0 (bs, 1 H), 6.45 (d, J=4 Hz, 1 H), 6.99 (s, 1 H), 7.00 (s, 1 H), 7.42 (d, J=4 Hz, 1 H). [M+H] calc'd for C$_{19}$H$_{25}$N$_3$O$_4$S$_2$ 424.5; found, 424.5.

Compound 3 was separated into its enantiomers under SFC conditions, using a chiral column (ChiralPak OJ-H) with mobile Phase A: liquid CO$_2$ and mobile Phase B: methanol at a flow rate of 20 min/ml. [M+H] calc'd for C$_{19}$H$_{25}$N$_3$O$_4$S$_2$ 424.5; found, 424.5

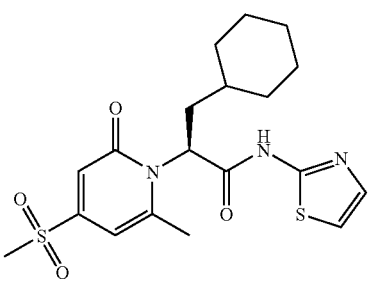

3A

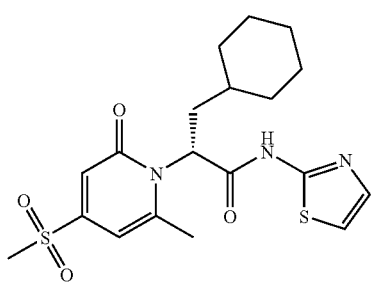

Example 4

3-cyclohexyl-2-(4-(ethylsulfonyl)-6-methyl-2-oxopyridin-1(2H)-yl)-N-(thiazol-2-yl)propanamide trifluoroacetic acid salt

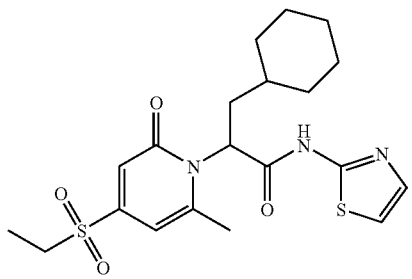

The title compound was synthesized using an analogous procedure to that described in connection with Example 3, except that sodium ethanethiolate was used. $^1$H NMR (400 MHz, CDCl$_3$) δ 0.95-1.30 (m, 5 H), 1.28 (t, J=4 Hz, 3 H), 1.4-1.90 (m, 7 H), 2.59 (s, 3 H), 2.73 (m, 1 H), 3.10 (q, J=4 Hz, 2 H), 4.8 (bs, 1 H), 6.54 (d, J=4 Hz, 1 H), 6.90 (d, J=4 Hz, 1 H), 7.10 (d, J=4 Hz, 1 H), 7.43 (d, J=4 Hz, 1 H). [M+H] calc'd for C$_{20}$H$_{27}$N$_3$O$_4$S$_2$ 438.5; found, 438.5.

Example 5

3-cyclohexyl-2-(4-(cyclopentylsulfonyl)-6-methyl-2-oxopyridin-1(2H)-yl)-N-(thiazol-2-yl)propanamide trifluoroacetic acid salt

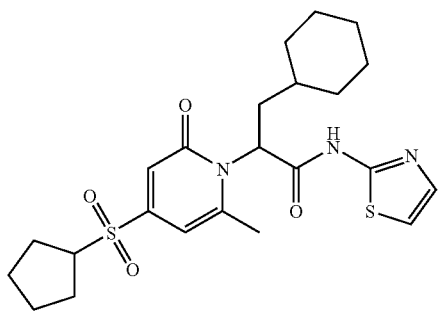

The title compound was synthesized using an analogous procedure to that described in connection with Example 3, except that sodium cyclopentylthiolate was used. $^1$H NMR (400 MHz, CDCl$_3$) δ 0.90-1.35 (m, 5 H), 1.45-2.20 (m, 16 H), 2.58 (s, 3 H), 2.71 (m, 1 H), 3.45 (m, 1 H), 6.54 (d, J=4 Hz, 1 H), 6.88 (d, J=4 Hz, 1 H), 7.10 (d, J=4 Hz, 1 H), 7.41 (d, J=4 Hz, 1 H). [M+H] calc'd for C$_{23}$H$_{31}$N$_3$O$_4$S$_2$ 478.6; found, 478.6.

Example 6

6-(3-cyclohexyl-2-(4-(cyclopentylsulfonyl)-6-methyl-2-oxopyridin-1(2H)-yl)propanamido)nicotinamide trifluoroacetic acid salt

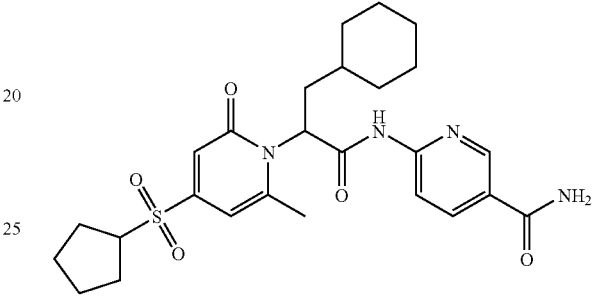

The title compound was synthesized using an analogous procedure to that described in connection with Example 3, except that sodium cyclopentylthiolate was used. $^1$H NMR (400 MHz, CDCl$_3$) δ 0.90-1.4 (m, 5 H), 1.6-2.20 (m, 16 H), 2.48 (m, 1 H), 2.59 (s, 3 H), 3.57 (m, 1 H), 6.56 (bs, 1 H), 6.96 (bs, 1 H), 8.26 (bs, 2 H), 8.77 (bs, 1 H). [M+H] calc'd for C$_{26}$H$_{34}$N$_4$O$_5$S 515.6; found 514.6.

Example 7

2-(6-methyl-4-(methylsulfonyl)-2-oxopyridin-1(2H)-yl)-3-(tetrahydro-2H-pyran-4-yl)-N-(thiazol-2-yl)propanamide trifluoroacetic acid salt

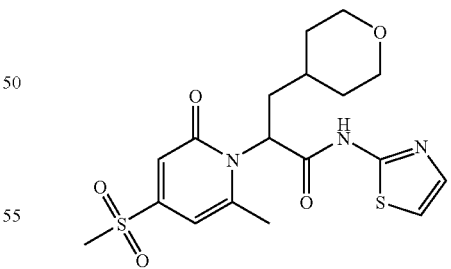

The title compound was synthesized using an analogous procedure to that described in connection with Example 3, except that 2-amino-3-(4-tetrahydropyranyl)-propionic acid was used in place of 2-amino-3-cyclohexylpropanoic acid in the first step . $^1$H NMR (400 MHz, CDCl$_3$) δ 1.3-1.9 (m, 7 H), 2.61 (s, 3 H), 2.87 (m, 1 H), 3.04 (s, 3 H), 3.45 (m, 2 H), 4.0 (m, 2 H), 4.89 (bs, 1 H), 6.61 (s, 1 H), 6.96 (s, 1 H), 7.14 (d, J=4 Hz, 1 H), 7.47 (d, J=4 Hz, 1 H), [M+H] calc'd for C$_{18}$H$_{23}$N$_3$O$_5$S 426.5; found 426.5.

Method D

Compounds designated in Table 1 below as being prepared using Method D were prepared using a procedure analogous to that described in connection with Example 8.

Example 8

3-cyclohexyl-2-(4-(cyclopentylsulfonyl)-2-oxopyridin-1(2H)-yl)-N-(thiazol-2-yl)propanamide trifluoroacetic acid salt

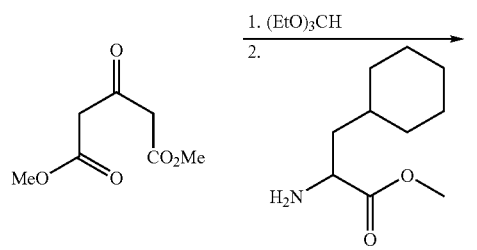

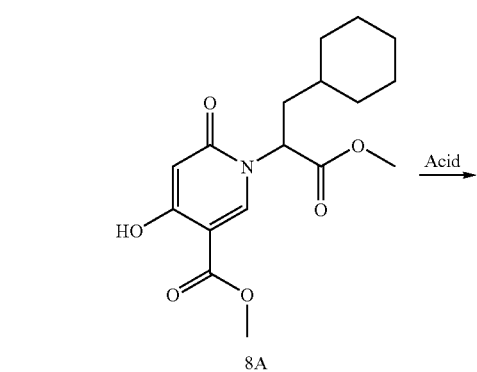

8A

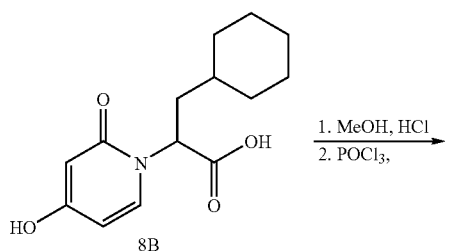

8B

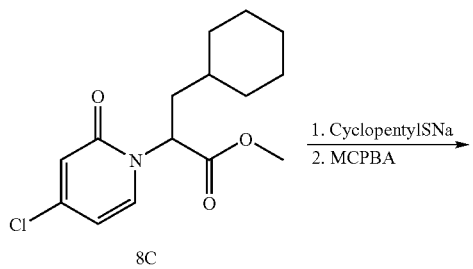

8C

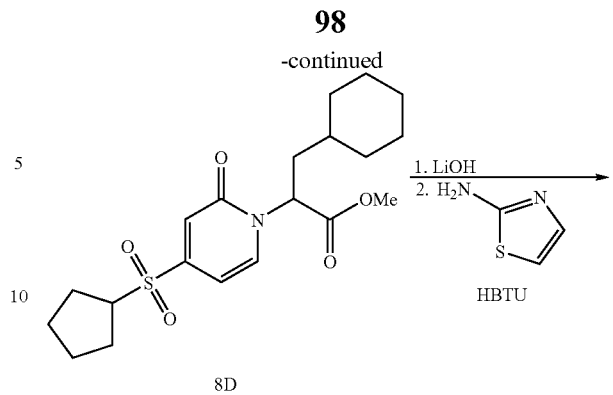

8D

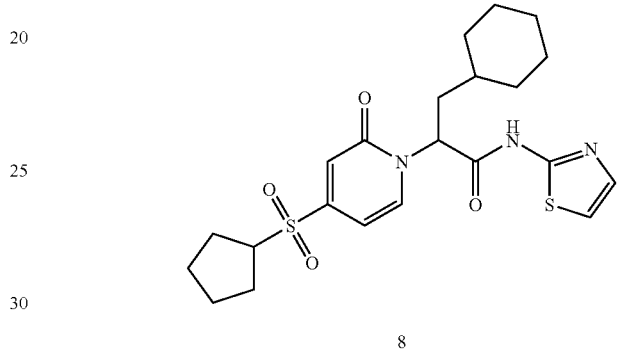

8

To dimethyl 1,3-acetonedicarboxylate (0.87 g) was added triethyl orthoformate (0.741 g) followed by acetic anhydride (0.969 g). The resulting solution was stirred for 1h at 135° C. The reaction mixture was cooled to room temperature and concentrated under reduced pressure. To the resulting residue at 0° C. was added methyl 2-amino-3-cyclohexylpropanoate in methanol (30 ml) and the solution was stirred at room temperature overnight. The reaction mixture was concentrated under reduced pressure, diluted with ethyl acetate, washed with water and brine, dried over Na$_2$SO$_4$, and concentrated in vacuo to yield compound 8A. [M+H] calc'd for C$_{17}$H$_{23}$NO$_6$, 338.37 found, 338.4.

Compound 8A (1.0 g) was dissolved in 30 ml of 48% concentrated HBr and the solution was refluxed at 170° C. for 2 days. The reaction mixture was concentrated under reduced pressure, diluted with ethyl acetate, washed with water, saturated bicarbonate solution and brine, dried over Na$_2$SO$_4$, and concentrated in vacuo to yield compound 8B. [M+H] calc'd for C$_{14}$H$_{19}$NO$_4$, 266.3 found, 266.3

The title compound was synthesized using compound 8B in an analogous procedure to that described in connection with Example 3. $^1$H NMR (400 MHz, CDCl$_3$) δ 0.90-1.25 (m, 5 H), 1.59-2.18 (m, 16 H), 3.51 (m, 1 H), 6.18 (t, J=8 Hz, 1 H), 6.96 (dd, J=4, 8 Hz, 2 H), 7.04 (d, J=4 Hz, 1 H), 7.59 (d, J=3 Hz, 1 H), 7.62 (d, J=4 Hz, 1 H), 7.95 (d, J=8 Hz, 1 H), [M+H] calc'd for C$_{22}$H$_{29}$N$_3$O$_4$S$_2$ 464.6; found 464.6.

Method E

Compounds designated in Table 1 below as being prepared using Method E were prepared using a procedure analogous to that described in connection with Example 9.

Example 9

3-(2-chloro-5-fluorophenyl)-N-(5-chlorothiazol-2-yl)-2-(4-(methylsulfonyl)-2-oxopyridin-1(2H)-yl)propanamide

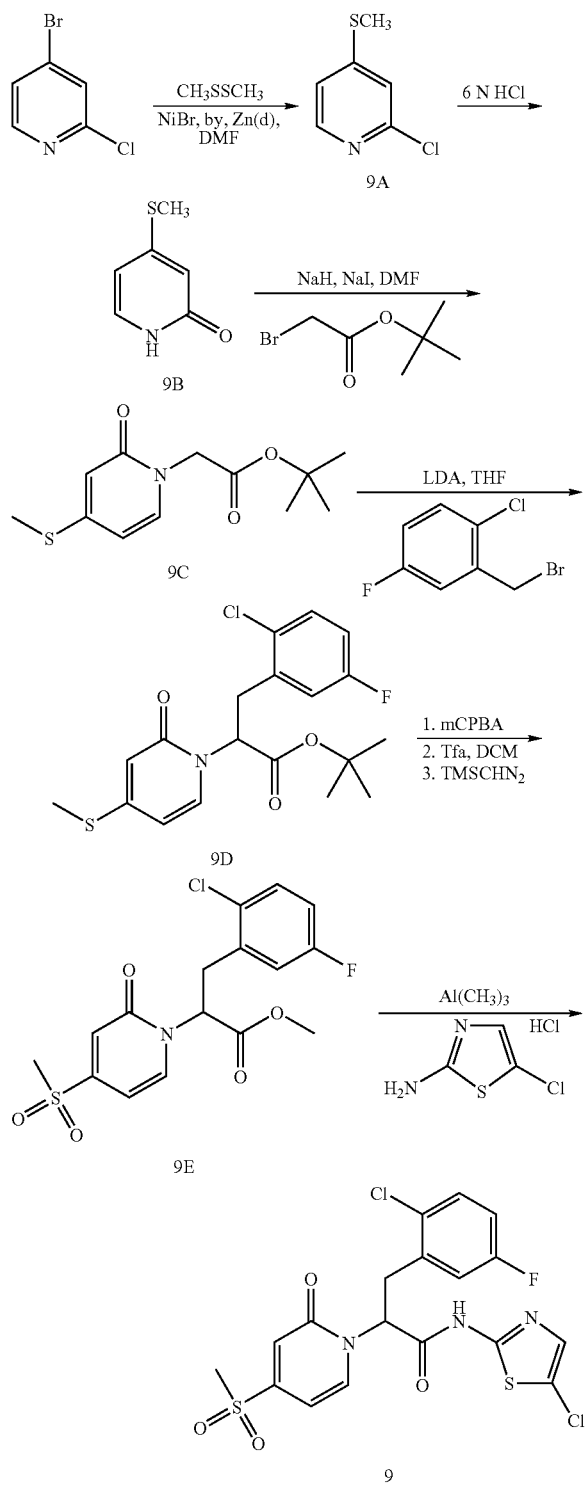

4-bromo-2-chloropyridine (5.0 g, 26 mmole), NiBr (0.567 g, 2.6 mmole), 2,2'-bipyridine (0.406 g, 2.6 mmole), Zinc dust (3.4 g, 52 mmole) and 1,2-dimethyldisulfane (1.2 g, 13 mmole) were added to a solution of DMF (25 mL) and the mixture was heated under $N_2$ for 18 h at 100° C. The solvent was removed from the crude reaction mixture under vacuum and the orange gum was treated with MeOH. The resulting ppt was filtered and discarded. The filtrate was purified with silica column chromatography using 5% MeOH in $CH_2Cl_2$; compound 9A was obtained as clear oil (1.1 g, 27% yield); [M+H] calc'd for $C_6H_7ClNS$, 159.99; found 160.1.

Compound 9A (2.0 g, 12.5 mmole) was added to a microwave vial with 6 N HCl (4 mL) and the mixture was heated at 200° C. for 1 h. The solvent was removed under vacuum and MeOH was added. The product 9B was isolated with preparative HPLC to afford a tan solid (0.75 g, 42% yield). $^1$H NMR (400 MHz, $CDCl_3$) δ 2.48 (s, 3 H) 6.36-6.43 (m, 2 H) 7.30 (d, J=7.33 Hz, 1 H); [M+H] calc'd for $C_6H_8NOS$, 142.02; found 142.1.

Compound 9B (0.228 g, 1.61 mmole) was dissolved in DMF (5 mL), the solution was chilled to 0° C. and NaH (0.043 g, 1.77 mmole) was added. When the reaction subsided, NaI (0.265 g, 1.77 mmole) was added along with tert-butyl 2-bromoacetate (0.345 g, 1.77 mmole) and the mixture was allowed to warm to RT over 3 h. Subsequently the solvent was removed under vacuum and the crude residue was subjected to column chromatography eluted with 1:1 EtOAc/Hexanes followed by 100% EtOAc to afford product 9C as a white solid (0.14 g, 34% yield). [M+H] calc'd for $C_{12}H_{18}NO_3S$, 256.09; found 256.1.

Compound 9C (0.140 g, 0.55 mmole) was dissolved in THF (10 mL) and cooled to −78° C. A solution of 1.8 M LDA (0.455 mL, 0.82 mmole) was added and the resultant orange soln. was stirred for 15 min. To this mixture 2-(bromomethyl)-1-chloro-4-fluorobenzene (0.184 g, 0.82 mmole) was added and the reaction was allowed to warm to RT overnight. The crude reaction mixture was partitioned between EtOAc and $H_2O$, the organic layer was dried over $Na_2SO_4$ and the solvent was removed under vacuum. The crude residue was subjected to column chromatography eluted with a Hexanes/EtOAc gradient to afford product 9D as a white solid (0.161 g, 74% yield). $[M^+-C_4H_9]$ calc'd for $C_{15}H_{14}ClFNO_3S$, 342.03; found 342.1.

Compound 9D (0.161 g, 0.41 mmole) was dissolved in $CH_2Cl_2$ (10 mL) the soln. was cooled to 0° C. and mCPBA (0.175 g, 1.01 mmole) was added. The cooling bath was removed after 20 min and the reaction mixture was stirred for an additional 2 h.

LC/MS indicated conversion to the desired sulfone; the reaction was washed with $NaHCO_3$ (saturated) and the organic layer was dried over $Na_2SO_4$. The crude residue was subjected to column chromatography affording the product (0.140 g) as an oil. This material was then treated with a 50% soln of TFA in $CH_2Cl_2$ (4 mL) for 15 min. The solvent was removed under vacuum, small amounts of MeOH were added and removed under vacuum to purge residual TFA (3×). MeOH was then added followed by trimethylsilyldiazomethane until a yellow color persisted. The reaction was quenched with AcOH and the solvent was removed under vacuum to afford crude 9E. [M+H] calc'd for $C_{16}H_{16}ClFNO_5S$, 388.03; found 388.0.

To 4 mL of chilled DCE (0° C.) was added 1M $(CH_3)_3Al$ (0.8 mL) and the mixture was stirred for 5 min. 5-chlorothiazol-2-amine hydrochloride (0.069 g, 0.40 mmole) was added and the reaction mixture was allowed to warm to RT over 40 min. A soln. of compound 9E (0.052 g, 0.134 mmole) in DCE (3 mL) was added and the reaction mixture was heated for 2 h at 110° C. The reaction was quenched with 1N HCl and extracted with $CH_2Cl_2$. The organics were dried over $Na_2SO_4$ and the solvent was removed under vacuum. Preparative HPLC of the crude residue afforded compound 9 as a tan solid (0.023 g, 35% yield). $^1$H NMR (400 MHz, MeOD) δ ppm 3.15 (s, 3 H) 3.49-3.67 (m, 1 H) 3.67-3.81 (m, 1 H) 5.86 (dd, J=9.35, 6.06 Hz, 1 H) 6.71 (dd, J=7.20, 1.89 Hz, 1 H) 6.94-7.10 (m, 3 H) 7.31 (s, 1 H) 7.39 (dd, J=8.72, 5.18 Hz, 1 H) 7.89 (d, J=7.33 Hz, 1 H); [M+H] calc'd for $C_{18}H_{15}C_{12}FN_3O_4S_2$, 489.98; found 489.8.

Method F

Compounds designated in Table 1 below as being prepared using Method F were prepared from Example 61 by a Suzuki coupling.

Method G

Compounds designated in Table 1 below as being prepared using Method G were prepared using a procedure analogous to that described in connection with Example 77.

Example 77

2-(3-chloro-4-(cyclopropylsulfonyl)-6-methyl-2-oxopyridin-1(2H)-yl)-N-(5-chlorothiazol-2-yl)-3-cyclohexylpropanamide

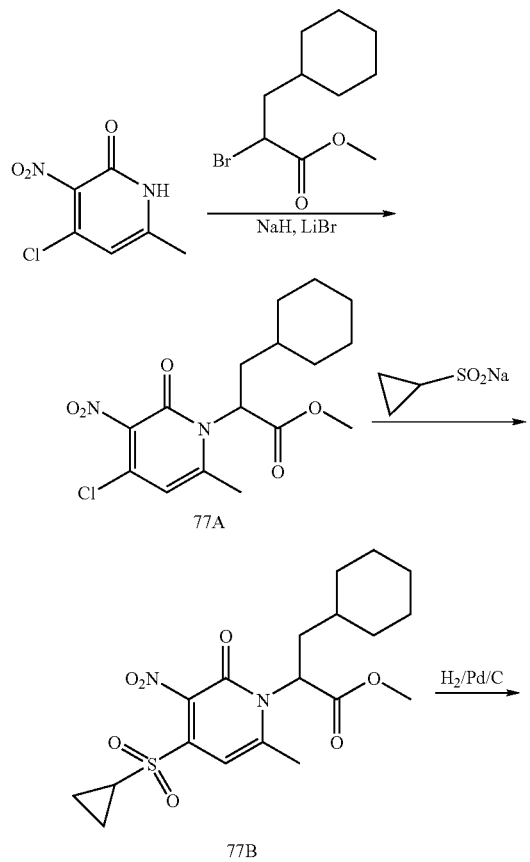

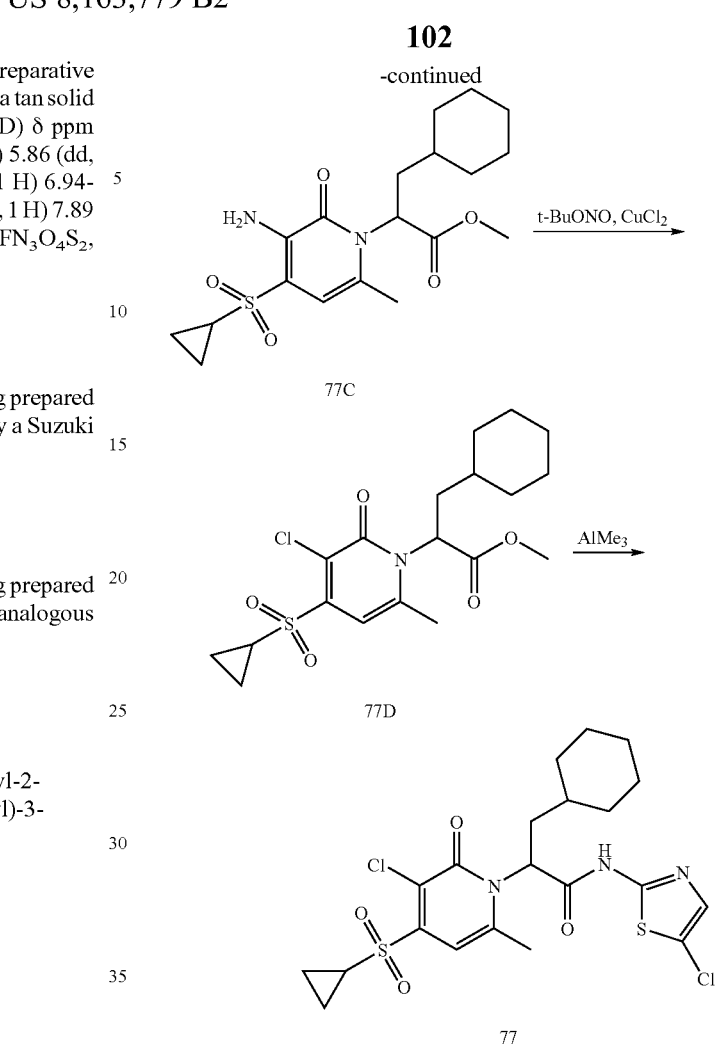

To 4-chloro-6-methyl-3-nitropyridin-2(1H)-one (1 g, 5.3 mmol) in 10 ml of DMF at 0° C. was added NaH (0.133 g, 5.56 mmol). After 10 minutes, LiBr (0.9 g, 10.6 mmol) was added and the reaction was allowed to stir at room temperature for 15 minutes followed by the addition of methyl 2-bromo-3-cyclohexylpropanoate in 3 ml of DMF. The reaction was heated at 65° C. overnight. The reaction mixture was extracted into ethyl acetate, and the organic layer was washed with water and brine, dried over $Na_2SO_4$, and concentrated in vacuo to yield an oil which was purified with silica chromatography using 75% EtOAc in hexanes to obtain compound 77A as an oil (1.32 g, 70% yield). [M+H] calc'd $C_{16}H_{21}ClN_2O_5$, 356.80; found, 356.9.

Compound 77A (0.38 g, 1.14 mmol) was dissolved in 5 ml of DMF and to this was added sodium cyclopropanesulfinate (0.13 g, 1.09 mmol). The reaction mixture was heated at overnight at 80° C. The reaction mixture was extracted into ethyl acetate, and the organic layer was washed with water and brine, dried over $Na_2SO_4$, and concentrated in vacuo to yield compound 77B as an oil in quantitative yield. [M+H] calc'd $C_{19}H_{26}N_2O_7S$, 427.48; found 427.6.

To compound 77B (0.44 g, 1.04 mmol) in 6 ml of EtOH was added a catalytic amount of Pd/C and the reaction mixture degassed and flushed with hydrogen gas. The reaction was stirred under hydrogen overnight. The Pd/C was filtered through celite and the filtrate was concentrated to obtain compound 77C as an oil in quantitative yield. [M+H] calc'd $C_{19}H_{28}N_2O_7S$, 429.48; found 429.6.

To t-butyl nitrite (0.160 g, 1.56 mmol) and cupric chloride (0.167 g, 1.24 mmol) in acetonitrile was added 77 C (0.41 g, 1.04 mmol) at room temperature and the solution was heated at 65° C. overnight. The reaction mixture was extracted into ethyl acetate, and the organic layer was washed with water and brine, dried over $Na_2SO_4$, and concentrated in vacuo to yield an oil which was purified with silica chromatography using 25% EtOAc in hexanes to obtain compound 77D as an oil (0.06 g, 14% yield). [M+H] calc'd $C_{19}H_{26}ClNO_5S$, 416.93; found, 417.0.

Compound 77 was obtained by treating compound 77D with 5-chloro-2-aminothiazole in the presence of $(CH_3)_3Al$ using the procedure described in connection with Example 9 (Method E)

Method H

Compounds designated in Table 1 below as being prepared using Method H were prepared using a procedure analogous to that described in connection with Example 79.

Example 79

3-cyclohexyl-2-(6-methyl-4-morpholino-2-oxopyridin-1(2H)-yl)-N-(thiazol-2-yl)propanamide

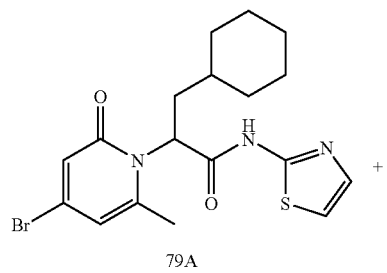

79A

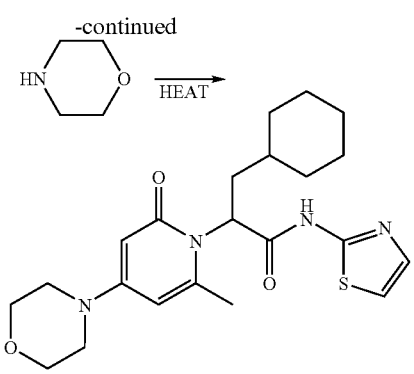

79

Compound 79A was synthesized using the procedure described in connection with Example 9 (Method C). Compound 79A (100 mg, 0.24 mmol) and morpholine (61.0 mg, 0.71 mmol) in DMF (3 ml) was heated at 140° C. overnight. The product was purified by HPLC to yield compound 79 86.7 mg. [M+H] calc'd for $C_{22}H_{30}N_4O_3S$ 431.57. $^1H$ NMR (400 MHz, MeOD). δ ppm 0.96 (m, 3H) 1.21 (m, 5H) 1.66 (m, 5H) 1.87 (m, 2H) 2.24 (m, 1H) 2.37 m, 4H), 3.76 (m, 5H) 5.58 (m, 1H) 6.16 (s, 1H) 6.64 (d, J=4 Hz, 1H) 7.02 (d, J=4 Hz, 1H).

Method I

Compounds designated in Table 1 below as being prepared using Method I were prepared using a procedure analogous to that described in connection with Example 137.

Example 137

N-(5-chlorothiazol-2-yl)-2-(4-(3-hydroxyprop-1-ynyl)-6-methyl-2-oxopyridin-1(2H)-yl)-3-(tetrahydro-2H-pyran-4-yl)propanamide

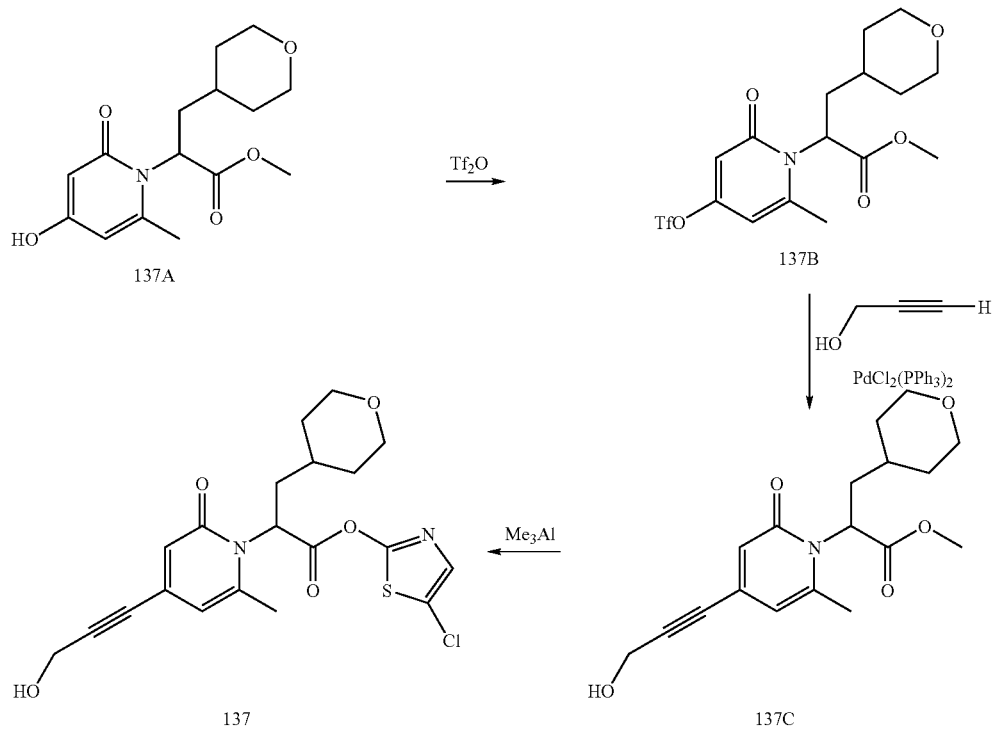

Compound 137A was synthesized using the procedure described in connection with Example 1 (Method A). Compound 137A (0.51 g, 1.75 mmol) was dissolved in methylene chloride (5 ml) and to this was added triethyl amine (0.365 ml, 2.625 mmol). The reaction mixture was cooled to 0° C. Tf₂O (0.353 ml, 2.10 mmol) was added slowly dropwise and the reaction mixture stirred for 1 h. Solvent removed in vacuo. The residue was dissolved in DMF (2 ml) and transferred to a microwave vail. Propargyl alcohol (0.173 ml, 1.93 mmol), PdCl₂(PPh₃)₂ (8.3 mg, 0.035 mmol), iPrNEt₃ (0.355 ml, 2.04 mmol) were added and the mixture heated in microwave at 100° C. for 15 min. The reaction mixture was diluted with ethyl acetate, filtered through celite and concentrated to yield compound 137B. [M+H] calc'd C18H24NO5, 334.16; found 334.21. The title compound (137) was synthesized using the procedure described in connection with Example 9 (Method E).

Method J

Compounds designated in Table 1 below as being prepared using Method J were prepared using a procedure analogous to that described in connection with Example 151.

Example 151

2-(4-(cyclopentylsulfonyl)-3,5,6-trimethy-2-oxopyridin-1(2H)-yl)-N-(5-fluorothiazol-2-yl)-3-(tetrahydro-2H-pyran-4-yl)propnamide

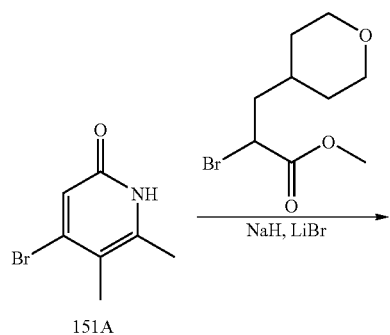

151A

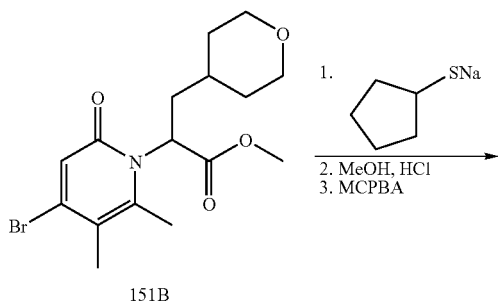

151B

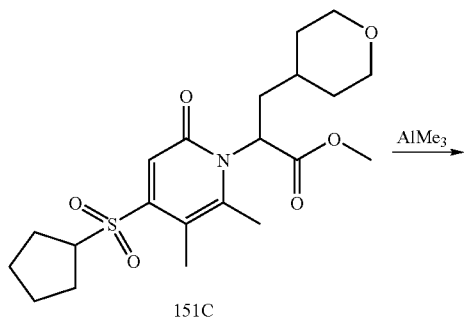

151C

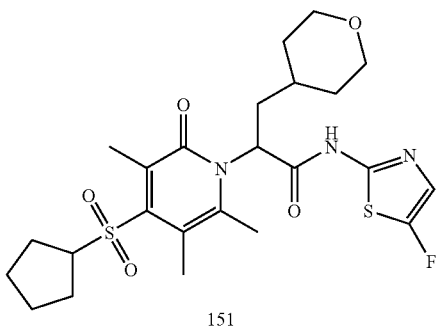

151

Compound 151A was synthesized as reported in *Tetrahedron* 62, 2006, 6945-6954. Compound 151B was synthesized using the procedure described in connection with Example 77 (Method G). Compound 151C was synthesized using the procedure described in connection with Example 3 (Method C) and the title compound (151) was synthesized using the procedure described in connection with Example 9 (Method E).

Method K

Compounds designated in Table 1 below as being prepared using Method K were prepared using a procedure analogous to that described in connection with Example 172.

Example 172

N-(5-chlorothiazol-2-yl)-2-(4-(cyclopropylsulfonyl)-6-methyl-2-oxopyridin-1(2H)-yl)-3-(tetrahydro-2H-pyran-4-yl)propanamide

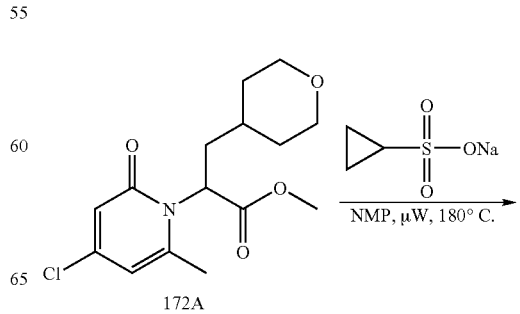

172A

107

-continued

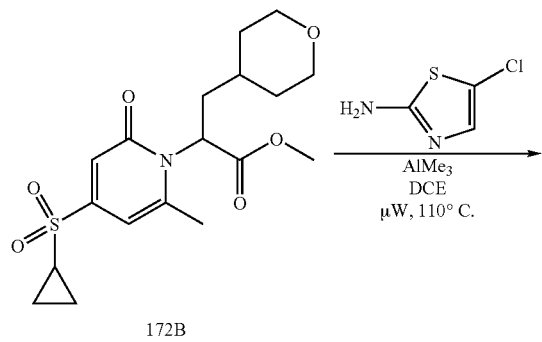

Compound 172A was synthesized using the procedure described in connection with Example 1 (Method A).

To the mixture of 172A (1.28 g, 4.08 mmol) and cyclopropylsulfinic acid sodium salt (1.08 g, 8.50 mmol) was added dry N-Methyl-2-pyrrolidone (NMP) (5.8 ml). The reaction was placed in microwave and heated for 45 minutes at 180° C. The reaction was cooled, diluted with EtOAc and filtered through celite. To the filtrate was added 1NHCl. And the layers were separated and the organic phase was washed with brine, dried over $Na_2SO_4$, and concentrated in vacuo to yield compound 172B.

To 5-chlorothiazol-2-amine hydrochloride (0.545 g, 3.19 mmole) in DCE (4 ml) was added 2M $(CH_3)_3Al$ (1.59 mL, 3.18 mmol) dropwise at 0° C. under $N_2$ for 15 minutes. Then the solution of compound 1B (0.204 g, 0.531 mmole) in 4 ml of DCE was added to the reaction mixture dropwise. After addition, the ice bath was removed, the reaction was stirred at room temperature for 0.5 hour, and then it was heated in a microwave at 110° C. for 1 hr. The reaction was quenched with 1N HCl and extracted with $CH_2Cl_2$. The organics were dried over $Na_2SO_4$ and the solvent was removed under vacuum. Preparative HPLC of the crude residue afforded compound 172. $^1$H NMR (400 MHz, CHLOROFORM-d) δ ppm 1.10-1.22 (m, 2H) 1.29-1.46 (m, 4H) 1.59-1.88 (m, 2 H) 2.36-2.61 (m, 4 H) 2.66 (d, J=3.79 Hz, 1 H) 3.40 (td, J=11.24, 5.81 Hz, 2 H) 3.97 (d, J=11.12 Hz, 5 H) 6.53 (br. s., 1 H) 6.95 (br. s., 1 H) 7.24 (s, 1 H).

108

Method L

Compounds designated in Table 1 below as being prepared using Method L were prepared using a procedure analogous to that described in connection with Example 174.

Example 174

N-(5-chlorothiazol-2-yl)-3-cyclohexyl-2-(6-methyl-2-oxo-4-(tetrahydro-2H-pyran-4-ylsulfonyl)pyridin-1(2H)-yl)propanamide

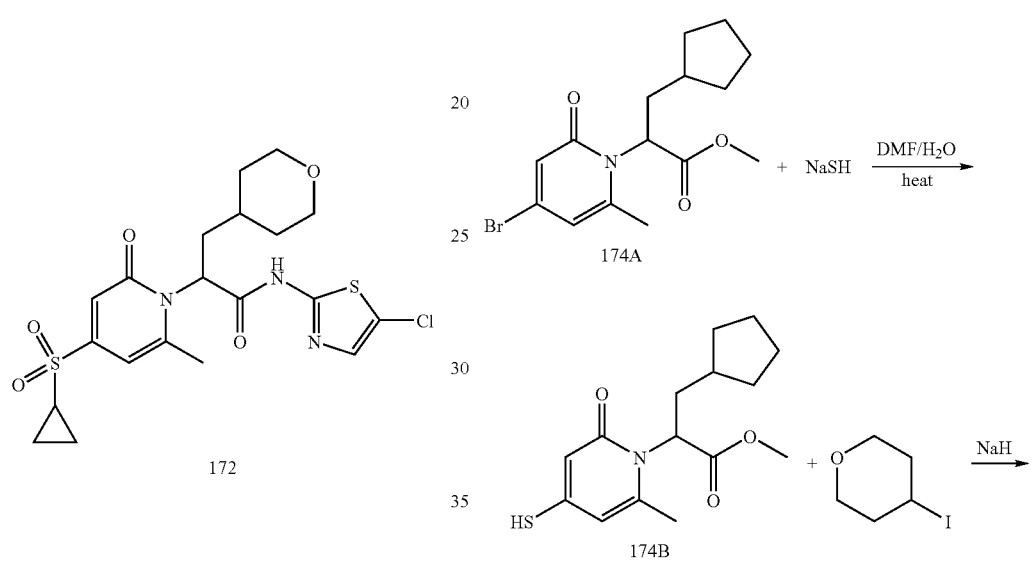

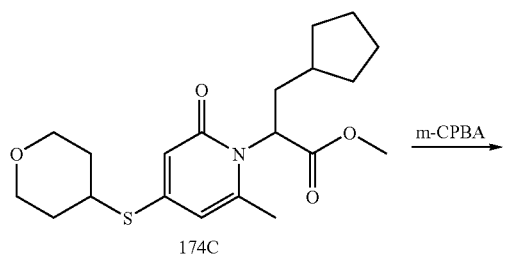

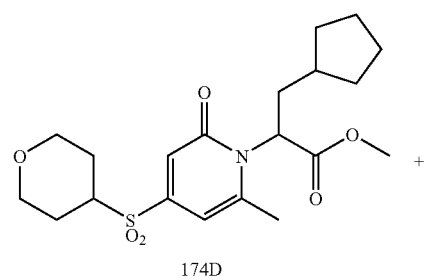

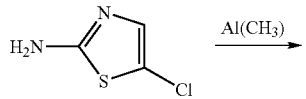

-continued

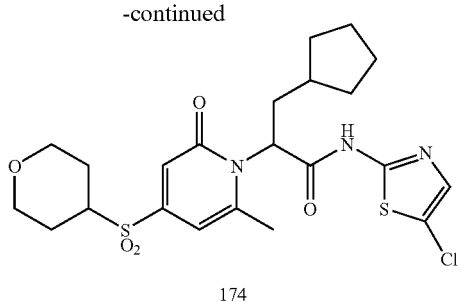

174

Compound 174A was synthesized using the procedure described in connection with compound 3. To a solution of compound 174A (1.315 g, 3.85 mmol) in DMF (14 ml) was added a solution of sodium sulfhydrate (323.0 mg, 5.77 mmol) in H$_2$O (3 ml). The reaction mixture was subjected to microwave heating at 100° C. for 30 minutes. The reaction solution was diluted with water and extracted with ethylacetate, dried over magnesium sulfate, concentrated under high vacuum to yield compound 174B 1.043 g. To a solution of compound 174B (500.0 mg, 1.69 mmol) in DMF (8 ml) was added sodium hydride at 0° C., followed by a solution of 4-iodotetrahydro-2H-pyran. The mixture was heated under nitrogen at 80° C. overnight. The reaction solution was diluted with water and extracted with ethylacetate, dried over magnesium sulfate, and concentrated under high vacuum to yield compound 174C (273 mg). Compound 174C was oxidized with m-chloroperoxybenzoic acid to yield compound 174D. Compound 174 was generated using the procedure described in connection with compound 9. [M+H] calc'd for C$_{22}$H$_{28}$ClN$_3$O$_5$S$_2$ 515.06; found 515. $^1$H NMR (400 MHz, MeOD). δ ppm 1.04 (m, 1H) 1.28 (m, 1H) 1.59 (m, 5H) 1.84 (m, 6H) 2.12 (m, 1H) 2.60 (m, 4H) 3.41 (m, 2H) 3.54 (m, 1H) 4.03 (m, 2H) 5.29 (m, 1H) 6.69 (s, 1H) 6.82 (s, 1H) 7.29 (s, 1H).

The above reaction schemes and variations thereof have been used to prepare the following compounds listed in Table 1.

TABLE 1

| Ex. | Structure | Method | LCMS ([M + H]) | NMR data |
|---|---|---|---|---|
| 1 | 3-cyclohexyl-2-(4-hydroxy-6-methyl-2-oxopyridin-1(2H)-yl)-N-(thiazol-2-yl)propanamide | A | calc'd for C$_{15}$H$_{21}$NO$_4$, 280.33; found, 280.3 | $^1$H NMR (400 MeOD) δ 0.8-1.93 (m, 13 H), 2.30 (m, 1H), 2.36 (s, 3 H), 5.67 (s, 1 H), 5.93 |
| 2 | 3-cyclohexyl-2-(4-methoxy-6-methyl-2-oxopyridin-1(2H)-yl)-N-(thiazol-2-yl)propanamide | B | calc'd for C$_{18}$H$_{23}$N$_3$O$_3$S, 376.49; found, 376.4. | $^1$H NMR (400 MHz, CDCl$_3$) δ 0.9-1.38 (m, 7 H), 1.58-1.82 (m, 5 H), 2.39 (s, 3 H), 2.46 (m, 1 H), 3.76 (s, 3 H), 5.81 (s, 1 H), 5.84 (s, 1 H), 6.97 (d, J = 4 Hz, 1 H), 7.42 (d, J = 4 Hz, 1 H). |
| 3 | 3-cyclohexyl-2-(6-methyl-4-(methylsulfonyl)-2-oxopyridin-1(2H)-yl)-N-(thiazol-2-yl)propanamide | C | calc'd for C$_{16}$H$_{22}$ClNO$_3$, 312.80 found, 312.8 | $^1$H NMR (400 MHz, CDCl$_3$) δ 0.8-1.7 (m, 13 H), 2.27 (s, 3 H), 2.35 (m, 1 H), 3.64 (s, 3 H), 6.03 (d, J = 4 Hz, 1 H), 6.40 (d, J = 4 Hz, 1 H). [M + H] |

TABLE 1-continued

| Ex. | Structure | Method | LCMS ([M + H]) | NMR data |
|---|---|---|---|---|
| 4 | 3-cyclohexyl-2-(4-(ethylsulfonyl)-6-methyl-2-oxopyridin-1(2H)-yl)-N-(thiazol-2-yl)propanamide | C | calc'd for $C_{20}H_{27}N_3O_4S_2$ 438.5; found, 438.5 | $^1$H NMR (400 MHz, CDCl$_3$) δ 0.95-1.30 (m, 5 H), 1.28 (t, J = 4 Hz, 3 H), 1.4-1.90 (m, 7 H), 2.59 (s, 3 H), 2.73 (m, 1 H), 3.10 (q, J = 4 Hz, 2 H), 4.8 (bs, H), 6.54 (d, J = 4 Hz, 1 H), 6.90 (d, J = 4 Hz, 1 H), 7.10 (d, J = 4 Hz, 1 H), 7.43 (d, J = 4 Hz, 1 H). |
| 5 | 3-cyclohexyl-2-(4-(cyclopentylsulfonyl)-6-methyl-2-oxopyridin-1(2H)-yl)-N-(thiazol-2-yl)propanamide | C | calc'd for $C_{23}H_{31}N_3O_4S_2$ 478.6; found, 478.6 | $^1$H NMR (400 MHz, CDCl$_3$) δ 0.90-1.35 (m, 5 H), 1.45-2.20 (m, 16 H), 2.58 (s, 3 H), 2.71 (m, 1 H), 3.45 (m, 1 H), 6.54 (d, J = 4 Hz, 1 H), 6.88 (d, J =4 Hz, 1 H), 7.10 (d, J = 4 Hz, 1 H), 7.41 (d, J = 4 Hz, 1 H). |
| 6 | 6-(3-cyclohexyl-2-(4-(cyclopentylsulfonyl)-6-methyl-2-oxopyridin-1(2H)-yl)propanamido)nicotinamide | C | calc'd for $C_{26}H_{34}N_4O_5S$ 515.6; found 514.6 | $^1$H NMR (400 MHz, CDCl$_3$) δ 0.90-1.4 (m, 5 H), 1.6-2.20 (m, 16 H), 2.48 (m, 1 H), 2.59 (s, 3 H), 3.57 (m, 1 H), 6.56 (bs, 1 H), 6.96 (bs, 1 H), 8.26 (bs, 2 H), 8.77 (bs, 1 H). |
| 7 | 2-(6-methyl-4-(methylsulfonyl)-2-oxopyridin-1(2H)-yl)-3-(tetrahydro-2H-pyran-4-yl)-N-(thiazol-2-yl)propanamide | C | calc'd for $C_{18}H_{23}N_3O_5S$ 426.5; found 426.5 | $^1$H NMR (400 MHz, CDCl$_3$) δ 1.3-1.9 (m, 7 H), 2.61 (s, 3 H), 2.87 (m, 1 H), 3.04 (s, 3 H), 3.45 (m, 2 H), 4.0 (m, 2 H), 4.89 (bs, 1 H), 6.61 (s, 1 H), 6.96 (s, 1 H), 7.14 (d, J = 4 Hz, 1 H), 7.47 (d, J = 4 Hz, 1 H). |

TABLE 1-continued

| Ex. | Structure | Method | LCMS ([M + H]) | NMR data |
|---|---|---|---|---|
| 8 | 3-cyclohexyl-2-(4-(cyclopentylsulfonyl)-2-oxopyridin-1(2H)-yl)-N-(thiazol-2-yl)propanamide | D | calc'd for $C_{22}H_{29}N_3O_4S_2$ 464.16; found 464.0 | $^1$H NMR (400 MHz, CDCl$_3$) δ 0.90-1.25 (m, 5 H), 1.59-2.18 (m, 16 H), 3.51 (m, 1 H), 6.18 (t, J = 8 Hz, 1 H), 6.96 (dd, J = 4, 8 Hz, 2 H), 7.04 (d, J = 4 Hz, 1 H), 7.59 (d, J = 3 Hz, 1 H), 7.62 (d, J = 4 Hz, 1 H), 7.95 (d, J = 8 Hz, 1 H) |
| 9 | 3-(2-chloro-5-fluorophenyl)-N-(5-chlorothiazol-2-yl)-2-(4-(methylsulfonyl)-2-oxopyridin-1(2H)-yl)propanamide | E | calc'd for $C_{18}H_{15}C_{12}FN_3O_4S_2$, 489.98; found 489.8. | $^1$H NMR (400 MHz, MeOD) δ ppm 3.15 (s, 3 H) 3.49-3.67 (m, 1 H) 3.67-3.81 (m, 1 H) 5.86 (dd, J = 9.35, 6.06 Hz, 1 H) 6.71 (dd, J = 7.20, 1.89 Hz, 1 H) 6.94-7.10 (m, 3 H) 7.31 (s, 1 H) 7.39 (dd, J = 8.72, 5.18 Hz, 1 H) 7.89 (d, J = 7.33 Hz, 1 H) |
| 10 | 2-(4-(cyclopentylsulfonyl)-6-methyl-2-oxopyridin-1(2H)-yl)-N-(thiazol-2-yl)-3-p-tolylpropanamide | C | calc'd for $C_{24}H_{27}N_3O_4S_2$ 486.14; found 486.02 | $^1$H NMR (400 MHz, CDCl$_3$) δ 1.62-2.09 (m, 11 H), 2.30 (s, 3 H), 3.45 (m, 1 H), 3.62 (m, 1 H), 3.74 (m, 1 H), 5.0 (bs, 1 H), 6.24 (s, 1 H), 6.92 (d, J = 8 Hz, 2 H), 6.97 (s, 1 H), 7.02 (m, 3 H), 7.41 (d, J = 3 Hz, 1 H) |
| 11 | 2-(4-(cyclopentylsulfonyl)-6-methyl-2-oxopyridin-1(2H)-yl)-4-methyl-N-(thiazol-2-yl)pentanamide | C | calc'd for $C_{20}H_{27}N_3O_4S_2$ 438.14; found 437.98 | $^1$H NMR (400 MHz, CDCl$_3$) δ 0.97 (d, J = 4 Hz, 3 H), 1.01 (d, J = 4 Hz, 3 H), 1.59-2.16 (m, 10 H), 2.52 (m, 1H), 2.58 (s, 3H), 3.48 (m, 1 H), 4.89 (bs, 1H), 6.52 (s, 1 H), 6.94 (s, 1 H), 7.06 (s, 1 H), 7.44 (s, 1 H). |

TABLE 1-continued

| Ex. | Structure | Method | LCMS ([M + H]) | NMR data |
|---|---|---|---|---|
| 12 | 2-(4-(cyclopentylsulfonyl)-6-methyl-2-oxopyridin-1(2H)-yl)-3-cyclopropyl-N-(thiazol-2-yl)propanamide | C | calc'd for $C_{20}H_{25}N_3O_4S_2$ 436.13; found 436.0 | $^1$H NMR (400 MHz, MeOD) δ 0.18 (m, 1 H), 0.39 (m, 1 H), 0.71 (m, 2 H), 0.82 (m, 1 H), 1.90 (m, 2 H), 2.04 (m, 2 H), 2.22 (m, 4 H), 2.42 (m, 1 H), 2.56 (m, 1 H), 2.89 (s, 3H), 3.81 (q, J = 8 Hz, 1 H), 5.41 (bs, 1H), 6.83 (s, 1 H), 7.10 (s, 1 H), 7.39 (s, 1 H), 7.71 (s, 1 H) |
| 13 | (S)-3-cyclohexyl-2-(4-(cyclopentylsulfonyl)-2-oxopyridin-1(2H)-yl)-N-(thiazol-2-yl)propanamide | C | calc'd for $C_{22}H_{29}N_3O_4S_2$ 464.16; found 464.10 | |
| 14 | 3-cyclopentyl-2-(4-(cyclopentylsulfonyl)-6-methyl-2-oxopyridin-1(2H)-yl)-N-(thiazol-2-yl)propanamide | C | calc'd for $C_{22}H_{29}N_3O_4S_2$ 464.16; found 464.10 | $^1$H NMR (400 MHz, CDCl$_3$) δ 1.06-1.26 (m, 2 H), 1.47-2.15 (m, 16 H), 2.53 (m, 1 H), 2.57 (s, 3 H), 3.48 (q, J = 8 Hz, 1 H), 4.90 (bs, 1 H), 6.51 (s, 1 H), 6.96 (s, 1 H), 7.03 (d, J = 4 Hz, 1 H), 7.44 (d, J = 4 Hz, 1 H) |
| 15 | N-(5-chlorothiazol-2-yl)-2-(4-(methylsulfonyl)-2-oxopyridin-1(2H)-yl)-3-(thiophen-3-yl)propanamide | E | calc'd for $C_{16}H_{15}ClN_3O_4S_3$ 443.98; found 443.8 | $^1$H NMR (400 MHz, MeOD) δ ppm 3.13 (s, 3 H) 3.48 (d, J = 9.85 Hz, 2 H) 6.00 (dd, J = 10.23, 5.94 Hz, 1 H) 6.71 (dd, J = 7.45, 1.89 Hz, 1 H) 6.95 (dd, J = 5.05, 1.01 Hz, 1 H) 6.99 (d, J = 2.02 Hz, 1 H) 7.10 (s, 1 H) 7.29 (d, J = 7.83 Hz, 1 H) 7.29 (s, 1 H) 7.76 (s, 1 H) 8.01 (d, J = 7.58 Hz, 1 H) |

TABLE 1-continued

| Ex. | Structure | Method | LCMS ([M + H]) | NMR data |
|---|---|---|---|---|
| 16 | 2-(4-(cyclopentylsulfonyl)-6-methyl-2-oxopyridin-1(2H)-yl)-3-(tetrahydro-2H-pyran-4-yl)-N-(thiazol-2-yl)propanamide | C | calc'd for $C_{22}H_{29}N_3O_5S_2$ 480.15; found 480.10 | $^1$H NMR (400 MHz, CDCl$_3$) δ 1.30-1.45 (m, 3 H), 1.6-2.15 (m, 12 H), 2.50 (s, 3 H), 2.65 (m, 1 H), 3.25 (bs, 2 H), 3.38 (m, 2 H), 3.55 (m, 1 H), 3.96 (m, 2 H), 6.51 (s, 1 H), 6.98 (s, 1 H), 7.02 (s, 1 H), 7.41 (s, 1H) |
| 17 | N-(5-chlorothiazol-2-yl)-3-(2,6-dichlorophenyl)-2-(4-(methylsulfonyl)-2-oxopyridin-1(2H)-yl)propanamide | E | calc'd for $C_{18}H_{15}Cl_3N_3O_4S_2$ 505.95; found 506.0 | $^1$H NMR (400 MHz, CDCl$_3$) δ ppm 3.06 (s, 3 H) 3.72 (dd, 1 H) 3.89 (dd, J = 14.15, 6.32 Hz, 1 H) 5.85 (br. s., 1 H) 6.64 (dd, J = 7.07, 1.77 Hz, 1 H) 7.11-7.21 (m, 3 H) 7.25 (s, 2 H) 7.73 (br. s., 1 H) |
| 18 | 2-(4-(cyclopentylsulfonyl)-6-methyl-2-oxopyridin-1(2H)-yl)-N-(thiazol-2-yl)hexanamide | C | calc'd for $C_{20}H_{27}N_3O_4S_2$ 438.14; found 438.10 | $^1$H NMR (400 MHz, CDCl$_3$) δ 0.91' (t, J = 8 Hz, 3 H), 1.09-2.16 (m, 14 H), 2.44 (m, 1H), 2.55 (s, 3H), 3.48 (m, 1 H), 4.89 (bs, 1H), 6.51 (s, 1 H), 6.95 (s, 1 H), 7.04 (d, J = 4 Hz, 1 H), 7.44 (s, 1 H). |
| 19 | 2-(4-(cyclopentylsulfonyl)-6-methyl-2-oxopyridin-1(2H)-yl)-5-methyl-N-(thiazol-2-yl)hexanamide | C | calc'd for $C_{21}H_{29}N_3O_4S_2$ 452.16; found 452.10 | $^1$H NMR (400 MHz, CDCl$_3$) δ 0.90 (d, J = 8 Hz, 3 H), 0.93 (d, J = 8 Hz, 3 H), 1.26-2.36 (m, 13 H), 2.48 (m, 1H), 2.55 (s, 3H), 3.55 (m, 1 H), 4.89 (bs, 1H), 6.54 (s, 1 H), 6.95 (s, 1 H), 7.08 (s, 1 H), 7.47 (s, 1 H). |

TABLE 1-continued

| Ex. | Structure | Method | LCMS ([M + H]) | NMR data |
|---|---|---|---|---|
| 20 | 2-(4-(cyclopentylsulfonyl)-6-methyl-2-oxopyridin-1(2H)-yl)-3-(3-methoxyphenyl)-N-(thiazol-2-yl)propanamide | C | calc'd for $C_{24}H_{27}N_3O_5S_2$, 502; found, 502 | $^1$H NMR (400 MHz, CHLOROFORM-d) δ ppm 1.60 (s, 3 H) 1.77-1.87 (m, 2 H) 1.87-1.98 (m, 2 H) 1.98-2.11 (m, 4H) 3.40-3.50 (m, 1 H) 3.55-3.64 (m, 1 H) 3.71 (s, 3 H) 3.76-3.91 (m, 1 H) 4.93-5.06 (m, 1 H) 6.26 (br. s., 1 H) 6.55 (br. s., 1 H) 6.65 (d, J = 7.58 Hz, 1 H) 6.77 (dd, J = 8.21, 2.65 Hz, 1 H) 7.01 (d, J = 2.78 Hz, 2 H) 7.16 (t, J = 7.96 Hz, 1 H) 7.44 (d, J = 3.54 Hz, 1 H) |
| 21 | 2-(4-(cyclopentylsulfonyl)-6-methyl-2-oxopyridin-1(2H)-yl)-3-(furan-2-yl)-N-(thiazol-2-yl)propanamide | C | calc'd for $C_{21}H_{23}N_3O_5S_2$ 462.11; found 462.0 | $^1$H NMR (400 MHz, CDCl$_3$) δ 1.59-2.11 (m, 9 H), 2.16 (s, 3H), 3.45 (m, 1 H), 3.76 (m, 2H), 5.10 (bs, 1 H), 6.00 (d, J = 4 Hz, 1 H), 6.26 (m, 1 H), 6.36 (s, 1 H), 6.94 (s, 2 H), 7.06 (d, J = 4 Hz, 1 H), 7.31 (s, 1 H), 7.41 (d, J = 4 Hz, 1 H) |
| 22 | (R)-N-(5-chlorothiazol-2-yl)-2-(4-(methylsulfonyl)-2-oxopyridin-1(2H)-yl)-3-(tetrahydro-2H-pyran-4-yl)propanamide | E | calc'd for $C_{17}H_{21}ClN_3O_5S_2$ 446.05; found 446.12 | $^1$H NMR (400 MHz, CDCl$_3$) δ ppm 1.39 (br. s., 1 H) 1.42 (d, J = 3.54 Hz, 2 H) 1.63 (d, J = 12.13 Hz, 1 H) 1.71 (br. s., 1 H) 1.86-2.09 (m, 1 H) 2.13-2.36 (m, 1 H) 3.10 (s, 3 H) 3.21-3.44 (m, 2 H) 3.97 (d, J = 11.62 Hz, 2 H) 5.93 (dd, J = 8.84, 6.32 Hz, 1 H) 6.75 (dd, J = 7.20, 1.89 Hz, 1 H) 7.34 (s, 1 H) 7.40 (d, J = 2.02 Hz, 1 H) 7.76 (d, J = 7.33 Hz, 1 H) |
| 23 | (S)-N-(5-chlorothiazol-2-yl)-2-(4-(methylsulfonyl)-2-oxopyridin-1(2H)-yl)-3- | E | calc'd for $C_{17}H_{21}ClN_3O_5S_2$ 446.05; found 446.12 | |

TABLE 1-continued

| Ex. | Structure | Method | LCMS ([M + H]) | NMR data |
|---|---|---|---|---|
| | (tetrahydro-2H-pyran-4-yl)propanamide | | | |
| 24 | 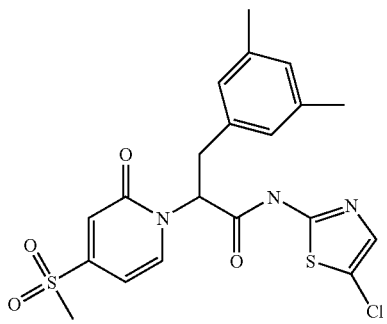<br>N-(5-chlorothiazol-2-yl)-3-(3,5-dimethylphenyl)-2-(4-(methylsulfonyl)-2-oxopyridin-1(2H)-yl)propanamide | E | calc'd for $C_{20}H_{21}ClN_3O_4S_2$ 466.06; found 466.1 | $^1$H NMR (400 MHz, CDCl$_3$) δ ppm 2.21 (s, 6 H) 3.04 (s, 3 H) 3.18-3.35 (m, 2 H) 3.44-3.62 (m, 1 H) 5.48 (br. s., 1 H) 6.57 (d, J = 6.82 Hz, 1 H) 6.71 (s, 2 H) 6.86 (s, 1 H) 7.18 (s, 1 H) 7.48 (d, J = 7.83 Hz, 1 H) |
| 25 | 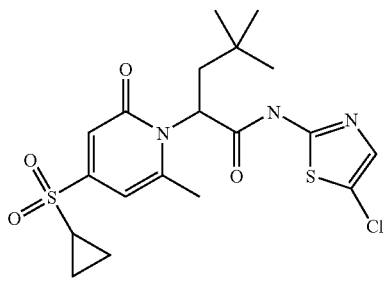<br>N-(5-chlorothiazol-2-yl)-2-(4-(cyclopropylsulfonyl)-6-methyl-2-oxopyridin-1(2H)-yl)-4,4-dimethylpentanamide | C | calc'd for $C_{19}H_{25}ClN_3O_4S_2$ 458.09; found 458.0 | $^1$H NMR (400 MHz, CDCl$_3$) δ ppm 0.96 (s, 9 H) 1.08-1.19 (m, 2 H) 1.22-1.29 (m, 2H) 1.36-1.41 (m, 1 H) 2.42-2.52 (m, 1 H) 2.64 (s, 3 H) 2.73-2.83 (m, 1 H) 4.88 (br. s., 1 H) 6.54 (br. s., 1 H) 6.93 (br. s., 1 H) 7.28 (br. s., 2 H) |
| 26 | 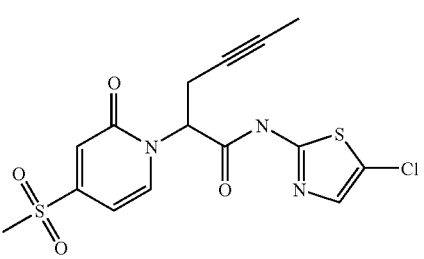<br>N-(5-chlorothiazol-2-yl)-2-(4-(methylsulfonyl)-2-oxopyridin-1(2H)-yl)hex-4-ynamide | E | calc'd for $C_{15}H_{15}ClN_3O_4S_2$ 400.01; found 400.1 | $^1$H NMR (400 MHz, CDCl$_3$) δ ppm 1.16-1.36 (m, 1 H) 1.26 (s, 0 H) 1.72 (s, 3 H) 2.05 (s, 0 H) 2.89-3.06 (m, 2H) 3.09 (s, 3H) 6.05 (t, J = 7.58 Hz, 1 H) 6.74 (d, J = 7.33 Hz, 1 H) 7.39 (s, 1 H) 7.53 (s, 1 H) 7.93 (d, J = 7.33 Hz, 1 H) |
| 27 | 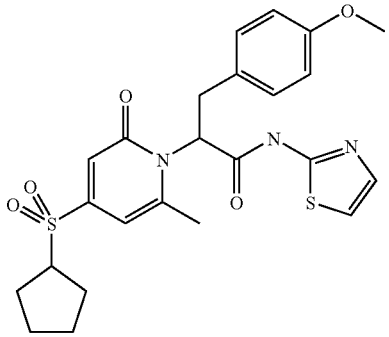<br>2-(4-(cyclopentylsulfonyl)-6-methyl-2-oxopyridin-1(2H)-yl)-3-(4-methoxyphenyl)-N-(thiazol-2-yl)propanamide | C | calc'd for $C_{24}H_{27}N_3O_5S_2$, 502; found, 502 | $^1$H NMR (400 MHz, DMSO-d$_6$) δ ppm 1.54-1.73 (m, 4 H) 1.76-1.87 (m, 4 H) 1.89 (s, 3 H) 3.26-3.35 (m, 1 H) 3.44-3.54 (m, 1 H) 3.67 (s, 3 H) 3.79-3.91 (m, 1 H) 5.30-5.40 (m, 1 H) 6.34 (d, J = 1.77 Hz, 1 H) 6.68 (s, 1 H) 6.73 (d, J = 8.34 Hz, 2 H) 6.91 (d, J = 8.34 Hz, 2 H) 7.21 (d, J = 3.54 Hz, 1 H) 7.44 (d, J = 3.54 Hz, 1 H) |

TABLE 1-continued

| Ex. | Structure | Method | LCMS ([M + H]) | NMR data |
|---|---|---|---|---|
| 28 | 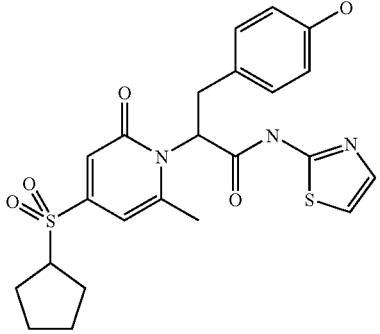<br>2-(4-(cyclopentylsulfonyl)-6-methyl-2-oxopyridin-1(2H)-yl)-3-(4-hydroxyphenyl)-N-(thiazol-2-yl)propanamide | C | calc'd for $C_{23}H_{25}N_3O_5S_2$, 488; found, 488 | $^1$H NMR (400 MHz, MeOD) δ ppm 1.64-1.86 (m, 4 H) 1.87-1.99 (m, 4 H) 2.01 (s, 3 H) 3.45-3.54 (m, 1 H) 3.55-3.64 (m, 1 H) 3.69-3.81 (m, 1 H) 5.42 (dd, J = 10.48, 3.92 Hz, 1 H) 6.48 (d, J = 1.26 Hz, 1 H) 6.60-6.66 (m, 2 H) 6.81-6.87 (m, 2 H) 6.91 (d, J = 1.77 Hz, 1 H) 7.39 (d, J = 4.04 Hz, 1 H) 7.60 (d, J = 4.04 Hz, 1 H) |
| 29 | 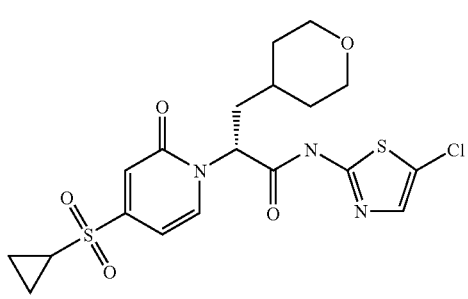<br>(R)-N-(5-chlorothiazol-2-yl)-2-(4-(cyclopropylsulfonyl)-2-oxopyridin-1(2H)-yl)-3-(tetrahydro-2H-pyran-4-yl)propanamide | C | calc'd for $C_{19}H_{23}ClN_3O_5S_2$, 472.07; found 472.1 | $^1$H NMR (400 MHz, MeOD) δ ppm 1.14-1.20 (m, 2 H) 1.22-1.42 (m, 7 H) 1.60 (d, J = 1.77 Hz, 1 H) 1.69 (d, J = 9.60 Hz, 1 H) 1.99-2.24 (m, 2 H) 2.67-2.86 (m, 1 H) 3.87 (br. s., 2 H) 5.94 (dd, J = 10.61, 5.31 Hz, 1 H) 6.80 (dd, J = 7.33, 2.02 Hz, 1 H) 7.00 (d, J = 2.02 Hz, 1 H) 7.33 (s, 1 H) 8.08 (d, J = 7.33 Hz, 1 H) |
| 30 | 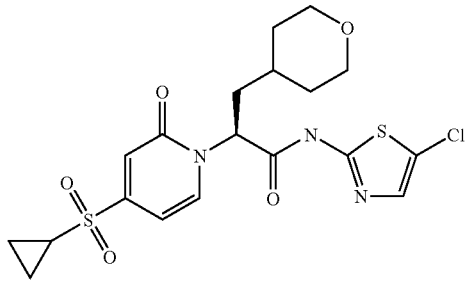<br>(S)-N-(5-chlorothiazol-2-yl)-2-(4-(cyclopropylsulfonyl)-2-oxopyridin-1(2H)-yl)-3-(tetrahydro-2H-pyran-4-yl)propanamide | E | calc'd for $C_{19}H_{23}ClN_3O_5S_2$ 472.07; found 472.1 | |
| 31 | 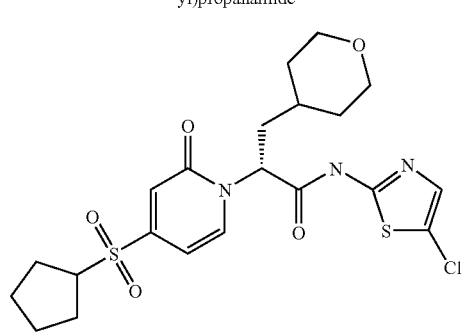<br>(R)-N-(5-chlorothiazol-2-yl)-2-(4-(cyclopentylsulfonyl)-2-oxopyridin-1(2H)-yl)-3-(tetrahydro-2H-pyran-4-yl)propanamide | D | calc'd for $C_{21}H_{26}ClN_3O_5S_2$ 500.10; found 500.00 | $^1$H NMR (400 MHz, CDCl$_3$) δ 1.30-2.24 (m, 15 H), 3.33 (m, 2 H), 3.50 (m, 1 H), 3.92 (m, 2 H), 6.35 (t, J = 8 Hz, 1 H), 6.74 (dd, J = 4, 8 Hz, 1 H), 7.99 (d, J = 4 Hz, 1 H), 8.04 (d, J = 8 Hz, 1 H) |

TABLE 1-continued

| Ex. | Structure | Method | LCMS ([M + H]) | NMR data |
|---|---|---|---|---|
| 32 | 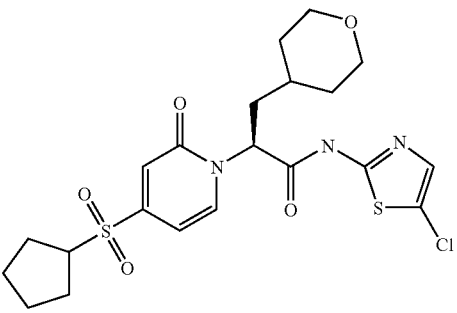 (S)-N-(5-chlorothiazol-2-yl)-2-(4-(cyclopentylsulfonyl)-2-oxopyridin-1(2H)-yl)-3-(tetrahydro-2H-pyran-4-yl)propanamide | D | calc'd for $C_{21}H_{26}ClN_3O_5S_2$ 500.10; found 500.00 | |
| 33 | 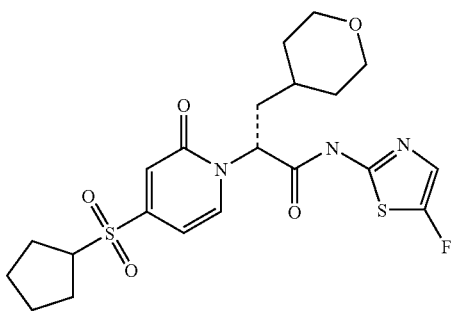 (R)-2-(4-(cyclopentylsulfonyl)-2-oxopyridin-1(2H)-yl)-N-(5-fluorothiazol-2-yl)-3-(tetrahydro-2H-pyran-4-yl)propanamide | D | calc'd for $C_{21}H_{26}FN_3O_5S_2$ 484.58; found 484.50 | $^1$H NMR (400 MHz, CDCl$_3$) δ 1.20-2.24 (m, 15 H), 3.34 (m, 2 H), 3.50 (m, 1 H), 3.92 (m, 2 H), 6.29 (t, J = 8 Hz, 1 H), 6.74 (dd, J = 4, 8 Hz, 1 H), 7.90 (d, J = 4 Hz, 1 H), 8.02 (d, J = 8 Hz, 1 H) |
| 34 | 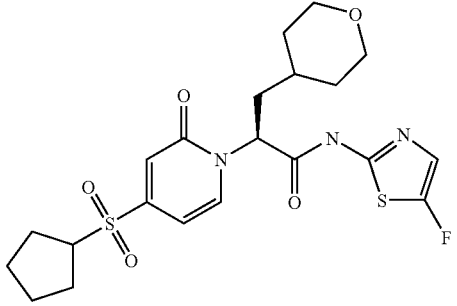 (S)-2-(4-(cyclopentylsulfonyl)-2-oxopyridin-1(2H)-yl)-N-(5-fluorothiazol-2-yl)-3-(tetrahydro-2H-pyran-4-yl)propanamide | D | calc'd for $C_{21}H_{26}FN_3O_5S_2$ 484.58; found 484.5 | |

TABLE 1-continued

| Ex. | Structure | Method | LCMS ([M + H]) | NMR data |
|---|---|---|---|---|
| 35 | 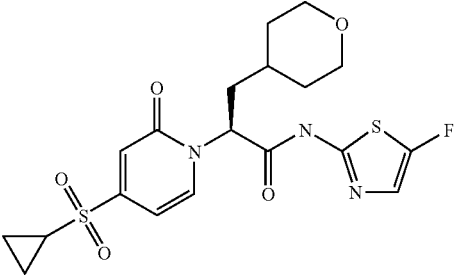<br>(S)-2-(4-(cyclopropylsulfonyl)-2-oxopyridin-1(2H)-yl)-N-(5-fluorothiazol-2-yl)-3-(tetrahydro-2H-pyran-4-yl)propanamide | E | calc'd for $C_{19}H_{23}FN_3O_5S_2$ 456.10; found 456.1 | $^1$H NMR (400 MHz, CHLOROFORM-d) δ ppm 1.04-1.54 (m, 8 H) 1.59-1.82 (m, 2 H) 2.01 (s, 1 H) 2.22 (d, J = 7.07 Hz, 1 H) 2.50 (dd, J = 12.51, 3.16 Hz, 1 H) 3.22-3.44 (m, 2 H) 3.84-4.07 (m, 2 H) 6.08 (t, J = 7.71 Hz, 1 H) 6.74 (dd, J = 7.20, 1.64 Hz, 1 H) 7.12 (br. s., 1 H) 7.53 (s, 1 H) 7.85 (d, J = 7.33 Hz, 1 H) |
| 36 | 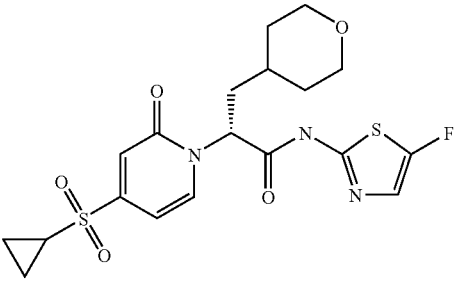<br>(R)-2-(4-(cyclopropylsulfonyl)-2-oxopyridin-1(2H)-yl)-N-(5-fluorothiazol-2-yl)-3-(tetrahydro-2H-pyran-4-yl)propanamide | E | calc'd for $C_{19}H_{23}FN_3O_5S_2$ 456.10; found 456.1 | |
| 37 | 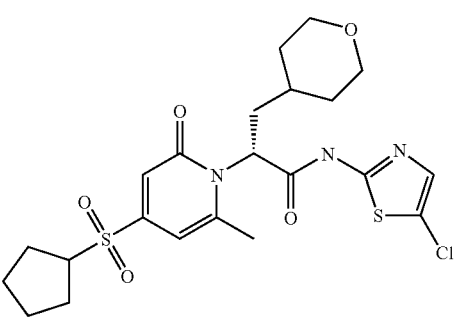<br>(R)-N-(5-chlorothiazol-2-yl)-2-(4-(cyclopentylsulfonyl)-6-methyl-2-oxopyridin-1(2H)-yl)-3-(tetrahydro-2H-pyran-4-yl)propanamide | D | calc'd for $C_{22}H_{28}ClN_3O_5S_2$ 514.12; found 514.10 | |

TABLE 1-continued

| Ex. | Structure | Method | LCMS ([M + H]) | NMR data |
|---|---|---|---|---|
| 38 | (S)-N-(5-chlorothiazol-2-yl)-2-(4-(cyclopentylsulfonyl)-6-methyl-2-oxopyridin-1(2H)-yl)-3-(tetrahydro-2H-pyran-4-yl)propanamide | D | calc'd for $C_{22}H_{28}ClN_3O_5S_2$ 514.12; found 514.10 | |
| 39 | (R)-2-(4-(cyclopentylsulfonyl)-6-methyl-2-oxopyridin-1(2H)-yl)-N-(5-fluorothiazol-2-yl)-3-(tetrahydro-2H-pyran-4-yl)propanamide | D | calc'd for $C_{22}H_{28}FN_3O_5S_2$ 498.15; found 498.1 | $^1$H NMR (400 MHz, CDCl$_3$) δ 1.30-2.24 (m, 14 H), 2.53 (s, 3 H), 2.57 (m, 1 H), 3.35 (m, 2 H), 3.49 (m, 1 H), 3.94 (m, 2 H), 4.92 (bs, 1 H), 6.50 (s, 1 H), 7.0 (s, 1 H), 7.02 (d, J = 4 Hz, 1 H) |
| 40 | (S)-2-(4-(cyclopentylsulfonyl)-6-methyl-2-oxopyridin-1(2H)-yl)-N-(5-fluorothiazol-2-yl)-3-(tetrahydro-2H-pyran-4-yl)propanamide | D | calc'd for $C_{22}H_{28}FN_3O_5S_2$ 498.15; found 498.1 | |

TABLE 1-continued

| Ex. | Structure | Method | LCMS ([M + H]) | NMR data |
|---|---|---|---|---|
| 41 | (R)-N-(5-chloropyridin-2-yl)-2-(4-(cyclopentylsulfonyl)-2-oxopyridin-1(2H)-yl)-3-(tetrahydro-2H-pyran-4-yl)propanamide | D | calc'd for $C_{23}H_{28}ClN_3O_5S$ 494.14; found 494.10 | $^1$H NMR (400 MHz, CDCl$_3$) δ 1.18-2.20 (m, 15 H), 3.36 (m, 2 H), 3.57 (m, 1 H), 3.95 (m, 2 H), 5.99 (t, J = 4 Hz, 1 H), 6.71 (d, J = 8 Hz, 1 H), 7.68 (d, J = 8 Hz, 1 H), 7.97 (d, J = 8 Hz, 1 H), 8.09 (d, J = 8 Hz, 1 H), 8.28 (s, 1 H) |
| 42 | (S)-N-(5-chloropyridin-2-yl)-2-(4-(cyclopentylsulfonyl)-2-oxopyridin-1(2H)-yl)-3-(tetrahydro-2H-pyran-4-yl)propanamide | D | calc'd for $C_{23}H_{28}ClN_3O_5S$ 494.14; found 494.10 | |
| 43 | N-(5-fluorothiazol-2-yl)-4,4-dimethyl-2-(6-methyl-2-oxo-4-tosylpyridin-1(2H)-yl)pentanamide | C | calc'd for $C_{23}H_{27}FN_3O_4S_2$ 492.13; found 492.2 | $^1$H NMR (400 MHz, CDCl$_3$) δ ppm 0.93 (s, 9 H) 2.44 (s, 3 H) 2.57 (br. s., 3H) 2.79 (d, J = 15.41 Hz, 2 H) 4.77 (br. s., 1 H) 6.50 (br. s., 1 H) 6.89 (br. s., 1 H) 7.02 (d, J = 2.02 Hz, 1 H) 7.35 (m, J = 8.34 Hz, 2 H) 7.81 (m, J = 8.08 Hz, 2 H) |

TABLE 1-continued

| Ex. | Structure | Method | LCMS ([M + H]) | NMR data |
|---|---|---|---|---|
| 44 | 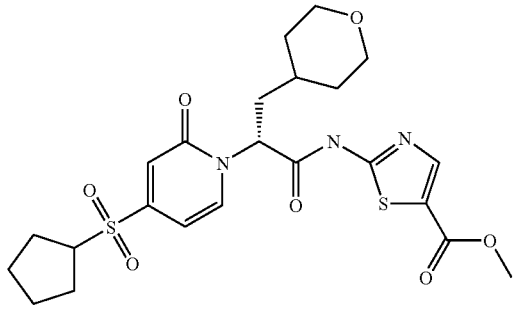<br>(R)-methyl 2-(2-(4-(cyclopentylsulfonyl)-2-oxopyridin-1(2H)-yl)-3-(tetrahydro-2H-pyran-4-yl)propanamido)thiazole-5-carboxylate | C | calc'd for $C_{23}H_{29}N_3O_7S_2$ 524.14; found 524.10 | $^1$H NMR (400 MHz, CDCl$_3$) δ 1.20-2.26 (m, 15 H), 3.33 (m, 2 H), 3.51 (m, 1 H), 3.88 (s, 3 H), 3.92 (m, 2 H), 6.42 (t, J = 8 Hz, 1 H), 6.77 (d, J = 8 Hz, 1 H), 8.03 (s, 1 H), 8.06 (d, J = 8 Hz, 1 H), 8.17 (s, 1 H) |
| 45 | 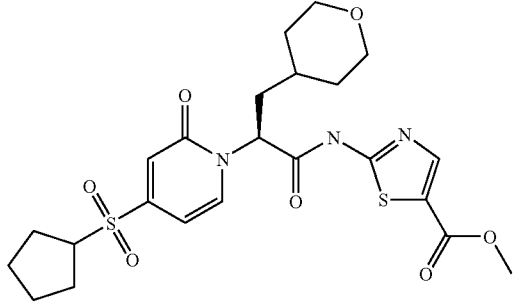<br>(S)-methyl 2-(2-(4-(cyclopentylsulfonyl)-2-oxopyridin-1(2H)-yl)-3-(tetrahydro-2H-pyran-4-yl)propanamido)thiazole-5-carboxylate | C | calc'd for $C_{23}H_{29}N_3O_7S_2$ 524.14; found 524.10 | |
| 46 | 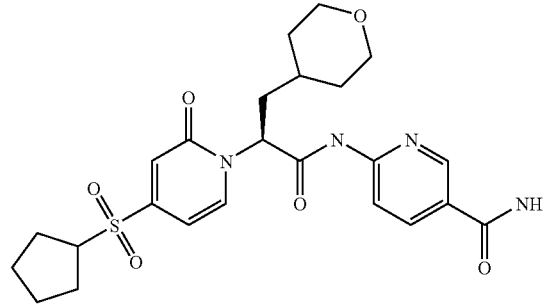<br>(S)-6-(2-(4-(cyclopentylsulfonyl)-2-oxopyridin-1(2H)-yl)-3-(tetrahydro-2H-pyran-4-yl)propanamido)nicotinamide | C | | |

TABLE 1-continued

| Ex. | Structure | Method | LCMS ([M + H]) | NMR data |
|---|---|---|---|---|
| 47 | (R)-6-(2-(4-(cyclopentylsulfonyl)-2-oxopyridin-1(2H)-yl)-3-(tetrahydro-2H-pyran-4-yl)propanamido)nicotinamide | C | calc'd for $C_{24}H_{30}N_4O_6S$ 503.19; found 503.10 | $^1$H NMR (400 MHz, CDCl$_3$) δ 1.35-2.22 (m, 15 H), 3.36 (m, 2H), 3.62 (m, 1 H), 3.95 (m, 2 H), 5.95 (m, 1 H), 6.74 (d, J = 4 Hz, 1 H), 7.12 (d, J = 8 Hz, 1 H), 7.95 (d, J = 8 Hz, 1 H), 8.08 (d, J = 8 Hz, 1 H), 8.30 (d, J = 8 Hz, 1 H), 8.82 (s, 1 H) |
| 48 | (R)-2-(4-(cyclopropylsulfonyl)-2-oxopyridin-1(2H)-yl)-N-(5-methoxythiazolo[5,4-b]pyridin-2-yl)-3-(tetrahydro-2H-pyran-4-yl)propanamide | E | calc'd for $C_{23}H_{27}N_4O_6S_2$ 519.14; found 519.3 | $^1$H NMR (400 MHz, CHLOROFORM-d) δ ppm 0.97-1.17 (m, 2 H) 1.18-1.46 (m, 5 H) 1.46-1.60 (m, 1 H) 1.68-1.81 (m, 2 H) 1.88-1.99 (m, 1 H) 2.18-2.33 (m, 1 H) 2.45 (br. s., 1 H) 3.25-3.42 (m, 2 H) 3.85-3.96 (m, 2 H) 3.98 (s, 3 H) 6.51 (br. s., 1 H) 6.76 (br. s., 1 H) 6.82 (d, J = 8.34 Hz, 1 H) 8.09-8.34 (m, 3 H) |
| 49 | (S)-2-(4-(cyclopropylsulfonyl)-2-oxopyridin-1(2H)-yl)-N-(5-methoxythiazolo[5,4-b]pyridin-2-yl)-3-(tetrahydro-2H-pyran-4-yl)propanamide | E | calc'd for $C_{23}H_{27}N_4O_6S_2$ 519.14; found 519.3 | 1H NMR (400 MHz, CHLOROFORM-d) δ ppm 0.97-1.17 (m, 2 H) 1.18-1.46 (m, 5 H) 1.46-1.60 (m, 1H) 1.68-1.81 (m, 2 H) 1.88-1.99 (m, 1 H) 2.18-2.33 (m, 1H) 2.45 (br. s., 1 H) 3.25-3.42 (m, 2 H) 3.85-3.96 (m, 2 H) 3.98 (s, 3 H) 6.51 (br. s., 1 H) 6.76 (br. s., 1 H) 6.82 (d, J = 8.34 Hz, 1 H) 8.09-8.34 (m, 3 H) |

TABLE 1-continued

| Ex. | Structure | Method | LCMS ([M + H]) | NMR data |
|---|---|---|---|---|
| 50 | 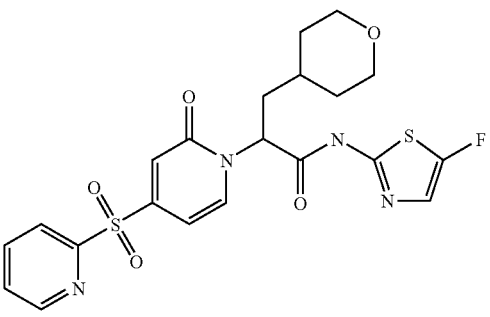<br>N-(5-fluorothiazol-2-yl)-2-(2-oxo-4-(pyridin-2-ylsulfonyl)pyridin-1(2H)-yl)-3-(tetrahydro-2H-pyran-4-yl)propanamide | E | calc'd for $C_{21}H_{22}FN_4O_5S_2$ 493.09; found 493.18 | $^1$H NMR (400 MHz, CHLOROFORM-d) δ ppm 1.13-1.35 (m, 3 H) 1.35-1.44 (m, 1 H) 1.53-1.76 (m, 2 H) 1.90 (ddd, J = 14.02, 8.21, 5.81 Hz, 1 H) 2.19 (dt, J = 14.08, 6.98 Hz, 1 H) 3.18-3.42 (m, 1 H) 3.79-3.99 (m, 2 H) 5.93 (t, J = 7.71 Hz, 1 H) 6.87 (dd, J = 7.33, 2.02 Hz, 1 H) 7.09 (d, J = 2.53 Hz, 1 H) 7.53 (d, J = 2.02 Hz, 1 H) 7.57 (dd, J = 12.50, 1.14 Hz, 1 H) 7.72 (d, J = 7.33 Hz, 1 H) 7.99 (td, J = 7.77, 1.64 Hz, 1 H) 8.19 (d, J = 7.83 Hz, 1 H) 8.73 (d, J = 4.55 Hz, 1 H) |
| 51 | 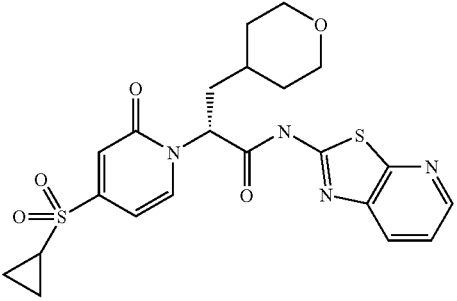<br>(R)-2-(4-(cyclopropylsulfonyl)-2-oxopyridin-1(2H)-yl)-3-(tetrahydro-2H-pyran-4-yl)-N-(thiazolo[5,4-b]pyridin-2-yl)propanamide | E | calc'd for $C_{22}H_{25}N_4O_5S_2$ 489.12, found 489.28 | $^1$H NMR (400 MHz, CHLOROFORM-d) δ ppm 0.66-0.95 (m, 1 H) 1.00-1.18 (m, 2 H) 1.18-1.36 (m, 2 H) 1.36-1.49 (m, 3 H) 1.76-1.83 (m, 2 H) 1.91-2.05 (m, 1 H) 2.25-2.36 (m, 1 H) 2.42-2.51 (m, 1 H) 3.30-3.42 (m, 2 H) 3.95 (dd, J = 11.49, 2.91 Hz, 2 H) 6.51 (t, J = 7.71 Hz, 1 H) 6.79 (dd, J = 7.33, 2.02 Hz, 1 H) 7.41 (dd, J = 8.21, 4.67 Hz, 1 H) 8.12 (d, J = 7.33 Hz, 1 H) 8.20 (d, J = 1.26 Hz, 1 H) 8.31 (dd, J = 8.34, 1.26 Hz, 1 H) 8.51 (d, J = 3.79 Hz, 1 H) |
| 52 | 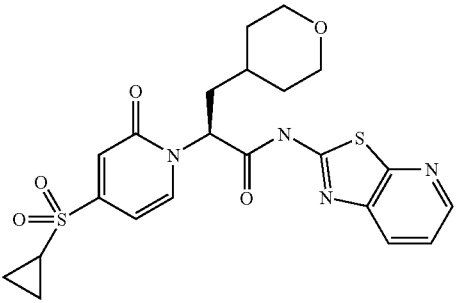<br>(S)-2-(4-(cyclopropylsulfonyl)-2-oxopyridin-1(2H)-yl)-3-(tetrahydro-2H-pyran-4-yl)-N-(thiazolo[5,4-b]pyridin-2-yl)propanamide | E | calc'd for $C_{22}H_{25}N_4O_5S_2$ 489.12, found 489.28 | $^1$H NMR (400 MHz, CHLOROFORM-d) δ ppm 0.66-0.95 (m, 1 H) 1.00-1.18 (m, 2 H) 1.18-1.36 (m, 2 H) 1.36-1.49 (m, 3 H) 1.76-1.83 (m, 2 H) 1.91-2.05 (m, 1 H) 2.25-2.36 (m, 1 H) 2.42-2.51 (m, 1 H) 3.30-3.42 (m, 2 H) 3.95 (dd, J = 11.49, 2.91 Hz, 2 H) 6.51 (t, J = 7.71 Hz, 1 H) 6.79 (dd, J = 7.33, 2.02 Hz, 1 H) 7.41 (dd, J = 8.21, 4.67 Hz, 1 H) 8.12 (d, J = 7.33 Hz, 1 H) 8.20 (d, J = 1.26 Hz, 1 H) 8.31 (dd, J = 8.34, 1.26 Hz, 1 H) 8.51 (d, J = 3.79 Hz, 1 H) |

TABLE 1-continued

| Ex. | Structure | Method | LCMS ([M + H]) | NMR data |
|---|---|---|---|---|
| 53 | 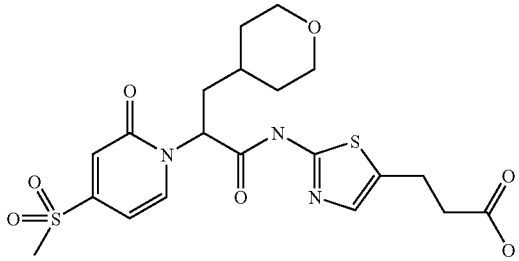<br>3-(2-(2-(4-(methylsulfonyl)-2-oxopyridin-1(2H)-yl)-3-(tetrahydro-2H-pyran-4-yl)propanamido)thiazol-5-yl)propanoic acid | E | calc'd for $C_{20}H_{26}N_3O_7S_2$, 484.11, found 484.27 | $^1$H NMR (400 MHz, CHLOROFORM-d) δ ppm 0.76-1.54 (m, 6 H) 1.65-1.72 (m, 1 H) 1.73-1.81 (m, 1 H) 2.12-2.28 (m, 2 H) 2.69 (t, J = 7.07 Hz, 2 H) 3.12 (t, J = 7.07 Hz, 2 H) 3.27 (s, 3 H) 3.91-4.01 (m, 2 H) 6.03 (dd, J = 10.23, 5.68 Hz, 1 H) 6.89 (dd, J = 7.33, 2.02 Hz, 1 H) 7.13 (d, J = 2.02 Hz, 1 H) 7.25 (s, 1 H) 8.16 (d, J = 7.33 Hz, 1 H) |
| 54 | 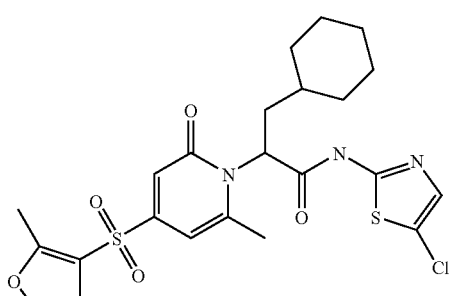<br>N-(5-chlorothiazol-2-yl)-3-cyclohexyl-2-(6-methyl-4-(2-methylfuran-3-ylsulfonyl)-2-oxopyridin-1(2H)-yl)propanamide | D | calc'd for $C_{23}H_{26}ClN_3O_5S_2$ 524.10; found 524.10 | $^1$H NMR (400 MHz, CDCl$_3$) δ 0.92-1.83 (m, 15 H), 2.53 (s,3 H), 2.57 (s, 3 H), 2.65 (m, 1 H), 4.88 (bs, 1 H), 6.53 (d, J = 3 Hz, 1 H), 6.58 (d, J = 4 Hz, 1 H), 6.88 (d, J = 3 Hz, 1 H), 7.26 (s, 1 H), 7.31 (d, J = 3 Hz, 1 H). |
| 55 | 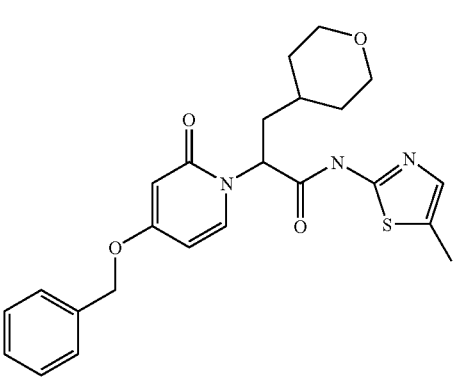<br>2-(4-(benzyloxy)-2-oxopyridin-1(2H)-yl)-N-(5-methylthiazol-2-yl)-3-(tetrahydro-2H-pyran-4-yl)propanamide | J | calc'd for $C_{24}H_{28}N_3O_4S$ 454.17; found 454.20 | $^1$H NMR (400 MHz, CHLOROFORM-d) δ ppm 1.31-1.50 (m, 3 H) 1.58 (d, J = 11.62 Hz, 1 H) 1.75 (d, J = 11.12 Hz, 1 H) 1.92-2.06 (m, 1 H) 2.18-2.30 (m, H) 2.44 (s, 3 H) 3.27-3.38 (m, 2 H) 3.94 (t, J = 12.38 Hz, 2 H) 5.01 (s, 2 H) 5.73 (dd, J = 9.98, 5.18 Hz, 1 H) 6.09-6.20 (m, 2 H) 7.14 (br. s., 1 H) 7.32 (d, J = 7.58 Hz, 1 H) 7.35-7.45 (m, 5 H). |

TABLE 1-continued

| Ex. | Structure | Method | LCMS ([M + H]) | NMR data |
|---|---|---|---|---|
| 56 | 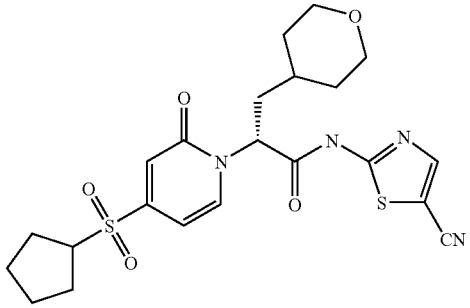<br>(R)-N-(5-cyanothiazol-2-yl)-2-(4-(cyclopentylsulfonyl)-2-oxopyridin-1(2H)-yl)-3-(tetrahydro-2H-pyran-4-yl)propanamide | D | calc'd for $C_{22}H_{26}N_4O_5S_2$ 491.13; found 491.10 | $^1$H NMR (400 MHz, CDCl$_3$) δ 1.26-2.16 (m, 15 H), 3.36 (m, 2 H), 3.59 (m, 1 H), 3.95 (m, 2 H), 5.98 (dd, J = 4, 8 Hz, 1 H), 6.72 (dd, J = 4, 8 Hz, 1 H), 7.12 (d, J = 4 Hz, 1 H), 7.92 (d, J = 8 Hz, 1 H) |
| 57 | 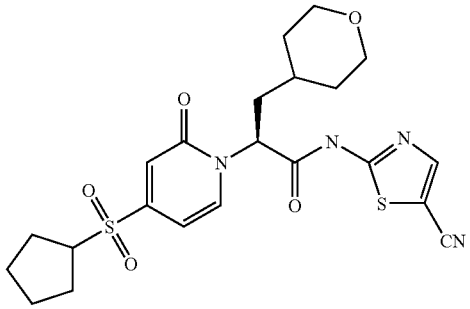<br>(S)-N-(5-cyanothiazol-2-yl)-2-(4-(cyclopentylsulfonyl)-2-oxopyridin-1(2H)-yl)-3-(tetrahydro-2H-pyran-4-yl)propanamide | D | calc'd for $C_{22}H_{26}N_4O_5S_2$ 491.13; found 491.10 | |
| 58 | 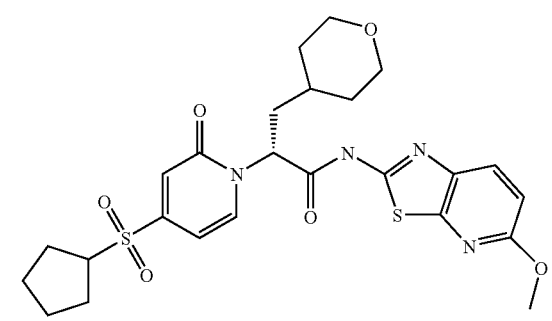<br>(R)-2-(4-(cyclopentylsulfonyl)-2-oxopyridin-1(2H)-yl)-N-(5-methoxythiazolo[5,4-b]pyridin-2-yl)-3-(tetrahydro-2H-pyran-4-yl)propanamide | D | calc'd for $C_{25}H_{30}N_4O_6S_2$ 547.16; found 547.10 | $^1$H NMR (400 MHz, d-DMSO) δ 1.25-2.24 (m, 15 H), 3.26 (m, 2 H), 3.85 (m, 1 H), 3.86 (m, 2 H), 3.95 (s, 3 H), 5.99 (dd, J = 4, 12 Hz, 1 H), 6.77 (d, J = 8 Hz, 1 H), 6.90 (d, J = 12 Hz), 6.97 (s, 1 H), 8.01 (d, J = 8 Hz, 1 H), 8.12 (d, J = 8 HZ, 1 H) |

TABLE 1-continued

| Ex. | Structure | Method | LCMS ([M + H]) | NMR data |
|---|---|---|---|---|
| 59 | (S)-2-(4-(cyclopentylsulfonyl)-2-oxopyridin-1(2H)-yl)-N-(5-methoxythiazolo[5,4-b]pyridin-2-yl)-3-(tetrahydro-2H-pyran-4-yl)propanamide | D | calc'd for $C_{25}H_{30}N_4O_6S_2$ 547.16; found 547.10 | |
| 60 | N-(5-chlorothiazol-2-yl)-3-cyclohexyl-2-(6-methyl-2-oxo-4-(thiophen-2-ylsulfonyl)pyridin-1(2H)-yl)propanamide | D | calc'd for $C_{22}H_{24}ClN_3O_4S_3$ 527.09; found 527.09 | $^1$H NMR (400 MHz, MeOD). δ ppm 0.99 (M, 2H) 1.20 (m, 3H) 1.36 (m, 1H) 1.69 (m, 5H) 1.76 (m, 1H) 2.49 (m, 4H), 5.21 (m, 1H) 6.72 (s, 1H) 6.88 (s, 1H) 7.26 (m, 2H) 7.89 (d, J = 4 Hz, 1H) 8.03 (d, J = 8 Hz, 1H) |
| 61 | (S)-2-(4-bromo-6-methyl-2-oxopyridin-1(2H)-yl)-3-cyclohexyl-N-(thiazol-2-yl)propanamide | C | calc'd for $C_{18}H_{22}BrN_3O_2S$ 425.36; found 425.36 | $^1$H NMR (400 MHz, MeOD). δ ppm 1.02 (m, 2H) 1.24 (m, 3H) 1.37 (m, 1H) 1.73 (m, 5H) 1.86 (m, 1H) 2.49 (m, 4H) 5.24 (m, 1H) 6.57 (s, 1H) 6.63 (s, 1H) 7.12 (d, J = 4 Hz, 1H) 7.42 (d, J = 0 Hz, 1H) |
| 62 | (S)-N-(5-methoxythiazolo[5,4-b]pyridin-2-yl)-2-(6-methyl-4-(2-methylfuran-3-ylsulfonyl)-2-oxopyridin-1(2H)-yl)-3-(tetrahydro-2H-pyran-4-yl)propanamide | D | calc'd for $C_{26}H_{28}N_4O_7S_2$ 573.14; found 573.14 | $^1$H NMR (400 MHz, d-MeOD) δ 1.25-1.37 (m, 3 H), 1.66-1.77 (m, 4 H), 2.58 (s, 3 H), 2.59 (s, 3 H), 2.67 (m, 1 H), 3.34 (m, 2 H), 3.45 (m, 1 H), 3.89 (m, 2 H), 3.96 (s, 3 H), 5.26 (bs, 1 H), 6.68 (s, 1 H), 6.75 (d, J = 4 Hz), 6.82 (d, J = 8 Hz, 1 H), 6.85 (d, J = 4 Hz, 1 H), 7.55 (d, J = 4 Hz, 1 H), 7.87 (d, J = 8 Hz, 1 H) |

TABLE 1-continued

| Ex. | Structure | Method | LCMS ([M + H]) | NMR data |
|---|---|---|---|---|
| 63 | 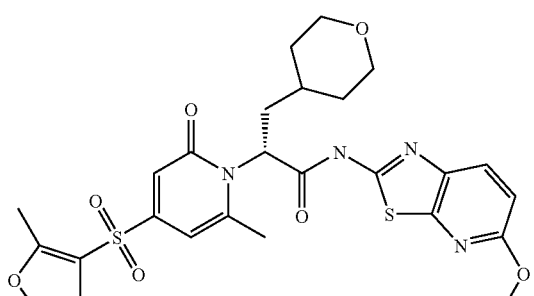(R)-N-(5-methoxythiazolo[5,4-b]pyridin-2-yl)-2-(6-methyl-4-(2-methylfuran-3-ylsulfonyl)-2-oxopyridin-1(2H)-yl)-3-(tetrahydro-2H-pyran-4-yl)propanamide | D | calc'd for $C_{26}H_{28}N_4O_7S_2$ 573.14; found 573.14 | |
| 64 | 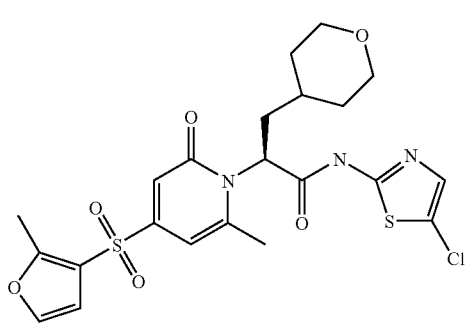(S)-N-(5-chlorothiazol-2-yl)-2-(6-methyl-4-(2-methylfuran-3-ylsulfonyl)-2-oxopyridin-1(2H)-yl)-3-(tetrahydro-2H-pyran-4-yl)propanamide | D | calc'd for $C_{22}H_{24}ClN_3O_6S_2$ 526.08; found 526.0 | $^1$H NMR (400 MHz, d-CDCl$_3$) δ 1.29-1.42 (m, 3 H), 1.61-1.75 (m, 4 H), 2.52 (s, 3 H), 2.58 (s, 3 H), 2.74 (m, 1 H), 3.36 (m, 2 H), 3.9 (m, 2 H), 4.75 (bs, 1 H), 6.50 (s, 1 H), 6.57 (d, J = 4 Hz), 6.89 (s, 1 H), 7.25 (s, 1 H), 7.33 (d, J = 4 Hz, 1 H) |
| 65 | 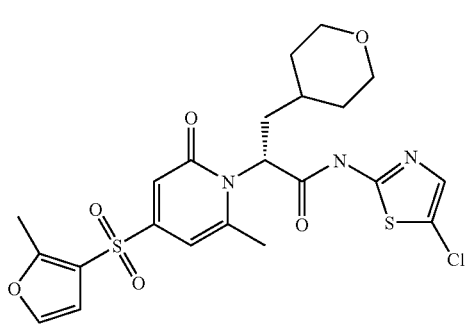(R)-N-(5-chlorothiazol-2-yl)-2-(6-methyl-4-(2-methylfuran-3-ylsulfonyl)-2-oxopyridin-1(2H)-yl)-3-(tetrahydro-2H-pyran-4-yl)propanamide | D | calc'd for $C_{22}H_{24}ClN_3O_6S_2$ 526.08; found 526.0 | |

TABLE 1-continued

| Ex. | Structure | Method | LCMS ([M + H]) | NMR data |
|---|---|---|---|---|
| 66 | 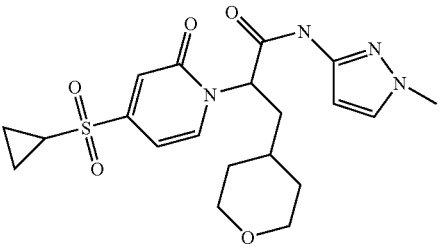<br>2-(4-(cyclopropylsulfonyl)-2-oxopyridin-1(2H)-yl)-N-(1-methyl-1H-pyrazol-3-yl)-3-(tetrahydro-2H-pyran-4-yl)propanamide | E | calc'd for $C_{20}H_{27}N_4O_5S$ 435.16; found 435.1 | $^1$H NMR (400 MHz, MeOD) δ ppm 1.05-1.20 (m, 2 H) 1.21-1.46 (m, 6 H) 1.62 (br. s., 2 H) 1.97-2.19 (m, 2 H) 2.78 (dd, J = 12.51, 3.16 Hz, 1 H) 3.34 (s, 2 H) 3.73-3.82 (m, 3 H) 3.84-4.00 (m, 2 H) 5.91 (dd, J = 9.73, 6.44 Hz, 1 H) 6.44 (d, J = 2.02 Hz, 1 H) 6.78 (dd, J = 7.20, 1.89 Hz, 1 H) 7.00 (d, J = 2.02 Hz, 1 H) 7.43 (d, J = 2.27 Hz, 1 H) 8.10 (d, J = 7.33 Hz, 1 H) |
| 67 | 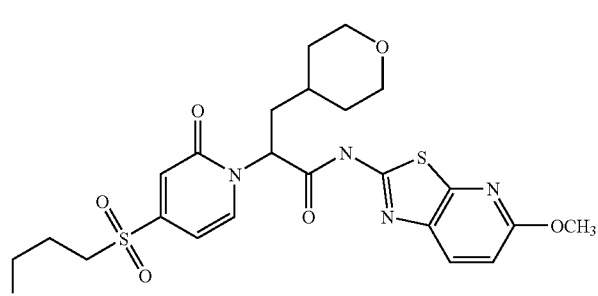<br>2-(4-(3-hydroxypropylsulfonyl)-2-oxopyridin-1(2H)-yl)-N-(5-methoxythiazolo[5,4-b]pyridin-2-yl)-3-(tetrahydro-2H-pyran-4-yl)propanamide | E | calc'd for $C_{23}H_{29}N_4O_7S_2$ 537.14; found 537.1 | $^1$H NMR (400 MHz, MeOD) δ ppm 1.21-1.45 (m, 2 H) 1.60 (d, J = 12.13 Hz, 1 H) 1.68 (d, J = 11.87 Hz, 1 H) 1.89 (dd, J = 9.98, 5.68 Hz, 1 H) 1.99-2.22 (m, 2 H) 3.16-3.40 (m, 4 H) 3.59 (t, J = 6.19 Hz, 2 H) 3.75-3.98 (m overlapping s, 5 H) 6.00 (dd, J = 10.61, 5.56 Hz, 1 H) 6.80 (d, J = 8.84 Hz, 1 H) 6.79 (dd, J = 7.20, 2.15 Hz, 1 H) 7.05 (d, J = 2.02 Hz, 1 H) 7.90 (d, J = 8.84 Hz, 1 H) 8.10 (d, J = 7.33 Hz, 1 H) |
| 68 | 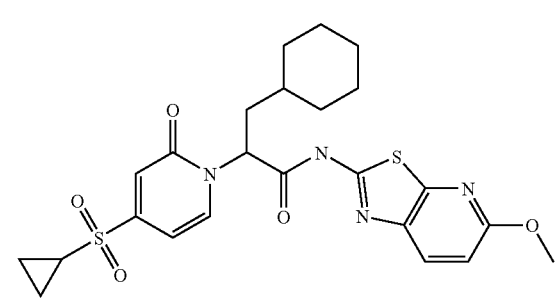<br>3-cyclohexyl-2-(4-(cyclopropylsulfonyl)-2-oxopyridin-1(2H)-yl)-N-(5-methoxythiazolo[5,4-b]pyridin-2-yl)propanamide | E | calc'd for $C_{24}H_{29}N_4O_5S_2$ 517.15; found 517.1 | $^1$H NMR (400 MHz, MeOD) δ ppm 0.98-1.34 (m, 10 H) 1.60-1.89 (m, 5 H) 2.00-2.21 (m, 2 H) 2.81 (dd, J = 12.76, 3.16 Hz, 1 H) 3.95 (s, 3 H) 6.00 (dd, J = 10.61, 5.56 Hz, 1 H) 6.78-6.91 (m, 2 H) 7.04 (d, J = 2.27 Hz, 1 H) 7.90-8.00 (m, 1 H) 8.10 (d, J = 7.33 Hz, 1 H) |
| 69 | 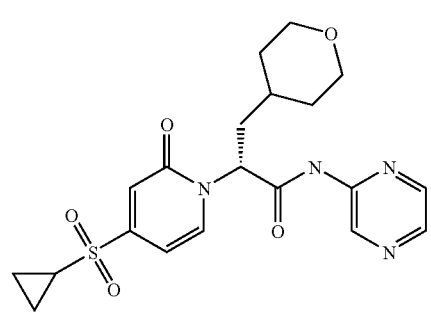<br>(R)-2-(4-(cyclopropylsulfonyl)-2-oxopyridin-1(2H)-yl)-N-(pyrazin-2-yl)-3-(tetrahydro-2H-pyran-4-yl)propanamide | E | calc'd for $C_{20}H_{25}N_4O_5S$ 433.15; found 433.1 | $^1$H NMR (400 MHz, MeOD) δ ppm 1.12-1.49 (m, 7 H) 1.57-1.77 (m, 2 H) 2.04-2.26 (m, 2 H) 2.73-2.87 (m, 1 H) 3.30 (d, J = 1.77 Hz, 2 H) 3.90 (dd, J = 9.85, 8.84 Hz, 2 H) 6.03 (dd, J = 10.86, 5.56 Hz, 1 H) 6.82 (dd, J = 7.33, 2.02 Hz, 1 H) 7.02 (d, J = 2.02 Hz, 1 H) 8.12 (d, J = 7.33 Hz, 1 H) 8.33 (d, J = 2.53 Hz, 1 H) 8.40 (d, J = 1.52 Hz, 1 H) 9.32 (s, 1 H) |

TABLE 1-continued

| Ex. | Structure | Method | LCMS ([M + H]) | NMR data |
|---|---|---|---|---|
| 70 | (S)-2-(4-(cyclopropylsulfonyl)-2-oxopyridin-1(2H)-yl)-N-(pyrazin-2-yl)-3-(tetrahydro-2H-pyran-4-yl)propanamide | E | calc'd for $C_{20}H_{25}N_4O_5S$ 433.15; found 433.1 | |
| 71 | (R)-2-(4-(3-hydroxypropylsulfonyl)-2-oxopyridin-1(2H)-yl)-N-(5-methoxythiazolo[5,4-b]pyridin-2-yl)-3-(tetrahydro-2H-pyran-4-yl)propanamide | E | calc'd for $C_{23}H_{29}N_4O_7S_2$ 537.14; found 537.1 | $^1$H NMR (400 MHz, MeOD) δ ppm 1.21-1.45 (m, 2 H) 1.60 (d, J = 12.13 Hz, 1 H) 1.68 (d, J = 11.87 Hz, 1 H) 1.89 (dd, J = 9.98, 5.68 Hz, 1 H) 1.99-2.22 (m, 2 H) 3.16-3.40 (m, 4 H) 3.59 (t, J = 6.19 Hz, 2 H) 3.75-3.98 (m overlapping s, 5 H) 6.00 (dd, J = 10.61, 5.56 Hz, 1 H) 6.80 (d, J = 8.84 Hz, 1 H) 6.79 (dd, J = 7.20, 2.15 Hz, 1 H) 7.05 (d, J = 2.02 Hz, 1 H) 7.90 (d, J = 8.84 Hz, 1 H) 8.10 (d, J = 7.33 Hz, 1 H) |
| 72 | (S)-2-(4-(3-hydroxypropylsulfonyl)-2-oxopyridin-1(2H)-yl)-N-(5-methoxythiazolo[5,4-b]pyridin-2-yl)-3-(tetrahydro-2H-pyran-4-yl)propanamide | E | calc'd for $C_{23}H_{29}N_4O_7S_2$ 537.14; found 537.1 | |
| 73 | (R)-2-(4-(cyclopropylsulfonyl)-2-oxopyridin-1(2H)-yl)-N-(1-methyl-1H-pyrazol-3-yl)-3-(tetrahydro-2H-pyran-4-yl)propanamide | E | calc'd for $C_{20}H_{27}N_4O_5S$ 435.16; found 435.1 | $^1$H NMR (400 MHz, MeOD) δ ppm 1.05-1.20 (m, 2 H) 1.21-1.46 (m, 6 H) 1.62 (br. s., 2 H) 1.97-2.19 (m, 2 H) 2.78 (dd, J = 12.51, 3.16 Hz, 1 H) 3.34 (s, 2 H) 3.73-3.82 (m, 3 H) 3.84-4.00 (m, 2 H) 5.91 (dd, J = 9.73, 6.44 Hz, 1 H) 6.44 (d, J = 2.02 Hz, 1 H) 6.78 (dd, J = 7.20, 1.89 Hz, 1 H) 7.00 (d, J = 2.02 Hz, 1 H) 7.43 (d, J = 2.27 Hz, 1 H) 8.10 (d, J = 7.33 Hz, 1 H) |

TABLE 1-continued

| Ex. | Structure | Method | LCMS ([M + H]) | NMR data |
|---|---|---|---|---|
| 74 | 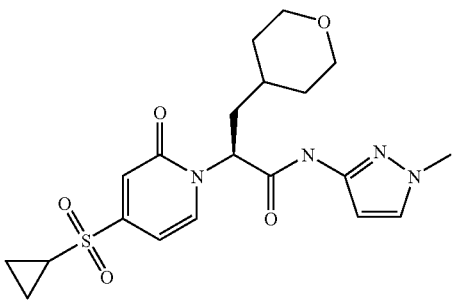<br>(S)-2-(4-(cyclopropylsulfonyl)-2-oxopyridin-1(2H)-yl)-N-(1-methyl-1H-pyrazol-3-yl)-3-(tetrahydro-2H-pyran-4-yl)propanamide | E | calc'd for $C_{20}H_{27}N_4O_5S$ 435.16; found 435.1 | |
| 75 | 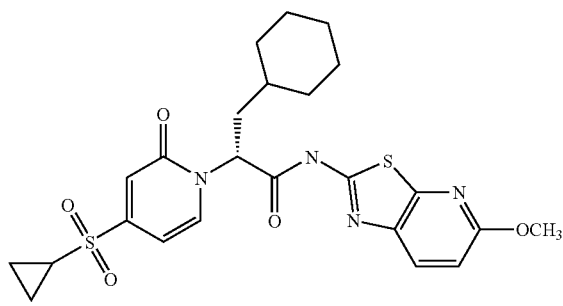<br>(R)-3-cyclohexyl-2-(4-(cyclopropylsulfonyl)-2-oxopyridin-1(2H)-yl)-N-(5-methoxythiazolo[5,4-b]pyridin-2-yl)propanamide | E | calc'd for $C_{24}H_{29}N_4O_5S_2$ 517.15; found 517.1 | |
| 76 | 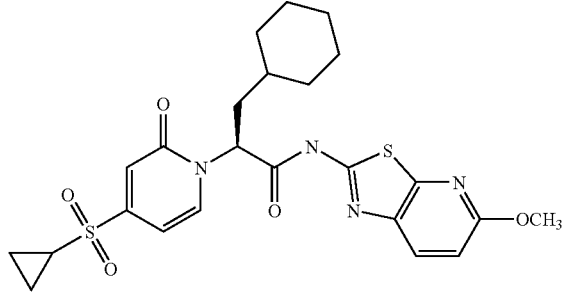<br>(S)-3-cyclohexyl-2-(4-(cyclopropylsulfonyl)-2-oxopyridin-1(2H)-yl)-N-(5-methoxythiazolo[5,4-b]pyridin-2-yl)propanamide | E | calc'd for $C_{24}H_{29}N_4O_5S_2$ 517.15; found 517.1 | |

TABLE 1-continued

| Ex. | Structure | Method | LCMS ([M + H]) | NMR data |
|---|---|---|---|---|
| 77 | 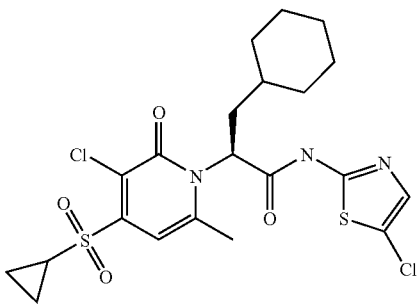<br>(S)-2-(3-chloro-4-(cyclopropylsulfonyl)-6-methyl-2-oxopyridin-1(2H)-yl)-N-(5-chlorothiazol-2-yl)-3-cyclohexylpropanamide | G | calc'd for $C_{21}H_{25}Cl_2N_3O_4S_2$ 518.07; found 518.0 | $^1$H NMR (400 MHz, CDCl$_3$) δ 0.90-2.10 (m, 17 H), 2.43 (s, 3 H), 3.08 (m, 1 H), 5.48 (m, 1 H), 7.28 (s, 1 H), 7.34 (s, 1 H) |
| 78 | 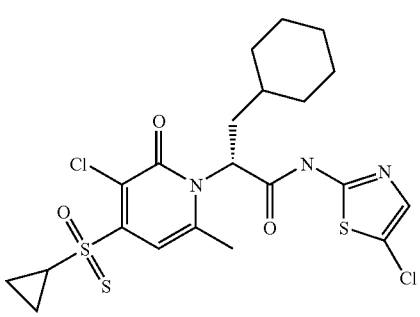<br>(R)-2-(3-chloro-4-(cyclopropylsulfonyl)-6-methyl-2-oxopyridin-1(2H)-yl)-N-(5-chlorothiazol-2-yl)-3-cyclohexylpropanamide | G | calc'd for $C_{21}H_{25}Cl_2N_3O_4S_2$ 518.07; found 518.0 | |
| 79 | 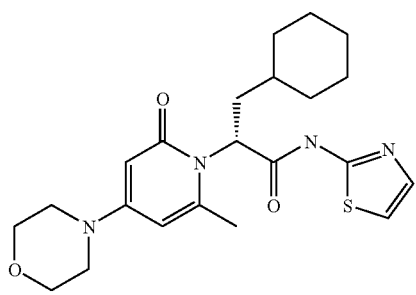<br>3-cyclohexyl-2-(6-methyl-4-morpholino-2-oxopyridin-1(2H)-yl)-N-(thiazol-2-yl)propanamide | H | calc'd for $C_{22}H_{30}N_4O_3S$ 431.57, found 431.557 | $^1$H NMR (400 MHz, MeOD). δ ppm 0.96 (m, 3H) 1.21 (m, 5H) 1.66 (m, 5 H) 1.87 (m, 2 H) 2.24 (m, 1 H) 2.37 m, 4H), 3.76 (m, 5H) 5.58 (m, 1H) 6.16 n (s, 1H) 6.64 (d, J = 4 Hz, 1H) 7.02 (d, J = 4 Hz, 1H) |
| 80 | 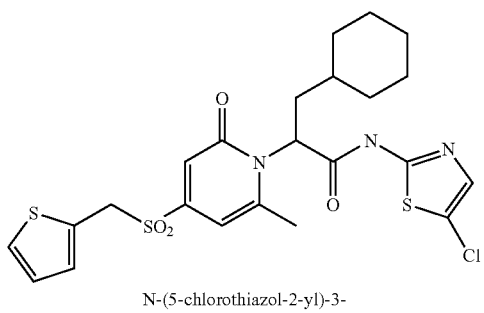<br>N-(5-chlorothiazol-2-yl)-3-cyclohexyl-2-(6-methyl-2-oxo-4-(thiophen-2-ylmethylsulfonyl)pyridin-1(2H)-yl)propanamide | C | calc'd for $C_{23}H_{26}ClN_3O_4S_3$ 541.12; found 541.12 | $^1$H NMR (400 MHz, MeOD). δ ppm 1.03 (m, 2H) 1.26 (m, 4H) 1.71 (m, 2H) 1.79 (m, 2H) 1.87 (m, 2H) 2.45 (m, 1H) 2.54 (s, 3H) 4.86 (d, J = 4 Hz, 2 H) 5.29 (m, 1H) 6.58 (s, 1H) 6.64 (s, 1H) 7.00 (t, J = 4, 4 Hz, 1 H) 7.07 (s, 1 H) 7.43 (d, J = 4 Hz, 1 H) |

TABLE 1-continued

| Ex. | Structure | Method | LCMS ([M + H]) | NMR data |
|---|---|---|---|---|
| 81 | 3-cyclohexyl-2-(4-(furan-2-ylmethylsulfonyl)-6-methyl-2-oxopyridin-1(2H)-yl)-N-(thiazol-2-yl)propanamide | C | calc'd for $C_{23}H_{27}N_3O_5S_2$, 490; found, 490 | $^1$H NMR (400 MHz, CHLOROFORM-d) δ ppm 0.88-1.06 (m, 2 H) 1.07-1.32 (m, 4 H) 1.64 (m, 4 H) 1.71 (br. s., 3 H) 2.32-2.45 (m, 1 H) 2.50 (m, 2 H) 4.45 (d, J = 2.78 Hz, 2 H) 4.83-5.02 (m, 1 H) 6.27 (br. s., 1 H) 6.37-6.41 (m, 1 H) 6.45-6.51 (m, 1 H) 6.87 (br. s., 1 H) 6.98-7.04 (m, 1 H) 7.41 (s, 1 H) 7.45 (t, J = 3.54 Hz, 1H) |
| 82 | 3-cyclohexyl-2-(4-(cyclopentylsulfonyl)-6-methyl-2-oxopyridin-1(2H)-yl)-N-(5-(4-fluorobenzyl)thiazol-2-yl)propanamide | C | calc'd for $C_{30}H_{36}FN_3O_4S_2$, 586; found, 586 | $^1$H NMR (400 MHz, CHLOROFORM-d) δ ppm 0.85-1.04 (m, 2 H) 1.06-1.30 (m, 4 H) 1.53-1.76 (m, 3 H) 1.75-1.87 (m, 4 H) 1.87-2.01 (m, 4 H) 2.01-2.18 (m, 4 H) 2.33-2.46 (m, 1 H) 2.46-2.61 (m, 2 H) 3.39-3.54 (m, 1 H) 4.02 (d, J = 7.07 Hz, 2 H) 4.77-5.00 (m, 1 H) 6.45 (br. s., 1 H) 6.91-7.05 (m, 3 H) 7.08-7.23 (m, 3 H) |
| 83 | N-(5-chlorothiazol-2-yl)-3-cyclohexyl-2-(4-(2,5-dimethylfuran-3-ylsulfonyl)-6-methyl-2-oxopyridin-1(2H)-yl)propanamide | C | calc'd for $C_{24}H_{28}ClN_3O_5S_2$ 539.08; found 539.08 | $^1$H NMR (400 MHz, MeOD). δ ppm 0.97 (m, 2H) 1.22 (m, 3H) 1.37 (m, 1H) 1.69 (m, 5H) 1.83 (m, 1H) 2.26 (s, 3H) 2.54 (m, 7H) 5.24 (m, 1H) 6.32 (s, 1H) 6.64 (s, 1H) 6.81 (s, 1H) 7.26 (s, 1H) |

TABLE 1-continued

| Ex. | Structure | Method | LCMS ([M + H]) | NMR data |
|---|---|---|---|---|
| 84 | 2-(4-(cyclopropylsulfonyl)-2-oxopyridin-1(2H)-yl)-N-(6-hydroxybenzo[d]thiazol-2-yl)-3-(tetrahydro-2H-pyran-4-yl)propanamide | E | calc'd for $C_{23}H_{26}N_3O_6S_2$ 504.12 found 504 | $^1$H NMR (400 MHz, MeOD) δ ppm 1.15 (dd, J = 7.83, 2.53 Hz, 2 H) 1.23-1.31 (m, 3 H) 1.34 (dd, J = 11.62, 4.80 Hz, 2 H) 1.42-1.53 (m, 1 H) 1.53-1.61 (m, 1 H) 1.82 (d, J = 12.63 Hz, 1 H) 2.27 (d, J = 14.40 Hz, 1 H) 2.26 (dd, J = 15.41, 4.04 Hz, 1 H) 2.80 (td, J = 8.21, 4.04 Hz, 1 H) 3.34 (t, J = 11.62 Hz, 2 H) 3.80-3.98 (m, 2 H) 5.57 (dd, J = 9.60, 5.31 Hz, 1 H) 6.81 (dd, J = 7.33, 2.02 Hz, 1 H) 7.05 (d, J = 2.02 Hz, 1 H) 7.19 (dd, J = 8.84, 2.27 Hz, 1 H) 7.45 (d, J = 8.84 Hz, 1 H) 7.55 (d, J = 2.27 Hz, 1 H) 8.04 (d, J = 7.07 Hz, 1 H) |
| 85 | (S)-N-(5-chlorothiazol-2-yl)-3-cyclohexyl-2-(6-methyl-2-oxo-4-(thiophen-2-ylmethylsulfonyl)pyridin-1(2H)-yl)propanamide | C | calc'd for $C_{23}H_{26}ClN_3O_4S_3$ 541.12; found 541.12 | $^1$H NMR (400 MHz, MeOD). δ ppm 1.03 (m, 2 H) 1.26 (m, 4 H) 1.71 (m, 2 H) 1.79 (m, 2 H) 1.87 (m, 2 H) 2.45 (m, 1 H) 2.54 (s, 3 H) 4.86 (d, J = 4 Hz, 2 H) 5.29 (m, 1 H) 6.58 (s, 1 H) 6.64 (s, 1 H) 7.00 (t, J = 4, 4 Hz, 1 H) 7.07 (s, 1 H) 7.43 (d, J = 4 Hz, 1 H) |
| 86 | (R)-N-(5-chlorothiazol-2-yl)-3-cyclohexyl-2-(6-methyl-2-oxo-4-(thiophen-2-ylmethylsulfonyl)pyridin-1(2H)-yl)propanamide | C | calc'd for $C_{23}H_{26}ClN_3O_4S_3$ 541.12; found 541.12 | $^1$H NMR (400 MHz, MeOD). δ ppm 1.03 (m, 2 H) 1.26 (m, 4 H) 1.71 (m, 2 H) 1.79 (m, 2 H) 1.87 (m, 2 H) 2.45 (m, 1 H) 2.54 (s, 3 H) 4.86 (d, J = 4 Hz, 2 H) 5.29 (m, 1 H) 6.58 (s, 1 H) 6.64 (s, 1 H) 7.00 (t, J = 4, 4 Hz, 1 H) 7.07 (s, 1 H) 7.43 (d, J = 4 Hz, 1 H |
| 87 | 3-cyclohexyl-2-(6-methyl-2-oxo-4-(pyrrolidin-1-yl)pyridin-1(2H)-yl)-N-(thiazol-2-yl)propanamide | H | calc'd for $C_{22}H_{30}N_4O_2S$ 415.57. found 415.57 | $^1$H NMR (400 MHz, MeOD). δ ppm 0.89 (m, 2 H) 1.21 (m, 4 H) 1.65 (m, 4 H) 1.87 (m, 2 H) 2.06 (m, 4 H) 2.30 (m, 2 H) 2.49 (s, 3 H) 3.43 (m, 4 H) 5.11 (m, 1 H) 6.06 (s, 1 H) 6.32 (s, 1 H) 6.87 (d, J = 4 Hz, 1 H) 7.34 (d, J = 4 Hz, 1 H) |

TABLE 1-continued

| Ex. | Structure | Method | LCMS ([M + H]) | NMR data |
|---|---|---|---|---|
| 88 | 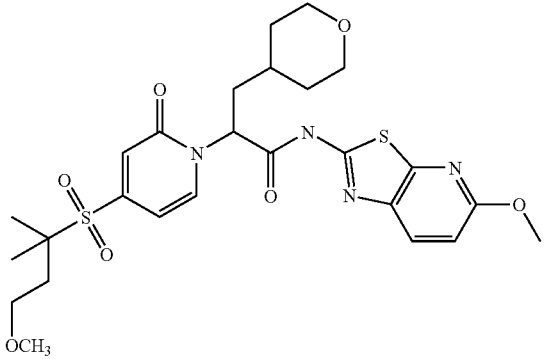 2-(4-(4-methoxy-2-methylbutan-2-ylsulfonyl)-2-oxopyridin-1(2H)-yl)-N-(5-methoxythiazolo[5,4-b]pyridin-2-yl)-3-(tetrahydro-2H-pyran-4-yl)propanamide | E | calc'd for $C_{26}H_{34}N_4O_7S_2$ 579.19; found 579.0 | $^1$H NMR (400 MHz, CDCl$_3$) δ ppm 1.28-1.49 (m, 9 H) 1.53-1.79 (m, 2 H) 2.01 (t, J = 6.57 Hz, 2 H) 2.07-2.29 (m, 2 H) 3.30 (d, J = 1.77 Hz, 5 H) 3.56 (t, J = 6.57 Hz, 2 H) 3.85-3.95 (m, 2 H) 3.96 (s, 3 H) 6.02 (dd, J = 10.36, 5.56 Hz, 1 H) 6.77 (dd, J = 7.33, 1.77 Hz, 1 H) 6.86 (d, J = 8.84 Hz, 1 H) 7.01 (d, J = 2.02 Hz, 1 H) 7.96 (d, J = 8.84 Hz, 1 H) 8.12 (d, J = 7.33 Hz, 1 H) |
| 89 | 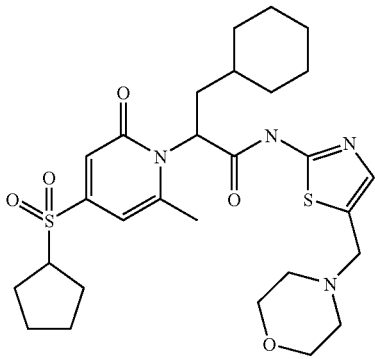 3-cyclohexyl-2-(4-(cyclopentylsulfonyl)-6-methyl-2-oxopyridin-1(2H)-yl)-N-(5-(morpholinomethyl)thiazol-2-yl)propanamide | C | calc'd for $C_{28}H_{40}N_4O_5S_2$, 577; found, 577 | $^1$H NMR (400 MHz, CHLOROFORM-d) δ ppm 0.89-1.10 (m, 2 H) 1.10-1.35 (m, 4 H) 1.36-2.19 (m, 15 H) 2.53-2.74 (m, 3 H) 2.89-3.75 (m, 5 H) 3.80-4.11 (m, 4 H) 4.33-4.64 (m, 2 H) 4.82-5.06 (m, 1 H) 6.68 (br. s., 1 H) 6.93 (br. s., 1 H) 7.67 (br. s., 1 H) |
| 90 | 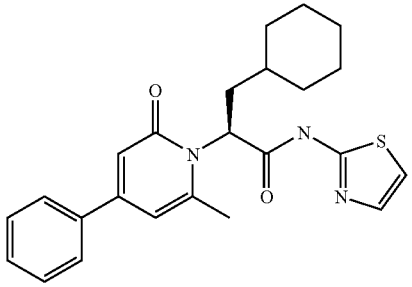 (S)-3-cyclohexyl-2-(6-methyl-2-oxo-4-phenylpyridin-1(2H)-yl)-N-(thiazol-2-yl)propanamide | F | calc'd for $C_{24}H_{28}N_3O_2S$ 422.19; found 421.9 | |

TABLE 1-continued

| Ex. | Structure | Method | LCMS ([M + H]) | NMR data |
|---|---|---|---|---|
| 91 | (S)-2-(4-(2-chlorophenyl)-6-methyl-2-oxopyridin-1(2H)-yl)-3-cyclohexyl-N-(thiazol-2-yl)propanamide | F | calc'd for $C_{24}H_{27}ClN_3O_2S$ 456.15; found 456.3 | |
| 92 | (S)-2-(4-(3-chlorophenyl)-6-methyl-2-oxopyridin-1(2H)-yl)-3-cyclohexyl-N-(thiazol-2-yl)propanamide | F | calc'd for $C_{24}H_{27}ClN_3O_2S$ 456.15; found 455.9 | |
| 93 | (S)-2-(4-(4-chlorophenyl)-6-methyl-2-oxopyridin-1(2H)-yl)-3-cyclohexyl-N-(thiazol-2-yl)propanamide | F | calc'd for $C_{24}H_{27}ClN_3O_2S$ 456.15; found 456.3 | |
| 94 | (S)-3-cyclohexyl-2-(4-(2-methoxyphenyl)-6-methyl-2-oxopyridin-1(2H)-yl)-N-(thiazol-2-yl)propanamide | F | calc'd for $C_{25}H_{30}N_3O_3S$ 452.20; found 451.9 | |

TABLE 1-continued

| Ex. | Structure | Method | LCMS ([M + H]) | NMR data |
|---|---|---|---|---|
| 95 | (S)-3-cyclohexyl-2-(4-(3-methoxyphenyl)-6-methyl-2-oxopyridin-1(2H)-yl)-N-(thiazol-2-yl)propanamide | F | calc'd for $C_{25}H_{30}N_3O_3S$ 452.20; found 452.3 | |
| 96 | (S)-3-cyclohexyl-2-(4-(4-methoxyphenyl)-6-methyl-2-oxopyridin-1(2H)-yl)-N-(thiazol-2-yl)propanamide | F | calc'd for $C_{25}H_{30}N_3O_3S$ 452.20; found 452.3 | |
| 97 | (S)-2-(4-(3-cyanophenyl)-6-methyl-2-oxopyridin-1(2H)-yl)-3-cyclohexyl-N-(thiazol-2-yl)propanamide | F | calc'd for $C_{25}H_{27}N_4O_2S$ 447.19; found 447.1 | |
| 98 | (S)-2-(4-(4-cyanophenyl)-6-methyl-2-oxopyridin-1(2H)-yl)-3-cyclohexyl-N-(thiazol-2-yl)propanamide | F | calc'd for $C_{25}H_{27}N_4O_2S$ 447.19; found 447.1 | |

TABLE 1-continued

| Ex. | Structure | Method | LCMS ([M + H]) | NMR data |
|---|---|---|---|---|
| 99 | (S)-3-cyclohexyl-2-(4-(furan-3-yl)-6-methyl-2-oxopyridin-1(2H)-yl)-N-(thiazol-2-yl)propanamide | F | calc'd for $C_{22}H_{26}N_3O_3S$ 412.17; found 412.3 | |
| 100 | (S)-3-cyclohexyl-2-(6-methyl-2-oxo-4-(pyridin-3-yl)pyridin-1(2H)-yl)-N-(thiazol-2-yl)propanamide | F | calc'd for $C_{23}H_{27}N_4O_2S$ 423.19; found 423.1 | |
| 101 | (S)-3-cyclohexyl-2-(6-methyl-4-(4-(methylsulfonyl)phenyl)-2-oxopyridin-1(2H)-yl)-N-(thiazol-2-yl)propanamide | F | calc'd for $C_{25}H_{30}N_3O_4S_2$ 500.17; found 500.3 | |
| 102 | (S)-3-cyclohexyl-2-(4-(4-(ethylsulfonyl)phenyl)-6-methyl-2-oxopyridin-1(2H)-yl)-N-(thiazol-2-yl)propanamide | F | calc'd for $C_{26}H_{32}N_3O_4S_2$ 514.18; found 514.3 | |

TABLE 1-continued

| Ex. | Structure | Method | LCMS ([M + H]) | NMR data |
|-----|-----------|--------|----------------|----------|
| 103 | 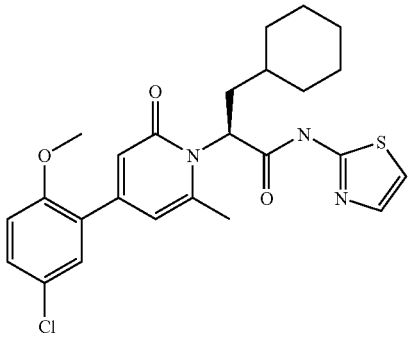<br>(S)-2-(4-(5-chloro-2-methoxyphenyl)-6-methyl-2-oxopyridin-1(2H)-yl)-3-cyclohexyl-N-(thiazol-2-yl)propanamide | F | calc'd for $C_{25}H_{29}ClN_3O_3S$ 486.16; found 486.3 | |
| 104 | 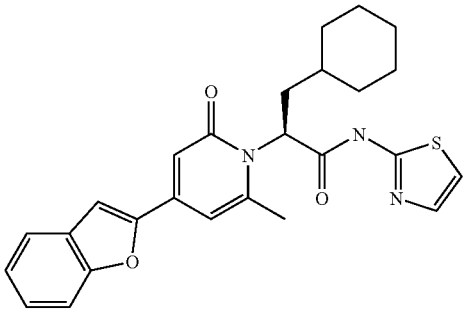<br>(S)-2-(4-(benzofuran-2-yl)-6-methyl-2-oxopyridin-1(2H)-yl)-3-cyclohexyl-N-(thiazol-2-yl)propanamide | F | calc'd for $C_{26}H_{28}N_3O_3S$ 462.19; found 462.3 | |
| 105 | 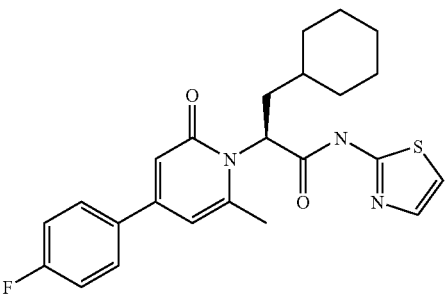<br>(S)-3-cyclohexyl-2-(4-(4-fluorophenyl)-6-methyl-2-oxopyridin-1(2H)-yl)-N-(thiazol-2-yl)propanamide | F | calc'd for $C_{24}H_{27}FN_3O_2S$ 440.18; found 440.3 | |

TABLE 1-continued

| Ex. | Structure | Method | LCMS ([M + H]) | NMR data |
|---|---|---|---|---|
| 106 | 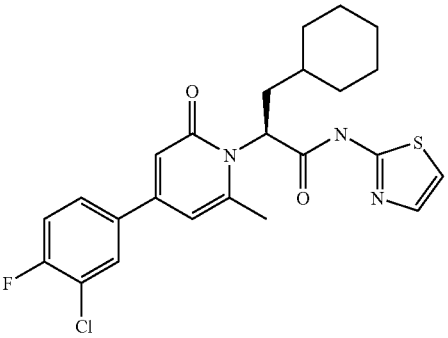<br>(S)-2-(4-(3-chloro-4-fluorophenyl)-6-methyl-2-oxopyridin-1(2H)-yl)-3-cyclohexyl-N-(thiazol-2-yl)propanamide | F | calc'd for $C_{24}H_{26}ClFN_3O_2S$ 474.14; found 473.9 | |
| 107 | 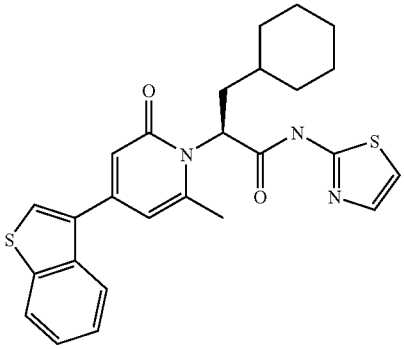<br>(S)-2-(4-(benzo[b]thiophen-3-yl)-6-methyl-2-oxopyridin-1(2H)-yl)-3-cyclohexyl-N-(thiazol-2-yl)propanamide | F | calc'd for $C_{26}H_{28}N_3O_2S_2$ 478.16; found 477.9 | |
| 108 | 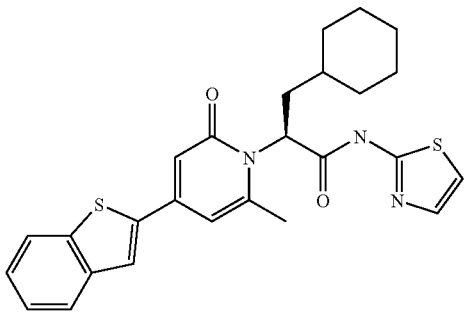<br>(S)-2-(4-(benzo[b]thiophen-2-yl)-6-methyl-2-oxopyridin-1(2H)-yl)-3-cyclohexyl-N-(thiazol-2-yl)propanamide | F | calc'd for $C_{26}H_{28}N_3O_2S_2$ 478.16; found 478.3 | |

TABLE 1-continued

| Ex. | Structure | Method | LCMS ([M + H]) | NMR data |
|---|---|---|---|---|
| 109 | (S)-3-cyclohexyl-2-(4-(3-fluorophenyl)-6-methyl-2-oxopyridin-1(2H)-yl)-N-(thiazol-2-yl)propanamide | F | calc'd for $C_{24}H_{27}FN_3O_2S$ 440.18; found 440.3 | |
| 110 | (S)-3-cyclohexyl-2-(4-(2-fluorophenyl)-6-methyl-2-oxopyridin-1(2H)-yl)-N-(thiazol-2-yl)propanamide | F | calc'd for $C_{24}H_{27}FN_3O_2S$ 440.18; found 440.3 | |
| 111 | (S)-3-cyclohexyl-2-(6-methyl-4-(4-methylthiophen-2-yl)-2-oxopyridin-1(2H)-yl)-N-(thiazol-2-yl)propanamide | F | calc'd for $C_{23}H_{28}N_3O_2S_2$ 442.16; found 442.3 | |
| 112 | (S)-3-cyclohexyl-2-(6-methyl-4-(3-(methylsulfonamido)phenyl)-2-oxopyridin-1(2H)-yl)-N-(thiazol-2-yl)propanamide | F | calc'd for $C_{25}H_{31}N_4O_4S_2$ 515.18; found 515.1 | |

TABLE 1-continued

| Ex. | Structure | Method | LCMS ([M + H]) | NMR data |
|---|---|---|---|---|
| 113 | (S)-3-cyclohexyl-2-(6-methyl-2-oxo-4-(1H-pyrazol-4-yl)pyridin-1(2H)-yl)-N-(thiazol-2-yl)propanamide | F | calc'd for $C_{21}H_{26}N_5O_2S$ 412.18; found 412.3 | |
| 114 | (S)-3-cyclohexyl-2-(6-methyl-4-(3-(N-methylsulfamoyl)phenyl)-2-oxopyridin-1(2H)-yl)-N-(thiazol-2-yl)propanamide | F | calc'd for $C_{25}H_{31}N_4O_4S_2$ 515.18; found 515.5 | |
| 115 | (S)-3-cyclohexyl-2-(6-methyl-4-(4-(N-methylsulfamoyl)phenyl)-2-oxopyridin-1(2H)-yl)-N-(thiazol-2-yl)propanamide | F | calc'd for $C_{25}H_{31}N_4O_4S_2$ 515.18; found 515.1 | |
| 116 | ethyl 2-(2-(4-(cyclopropylsulfonyl)-2-oxopyridin-1(2H)-yl)-3-(tetrahydro-2H-pyran-4-yl)propanamido)thiazole-5-carboxylate | E | calc'd for $C_{22}H_{28}N_3O_7S_2$ 510.13; found 510 | 1H NMR (400 MHz, CHLOROFORM-d) δ ppm 1.15 (ddd, J = 7.96, 4.17, 4.04 Hz, 2 H) 1.25 (s, 1 H) 1.30-1.55 (m, 2 H) 1.37 (t, J = 7.20 Hz, 6 H) 1.61-1.76 (m, 2 H) 1.98 (d, J = 6.06 Hz, 1 H) 2.25 (d, J = 7.07 Hz, 1 H) 2.49 (dd, J = 12.63, 3.28 Hz, 1 H) 3.25-3.35 (m, 2 H) 3.92 (br. s., 1 H) 3.95 (d, J = 1.77 Hz, 1 H) 4.35 (q, J = 7.16 Hz, 2 H) 6.14 (t, J = 7.58 Hz, 1 H) 6.75 (dd, J = 7.20, 1.89 Hz, 1 H) 7.59 (d, J = 1.52 Hz, 1 H) 7.87 (d, J = 7.33 Hz, 1 H) 8.13 (s, 1 H) |

TABLE 1-continued

| Ex. | Structure | Method | LCMS ([M + H]) | NMR data |
|---|---|---|---|---|
| 117 | 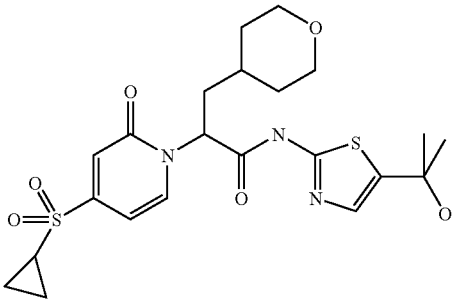<br>2-(4-(cyclopropylsulfonyl)-2-oxopyridin-1(2H)-yl)-N-(5-(2-hydroxypropan-2-yl)thiazol-2-yl)-3-(tetrahydro-2H-pyran-4-yl)propanamide | E | calc'd for $C_{22}H_{30}N_3O_6S_2$ 496.15; found 496.03 | $^1$H NMR (400 MHz, CHLOROFORM-d). δ ppm 1.17 (d, J = 7.83 Hz, 2 H) 1.22-1.46 (m, 6 H) 1.54-1.68 (m, 7 H) 1.68-1.74 (m, 1 H) 2.03-2.22 (m, 3 H) 2.80 (dd, J = 12.13, 3.28 Hz, 1 H) 3.24-3.40 (m, 1 H) 3.88 (d, J = 10.36 Hz, 2 H) 5.96 (dd, J = 10.23, 5.43 Hz, 1 H) 6.81 (d, J = 7.33 Hz, 1 H) 7.01 (s, 1 H) 8.09 (d, J = 7.33 Hz, 1 H) |
| 118 | 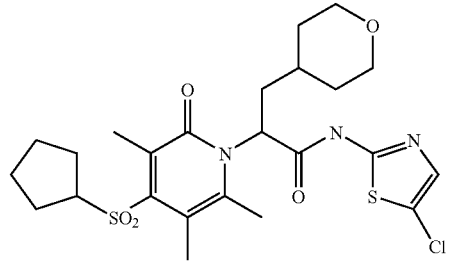<br>N-(5-chlorothiazol-2-yl)-2-(4-(cyclopentylsulfonyl)-3,5,6-trimethyl-2-oxopyridin-1(2H)-yl)-3-(tetrahydro-2H-pyran-4-yl)propanamide | J | calc'd for $C_{24}H_{32}ClN_3O_5S_2$ 543.11. found 543.11 | $^1$H NMR (400 MHz, CHLOROFORM-d). δ ppm 1.41 (m, 2 H) 1.68 (m, 4 H) 1.89 (m, 6 H) 2.08 (m, 3 H) 2.38 (s, 3 H) 2.54 (s, 2 H) 2.67 (s, 3 H) 3.35 (m, 2 H) 3.62 (m, 1 H) 3.97 (m, 2 H) 5.44 (m, 1 H) 7.25 (s, 1 H) |
| 119 | 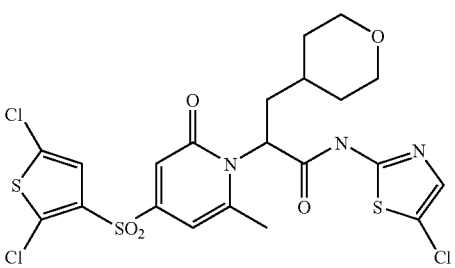<br>N-(5-chlorothiazol-2-yl)-2-(4-(2,5-dichlorothiophen-3-ylsulfonyl)-6-methyl-2-oxopyridin-1(2H)-yl)-3-(tetrahydro-2H-pyran-4-yl)propanamide | C | calc'd for $C_{21}H_{20}Cl_3N_3O_5S_3$ 597.96. found 597.9 | $^1$H NMR (400 MHz, CHLOROFORM-d). δ ppm 1.39 (m, 2H) 1.67 (m, 2H) 1.80 (m, 2H) 1.99 (m, 2H) 2.51 (s, 3H) 3.36 (m, 2H) 3.95 (m, 2H) 5.71 (m, 1H) 7.22 (s, 1H) 7.26 (s, 1H) 7.34 (s, 1H |

TABLE 1-continued

| Ex. | Structure | Method | LCMS ([M + H]) | NMR data |
|-----|-----------|--------|----------------|----------|
| 120 | (R)-2-(4-(4-methoxy-2-methylbutan-2-ylsulfonyl)-2-oxopyridin-1(2H)-yl)-N-(5-methoxythiazolo[5,4-b]pyridin-2-yl)-3-(tetrahydro-2H-pyran-4-yl)propanamide | E | calc'd for $C_{26}H_{34}N_4O_7S_2$ 579.19; found 579.0 | |
| 121 | (S)-2-(4-(4-methoxy-2-methylbutan-2-ylsulfonyl)-2-oxopyridin-1(2H)-yl)-N-(5-methoxythiazolo[5,4-b]pyridin-2-yl)-3-(tetrahydro-2H-pyran-4-yl)propanamide | E | calc'd for $C_{26}H_{34}N_4O_7S_2$ 579.19; found 579.0 | |
| 122 | (R)-3-cyclohexyl-2-(4-(cyclopropylsulfonyl)-6-methyl-2-oxopyridin-1(2H)-yl)-N-(5-methoxythiazolo[5,4-b]pyridin-2-yl)propanamide | D | calc'd for $C_{25}H_{30}N_4O_5S_2$ 531.17; found 531.10 | |

| Ex. | Structure | Method | LCMS ([M + H]) | NMR data |
|---|---|---|---|---|
| 123 | (S)-3-cyclohexyl-2-(4-(cyclopropylsulfonyl)-6-methyl-2-oxopyridin-1(2H)-yl)-N-(5-methoxythiazolo[5,4-b]pyridin-2-yl)propanamide | D | calc'd for $C_{25}H_{30}N_4O_5S_2$ 531.17; found 531.10 | $^1$H NMR (400 MHz, d-CDCl$_3$) δ 0.97-1.39 (m, H), 1.65-1.78 (m, 6 H), 2.51 (m, 2 H), 2.58 (s, 3 H), 4.00 (s, 3 H), 5.0 (bs, 1 H), 6.52 (s, 1 H), 6.82 (d, J = 8 Hz), 7.0 (s, 1 H), 7.85 (d, J = 8 Hz, 1 H) |
| 124 | 2-(7-chloro-4-oxothieno[3,2-c]pyridin-5(4H)-yl)-N-(5-chlorothiazol-2-yl)-3-cyclohexylpropanamide | J | calc'd for $C_{19}H_{19}Cl_2N_3O_2S_2$ 457.41; found 457.40 | $^1$H NMR (400 MHz, d-DMSO) δ 0.97-1.25 (m, 7 H), 1.58-1.80 (m, 5 H), 1.98-2.11 (m, 1 H), 6.0 (q, J = 4, 8 Hz, 1 H), 7.33 (s, 1 H), 7.59 (s, 2 H), 7.71 (s, 1 H) |
| 125 | 2-(4-((S)-3-hydroxypyrrolidin-1-yl)-2-oxopyridin-1(2H)-yl)-N-(5-methoxythiazolo[5,4-b]pyridin-2-yl)-3-(tetrahydro-2H-pyran-4-yl)propanamide | E | calc'd for $C_{24}H_{30}N_5O_5S$ 500.19; found 499.9 | $^1$H NMR (400 MHz, MeOD) δ ppm 1.30-1.44 (m, 4 H) 1.58 (d, J = 11.37 Hz, 1 H) 1.71 (d, J = 11.87 Hz, 1 H) 2.00-2.19 (m, 4 H) 2.20-2.24 (m, 2 H) 3.54 (br. s., 2 H) 3.88 (t, J = 11.37 Hz, 4 H) 3.93 (s, 3 H) 4.53 (d, J = 2.02 Hz, 1 H) 5.85 (dd, J = 11.12, 5.05 Hz, 1 H) 6.31 (d, J = 7.83 Hz, 1 H) 6.83 (d, J = 7.83 Hz, 1 H) 7.77 (d, J = 7.83 Hz, 1 H) 7.92 (d, J = 9.09 Hz, 1 H) |
| 126 | (S)-3-cyclohexyl-2-(6-methyl-4-(3-(methylsulfonyl)phenyl)-2-oxopyridin-1(2H)-yl)-N-(thiazol-2-yl)propanamide | F | calc'd for $C_{25}H_{30}N_3O_4S_2$ 500.17; found 500.3 | |

TABLE 1-continued

| Ex. | Structure | Method | LCMS ([M + H]) | NMR data |
|---|---|---|---|---|
| 127 | 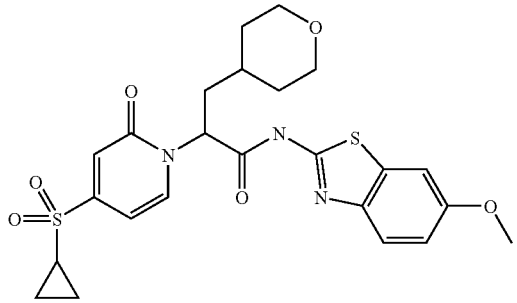<br>2-(4-(cyclopropylsulfonyl)-2-oxopyridin-1(2H)-yl)-N-(6-methoxybenzo[d]thiazol-2-yl)-3-(tetrahydro-2H-pyran-4-yl)propanamide | E | calc'd for $C_{24}H_{28}N_3O_6S_2$ 518.13; found 518.3 | 1H NMR (400 MHz, CHLOROFORM-d) δ ppm 1.16 (d, J = 7.83 Hz, 2 H) 1.25-1.50 (m, 5 H) 1.63 (br. s., 1 H) 1.72 (d, J = 10.36 Hz, 1 H) 2.01 (d, J = 8.08 Hz, 1 H) 2.21 (d, J = 7.33 Hz, 1 H) 2.53 (ddd, J = 7.64, 4.99, 3.03 Hz, 1 H) 2.69-3.05 (m, 1 H) 3.24-3.45 (m, 2 H) 3.69-3.91 (m, 3 H) 3.94 (d, J = 10.61 Hz, 2 H) 5.96-6.08 (m, 1 H) 6.73 (dd, J = 7.33, 2.02 Hz, 1 H) 7.09 (dd, J = 8.97, 2.40 Hz, 1 H) 7.27-7.31 (m, 2 H) 7.58-7.81 (m, 1 H) 7.89 (dd, J = 7.33, 2.02 Hz, 1 H) |
| 128 | 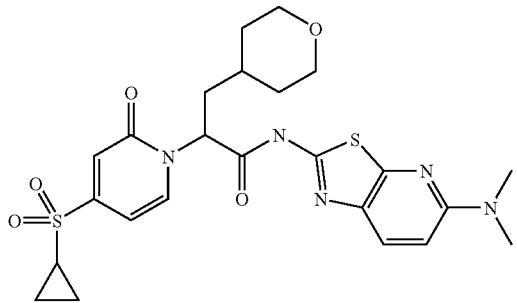<br>2-(4-(cyclopropylsulfonyl)-2-oxopyridin-1(2H)-yl)-N-(5-(dimethylamino)thiazolo[5,4-b]pyridin-2-yl)-3-(tetrahydro-2H-pyran-4-yl)propanamide | E | calc'd for $C_{24}H_{30}N_5O_5S_2$ 532.16; found 532 | 1H NMR (400 MHz, MeOD) δ ppm 1.18 (d, J = 7.83 Hz, 2 H) 1.24-1.36 (m, 3 H) 1.36-1.49 (m, 3 H) 1.60-1.68 (m, 1 H) 1.68-1.78 (m, 1 H) 2.07-2.17 (m, 1 H) 2.18-2.32 (m, 1 H) 2.81 (t, J = 4.80 Hz, 1 H) 3.28 (s, 6 H) 3.29-3.40 (m, 2 H) 3.84-3.97 (m, 2 H) 5.99 (dd, J = 10.74, 5.18 Hz, 1 H) 6.83 (dd, J = 7.33, 2.02 Hz, 1 H) 7.03 (d, J = 2.02 Hz, 1 H) 7.08 (d, J = 9.35 Hz, 1 H) 8.06-8.18 (m, 2 H) |
| 129 | 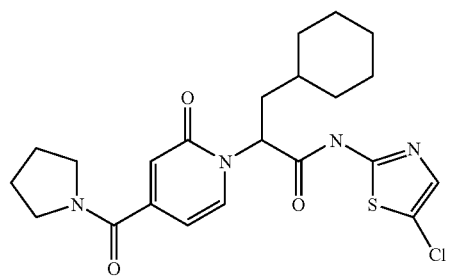<br>N-(5-chlorothiazol-2-yl)-3-cyclohexyl-2-(2-oxo-4-(pyrrolidine-1-carbonyl)pyridin-1(2H)-yl)propanamide | H | calc'd for $C_{22}H_{27}ClN_4O_3S$ 463.99; found 463.99 | $^1$H NMR (400 MHz, MeOD). δ ppm 1.14 (m, 6 H) 1.69 (m, 4 H) 1.80 (m, 1 H) 1.95 (m, 5 H) 2.09 (m, 1 H) 3.48 (m, 4 H) 5.94 (m, 1 H) 6.50 (d, J = 8 Hz, 1 H) 6.62 (s, 1 H) 7.34 (s, 1 H) 7.90 (d, J = 8 Hz, 1 H) |

TABLE 1-continued

| Ex. | Structure | Method | LCMS ([M + H]) | NMR data |
|---|---|---|---|---|
| 130 | 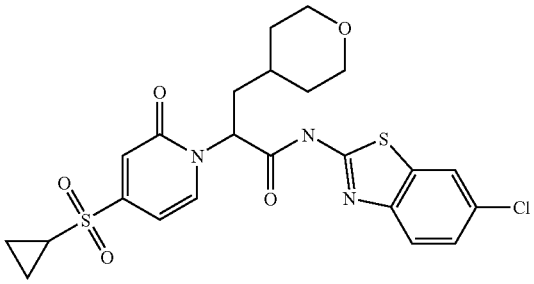<br>N-(6-chlorobenzo[d]thiazol-2-yl)-2-(4-(cyclopropylsulfonyl)-2-oxopyridin-1(2H)-yl)-3-(tetrahydro-2H-pyran-4-yl)propanamide | E | calc'd for C$_{23}$H$_{25}$ClN$_3$O$_5$S$_2$ 522.08; found 522 | $^1$H NMR (400 MHz, CHLOROFORM-d) δ ppm 1.10-1.22 (m, 1 H) 1.17 (d, J = 7.83 Hz, 1 H) 1.40 (dd, J = 12.38, 5.56 Hz, 3 H) 1.36-1.48 (m, 2 H) 1.64 (d, J = 12.13 Hz, 1 H) 1.69-1.77 (m, 1 H) 1.95-2.07 (m, 1 H) 2.10-2.21 (m, 1 H) 2.54 (dd, 12.51, 3.16 Hz, 1 H) 3.32-3.42 (m, 3 H) 3.90-4.00 (m, 2 H) 6.04 (dd, J = 9.60, 6.32 Hz, 1 H) 6.73 (dd, J = 7.33, 2.02 Hz, 1 H) 7.15 (d, J = 1.77 Hz, 1 H) 7.41 (dd, J = 8.59, 2.02 Hz, 1 H) 7.73 (d, J = 8.59 Hz, 1 H) 7.79 (d, J = 2.02 Hz, 1 H) 7.91 (d, J = 7.33 Hz, 1 H) |
| 131 | 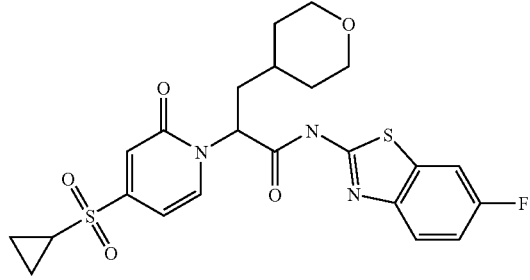<br>2-(4-(cyclopropylsulfonyl)-2-oxopyridin-1(2H)-yl)-N-(6-fluorobenzo[d]thiazol-2-yl)-3-(tetrahydro-2H-pyran-4-yl)propanamide | E | calc'd for C$_{23}$H$_{25}$FN$_3$O$_5$S$_2$ 506.11; found 506 | 1H NMR (400 MHz, CHLOROFORM-d) δ ppm 1.18 (d, J = 7.58 Hz, 1 H) 1.13-1.24 (m, 1 H) 1.31-1.49 (m, 5 H) 1.60-1.69 (m, 1 H) 1.69-1.79 (m, 1 H) 1.96-2.10 (m, 1 H) 2.10-2.23 (m, 1 H) 2.56 (dd, J = 7.45, 4.93 Hz, 1 H) 3.30-3.36 (m, 3 H) 3.92-4.01 (m, 2 H) 6.06 (dd, J = 9.47, 6.19 Hz, 1 H) 6.74 (d, J = 7.33 Hz, 1 H) 7.15 (s, 1 H) 7.19 (t, J = 8.21 Hz, 1 H) 7.51 (d, J = 7.83 Hz, 1 H) 7.76 (dd, J = 8.72, 4.67 Hz, 1 H) 7.93 (d, J = 6.82 Hz, 1 H) |
| 132 | 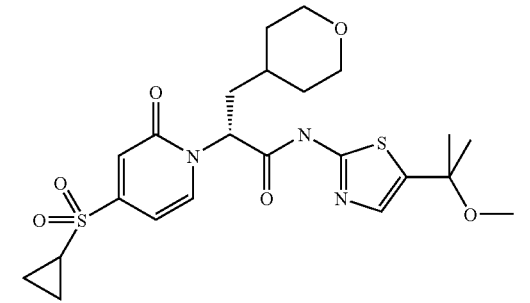<br>(R)-2-(4-(cyclopropylsulfonyl)-2-oxopyridin-1(2H)-yl)-N-(5-(2-methoxypropan-2-yl)thiazol-2-yl)-3-(tetrahydro-2H-pyran-4-yl)propanamide | E | calc'd for C$_{23}$H$_{32}$N$_3$O$_6$S$_2$ 510.17; found 510 | 1H NMR (400 MHz, CHLOROFORM-d) δ ppm 0.71-0.94 (m, 2 H) 1.10-1.80 (m, 14 H) 1.87-2.02 (m, 1 H) 2.17-2.33 (m, 1 H) 2.48 (t, J = 4.17 Hz, 1 H) 3.12 (s, 3 H) 3.24-3.41 (m, 2 H) 3.93 (d, J = 14.40 Hz, 2 H) 6.09 (s, 1 H) 6.70 (d, J = 7.07 Hz, 1 H) 7.36 (s, 1 H) 7.51 (s, 1 H) 7.88 (d, J = 7.33 Hz, 1 H) |

TABLE 1-continued

| Ex. | Structure | Method | LCMS ([M + H]) | NMR data |
|---|---|---|---|---|
| 133 | (S)-2-(4-(cyclopropylsulfonyl)-2-oxopyridin-1(2H)-yl)-N-(5-(2-methoxypropan-2-yl)thiazol-2-yl)-3-(tetrahydro-2H-pyran-4-yl)propanamide | E | calc'd for $C_{23}H_{32}N_3O_6S_2$ 510.17; found 510 | 1H NMR (400 MHz, CHLOROFORM-d) δ ppm 0.71-0.94 (m, 2 H) 1.10-1.80 (m, 14 H) 1.87-2.02 (m, 1 H) 2.17-2.33 (m, 1 H) 2.48 (t, J = 4.17 Hz, 1 H) 3.12 (s, 3 H) 3.24-3.41 (m, 2 H) 3.93 (d, J = 14.40 Hz, 2 H) 6.09 (s, 1 H) 6.70 (d, J = 7.07 Hz, 1 H) 7.36 (s, 1 H) 7.51 (s, 1 H) 7.88 (d, J = 7.33 Hz, 1 H) |
| 134 | N-(5-chlorothiazol-2-yl)-2-(6-methyl-2-oxo-4-(thiophen-2-ylmethylsulfonyl)pyridin-1(2H)-yl)-3-(tetrahydro-2H-pyran-4-yl)propanamide | C | calc'd for $C_{22}H_{24}ClN_3O_5S_3$ 543.09; found 543.09 | $^1$H NMR (400 MHz, CHLOROFORM-d). δ ppm 1.36 (m, 2 H) 1.59 (m, 3 H) 2.18 (m, 1 H) 2.50 (m, 4 H) 3.35 (m, 2 H) 3.95 (m, 2 H) 4.60 (s, 2 H) 4.97 (m, 1 H) 6.26 (s, 1 H) 6.85 (s, 1 H) 7.02 (m, 1 H) 7.07 (d, J = 4 Hz, 1 H) 7.27 (s, 1 H) 7.34 (d, J = 4 Hz, 1 H) |
| 135 | (S)-N-(5-chlorothiazol-2-yl)-2-(4-(cyclopentylsulfonyl)-3,5,6-trimethyl-2-oxopyridin-1(2H)-yl)-3-(tetrahydro-2H-pyran-4-yl)propanamide | J | calc'd for $C_{24}H_{32}ClN_3O_5S_2$ 543.11. found 543 | $^1$H NMR (400 MHz, CHLOROFORM-d). δ ppm 1.41 (m, 2 H) 1.68 (m, 4 H) 1.89 (m, 6 H) 2.08 (m, 3 H) 2.38 (s, 3 H) 2.54 (s, 3 H) 2.67 (s, 3 H) 3.35 (m, 2 H) 3.62 (m, 1 H) 3.97 (m, 2 H) 5.44 (m, 1 H) 7.25 (s, 1 H) |
| 136 | (R)-N-(5-chlorothiazol-2-yl)-2-(4-(cyclopentylsulfonyl)-3,5,6-trimethyl-2-oxopyridin-1(2H)-yl)-3-(tetrahydro-2H-pyran-4-yl)propanamide | J | calc'd for $C_{24}H_{32}ClN_3O_5S_2$ 543.11. found 543 | 1H NMR (400 MHz, CHLOROFORM-d). δ ppm 1.41 (m, 2 H) 1.68 (m, 4 H) 1.89 (m, 6 H) 2.08 (m, 3 H) 2.38 (s, 3 H) 2.54 (s, 3 H) 2.67 (s, 3 H) 3.35 (m, 2 H) 3.62 (m, 1 H) 3.97 (m, 2 H) 5.44 (m, 1 H) 7.25 (s, 1 H) |

TABLE 1-continued

| Ex. | Structure | Method | LCMS ([M + H]) | NMR data |
|---|---|---|---|---|
| 137 | N-(5-chlorothiazol-2-yl)-2-(4-(3-hydroxyprop-1-ynyl)-6-methyl-2-oxopyridin-1(2H)-yl)-3-(tetrahydro-2H-pyran-4-yl)propanamide | I | calc'd for $C_{20}H_{23}ClN_3O_4S$ 436.10. found 436.30 | 1H NMR (400 MHz, CHLOROFORM-d) δ ppm 1.21-1.42 (m, 2 H) 1.51-1.73 (m, 3 H) 2.26-2.65 (m, 2 H) 2.37 (s, 3 H) 3.26-3.38 (m, 2 H) 3.90 (d, J = 9.60 Hz, 2 H) 4.42 (s, 2 H) 6.03-6.13 (m, 1 H) 6.48 (s, 1 H) 7.19 (s, 1 H) 7.22 (s, 1 H) |
| 138 | 2-(4-(cyclopropylsulfonyl)-2-oxopyridin-1(2H)-yl)-N-(5-(4-fluorobenzyl)thiazol-2-yl)-3-(tetrahydro-2H-pyran-4-yl)propanamide | E | calc'd for $C_{26}H_{29}FN_3O_5S_2$ 546.15; found 546 | 1H NMR (400 MHz, CHLOROFORM-d) δ ppm 1.16 (d, J = 7.83 Hz, 2 H) 1.33-1.50 (m, 5 H) 1.61 (br. s., 1 H) 1.70 (br. s., 1 H) 1.96 (d, J = 4.80 Hz, 1 H) 2.23 (d, J = 6.82 Hz, 1 H) 2.50 (dd, J = 12.51, 3.16 Hz, 1 H) 3.25-3.40 (m, 2 H) 3.94 (d, J = 11.12 Hz, 2 H) 3.94 (br. s., 1 H) 4.08 (s, 2 H) 5.93 (t, J = 7.58 Hz, 1 H) 6.69 (dd, J = 7.20, 1.89 Hz, 1 H) 7.02 (t, J = 8.46 Hz, 2 H) 7.19 (dd, J = 8.34, 5.31 Hz, 2 H) 7.24 (s, 1 H) 7.33 (s, 1 H) 7.75 (d, J = 7.33 Hz, 1 H) |
| 139 | 2-(2-oxo-5-(pyrrolidin-1-ylsulfonyl)pyridin-1(2H)-yl)-3-(tetrahydro-2H-pyran-4-yl)-N-(thiazol-2-yl)propanamide | J | calc'd for $C_{20}H_{27}N_4O_5S_2$ 467.13; found 467.30 | 1H NMR (400 MHz, CHLOROFORM-d) δ ppm 1.23-1.38 (m, 2 H) 1.39-1.51 (m, 1 H) 1.57-1.71 (m, 2 H) 1.83-1.91 (m, 4 H) 2.03 (ddd, J = 14.21, 8.78, 5.81 Hz, 1 H) 2.18 (ddd, J = 14.27, 7.33, 7.20 Hz, 1 H) 3.19-3.38 (m, 6 H) 3.82-3.92 (m, 2 H) 6.18 (t, J = 7.96 Hz, 1 H) 6.82 (d, J = 9.35 Hz, 1 H) 7.06 (d, J = 3.54 Hz, 1 H) 7.69 (d, J = 3.54 Hz, 1 H) 7.72 (dd, J = 9.60, 2.53 Hz, 1 H) 8.38 (d, J = 2.27 Hz, 1 H) |

TABLE 1-continued

| Ex. | Structure | Method | LCMS ([M + H]) | NMR data |
|---|---|---|---|---|
| 140 | 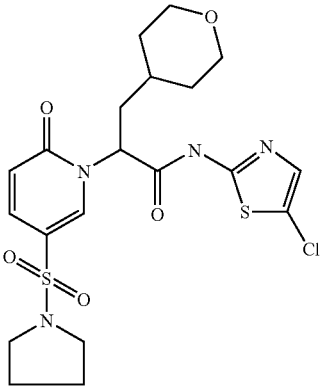<br>N-(5-chlorothiazol-2-yl)-2-(2-oxo-5-(pyrrolidin-1-ylsulfonyl)pyridin-1(2H)-yl)-3-(tetrahydro-2H-pyran-4-yl)propanamide | J | calc'd for $C_{20}H_{26}ClN_4O_5S_2$, 501.10; found 501.30 | $^1$H NMR (400 MHz, CHLOROFORM-d) δ ppm 1.26-1.39 (m, 2 H) 1.40-1.49 (m, 1 H) 1.64 (d, J = 12.13 Hz, 2 H) 1.88 (d, J = 13.39 Hz, 4 H) 1.96-2.07 (m, 1 H) 2.12-2.26 (m, 1 H) 3.15-3.43 (m, 6 H) 3.75-4.01 (m, 2 H) 6.07-6.27 (m, 1 H) 6.91 (d, J = 9.60 Hz, 1 H) 7.37 (s, 1 H) 7.75 (dd, J = 9.47, 2.40 Hz, 1 H) 8.35 (s, 1 H) |
| 141 | 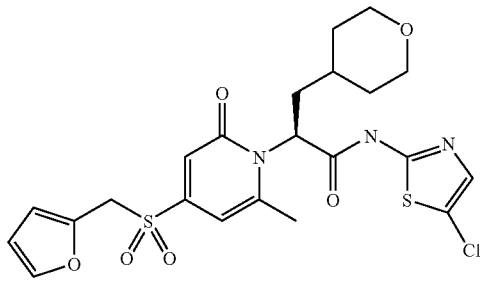<br>(S)-N-(5-chlorothiazol-2-yl)-2-(4-(furan-2-ylmethylsulfonyl)-6-methyl-2-oxopyridin-1(2H)-yl)-3-(tetrahydro-2H-pyran-4-yl)propanamide | C | calc'd for $C_{22}H_{24}ClN_3O_6S_2$, 527; found, 527 | $^1$H NMR (400 MHz, CHLOROFORM-d) δ ppm 1.27-1.44 (m, 2 H) 1.44-1.55 (m, 1 H) 1.63 (br. s., 3 H) 2.38-2.60 (m, 4 H) 3.26-3.41 (m, J = 11.81, 11.81, 7.07, 1.89 Hz, 2 H) 3.90-4.02 (m, 2 H) 4.48 (s, 2 H) 4.84-5.03 (m, 1 H) 6.27 (br. s., 1 H) 6.41 (dd, J = 3.28, 1.77 Hz, 1 H) 6.49 (d, J = 3.28 Hz, 1 H) 6.89 (s, 1 H) 7.28 (s, 1 H) 7.40 (d, J = 1.77 Hz, 1 H) |
| 142 | 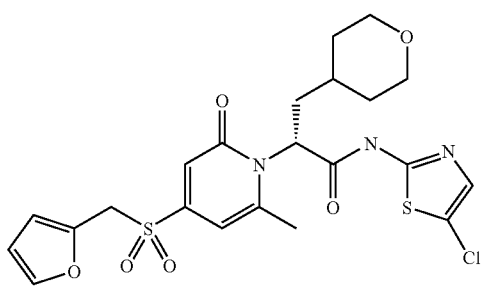<br>(R)-N-(5-chlorothiazol-2-yl)-2-(4-(furan-2-ylmethylsulfonyl)-6-methyl-2-oxopyridin-1(2H)-yl)-3-(tetrahydro-2H-pyran-4-yl)propanamide | C | calc'd for $C_{22}H_{24}ClN_3O_6S_2$, 527; found, 527 | $^1$H NMR (400 MHz, CHLOROFORM-d) δ ppm 1.27-1.44 (m, 2 H) 1.44-1.55 (m, 1 H) 1.63 (br. s., 3 H) 2.38-2.60 (m, 4 H) 3.26-3.41 (m, J = 11.81, 11.81, 7.07, 1.89 Hz, 2 H) 3.90-4.02 (m, 2 H) 4.48 (s, 2 H) 4.84-5.03 (m, 1 H) 6.27 (br. s., 1 H) 6.41 (dd, J = 3.28, 1.77 Hz, 1 H) 6.49 (d, J = 3.28 Hz, 1 H) 6.89 (s, 1 H) 7.28 (s, 1 H) 7.40 (d, J = 1.77 Hz, 1 H) |

TABLE 1-continued

| Ex. | Structure | Method | LCMS ([M + H]) | NMR data |
|---|---|---|---|---|
| 143 | 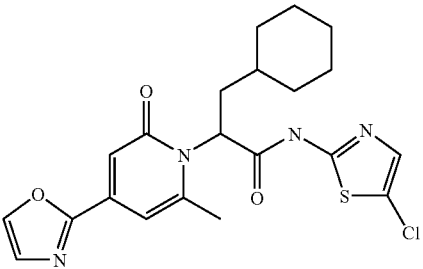<br>N-(5-chlorothiazol-2-yl)-3-cyclohexyl-2-(6-methyl-4-(oxazol-2-yl)-2-oxopyridin-1(2H)-yl)propanamide | F | calc'd for $C_{21}H_{23}ClN_4O_3S$ 447.12; found 447.10 | $^1$H NMR (400 MHz, d-DMSO) δ 0.87-0.97 (m, 2 H), 1.1-1.22 (m, 5 H), 1.53-1.81 (m, 6 H), 1.98-2.11 (m, 1 H), 2.44 (m, 1 H), 2.51 (s, 3 H), 6.71 (s, 1 H), 6.77 (s, 1 H), 7.47 (s, 1 H), 7.51 (s, 3 H), 8.36 (s, 1 H), |
| 144 | 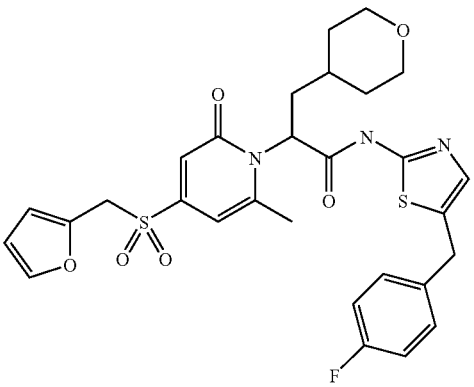<br>N-(5-(4-fluorobenzyl)thiazol-2-yl)-2-(4-(furan-2-ylmethylsulfonyl)-6-methyl-2-oxopyridin-1(2H)-yl)-3-(tetrahydro-2H-pyran-4-yl)propanamide | C | calc'd for $C_{29}H_{30}FN_3O_6S_2$, 600; found, 600 | $^1$H NMR (400 MHz, CHLOROFORM-d) δ ppm 1.23-1.43 (m, 2 H) 1.45-1.80 (m, 4 H) 2.33-2.61 (m, 4 H) 3.27-3.40 (m, 2 H) 3.94 (dd, J = 11.49, 3.66 Hz, 2 H) 4.04 (s, 2 H) 4.46 (s, 2 H) 4.80-4.97 (m, 1 H) 6.25 (br. s., 1 H) 6.37-6.43 (m, 1 H) 6.48 (d, J = 3.28 Hz, 1 H) 6.87 (br. s., 1 H) 6.94-7.04 (m, 2 H) 7.14 (s, 1 H) 7.15-7.23 (m, 2 H) 7.41 (s, 1 H) |
| 145 | 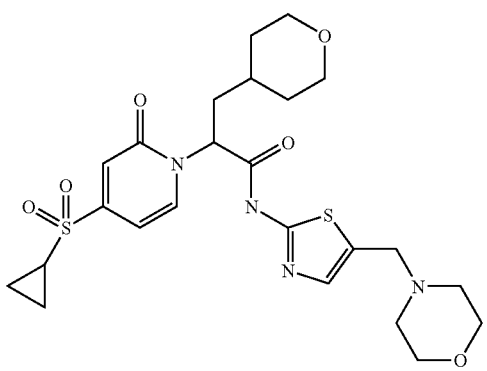<br>2-(4-(cyclopropylsulfonyl)-2-oxopyridin-1(2H)-yl)-N-(5-(morpholinomethyl)thiazol-2-yl)-3-(tetrahydro-2H-pyran-4-yl)propanamide | E | calc'd for $C_{24}H_{33}N_4O_6S_2$ 537.18; found 537 | 1H NMR (400 MHz, MeOD) δ ppm 1.20 (d, J = 7.83 Hz, 1 H) 1.27-1.50 (m, 5 H) 1.58-1.78 (m, 2 H) 2.13 (t, J = 6.57 Hz, 1 H) 2.74 (dd, J = 12.63, 3.03 Hz, 1 H) 3.17-3.42 (m, 4 H) 3.33 (d, J = 1.77 Hz, 6 H) 3.79-4.03 (m, 5 H) 4.53 (s, 2 H) 6.00 (dd, J = 9.35, 6.32 Hz, 1 H) 6.81 (dd, J = 7.33, 2.02 Hz, 1 H) 7.05 (d, J = 1.77 Hz, 1 H) 7.63 (s, 1 H) 8.05 (d, J = 7.33 Hz, 1 H) |

TABLE 1-continued

| Ex. | Structure | Method | LCMS ([M + H]) | NMR data |
|---|---|---|---|---|
| 146 | N-(5-chlorothiazol-2-yl)-2-(2-oxo-4-(2,2,2-trifluoroethylsulfonyl)pyridin-1(2H)-yl)-3-(tetrahydro-2H-pyran-4-yl)propanamide | E | calc'd for $C_{18}H_{20}ClF_3N_3O_5S_2$ 514.04; found 514.1 | 1H NMR (400 MHz, d-CDCl$_3$) δ ppm 1.36 (d, J = 15.92 Hz, 2 H) 1.55-1.74 (m, 4 H) 1.93 (d, J = 6.32 Hz, 1 H) 2.21 (d, J = 6.57 Hz, 1 H) 3.24-3.37 (m, 3 H) 3.88-3.96 (m, 2 H) 6.19-6.29 (m, 1 H) 6.76 (d, 1 H) 7.34 (s, 1 H) 7.94 (s, 1 H) 8.07 (d, J = 7.33 Hz, 1 H) |
| 147 | 2-(4-(cyclopropylsulfonyl)-2-oxopyridin-1(2H)-yl)-N-(5-((4-methylpiperazin-1-yl)methyl)thiazol-2-yl)-3-(tetrahydro-2H-pyran-4-yl)propanamide | E | calc'd for $C_{25}H_{36}N_5O_5S_2$ 550.21; found 550 | 1H NMR (400 MHz, MeOD) δ ppm 1.21 (d, J = 8.59 Hz, 2 H) 1.38 (d, J = 4.80 Hz, 4 H) 1.36 (br. s., 1 H) 1.57-1.78 (m, 2 H) 2.05 (br. s., 1 H) 2.11 (br. s., 1 H) 2.50-2.60 (m, 3H) 2.79-2.97 (m, 4 H) 3.26-3.42 (m, 6 H) 3.81 (s, 2 H) 3.95 (d, J = 11.62 Hz, 2 H) 4.51 (br. s., 2 H) 6.01 (dd, J = 9.73, 5.94 Hz, 1 H) 6.75 (d, J = 7.33 Hz, 1 H) 7.09 (s, 1 H) 7.32 (s, 1 H) 7.96 (d, J = 7.33 Hz, 1 H) |
| 148 | (R)-N-(5-chlorothiazol-2-yl)-2-(2-oxo-4-(2,2,2-trifluoroethylsulfonyl)pyridin-1(2H)-yl)-3-(tetrahydro-2H-pyran-4-yl)propanamide | E | calc'd for $C_{18}H_{20}ClF_3N_3O_5S_2$ 514.04; found 514.1 | |
| 149 | (S)-N-(5-chlorothiazol-2-yl)-2-(2-oxo-4-(2,2,2-trifluoroethylsulfonyl)pyridin-1(2H)-yl)-3-(tetrahydro-2H-pyran-4-yl)propanamide | E | calc'd for $C_{18}H_{20}ClF_3N_3O_5S_2$ 514.04; found 514.1 | |

TABLE 1-continued

| Ex. | Structure | Method | LCMS ([M + H]) | NMR data |
|---|---|---|---|---|
| 150 | 2-(4-(cyclopropylsulfonyl)-2-oxopyridin-1(2H)-yl)-N-(5-((4-(2-(dimethylamino)-2-oxoethyl)piperazin-1-yl)methyl)thiazol-2-yl)-3-(tetrahydro-2H-pyran-4-yl)propanamide | E | calc'd for $C_{28}H_{41}N_6O_6S_2$ 621.25; found 621 | 1H NMR (400 MHz, CHLOROFORM-d) δ ppm 1.19 (d, J = 7.83 Hz, 2 H) 1.39 (dd, J = 10.23, 7.45 Hz, 3 H) 1.27-1.50 (m, 2 H) 1.65 (d, J = 9.85 Hz, 1 H) 1.72 (d, J = 10.11 Hz, 1 H) 1.84-2.08 (m, 1 H) 2.08-2.31 (m, 1 H) 2.58 (dd, J = 12.63, 3.28 Hz, 1 H) 2.98 (d, J = 5.31 Hz, 6 H) 3.01-3.09 (m, 4 H) 3.28-3.42 (m, 6 H) 3.87-4.00 (m, 4 H) 4.04 (s, 2 H) 4.09-4.23 (m, 1 H) 6.00 (dd, J = 9.47, 6.19 Hz, 1 H) 6.74 (dd, J = 7.33, 2.02 Hz, 1 H) 7.12 (d, J = 2.02 Hz, 1 H) 7.42 (s, 1 H) 7.93 (d, J = 7.33 Hz, 1 H) |
| 151 | (S)-2-(4-(cyclopentylsulfonyl)-5,6-dimethyl-2-oxopyridin-1(2H)-yl)-N-(5-fluorothiazol-2-yl)-3-(tetrahydro-2H-pyran-4-yl)propanamide | J | calc'd for $C_{23}H_{30}FN_3O_5S_2$ 512.16; found 512.10 | $^1$H NMR (400 MHz, d-CDCl$_3$) δ 1.32-1.45 (m, 2 H), 1.64-2.04 (m, 12 H), 2.12-2.20 (m, 1 H), 2.47 (s, 3 H), 2.53 (s, 3 H), 3.35 (m, 2 H), 3.60 (m, 1 H), 3.94 (m, 2 H), 5.67 (dd, J = 4, 8 Hz, 1 H), 7.04 (d, J = 3 Hz, 1 H), 7.33 (s, 1 H) |
| 152 | 2-(4-(cyclopropylsulfonyl)-6-methyl-2-oxopyridin-1(2H)-yl)-N-(5-fluorothiazol-2-yl)-3-(tetrahydro-2H-pyran-4-yl)propanamide | C | calc'd for $C_{20}H_{25}FN_3O_5S_2$ 470.11; found 470 | 1H NMR (400 MHz, CHLOROFORM-d) δ ppm 1.17 (dd, J = 7.83, 2.02 Hz, 2 H) 1.35-1.48 (m, 4 H) 1.53-1.78 (m, 3 H) 2.45-2.57 (m, 4 H) 2.58-2.69 (m, 1 H) 3.32-3.47 (m, 1 H) 3.39 (s, 3 H) 3.96 (dd, J = 11.49, 2.40 Hz, 2 H) 6.52 (s, 1 H) 6.97 (s, 1 H) 7.00 (d, J = 2.53 Hz, 1 H) |

TABLE 1-continued

| Ex. | Structure | Method | LCMS ([M + H]) | NMR data |
|---|---|---|---|---|
| 153 | (R)-2-(4-(cyclopentylsulfonyl)-5,6-dimethyl-2-oxopyridin-1(2H)-yl)-N-(5-fluorothiazol-2-yl)-3-(tetrahydro-2H-pyran-4-yl)propanamide | J | calc'd for $C_{23}H_{30}FN_3O_5S_2$ 512.16; found 512.10 | |
| 154 | (R)-2-(3-amino-4-(cyclopropylsulfonyl)-6-methyl-2-oxopyridin-1(2H)-yl)-3-cyclopentyl-N-(5-fluorothiazol-2-yl)propanamide | G | calc'd for $C_{20}H_{25}FN_4O_4S_2$ 469.13; found 469.10 | $^1$H NMR (400 MHz, CDCl$_3$) δ 1.04-1.80 (m, 15 H), 2.39 (s, 3 H), 2.46 (m, 1 H), 2.61 (m, 1 H), 4.85 (bs, 1 H), 5.90 bs, 2 H), 6.29 (s, 1 H), 7.02 (d, J = 3 Hz, 1 H) |
| 155 | (S)-2-(3-amino-4-(cyclopropylsulfonyl)-6-methyl-2-oxopyridin-1(2H)-yl)-3-cyclopentyl-N-(5-fluorothiazol-2-yl)propanamide | G | calc'd for $C_{20}H_{25}FN_4O_4S_2$ 469.13; found 469.10 | |

TABLE 1-continued

| Ex. | Structure | Method | LCMS ([M + H]) | NMR data |
|---|---|---|---|---|
| 156 | 2-(5-acetamido-2-oxopyridin-1(2H)-yl)-N-(5-chlorothiazol-2-yl)-3-(tetrahydro-2H-pyran-4-yl)propanamide | E | calc'd for $C_{18}H_{22}ClN_4O_4S$ 425.10; found 424.91 | $^1$H NMR (400 MHz, MeOD) δ ppm 1.31-1.40 (m, 3 H) 1.71 (dd, 2 H) 1.99-2.24 (m, 5 H) 3.24-3.46 (m, 2 H) 3.85-4.01 (m, 2 H) 5.91 (dd, J = 10.36, 5.31 Hz, 1 H) 6.58 (d, J = 9.60 Hz, 1 H) 7.33 (s, 1 H) 7.54 (dd, J = 9.60, 2.27 Hz, 1 H) 8.35 (d, J = 2.02 Hz, 1 H) |
| 157 | N-(5-chlorothiazol-2-yl)-2-(4-(cyclopropylsulfonyl)-6-methyl-2-oxopyridin-1(2H)-yl)-3-(tetrahydro-2H-pyran-4-yl)propanamide | C | calc'd for $C_{20}H_{25}ClN_3O_5S_2$ 486.08; found 486 | 1H NMR (400 MHz, CHLOROFORM-d) δ ppm 1.10-1.22 (m, 2 H) 1.29-1.46 (m, 4 H) 1.59-1.88 (m, 2 H) 2.36-2.61 (m, 4 H) 2.66 (d, J = 3.79 Hz, 1 H) 3.40 (td, J = 11.24, 5.81 Hz, 2 H) 3.97 (d, J = 11.12 Hz, 5 H) 6.53 (br. s., 1 H) 6.95 (br. s., 1 H) 7.24 (s, 1 H) |
| 158 | N-(5-chlorothiazol-2-yl)-2-(4-(3-fluorophenylsulfonyl)-6-methyl-2-oxopyridin-1(2H)-yl)-3-(tetrahydro-2H-pyran-4-yl)propanamide | C | calc'd for $C_{23}H_{24}ClFN_3O_5S_2$ 540.08; found 540 | 1H NMR (400 MHz, CHLOROFORM-d) δ ppm 1.34 (t, J = 12.51 Hz, 2 H) 1.67 (br. s., 4 H) 2.50 (s, 3 H) 2.72 (br. s., 1 H) 3.29-3.44 (m, 3 H) 3.95 (br. s., 2 H) 6.50 (s, 1 H) 6.94 (s, 1 H) 7.23 (s, 1 H) 7.38 (td, J = 8.21, 2.27 Hz, 1 H) 7.57 (td, J = 7.96, 5.31 Hz, 1 H) 7.65 (d, J = 7.58 Hz, 1 H) 7.73 (d, J = 7.83 Hz, 1H) |

TABLE 1-continued

| Ex. | Structure | Method | LCMS ([M + H]) | NMR data |
|---|---|---|---|---|
| 159 | 2-(4-(3-fluorophenylsulfonyl)-6-methyl-2-oxopyridin-1(2H)-yl)-N-(5-fluorothiazol-2-yl)-3-(tetrahydro-2H-pyran-4-yl)propanamide | C | calc'd for $C_{23}H_{24}F_2N_3O_5S_2$ 524.10; found 524 | $^1$H NMR (400 MHz, CHLOROFORM-d) δ ppm 1.34 (br. s., 2 H) 1.63 (d, J = 11.87 Hz, 4 H) 2.47 (br. s., 2 H) 2.61 (br. s. 1 H) 3.32-3.43 (m, 4 H) 3.95 (d, J = 11.12 Hz, 2 H) 6.47 (s, 1 H) 6.98 (br. s., 1 H) 7.34-7.47 (m, 3 H) 7.53-7.73 (m, 1 H) 7.76-7.80 (m, 1 H) |
| 160 | N-(5-chlorothiazol-2-yl)-2-(4-(1,1-dioxotetrahydrothiopyran-4-ylsulfonyl)-6-methyl-2-oxopyridin-1(2H)-yl)-3-cyclohexylpropanamide | L | calc'd for $C_{23}H_{30}ClN_3O_6S_3$ 577.15; found 577 | $^1$H NMR (400 MHz, MeOD). δ ppm 1.03 (m, 2 H) 1.24 (m, 3 H) 1.40 (m, 1 H) 1.73 (m, 5 H) 1.89 (m, 1 H) 2.27 (m, 2 H) 2.52 (m, 3 H) 2.60 (s, 3 H) 3.22 (m, 4 H) 3.61 (m, 1 H) 5.32 (m, 1 H) 6.69 (s, 1 H) 6.86 (s, 1 H) 7.29 (s, 1 H) |
| 161 | N-(5-fluorothiazol-2-yl)-2-(4-(1,1-dioxotetrahydrothiopyran-4-ylsulfonyl)-6-methyl-2-oxopyridin-1(2H)-yl)-3-cyclohexylpropanamide | L | calc'd for $C_{23}H_{30}FN_3O_6S_3$ 560.70; found 5607.06 (s, 1 H) | $^1$H NMR (400 MHz, MeOD). δ ppm 1.03 (m, 2 H) 1.24 (m, 3 H) 1.43 (m, 1 H) 1.72 (m, 5 H) 1.90 (m, 1 H) 2.29 (m, 2 H) 2.50 9m, 3 H) 2.60 (s, 3 H) 3.22 (m, 4 H) 3.61 (m, 1 H) 5.31 (m, 1 H) 6.69 (s, 1 H) 6.86 (s, 1 H) 7.06 (s, 1 H) |
| 162 | (S)-3-cyclopentyl-2-(4-(cyclopropylsulfonyl)-6-methyl-2-oxopyridin-1(2H)-yl)-N-(5-fluorothiazol-2-yl)propanamide | D | calc'd for $C_{20}H_{24}FN_3O_4S_2$ 454.12; found 454.10 | $^1$H NMR (400 MHz, CDCl$_3$) δ 1.07-1.80 (m, 14 H), 2.45 (m, 1 H), 2.50 (m, 1 H), 2.55 (s, 3 H), 4.89 (bs, 1 H), 6.50 (s, 1 H), 6.97 (s, 1 H), 7.01 (d, J = 4 Hz, 1 H) |

TABLE 1-continued

| Ex. | Structure | Method | LCMS ([M + H]) | NMR data |
|---|---|---|---|---|
| 163 | (R)-3-cyclopentyl-2-(4-(cyclopropylsulfonyl)-6-methyl-2-oxopyridin-1(2H)-yl)-N-(5-fluorothiazol-2-yl)propanamide | D | calc'd for $C_{20}H_{24}FN_3O_4S_2$ 454.12; found 454.10 | |
| 164 | (R)-2-(4-(cyclopentylsulfonyl)-6-methyl-2-oxopyridin-1(2H)-yl)-N-(5-fluoropyridin-2-yl)-3-(tetrahydro-2H-pyran-4-yl)propanamide | D | calc'd for $C_{24}H_{30}FN_3O_5S$ 492.19; found 492.10 | $^1$H NMR (400 MHz, d-CDCl$_3$) δ 1.26-2.14 (m, 14 H), 2.54 (s, 3 H), 2.55 (m, 1 H), 3.36 (m, 2 H), 3.50 (m, 1 H), 3.95 (m, 2 H), 4.90 (bs, 1 H), 6.49 (s, 1 H), 7.03 (s, 1 H), 7.44 (m, 1 H), 8.14 (s, 1 H), 8.17 (m, 1 H) |
| 165 | (S)-2-(4-(cyclopentylsulfonyl)-6-methyl-2-oxopyridin-1(2H)-yl)-N-(5-fluoropyridin-2-yl)-3-(tetrahydro-2H-pyran-4-yl)propanamide | D | calc'd for $C_{24}H_{30}FN_3O_5S$ 492.19; found 492.10 | |
| 166 | (S)-N-(5-chloropyridin-2-yl)-2-(4-(cyclopentylsulfonyl)-6-methyl-2-oxopyridin-1(2H)-yl)-3-(tetrahydro-2H-pyran-4-yl)propanamide | D | calc'd for $C_{24}H_{30}ClN_3O_5S$ 508.16; found 508.10 | $^1$H NMR (400 MHz, d-CDCl$_3$) δ 1.33-2.12 (m, 14 H), 2.55 (s, 3 H), 2.56 (m, 1 H), 3.36 (m, 2 H), 3.50 (m, 1 H), 3.96 (m, 2 H), 4.90 (bs, 1 H), 6.49 (s, 1 H), 7.03 (s, 1 H), 7.67 (dd, J = 4, 8 Hz, 1 H), 8.14 (d, J = 8 Hz, 1 H), 8.23 (d, J = 4 Hz, 1 H) |

TABLE 1-continued

| Ex. | Structure | Method | LCMS ([M + H]) | NMR data |
|---|---|---|---|---|
| 167 | 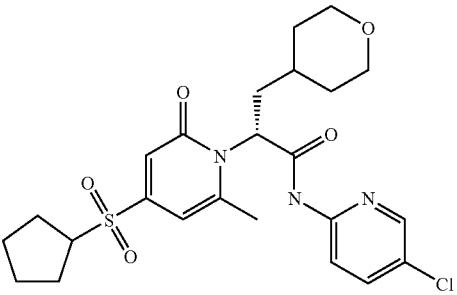<br>(R)-N-(5-chloropyridin-2-yl)-2-(4-(cyclopentylsulfonyl)-6-methyl-2-oxopyridin-1(2H)-yl)-3-(tetrahydro-2H-pyran-4-yl)propanamide | D | calc'd for $C_{24}H_{30}ClN_3O_5S$ 508.16; found 508.10 | |
| 168 | 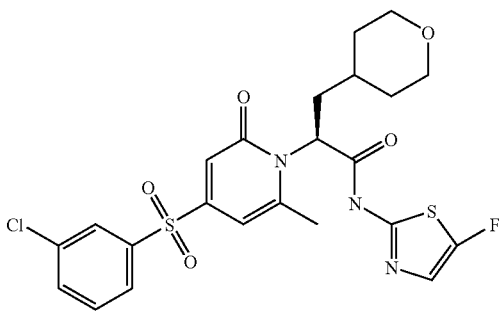<br>(S)2-(4-(3-chlorophenylsulfonyl)-6-methyl-2-oxopyridin-1(2H)-yl)-N-(5-fluorothiazol-2-yl)-3-(tetrahydro-2H-pyran-4-yl)propanamide | D | calc'd for $C_{23}H_{23}ClFN_3O_5S_2$ 540.08; found 540.0 | $^1$H NMR (400 MHz, d-CDCl$_3$) δ 1.10-1.68 (m, 7 H), 2.49 (s, 3 H), 2.62 (m, 1 H), 3.31 (m, 2 H), 3.84 (m, 2 H), 4.90 (bs, 1 H), 6.60 (s, 1 H), 6.85 (s, 1 H), 7.03 (d, J = 3 Hz, 1 H), 7.68 (t, J = 8 Hz, 1 H), 7.76 (m, 1 H), 7.96 (m, 1 H), 8.01 (d, J = 8 Hz, 1 H) |
| 169 | 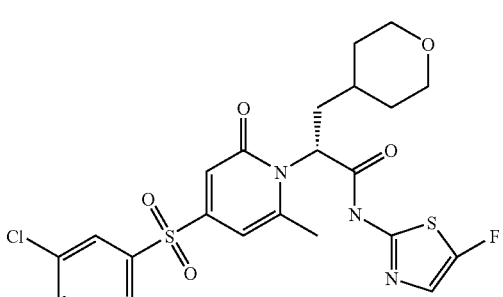<br>(R)-2-(4-(3-chlorophenylsulfonyl)-6-methyl-2-oxopyridin-1(2H)-yl)-N-(5-fluorothiazol-2-yl)-3-(tetrahydro-2H-pyran-4-yl)propanamide | D | calc'd for $C_{23}H_{23}ClFN_3O_5S_2$ 540.08; found 540.0 | |

TABLE 1-continued

| Ex. | Structure | Method | LCMS ([M + H]) | NMR data |
|---|---|---|---|---|
| 170 | (R)-3-cyclopentyl-2-(4-(cyclopropylsulfonyl)-6-methyl-2-oxopyridin-1(2H)-yl)-N-(pyrazin-2-yl)propanamide | D | calc'd for $C_{21}H_{26}N_4O_4S$ 431.17; found 431.10 | $^1$H NMR (400 MHz, CDCl$_3$) δ 1.12-1.17 (m, 4 H), 1.35-1.78 (m, 11 H), 2.49 (m, 1 H), 2.59 (s, 3 H), 4.90 (bs, 1 H), 6.51 (s, 1 H), 7.00 (s, 1 H), 8.27 (t, J = 4 Hz, 1 H), 8.36 (d, J = 4 Hz, 1 H), 9.48 (s, 1 H) |
| 171 | (S)-3-cyclopentyl-2-(4-(cyclopropylsulfonyl)-6-methyl-2-oxopyridin-1(2H)-yl)-N-(pyrazin-2-yl)propanamide | D | calc'd for $C_{21}H_{26}N_4O_4S$ 431.17; found 431.10 | |
| 172 | (S)-N-(5-chlorothiazol-2-yl)-2-(4-(cyclopropylsulfonyl)-6-methyl-2-oxopyridin-1(2H)-yl)-3-(tetrahydro-2H-pyran-4-yl)propanamide | K | calc'd for $C_{20}H_{25}ClN_3O_5S_2$ 486.08; found 486 | 1H NMR (400 MHz, CHLOROFORM-d) δ ppm 1.10-1.22 (m, 2 H) 1.29-1.46 (m, 4 H) 1.59-1.88 (m, 2 H) 2.36-2.61 (m, 4 H) 2.66 (d, J = 3.79 Hz, 1 H) 3.40 (td, J = 11.24, 5.81 Hz, 2 H) 3.97 (d, J = 11.12 Hz, 5 H) 6.53 (br. s., 1 H) 6.95 (br. s., 1 H) 7.24 (s, 1 H) |
| 173 | (R)-N-(5-chlorothiazol-2-yl)-2-(4-(cyclopropylsulfonyl)-6-methyl-2-oxopyridin-1(2H)-yl)-3-(tetrahydro-2H-pyran-4-yl)propanamide | K | calc'd for $C_{20}H_{25}ClN_3O_5S_2$ 486.08; found 486 | 1H NMR (400 MHz, CHLOROFORM-d) δ ppm 1.10-1.22 (m, 2 H) 1.29-1.46 (m, 4 H) 1.59-1.88 (m, 2 H) 2.36-2.61 (m, 4 H) 2.66 (d, J = 3.79 Hz, 1 H) 3.40 (td, J = 11.24, 5.81 Hz, 2 H) 3.97 (d, J = 11.12 Hz, 5 H) 6.53 (br. s., 1 H) 6.95 (br. s., 1 H) 7.24 (s, 1 H) |

TABLE 1-continued

| Ex. | Structure | Method | LCMS ([M + H]) | NMR data |
|---|---|---|---|---|
| 174 | N-(5-chlorothiazol-2-yl)-3-cyclopentyl-2-(6-methyl-2-oxo-4-(tetrahydro-2H-pyran-4-ylsulfonyl)pyridin-1(2H)-yl)propanamide | L | calc'd for $C_{22}H_{28}ClN_3O_5S_2$ 515.06; found 515 | $^1$H NMR (400 MHz, MeOD). δ ppm 1.04 (m, 1 H) 1.28 (m, 1 H) 1.59 (m, 5 H) 1.84 (m, 6 H) 2.12 (m, 1 H) 2.60 (m, 4 H) 3.41 (m, 2 H) 3.54 (m, 1 H) 4.03 (m, 2 H) 5.29 (m, 1 H) 6.69 (s, 1 H) 6.82 (s, 1 H) 7.29 (s, 1 H) |
| 175 | 3-cyclopentyl-N-(5-fluorothiazol-2-yl)-2-(6-methyl-2-oxo-4-(tetrahydro-2H-pyran-4-ylsulfonyl)pyridin-1(2H)-yl)propanamide | L | calc'd for $C_{22}H_{28}FN_3O_5S_2$ 498.61; found 498 | $^1$H NMR (400 MHz, MeOD). δ ppm 1.02 (m, 1 H) 1.26 (m, 1 H) 1.58 (m, 5 H) 1.83 (m, 6 H) 2.11 (m, 1 H) 2.56 (m, 4 H) 3.40 (t, J = 12, 8 Hz, 2 H) 3.52 (m, 1 H) 4.01 (m, 2 H) 5.28 (m, 1 H) 6.67 (s, 1H) 6.81 (s, 1 H) 7.05 (s, 1 H) |
| 176 | 2-(4-(cyclopentylsulfonyl)-6-methyl-2-oxopyridin-1(2H)-yl)-N-(1-methyl-1H-pyrazol-3-yl)-3-(tetrahydro-2H-pyran-4-yl)propanamide | D | calc'd for $C_{23}H_{32}N_4O_5S$ 477.21 found 477.20 | $^1$H NMR (400 MHz, d-CDCl$_3$) δ 1.26-1.43 (m, 2 H), 1.62-2.13 (m, 13 H), 2.54 (s, 3 H), 2.76 (m, 1 H), 3.39 (m, 2 H), 3.44 (m, 1 H), 3.96 (s, 3 H), 3.98 (m, 2 H), 4.80 (bs, 1 H), 6.54 (s, 1 H), 6.88 (s, 1 H), 6.95 (s, 1 H), 7.36 (d, J = 4 Hz, 1 H) |
| 177 | 2-(4-(cyclopentylsulfonyl)-6-methyl-2-oxopyridin-1(2H)-yl)-N-(pyrazin-2-yl)-3-(tetrahydro-2H-pyran-4-yl)propanamide | D | calc'd for $C_{23}H_{30}N_4O_5S$ 475.19; found 475.10 | $^1$H NMR (400 MHz, d-CDCl$_3$) δ 1.26-2.12 (m, 14 H), 2.60 (s, 3 H), 2.76 (m, 1 H), 3.44 (m, 2 H), 3.50 (m, 1 H), 4.06 (s, 2 H), 4.95 (bs, 1 H), 6.62 (s, 1 H), 7.05 (s, 1 H), 8.34 (s, 1 H), 8.47 (s, 1 H), 9.65 (s, 1 H) |

TABLE 1-continued

| Ex. | Structure | Method | LCMS ([M + H]) | NMR data |
|---|---|---|---|---|
| 178 | N-(5-chlorothiazol-2-yl)-3-cyclopentyl-2-(4-(cyclopropylsulfonyl)-6-methyl-2-oxopyridin-1(2H)-yl)propanamide | D | calc'd for $C_{20}H_{24}ClN_3O_4S_2$ 470 09; found 470.0 | $^1$H NMR (400 MHz, CDCl$_3$) δ 1.09-2.15 (m, 14 H), 2.46 (m, 1 H), 2.57 (s, 3 H), 2.62 (m, 1 H), 4.95 (bs, 1 H), 6.54 (s, 1 H), 6.91 (s, 1 H), 7.26 (s, 1 H) |
| 179 | 2-(5-chloro-4-(cyclopropylsulfonyl)-2-oxopyridin-1(2H)-yl)-N-(5-chlorothiazol-2-yl)-3-(tetrahydro-2H-pyran-4-yl)propanamide | H | calc'd for $C_{19}H_{21}Cl_2N_3O_5S_2$ 507.43; found 507 | $^1$H NMR (400 MHz, CHLOROFORM-d). δ ppm 1.21 (m, 3 H) 1.43 (m, 4 H) 1.69 (d, J = 12 Hz, 2 H) 1.93 (m, 1 H) 2.21 (m, 1 H) 2.96 (m, 1 H) 3.33 (m, 2 H) 3.92 (m, 2 H) 6.21 (t, J = 4, 8 Hz, 1 H) 7.37 (s, 1 H) 8.02 (s, 1 H) 8.04 (s, 1 H) |
| 180 | (S)-6-(3-cyclopentyl-2-(4-(cyclopropylsulfonyl)-6-methyl-2-oxopyridin-1(2H)-yl)propanamido)nicotinamide | D | calc'd for $C_{23}H_{28}N_4O_5S$ 473.18; found 473.10 | |
| 181 | (R)-6-(2-(4-(cyclopentylsulfonyl)-6-methyl-2-oxopyridin-1(2H)-yl)-3-(tetrahydro-2H-pyran-4-yl)propanamido)nicotinamide | D | calc'd for $C_{25}H_{32}N_4O_6S$ 517.20; found 517.20 | $^1$H NMR (400 MHz, CDCl$_3$) δ 1.20-2.09 (m, 14 H), 2.56 (s, 3 H), 2.59 (m, 1 H), 3.36 (m, 2 H), 3.50 (m, 1 H), 3.97 (m, 2 H), 4.95 (bs, 1 H), 6.51 (s, 1 H), 7.04 (s, 1 H), 7.96 (m, 1 H), 8.30 (d, J = 8 Hz, 1 H), 8.57 (d, J = 4 Hz, 1 H) |

TABLE 1-continued

| Ex. | Structure | Method | LCMS ([M + H]) | NMR data |
|---|---|---|---|---|
| 182 | 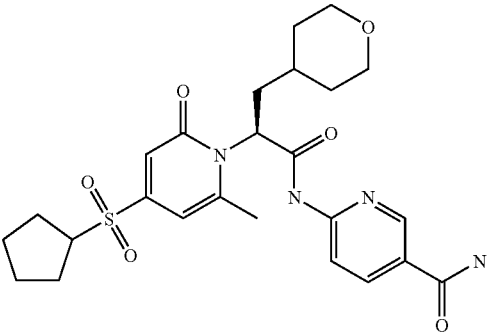 (S)-6-(2-(4-(cyclopentylsulfonyl)-6-methyl-2-oxopyridin-1(2H)-yl)-3-(tetrahydro-2H-pyran-4-yl)propanamido)nicotinamide | D | calc'd for $C_{25}H_{32}N_4O_6S$ 517.20; found 517.20 | |
| 183 | 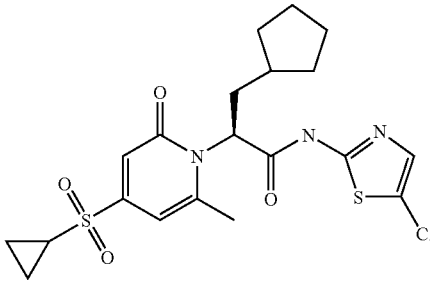 (S)-N-(5-chlorothiazol-2-yl)-3-cyclopentyl-2-(4-(cyclopropylsulfonyl)-6-methyl-2-oxopyridin-1(2H)-yl)propanamide | D | calc'd for $C_{20}H_{24}ClN_3O_4S_2$ 470.09; found 470.0 | |
| 184 | 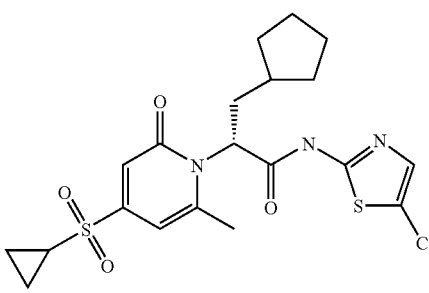 (R)-N-(5-chlorothiazol-2-yl)-3-cyclopentyl-2-(4-(cyclopropylsulfonyl)-6-methyl-2-oxopyridin-1(2H)-yl)propanamide | D | calc'd for $C_{20}H_{24}ClN_3O_4S_2$ 470.09; found 470.0 | |

TABLE 1-continued

| Ex. | Structure | Method | LCMS ([M + H]) | NMR data |
|---|---|---|---|---|
| 185 | 2-(5-chloro-4-(cyclopentylsulfonyl)-2-oxopyridin-1(2H)-yl)-N-(5-chlorothiazol-2-yl)-3-(tetrahydro-2H-pyran-4-yl)propanamide | H | calc'd for $C_{21}H_{25}Cl_2N_3O_5S_2$ 535.48; found 535 | $^1$H NMR (400 MHz, CHLOROFORM-d). δ ppm 1.39 (m, 3 H) 1.86 (m, 10 H) 2.22 ((m, 2 H) 3.33 (m, 2 H) 3.95 (m, 3 H) 6.22 (t, J = 4, 8 Hz, 1 H) 7.37 (s, 1 H) 8.04 (s, 1 H) 8.16 (s, 1 H |
| 186 | 2-(5-chloro-4-(cyclopentylsulfonyl)-2-oxopyridin-1(2H)-yl)-N-(5-fluorothiazol-2-yl)-3-(tetrahydro-2H-pyran-4-yl)propanamide | H | calc'd for $C_{21}H_{25}ClFN_3O_5S_2$ 519.02; found 519 | $^1$H NMR (400 MHz, CHLOROFORM-d). δ ppm 1.39 (m, 5 H) 1.69 (m, 3 H) 1.95 (m, 5 H) 2.19 (m, 2 H) 3.39 (m, 2 H) 4.00 (m, 3 H) 5.94 (t, J = 8, 8 Hz, 1 H) 7.14 (d, J = 4 Hz, 1 H) 7.70 (s, 1 H) 7.80 (s, 1 H) |
| 187 | (S)-N-(5-chlorothiazol-2-yl)-2-(4-(1,1-dioxotetrahydrothiopyran-4-ylsulfonyl)-6-methyl-2-oxopyridin-1(2H)-yl)-3-cyclohexyipropanamide | L | calc'd for $C_{23}H_{30}ClN_3O_6S_3$ 577.15; found 577 | $^1$H NMR (400 MHz, MeOD). δ ppm 1.03 (m, 2 H) 1.24 (3 H) 1.40 (m, 1 H) 1.73 (m, 5 H) 1.89 (m, 1 H) 2.27 (m, 2 H) 2.52 (m, 3 H) 2.60 (s, 3 H) 3.22 (m, 4 H) 3.61 (m, 1 H) 5.32 (m, 1 H) 6.69 (s, 1 H) 6.86 (s, 1 H) 7.29 (s, 1 H) |
| 188 | (R)-N-(5-chlorothiazol-2-yl)-2-(4-(1,1-dioxotetrahydrothiopyran-4-ylsulfonyl)-6-methyl-2-oxopyridin-1(2H)-yl)-3-cyclohexylpropanamide | L | calc'd for $C_{23}H_{30}ClN_3O_6S_3$ 577.15; found 577 | $^1$H NMR (400 MHz, MeOD). δ ppm 1.03 (m, 2 H) 1.24 (3 H) 1.40 (m, 1 H) 1.73 (m, 5 H) 1.89 (m, 1 H) 2.27 (m, 2 H) 2.52 (m, 3 H) 2.60 (s, 3 H) 3.22 (m, 4 H) 3.61 (m, 1 H) 5.32 (m, 1 H) 6.69 (s, 1 H) 6.86 (s, 1 H) 7.29 (s, 1 H) |

TABLE 1-continued

| Ex. | Structure | Method | LCMS ([M + H]) | NMR data |
|---|---|---|---|---|
| 189 | 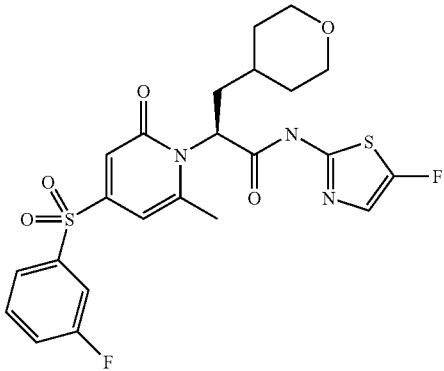<br>(S)-2-(4-(3-fluorophenylsulfonyl)-6-methyl-2-oxopyridin-1(2H)-yl)-N-(5-fluorothiazol-2-yl)-3-(tetrahydro-2H-pyran-4-yl)propanamide | K | calc'd for $C_{23}H_{24}F_2N_3O_5S_2$ 524.10; found 524 | $^1$H NMR (400 MHz, CHLOROFORM-d) δ ppm 1.34 (br. s., 2 H) 1.63 (d, J = 11.87 Hz, 4 H) 2.47 (br. s., 2 H) 2.61 (br. s., 1 H) 3.32-3.43 (m, 4 H) 3.95 (d, J = 11.12 Hz, 2 H) 6.47 (s, 1 H) 6.98 (br. s., 1 H) 7.34-7.47 (m, 3 H) 7.53-7.73 (m, 1 H) 7.76-7.80 (m, 1 H) |
| 190 | 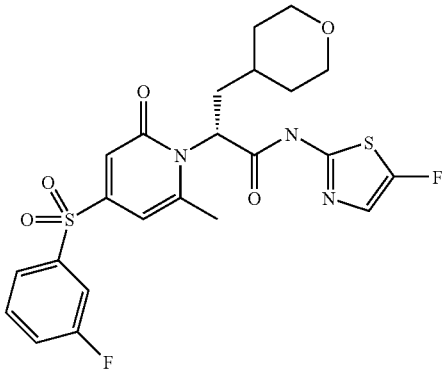<br>(R)-2-(4-(3-fluorophenylsulfonyl)-6-methyl-2-oxopyridin-1(2H)-yl)-N-(5-fluorothiazol-2-yl)-3-(tetrahydro-2H-pyran-4-yl)propanamide | K | calc'd for $C_{23}H_{24}F_2N_3O_5S_2$ 524.10; found 524 | $^1$H NMR (400 MHz, CHLOROFORM-d) δ ppm 1.34 (br. s., 2 H) 1.63 (d, J = 11.87 Hz, 4 H) 2.47 (br. s., 2 H) 2.61 (br. s., 1 H) 3.32-3.43 (m, 4 H) 3.95 (d, J = 11.12 Hz, 2 H) 6.47 (s, 1 H) 6.98 (br. s., 1 H) 7.34-7.47 (m, 3 H) 7.53-7.73 (m, 1 H) 7.76-7.80 (m, 1 H) |
| 191 | 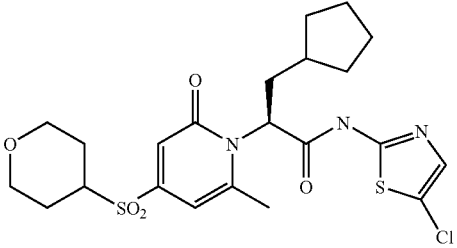<br>(S)-N-(5-chlorothiazol-2-yl)-3-cyclopentyl-2-(6-methyl-2-oxo-4-(tetrahydro-2H-pyran-4-ylsulfonyl)pyridin-1(2H)-yl)propanamide | L | calc'd for $C_{22}H_{28}ClN_3O_5S_2$ 515.06; found 515 | $^1$H NMR (400 MHz, MeOD). δ ppm 1.04 (m, 1 H) 1.28 (m, 1 H) 1.59 (m, 5 H) 1.84 (m, 6 H) 2.12 (m, 1 H) 2.60 (m, 4 H) 3.41 (m, 2 H) 3.54 (m, 1 H) 4.03 (m, 2 H) 5.29 (m, 1 H) 6.69 (s, 1 H) 6.82 (s, 1 H) 7.29 (s, 1 H) |

TABLE 1-continued

| Ex. | Structure | Method | LCMS ([M + H]) | NMR data |
|---|---|---|---|---|
| 192 | (R)-N-(5-chlorothiazol-2-yl)-3-cyclopentyl-2-(6-methyl-2-oxo-4-(tetrahydro-2H-pyran-4-ylsulfonyl)pyridin-1(2H)-yl)propanamide | L | calc'd for $C_{22}H_{28}ClN_3O_5S_2$ 515.06; found 515 | |
| 193 | (S)-3-cyclopentyl-N-(5-fluorothiazol-2-yl)-2-(6-methyl-2-oxo-4-(tetrahydro-2H-pyran-4-ylsulfonyl)pyridin-1(2H)-yl)propanamide | L | calc'd for $C_{22}H_{28}FN_3O_5S_2$ 498.61; found 498 | $^1$H NMR (400 MHz, MeOD). δ ppm 1.02 (m, 1 H) 1.26 (m, 1 H) 1.58 (m, 5 H) 1.83 (m, 6 H) 2.11 (m, 1 H) 2.56 (m, 4 H) 3.40 (t, J = 12, 8 Hz, 2 H) 3.52 (m, 1 H) 4.01 (m, 2 H) 5.28 (m, 1 H) 6.67 (s, 1 H) 6.81 (s, 1 H) 7.05 (s, 1 H) |
| 194 | (R)-3-cyclopentyl-N-(5-fluorothiazol-2-yl)-2-(6-methyl-2-oxo-4-(tetrahydro-2H-pyran-4-ylsulfonyl)pyridin-1(2H)-yl)propanamide | L | calc'd for $C_{22}H_{28}FN_3O_5S_2$ 498.61; found 498 | |
| 195 | (R)-2-(5-chloro-4-(cyclopropylsulfonyl)-2-oxopyridin-1(2H)-yl)-N-(5-chlorothiazol-2-yl)-3-(tetrahydro-2H-pyran-4-yl)propanamide | H | calc'd for $C_{19}H_{21}Cl_2N_3O_5S_2$ 507.43; found 507 | |

TABLE 1-continued

| Ex. | Structure | Method | LCMS ([M + H]) | NMR data |
|---|---|---|---|---|
| 196 | (S)-2-(5-chloro-4-(cyclopropylsulfonyl)-2-oxopyridin-1(2H)-yl)-N-(5-chlorothiazol-2-yl)-3-(tetrahydro-2H-pyran-4-yl)propanamide | H | calc'd for $C_{19}H_{21}Cl_2N_3O_5S_2$ 507.43; found 507 | $^1$H NMR (400 MHz, CHLOROFORM-d). δ ppm 1.21 (m, 3 H) 1.43 (m, 4 H) 1.69 (d, J = 12 Hz, 2 H) 1.93 (m, 1 H) 2.21 (m, 1 H) 2.96 (m, 1 H) 3.33 (m, 2 H) 3.92 (m, 2 H) 6.21 (t, J = 4, 8 Hz, 1 H) 7.37 (s, 1 H) 8.02 (s, 1 H) 8.04 (s, 1 H) |
| 197 | (R)-2-(5-chloro-4-(cyclopropylsulfonyl)-2-oxopyridin-1(2H)-yl)-N-(5-fluorothiazol-2-yl)-3-(tetrahydro-2H-pyran-4-yl)propanamide | H | calc'd for $C_{19}H_{21}ClFN_3O_5S_2$ 489.97; found 490.0 | |
| 198 | (S)-2-(5-chloro-4-(cyclopropylsulfonyl)-2-oxopyridin-1(2H)-yl)-N-(5-fluorothiazol-2-yl)-3-(tetrahydro-2H-pyran-4-yl)propanamide | H | calc'd for $C_{19}H_{21}ClFN_3O_5S_2$ 489.97; found 490.0 | $^1$H NMR (400 MHz, CHLOROFORM-d). δ ppm 1.21 (m, 3 H) 1.39 (m, 4H) 1.69 (d, J = 12 Hz, 2 H) 1.92 (m, 1 H) 2.20 (m, 1 H) 2.96 (m, 1 H) 3.33 (m, 2 H) 3.92 (m, 2 H) 6.18 (t, J = 8, 4 Hz, 1 H) 7.13 (s, 1 H) 7.96 (s, 1 H) 8.02 (s, 1 H) |
| 199 | 3-cyclohexyl-2-(1-oxoisoquinolin-2(1H)-yl)-N-(thiazol-2-yl)propanamide | J | calc'd for $C_{21}H_{24}N_3O_2S$ 382.15; found 282.0 | $^1$H NMR (400 MHz, CHLOROFORM-d) δ ppm 0.82-1.00 (m, 2 H) 1.01-1.14 (m, 3 H) 1.50-1.64 (m, 1 H) 1.69 (d, J = 12.63 Hz, 1 H) 1.77 (d, J = 12.63 Hz, 1 H) 1.92-2.04 (m, 1 H) 2.14 (ddd, J = 14.21, 7.58, 7.26 Hz, 1 H) 6.15 (t, J = 7.83 Hz, 1 H) 6.63 (d, J = 8.59 Hz, 1 H) 7.02 (d, J = 5.56 Hz, 1 H) 7.43 (d, J = 7.58 Hz, 1 H) 7.48-7.56 (m, 2 H) 7.67 (t, J = 7.45 Hz, 1 H) 7.75 (d, J = 4.29 Hz, 1 H) 8.48 (d, J = 8.08 Hz, 1 H) 11.89 (br. s., 1 H) |

TABLE 1-continued

| Ex. | Structure | Method | LCMS ([M + H]) | NMR data |
|---|---|---|---|---|
| 200 | 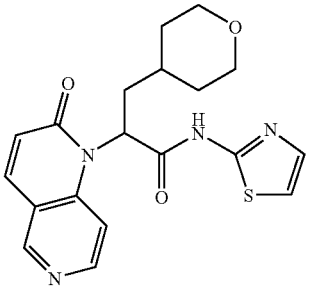<br>2-(2-oxo-1,6-naphthyridin-1(2H)-yl)-3-(tetrahydro-2H-pyran-4-yl)-N-(thiazol-2-yl)propanamide | J | calc'd for $C_{19}H_{21}N_4O_3S$ 385.13; found 385.26 | $^1$H NMR (400 MHz, CHLOROFORM-d) δ ppm 1.34 (td, J = 12.38, 4.29 Hz, 2 H) 1.59-1.70 (m, 2 H) 1.76-1.87 (m, 1 H) 1.87-1.93 (m, 1 H) 2.03-2.16 (m, 1 H) 3.21-3.39 (m, 4 H) 5.77 (dd, J = 9.60, 3.79 Hz, 1 H) 6.93 (d, J = 3.54 Hz, 1 H) 7.33-7.41 (m, 2 H) 7.88 (d, J = 6.82 Hz, 1 H) 8.38-8.51 (m, 2 H) 9.32 (s, 1 H) |

Biological Testing

The activity of compounds as glucokinase activators may be assayed in vitro, in vivo or in a cell line. Provided below is an enzymatic glucokinase activity assay.

Purified glucokinase may be obtained as follows. DNA encoding residues 12-465 of the full-length sequence of the human enzyme may be amplified by PCR and cloned into the HindIII and EcoRI sites of pFLAG-CTC (Sigma). SEQ. I.D. No. 1 corresponds to residues 12-465 of glucokinase.

The expression of recombinant glucokinase protein may be carried out by transformation and growth of DH10b-T1r *E. coli* cells incorporating the (pFLAG-CTC) plasmid in LB media. Protein expression can be induced in this system by the addition of IPTG to the culture medium.

Recombinant protein may be isolated from cellular extracts by passage over Sepharose Q Fast Flow resin (Pharmacia). This partially purified GK extract may then be further purified by a second passage over Poros HQ 10 (Applied Biosystems). The purity of GK may be determined on denaturing SDS-PAGE gel. Purified GK may then be concentrated to a final concentration of 20.0 mg/ml. After flash freezing in liquid nitrogen, the proteins can be stored at −78° C. in a buffer containing 25 mM TRIS-HCl pH 7.6, 50 mM NaCl, and 0.5 mM TCEP.

It should be noted that a variety of other expression systems and hosts are also suitable for the expression of glucokinase, as would be readily appreciated by one of skill in the art.

The activation properties of compounds for GK may be determined using a black 384-well-plate format under the following reaction conditions: 25 mM Hepes pH 7.2, 25 mM NaCl, 10 mM $MgCl_2$, 0.01% Brij35, 1 mM DTT, 5 μM ATP, 5 mM Glucose 2% DMSO. The amount of ATP consumed may be determined quantitatively by addition of equal volume of luciferase reagent (luciferase+beetle luciferin—KinaseGlo Luminescent Kinase Assay kit from Promega). The luminescence intensity may be measured by using the Analyst HT from LJL Biosystems.

The assay reaction may be initiated as follows: 4 μl of substrate mixture (12.5 μM ATP and 12.5 mM Glucose) was added to each well of the plate, followed by the addition of 2 μl of activator (2 fold serial dilutions for 11 data points for each activator) containing 10% DMSO. 4 μL of 1.25 nM GK solution may be added to initiate the reaction. The reaction mixture may then be incubated at room temperature for 60 min, and quenched and developed by addition of 10 μL of luciferase reagent. Luminescence intensities of the resulting reaction mixtures may be measured after a 10 min incubation at room temperature. The luminescence intensity may be measured by using the Analyst HT from LJL Biosystems.

$pK_{act}$ values may be calculated by non-linear curve fitting of the compound concentrations and luminescence intensities to a standard inhibition/activation equation. $K_{act}$ is the concentration that displays 50% of the maximal increase in GK activity observed using a saturating activator concentration.

$pK_{act}$ values for select compounds of the present invention are given in Table 2.

TABLE 2

$pK_{act}$ and % $ACT_{max}$ of Exemplified Compounds Against GK

| Ex. | $pK_{act}$ |
|---|---|
| 1 | <4.8 |
| 2 | <4.8 |
| 3 | 4.8-5.8 |
| 4 | 4.8-5.8 |
| 5 | >5.8 |
| 6 | >5.8 |
| 7 | <4.8 |
| 8 | >5.8 |
| 9 | <4.8 |
| 10 | <4.8 |
| 11 | >5.8 |
| 12 | 4.8-5.8 |
| 13 | >5.8 |
| 14 | >5.8 |
| 15 | <4.8 |
| 16 | 4.8-5.8 |
| 17 | <4.8 |
| 18 | 4.8-5.8 |
| 19 | 4.8-5.8 |
| 20 | <4.8 |
| 21 | <4.8 |
| 22 | <4.8 |
| 23 | 4.8-5.8 |
| 24 | <4.8 |
| 25 | >5.8 |
| 26 | <4.8 |
| 27 | <4.8 |
| 28 | <4.8 |
| 29 | <4.8 |
| 30 | >5.8 |
| 31 | <4.8 |
| 32 | >5.8 |
| 33 | 4.8-5.8 |
| 34 | >5.8 |
| 35 | >5.8 |
| 36 | <4.8 |
| 37 | 4.8-5.8 |
| 38 | >5.8 |

TABLE 2-continued pK$_{act}$ and %ACT$_{max}$ of Exemplified Compounds Against GK

| Ex. | pK$_{act}$ |
|---|---|
| 39 | <4.8 |
| 40 | >5.8 |
| 41 | <4.8 |
| 42 | >5.8 |
| 43 | 4.8-5.8 |
| 45 | >5.8 |
| 46 | >5.8 |
| 47 | <4.8 |
| 48 | 4.8-5.8 |
| 49 | >5.8 |
| 50 | >5.8 |
| 51 | <4.8 |
| 52 | 4.8-5.8 |
| 53 | <4.8 |
| 54 | >5.8 |
| 55 | 4.8-5.8 |
| 56 | <4.8 |
| 57 | 4.8-5.8 |
| 58 | <4.8 |
| 59 | >5.8 |
| 60 | >5.8 |
| 61 | <4.8 |
| 62 | 4.8-5.8 |
| 63 | <4.8 |
| 64 | 4.8-5.8 |
| 65 | <4.8 |
| 66 | <4.8 |
| 67 | <4.8 |
| 68 | >5.8 |
| 69 | <4.8 |
| 71 | <4.8 |
| 72 | 4.8-5.8 |
| 73 | <4.8 |
| 74 | 4.8-5.8 |
| 75 | 4.8-5.8 |
| 76 | >5.8 |
| 77 | >5.8 |
| 78 | 4.8-5.8 |
| 79 | <4.8 |
| 80 | 4.8-5.8 |
| 81 | >5.8 |
| 82 | >5.8 |
| 83 | >5.8 |
| 84 | <4.8 |
| 85 | >5.8 |
| 87 | <4.8 |
| 88 | 4.8-5.8 |
| 89 | >5.8 |
| 90 | <4.8 |
| 91 | <4.8 |
| 92 | <4.8 |
| 93 | <4.8 |
| 95 | 4.8-5.8 |
| 96 | <4.8 |
| 97 | <4.8 |
| 98 | 4.8-5.8 |
| 99 | <4.8 |
| 100 | 4.8-5.8 |
| 101 | <4.8 |
| 102 | <4.8 |
| 103 | <4.8 |
| 104 | <4.8 |
| 105 | <4.8 |
| 106 | <4.8 |
| 107 | <4.8 |
| 108 | <4.8 |
| 109 | <4.8 |
| 110 | <4.8 |
| 111 | <4.8 |
| 112 | <4.8 |
| 113 | <4.8 |
| 114 | 4.8-5.8 |
| 115 | <4.8 |
| 117 | <4.8 |
| 118 | >5.8 |
| 119 | 4.8-5.8 |
| 120 | <4.8 |
| 121 | 4.8-5.8 |
| 122 | 4.8-5.8 |
| 123 | >5.8 |
| 124 | <4.8 |
| 125 | <4.8 |
| 126 | <4.8 |
| 127 | 4.8-5.8 |
| 128 | >5.8 |
| 129 | 4.8-5.8 |
| 130 | 4.8-5.8 |
| 131 | 4.8-5.8 |
| 132 | 4.8-5.8 |
| 133 | 4.8-5.8 |
| 134 | >5.8 |
| 135 | >5.8 |
| 136 | 4.8-5.8 |
| 137 | <4.8 |
| 138 | 4.8-5.8 |
| 139 | 4.8-5.8 |
| 140 | 4.8-5.8 |
| 141 | >5.8 |
| 142 | <4.8 |
| 143 | 4.8-5.8 |
| 144 | 4.8-5.8 |
| 145 | <4.8 |
| 146 | <4.8 |
| 147 | <4.8 |
| 148 | <4.8 |
| 149 | 4.8-5.8 |
| 150 | <4.8 |
| 151 | >5.8 |
| 153 | >5.8 |
| 154 | 4.8-5.8 |
| 155 | 4.8-5.8 |
| 156 | <4.8 |
| 157 | 4.8-5.8 |
| 158 | >5.8 |
| 159 | 4.8-5.8 |
| 160 | 4.8-5.8 |
| 161 | 4.8-5.8 |
| 162 | >5.8 |
| 163 | <4.8 |
| 164 | <4.8 |
| 165 | 4.8-5.8 |
| 166 | >5.8 |
| 167 | <4.8 |
| 168 | >5.8 |
| 169 | <4.8 |
| 170 | <4.8 |
| 171 | 4.8-5.8 |
| 172 | >5.8 |
| 173 | <4.8 |
| 174 | 4.8-5.8 |
| 175 | 4.8-5.8 |
| 176 | <4.8 |
| 177 | <4.8 |
| 178 | >5.8 |
| 179 | 4.8-5.8 |
| 180 | 4.8-5.8 |
| 181 | <4.8 |
| 182 | 4.8-5.8 |
| 183 | >5.8 |
| 185 | 4.8-5.8 |
| 186 | 4.8-5.8 |
| 187 | 4.8-5.8 |
| 188 | <4.8 |
| 189 | 4.8-5.8 |
| 190 | <4.8 |
| 191 | 4.8-5.8 |
| 192 | <4.8 |
| 193 | 4.8-5.8 |
| 194 | <4.8 |
| 195 | <4.8 |
| 196 | 4.8-5.8 |

TABLE 2-continued pK$_{act}$ and % ACT$_{max}$ of Exemplified Compounds Against GK

| Ex. | pK$_{act}$ |
|-----|-----------|
| 197 | <4.8 |
| 198 | 4.8-5.8 |

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A compound of the formula:

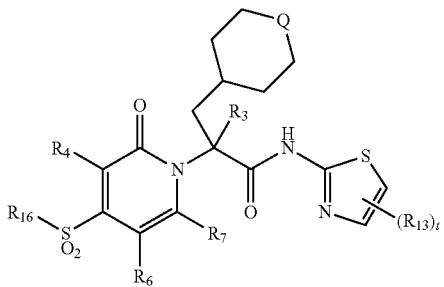

or a pharmaceutically acceptable salt thereof, wherein
t is selected from the group consisting of 0, 1 and 2;
Q is selected from the group consisting of O and $CH_2$;
$R_3$ is selected from the group consisting of hydrogen, $(C_{1-10})$alkyl, halo$(C_{1-10})$alkyl, amino $(C_{1-10})$alkyl, $(C_{3-12})$cycloalkyl$(C_{1-5})$alkyl, aryl$(C_{1-10})$alkyl, $(C_{9-12})$bicycloaryl$(C_{1-5})$alkyl, $(C_{3-12})$cycloalkyl, $(C_{9-12})$bicycloalkyl, aryl, and $(C_{9-12})$bicycloaryl, each substituted or unsubstituted;
$R_4$, $R_6$ and $R_7$ are each independently selected from the group consisting of hydrogen, halo, nitro, cyano, hydroxy, alkoxy, aryloxy, amino, $(C_{1-10})$alkylamino, —CO—NH—$R_{16}$, —NH—CO—$R_{16}$, —SO$_2$—$R_{16}$, —NH—SO$_2$—$R_{16}$, —SO$_2$—NH—$R_{16}$, $(C_{1-10})$alkyl, halo$(C_{1-10})$alkyl, amino$(C_{1-10})$alkyl, $(C_{3-12})$cycloalkyl$(C_{1-5})$alkyl, aryl$(C_{1-10})$alkyl, $(C_{9-12})$bicycloaryl$(C_{1-5})$alkyl, $(C_{3-12})$cycloalkyl, $(C_{9-12})$bicycloalkyl, aryl, and $(C_{9-12})$bicycloaryl, each substituted or unsubstituted;

each $R_{13}$ is independently selected from the group consisting of hydrogen, halo, nitro, cyano, hydroxy, alkoxy, aryloxy, amino, $(C_{1-10})$alkylamino, $(C_{1-10})$alkyl, halo$(C_{1-10})$alkyl, amino$(C_{1-10})$alkyl, $(C_{3-12})$cycloalkyl$(C_{1-5})$alkyl, aryl$(C_{1-10})$alkyl, $(C_{9-12})$bicycloaryl$(C_{1-5})$alkyl, $(C_{3-12})$cycloalkyl, $(C_{9-12})$bicycloalkyl, aryl, and $(C_{9-12})$bicycloaryl, each substituted or unsubstituted; and each $R_{16}$ is independently selected from the group consisting of hydrogen, halo, nitro, cyano, hydroxy, $(C_{1-10})$alkoxy, $(C_{4-12})$aryloxy, aminocarbonyl, amino, $(C_{1-10})$alkylamino, $(C_{1-10})$alkyl, halo$(C_{1-10})$alkyl, hydroxy$(C_{1-10})$alkyl, aza$(C_{1-10})$alkyl, $(C_{1-10})$oxaalkyl, $(C_{1-10})$oxoalkyl, $(C_{3-12})$cycloalkyl$(C_{1-5})$alkyl, aryl$(C_{1-10})$alkyl, $(C_{9-12})$bicycloaryl$(C_{1-5})$alkyl, $(C_{3-12})$cycloalkyl, $(C_{9-12})$bicycloalkyl, $(C_{4-12})$aryl, and $(C_{9-12})$bicycloaryl, each substituted or unsubstituted, wherein each optional substituent is independently selected from the group consisting of halo, nitro, cyano, hydroxy, $(C_{1-10})$alkoxy, $(C_{4-12})$aryloxy, aminocarbonyl, amino, $(C_{1-10})$alkylamino, $(C_{1-10})$alkyl, halo$(C_{1-10})$alkyl, hydroxy$(C_{1-10})$alkyl, $(C_{1-10})$azaalkyl, $(C_{3-12})$cycloalkyl$(C_{1-5})$alkyl, aryl$(C_{1-10})$alkyl, $(C_{9-12})$bicycloaryl$(C_{1-5})$alkyl, $(C_{3-12})$cycloalkyl, $(C_{9-12})$bicycloalkyl, $(C_{4-12})$aryl, and $(C_{9-12})$bicycloaryl.

2. The compound or pharmaceutically acceptable salt according to claim 1, wherein the thiazolyl ring is:

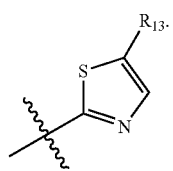

3. The compound or pharmaceutically acceptable salt according to claim 1, wherein $R_3$ is selected from the group consisting of $(C_{1-10})$alkyl, halo$(C_{1-10})$alkyl, amino$(C_{1-10})$alkyl, $(C_{3-12})$cycloalkyl$(C_{1-5})$alkyl, aryl$(C_{1-10})$alkyl, $(C_{9-12})$bicycloaryl$(C_{1-5})$alkyl, $(C_{3-12})$cycloalkyl, $(C_{9-12})$bicycloalkyl, aryl, and $(C_{9-12})$bicycloaryl, each substituted or unsubstituted.

4. The compound or pharmaceutically acceptable salt according to claim 1, wherein $R_3$ is selected from the group consisting of hydrogen, $(C_{1-10})$alkyl, $(C_{3-12})$cycloalkyl$(C_{1-5})$alkyl, and aryl$(C_{1-10})$alkyl, each substituted or unsubstituted.

5. The compound or pharmaceutically acceptable salt according to claim 1, wherein $R_3$ is selected from the group consisting of $(C_{1-10})$alkyl, $(C_{3-12})$cycloalkyl$(C_{1-5})$alkyl, and aryl$(C_{1-10})$alkyl, each substituted or unsubstituted.

6. The compound or pharmaceutically acceptable salt according to claim 1, wherein $R_3$ is selected from the group consisting of hydrogen, butyl, cyclohexylmethyl, benzyl, and phenyl.

7. The compound or pharmaceutically acceptable salt according to claim 1, wherein $R_3$ is selected from the group consisting of butyl, cyclohexylmethyl, benzyl, and phenyl.

8. The compound or pharmaceutically acceptable salt according to claim 1, wherein $R_4$ is selected from the group consisting of halo, $(C_{1-10})$alkyl, $(C_{1-10})$alkoxy, —CO—NH—$R_{16}$, —NH—CO—$R_{16}$, —SO$_2$—$R_{16}$, —NH—SO$_2$—$R_{16}$, and —SO$_2$—NH—$R_{16}$.

9. The compound or pharmaceutically acceptable salt according to claim 1, wherein $R_4$ is a substituted or unsubstituted $(C_{1-5})$alkyl.

10. The compound or pharmaceutically acceptable salt according to claim 1, wherein $R_4$ is methyl.

11. The compound or pharmaceutically acceptable salt according to claim 1, wherein $R_6$ is selected from the group consisting of hydrogen, halo, $(C_{1-10})$alkyl, $(C_{1-10})$alkoxy, —CO—NH—$R_{16}$, —NH—CO—$R_{16}$, —SO$_2$—$R_{16}$, —NH—SO$_2$—$R_{16}$, and —SO$_2$—NH—$R_{16}$.

12. The compound or pharmaceutically acceptable salt according to claim 1, wherein $R_6$ is hydrogen.

13. The compound or pharmaceutically acceptable salt according to claim 1, wherein $R_6$ is a substituted or unsubstituted $(C_{1-5})$alkyl.

14. The compound or pharmaceutically acceptable salt according to claim 1, wherein $R_6$ is methyl.

15. The compound or pharmaceutically acceptable salt according to claim 1, wherein $R_7$ is selected from the group consisting of hydrogen, halo, $(C_{1-10})$alkyl, $(C_{1-10})$alkoxy, —CO—NH—$R_{16}$, —NH—CO—$R_{16}$, —SO$_2$—$R_{16}$, —NH—SO$_2$—$R_{16}$, and —SO$_2$—NH—$R_{16}$.

16. The compound or pharmaceutically acceptable salt according to claim 1, wherein $R_7$ is methyl.

17. A compound selected from the group consisting of:
3-cyclohexyl-2-(6-methyl-4-(methylsulfonyl)-2-oxopyridin-1(2H)-yl)-N-(thiazol-2-yl)propanamide;
3-cyclohexyl-2-(4-(ethylsulfonyl)-6-methyl-2-oxopyridin-1(2H)-yl)-N-(thiazol-2-yl)propanamide;
3-cyclohexyl-2-(4-(cyclopentylsulfonyl)-6-methyl-2-oxopyridin-1(2H)-yl)-N-(thiazol-2-yl)propanamide;
2-(6-methyl-4-(methylsulfonyl)-2-oxopyridin-1(2H)-yl)-3-(tetrahydro-2H-pyran-4-yl)-N-(thiazol-2-yl)propanamide;
3-cyclohexyl-2-(4-(cyclopentylsulfonyl)-2-oxopyridin-1(2H)-yl)-N-(thiazol-2-yl)propanamide;
(S)-3-cyclohexyl-2-(4-(cyclopentylsulfonyl)-2-oxopyridin-1(2H)-yl)-N-(thiazol-2-yl)propanamide;
2-(4-(cyclopentylsulfonyl)-6-methyl-2-oxopyridin-1(2H)-yl)-3-(tetrahydro-2H-pyran-4-yl)-N-(thiazol-2-yl)propanamide;
(R)-N-(5-chlorothiazol-2-yl)-2-(4-(methylsulfonyl)-2-oxopyridin-1(2H)-yl)-3-(tetrahydro-2H-pyran-4-yl)propanamide;
(S)-N-(5-chlorothiazol-2-yl)-2-(4-(methylsulfonyl)-2-oxopyridin-1(2H)-yl)-3-(tetrahydro-2H-pyran-4-yl)propanamide;
(R)-N-(5-chlorothiazol-2-yl)-2-(4-(cyclopropylsulfonyl)-2-oxopyridin-1(2H)-yl)-3-(tetrahydro-2H-pyran-4-yl)propanamide;
(S)-N-(5-chlorothiazol-2-yl)-2-(4-(cyclopropylsulfonyl)-2-oxopyridin-1(2H)-yl)-3-(tetrahydro-2H-pyran-4-yl)propanamide;
(R)-N-(5-chlorothiazol-2-yl)-2-(4-(cyclopentylsulfonyl)-2-oxopyridin-1(2H)-yl)-3-(tetrahydro-2H-pyran-4-yl)propanamide;
(S)-N-(5-chlorothiazol-2-yl)-2-(4-(cyclopentylsulfonyl)-2-oxopyridin-1(2H)-yl)-3-(tetrahydro-2H-pyran-4-yl)propanamide;
(R)-2-(4-(cyclopentylsulfonyl)-2-oxopyridin-1(2H)-yl)-N-(5-fluorothiazol-2-yl)-3-(tetrahydro-2H-pyran-4-yl)propanamide;
(S)-2-(4-(cyclopentylsulfonyl)-2-oxopyridin-1(2H)-yl)-N-(5-fluorothiazol-2-yl)-3-(tetrahydro-2H-pyran-4-yl)propanamide;
(S)-2-(4-(cyclopropylsulfonyl)-2-oxopyridin-1(2H)-yl)-N-(5-fluorothiazol-2-yl)-3-(tetrahydro-2H-pyran-4-yl)propanamide;
(R)-2-(4-(cyclopropylsulfonyl)-2-oxopyridin-1(2H)-yl)-N-(5-fluorothiazol-2-yl)-3-(tetrahydro-2H-pyran-4-yl)propanamide;
(R)-N-(5-chlorothiazol-2-yl)-2-(4-(cyclopentylsulfonyl)-6-methyl-2-oxopyridin-1(2H)-yl)-3-(tetrahydro-2H-pyran-4-yl)propanamide;
(S)-N-(5-chlorothiazol-2-yl)-2-(4-(cyclopentylsulfonyl)-6-methyl-2-oxopyridin-1(2H)-yl)-3-(tetrahydro-2H-pyran-4-yl)propanamide;
(R)-2-(4-(cyclopentylsulfonyl)-6-methyl-2-oxopyridin-1(2H)-yl)-N-(5-fluorothiazol-2-yl)-3-(tetrahydro-2H-pyran-4-yl)propanamide;
(S)-2-(4-(cyclopentylsulfonyl)-6-methyl-2-oxopyridin-1(2H)-yl)-N-(5-fluorothiazol-2-yl)-3-(tetrahydro-2H-pyran-4-yl)propanamide;
(R)-methyl 2-(2-(4-(cyclopentylsulfonyl)-2-oxopyridin-1(2H)-yl)-3-(tetrahydro-2H-pyran-4-yl)propanamido)thiazole-5-carboxylate;
(S)-methyl 2-(2-(4-(cyclopentylsulfonyl)-2-oxopyridin-1(2H)-yl)-3-(tetrahydro-2H-pyran-4-yl)propanamido)thiazole-5-carboxylate;
3-(2-(2-(4-(methylsulfonyl)-2-oxopyridin-1(2H)-yl)-3-(tetrahydro-2H-pyran-4-yl)propanamido)thiazol-5-yl)propanoic acid;
(R)-N-(5-cyanothiazol-2-yl)-2-(4-(cyclopentylsulfonyl)-2-oxopyridin-1(2H)-yl)-3-(tetrahydro-2H-pyran-4-yl)propanamide;
(S)-N-(5-cyanothiazol-2-yl)-2-(4-(cyclopentylsulfonyl)-2-oxopyridin-1(2H)-yl)-3-(tetrahydro-2H-pyran-4-yl)propanamide;
(S)-2-(3-chloro-4-(cyclopropylsulfonyl)-6-methyl-2-oxopyridin-1(2H)-yl)-N-(5-chlorothiazol-2-yl)-3-cyclohexylpropanamide;
(R)-2-(3-chloro-4-(cyclopropylsulfonyl)-6-methyl-2-oxopyridin-1(2H)-yl)-N-(5-chlorothiazol-2-yl)-3-cyclohexylpropanamide;

3-cyclohexyl-2-(4-(cyclopentylsulfonyl)-6-methyl-2-oxopyridin-1(2H)-yl)-N-(5-(4-fluorobenzyl)thiazol-2-yl)propanamide;

ethyl 2-(2-(4-(cyclopropylsulfonyl)-2-oxopyridin-1(2H)-yl)-3-(tetrahydro-2H-pyran-4-yl)propanamido)thiazole-5-carboxylate;

2-(4-(cyclopropylsulfonyl)-2-oxopyridin-1(2H)-yl)-N-(5-(2-hydroxypropan-2-yl)thiazol-2-yl)-3-(tetrahydro-2H-pyran-4-yl)propanamide;

N-(5-chlorothiazol-2-yl)-2-(4-(cyclopentylsulfonyl)-3,5,6-trimethyl-2-oxopyridin-1(2H)-yl)-3-(tetrahydro-2H-pyran-4-yl)propanamide;

(R)-2-(4-(cyclopropylsulfonyl)-2-oxopyridin-1(2H)-yl)-N-(5-(2-methoxypropan-2-yl) thiazol-2-yl)-3-(tetrahydro-2H-pyran-4-yl)propanamide;

(S)-2-(4-(cyclopropylsulfonyl)-2-oxopyridin-1(2H)-yl)-N-(5-(2-methoxypropan-2-yl)thiazol-2-yl)-3-(tetrahydro-2H-pyran-4-yl)propanamide;

(S)-N-(5-chlorothiazol-2-yl)-2-(4-(cyclopentylsulfonyl)-3,5,6-trimethyl-2-oxopyridin-1(2H)-yl)-3-(tetrahydro-2H-pyran-4-yl)propanamide;

(R)-N-(5-chlorothiazol-2-yl)-2-(4-(cyclopentylsulfonyl)-3,5,6-trimethyl-2-oxopyridin-1(2H)-yl)-3-(tetrahydro-2H-pyran-4-yl)propanamide;

2-(4-(cyclopropylsulfonyl)-2-oxopyridin-1(2H)-yl)-N-(5-(4-fluorobenzyl)thiazol-2-yl)-3-(tetrahydro-2H-pyran-4-yl)propanamide;

N-(5-chlorothiazol-2-yl)-2-(2-oxo-4-(2,2,2-trifluoroethylsulfonyl)pyridin-1(2H)-yl)-3-(tetrahydro-2H-pyran-4-yl)propanamide;

(R)-N-(5-chlorothiazol-2-yl)-2-(2-oxo-4-(2,2,2-trifluoroethylsulfonyl)pyridin-1(2H)-yl)-3-(tetrahydro-2H-pyran-4-yl)propanamide;

(S)-N-(5-chlorothiazol-2-yl)-2-(2-oxo-4-(2,2,2-trifluoroethylsulfonyl)pyridin-1(2H)-yl)-3-(tetrahydro-2H-pyran-4-yl)propanamide;

(S)-2-(4-(cyclopentylsulfonyl)-5,6-dimethyl-2-oxopyridin-1(2H)-yl)-N-(5-fluorothiazol-2-yl)-3-(tetrahydro-2H-pyran-4-yl)propanamide;

2-(4-(cyclopropylsulfonyl)-6-methyl-2-oxopyridin-1(2H)-yl)-N-(5-fluorothiazol-2-yl)-3-(tetrahydro-2H-pyran-4-yl)propanamide;

(R)-2-(4-(cyclopentylsulfonyl)-5,6-dimethyl-2-oxopyridin-1(2H)-yl)-N-(5-fluorothiazol-2-yl)-3-(tetrahydro-2H-pyran-4-yl)propanamide;

N-(5-chlorothiazol-2-yl)-2-(4-(cyclopropylsulfonyl)-6-methyl-2-oxopyridin-1(2H)-yl)-3-(tetrahydro-2H-pyran-4-yl)propanamide;

N-(5-chlorothiazol-2-yl)-2-(4-(3-fluorophenylsulfonyl)-6-methyl-2-oxopyridin-1(2H)-yl)-3-(tetrahydro-2H-pyran-4-yl)propanamide;

2-(4-(3-fluorophenylsulfonyl)-6-methyl-2-oxopyridin-1(2H)-yl)-N-(5-fluorothiazol-2-yl)-3-(tetrahydro-2H-pyran-4-yl)propanamide;

(S)-2-(4-(3-chlorophenylsulfonyl)-6-methyl-2-oxopyridin-1(2H)-yl)-N-(5-fluorothiazol-2-yl)-3-(tetrahydro-2H-pyran-4-yl)propanamide;

(R)-2-(4-(3-chlorophenylsulfonyl)-6-methyl-2-oxopyridin-1(2H)-yl)-N-(5-fluorothiazol-2-yl)-3-(tetrahydro-2H-pyran-4-yl)propanamide;

(S)-N-(5-chlorothiazol-2-yl)-2-(4-(cyclopropylsulfonyl)-6-methyl-2-oxopyridin-1(2H)-yl)-3-(tetrahydro-2H-pyran-4-yl)propanamide;

(R)-N-(5-chlorothiazol-2-yl)-2-(4-(cyclopropylsulfonyl)-6-methyl-2-oxopyridin-1(2H)-yl)-3-(tetrahydro-2H-pyran-4-yl)propanamide;

2-(5-chloro-4-(cyclopropylsulfonyl)-2-oxopyridin-1(2H)-yl)-N-(5-chlorothiazol-2-yl)-3-(tetrahydro-2H-pyran-4-yl)propanamide;

2-(5-chloro-4-(cyclopentylsulfonyl)-2-oxopyridin-1(2H)-yl)-N-(5-chlorothiazol-2-yl)-3-(tetrahydro-2H-pyran-4-yl)propanamide;

2-(5-chloro-4-(cyclopentylsulfonyl)-2-oxopyridin-1(2H)-yl)-N-(5-fluorothiazol-2-yl)-3-(tetrahydro-2H-pyran-4-yl)propanamide;

(S)-2-(4-(3-fluorophenylsulfonyl)-6-methyl-2-oxopyridin-1(2H)-yl)-N-(5-fluorothiazol-2-yl)-3-(tetrahydro-2H-pyran-4-yl)propanamide;

(R)-2-(4-(3-fluorophenylsulfonyl)-6-methyl-2-oxopyridin-1(2H)-yl)-N-(5-fluorothiazol-2-yl)-3-(tetrahydro-2H-pyran-4-yl)propanamide;

(R)-2-(5-chloro-4-(cyclopropylsulfonyl)-2-oxopyridin-1(2H)-yl)-N-(5-chlorothiazol-2-yl)-3-(tetrahydro-2H-pyran-4-yl)propanamide;

(S)-2-(5-chloro-4-(cyclopropylsulfonyl)-2-oxopyridin-1(2H)-yl)-N-(5-chlorothiazol-2-yl)-3-(tetrahydro-2H-pyran-4-yl)propanamide;

(R)-2-(5-chloro-4-(cyclopropylsulfonyl)-2-oxopyridin-1(2H)-yl)-N-(5-fluorothiazol-2-yl)-3-(tetrahydro-2H-pyran-4-yl)propanamide;

(S)-2-(5-chloro-4-(cyclopropylsulfonyl)-2-oxopyridin-1(2H)-yl)-N-(5-fluorothiazol-2-yl)-3-(tetrahydro-2H-pyran-4-yl)propanamide; and a pharmaceutically acceptable salt of any one of the aforementioned compounds.

18. A pharmaceutical composition comprising a compound or pharmaceutically acceptable salt as defined in claim 1; and one or more pharmaceutically acceptable excipients.

* * * * *

SEQUENCE LISTING

```
<160> NUMBER OF SEQ ID NOS: 1

<210> SEQ ID NO 1
<211> LENGTH: 458
<212> TYPE: PRT
<213> ORGANISM: Homo sapiens
<220> FEATURE:
<221> NAME/KEY: MISC_FEATURE
<222> LOCATION: (5)..(458)
<223> OTHER INFORMATION: Amino Acid Sequence residues 13-466 of human
      Glucokinase

<400> SEQUENCE: 1

Met Lys Leu Met Ala Leu Thr Leu Val Glu Gln Ile Leu Ala Glu Phe
1               5                   10                  15

Gln Leu Gln Glu Glu Asp Leu Lys Lys Val Met Arg Arg Met Gln Lys
                20                  25                  30

Glu Met Asp Arg Gly Leu Arg Leu Glu Thr His Glu Glu Ala Ser Val
            35                  40                  45

Lys Met Leu Pro Thr Tyr Val Arg Ser Thr Pro Glu Gly Ser Glu Val
    50                  55                  60

Gly Asp Phe Leu Ser Leu Asp Leu Gly Gly Thr Asn Phe Arg Val Met
65                  70                  75                  80

Leu Val Lys Val Gly Glu Gly Glu Glu Gly Gln Trp Ser Val Lys Thr
                85                  90                  95

Lys His Gln Met Tyr Ser Ile Pro Glu Asp Ala Met Thr Gly Thr Ala
            100                 105                 110

Glu Met Leu Phe Asp Tyr Ile Ser Glu Cys Ile Ser Asp Phe Leu Asp
        115                 120                 125

Lys His Gln Met Lys His Lys Lys Leu Pro Leu Gly Phe Thr Phe Ser
    130                 135                 140

Phe Pro Val Arg His Glu Asp Ile Asp Lys Gly Ile Leu Leu Asn Trp
145                 150                 155                 160

Thr Lys Gly Phe Lys Ala Ser Gly Ala Glu Gly Asn Asn Val Val Gly
                165                 170                 175

Leu Leu Arg Asp Ala Ile Lys Arg Arg Gly Asp Phe Glu Met Asp Val
            180                 185                 190

Val Ala Met Val Asn Asp Thr Val Ala Thr Met Ile Ser Cys Tyr Tyr
        195                 200                 205

Glu Asp His Gln Cys Glu Val Gly Met Ile Val Gly Thr Gly Cys Asn
    210                 215                 220

Ala Cys Tyr Met Glu Glu Met Gln Asn Val Glu Leu Val Glu Gly Asp
225                 230                 235                 240

Glu Gly Arg Met Cys Val Asn Thr Glu Trp Gly Ala Phe Gly Asp Ser
                245                 250                 255

Gly Glu Leu Asp Glu Phe Leu Leu Glu Tyr Asp Arg Leu Val Asp Glu
            260                 265                 270
```

| | | | | | | | | | | | | |
|---|---|---|---|---|---|---|---|---|---|---|---|---|
| Ser | Ser | Ala | Asn | Pro | Gly | Gln | Gln | Leu | Tyr | Glu | Lys | Leu | Ile | Gly | Gly |
| | 275 | | | | | 280 | | | | | 285 | | | | |
| Lys | Tyr | Met | Gly | Glu | Leu | Val | Arg | Leu | Val | Leu | Leu | Arg | Leu | Val | Asp |
| | 290 | | | | | 295 | | | | | 300 | | | | |
| Glu | Asn | Leu | Leu | Phe | His | Gly | Glu | Ala | Ser | Glu | Gln | Leu | Arg | Thr | Arg |
| 305 | | | | | 310 | | | | | 315 | | | | | 320 |
| Gly | Ala | Phe | Glu | Thr | Arg | Phe | Val | Ser | Gln | Val | Glu | Ser | Asp | Thr | Gly |
| | | | | 325 | | | | | 330 | | | | | 335 | |
| Asp | Arg | Lys | Gln | Ile | Tyr | Asn | Ile | Leu | Ser | Thr | Leu | Gly | Leu | Arg | Pro |
| | | | 340 | | | | | 345 | | | | | 350 | | |
| Ser | Thr | Thr | Asp | Cys | Asp | Ile | Val | Arg | Arg | Ala | Cys | Glu | Ser | Val | Ser |
| | | 355 | | | | | 360 | | | | | 365 | | | |
| Thr | Arg | Ala | Ala | His | Met | Cys | Ser | Ala | Gly | Leu | Ala | Gly | Val | Ile | Asn |
| | 370 | | | | | 375 | | | | | 380 | | | | |
| Arg | Met | Arg | Glu | Ser | Arg | Ser | Glu | Asp | Val | Met | Arg | Ile | Thr | Val | Gly |
| 385 | | | | | 390 | | | | | 395 | | | | | 400 |
| Val | Asp | Gly | Ser | Val | Tyr | Lys | Leu | His | Pro | Ser | Phe | Lys | Glu | Arg | Phe |
| | | | | 405 | | | | | 410 | | | | | 415 | |
| His | Ala | Ser | Val | Arg | Arg | Leu | Thr | Pro | Ser | Cys | Glu | Ile | Thr | Phe | Ile |
| | | | 420 | | | | | 425 | | | | | 430 | | |
| Glu | Ser | Glu | Glu | Gly | Ser | Gly | Arg | Gly | Ala | Ala | Leu | Val | Ser | Ala | Val |
| | | 435 | | | | | 440 | | | | | 445 | | | |
| Ala | Cys | Lys | Lys | Ala | Cys | Met | Leu | Gly | Gln | | | | | | |
| | 450 | | | | | 455 | | | | | | | | | |